United States Patent
Abrahmsén et al.

(10) Patent No.: US 10,323,066 B2
(45) Date of Patent: Jun. 18, 2019

(54) NEONATAL FC RECEPTOR BINDING DIMER AND METHODS OF USE

(71) Applicant: Affibody AB, Solna (SE)

(72) Inventors: Lars Abrahmsén, Stockholm (SE); Caroline Ekblad, Saltsjö-boo (SE); Elin Gunneriusson, Saltsjöbaden (SE); Torbjörn Gräslund, Hägersten (SE); Johan Seijsing, Stockholm (SE); John Löfblom, Huddinge (SE); Malin Lindborg, Saltsjö-boo (SE); Fredrik Frejd, Stockholm (SE); Lindvi Gudmundsdotter, Stockholm (SE)

(73) Assignee: AFFIBODY AB, Solna (SE)

( * ) Notice: Subject to any disclaimer, the term of this patent is extended or adjusted under 35 U.S.C. 154(b) by 0 days.

(21) Appl. No.: 15/510,900

(22) PCT Filed: Sep. 17, 2015

(86) PCT No.: PCT/EP2015/071339
§ 371 (c)(1),
(2) Date: Mar. 13, 2017

(87) PCT Pub. No.: WO2016/042083
PCT Pub. Date: Mar. 24, 2016

(65) Prior Publication Data
US 2017/0260238 A1 Sep. 14, 2017

(30) Foreign Application Priority Data
Sep. 17, 2014 (EP) ..................................... 14185140

(51) Int. Cl.
| C07K 14/31 | (2006.01) |
| C07K 14/00 | (2006.01) |
| C07K 14/735 | (2006.01) |
| C07K 14/74 | (2006.01) |
| A61K 38/00 | (2006.01) |

(52) U.S. Cl.
CPC .............. *C07K 14/00* (2013.01); *C07K 14/31* (2013.01); *C07K 14/70535* (2013.01); *C07K 14/70539* (2013.01); *A61K 38/00* (2013.01); *C07K 2319/00* (2013.01); *C07K 2319/30* (2013.01); *C07K 2319/74* (2013.01)

(58) Field of Classification Search
None
See application file for complete search history.

(56) References Cited

U.S. PATENT DOCUMENTS

| 6,602,977 | B1 | 8/2003 | Ljungqvist et al. |
| 8,906,844 | B2 | 12/2014 | Mezo et al. |
| 9,012,603 | B2 | 4/2015 | Mezo et al. |
| 9,045,564 | B2 | 6/2015 | Gao et al. |
| 9,260,520 | B2 | 2/2016 | Tenhoor et al. |
| 9,975,943 | B2 * | 5/2018 | Ekblad ................ C07K 14/745 |
| 9,982,022 | B2 * | 5/2018 | Nordling ............... C07K 1/047 |
| 2016/0031967 | A1 | 2/2016 | Ekblad et al. |

FOREIGN PATENT DOCUMENTS

| WO | 2006118772 | | 11/2006 |
| WO | 2009016043 | A2 | 2/2009 |
| WO | 2009077175 | A1 | 6/2009 |
| WO | 2010054699 | A1 | 5/2010 |
| WO | 2011056124 | A1 | 5/2011 |
| WO | 2014064237 | A1 | 5/2014 |

OTHER PUBLICATIONS

Tian et al., Bivalent Ligands with Long Nanometer-Scale Flexible Linkers, Dec. 29, 2008, Biochemistry 48:264-275.*
A. Mezo et al., "Reduction of IgG in Nonhuman Primates by a Peptide Antagonist of the Neonatal Fc Receptor FcRn," PNAS; Feb. 19, 2008, pp. 2337-2342, vol. 105, No. 7.
A. Orlova et al., "Tumor Imaging Using a Picomolar Affinity HER2 Binding Affibody Molecule," American Association for Cancer Research; Apr. 15, 2006, pp. 4339-4348, vol. 66, No. 8.
C. Gronwall et al., "Selection and Characterization of Affibody ligands binding to Alzheimer Amyloid B Peptides," Journal of Biotechnology; 2007, pp. 162-183, vol. 128.
C. Vaccaro et al., "Engineering the Fc Region of Immunoglobulin G to modulate In Vivo Antibody Levels," Nature Biotechnology; Oct. 2005, pp. 1283-1288, vol. 23, No. 10.
Roopenian, et al., "FcRn: The Neonatal Fc Receptor Comes of Age," Nature Reviews Immunology; Sep. 2007, pp. 715-725, vol. 7.
D. Suter et al., "Rapid Generation of Stable Transgenic Embryonic Stem Cell Lines Using Modular Lentivectors," Stem Cells; 2006, pp. 615-623, vol. 24.
International Preliminary Report on Patentability; International Application No. PCT/EP20015/071339; International Filing Date: Sep. 17, 2015; dated Jan. 12, 2016; 6 pages.
International Search Report; International Application No. PCT/EP2015/071339; International Filing Date: Sep. 17, 2015; dated Jan. 12, 2016; 4 pages.
J. Anderson et al., "Extending Half-life by Indirect Targeting of the Neonatal Fc Receptor (FcRN) Using a Minimal Albumin Binding Domain," Journal of Biological Chemistry; Feb. 18, 2011, pp. 5234-5241, vol. 286, No. 7.

(Continued)

*Primary Examiner* — John D Ulm
(74) *Attorney, Agent, or Firm* — Cantor Colburn LLP

(57) ABSTRACT

The present disclosure relates to dimers of engineered polypeptides having a binding affinity for the neonatal Fc receptor FcRn, and provides an FcRn binding dimer, comprising a first monomer unit, a second monomer unit and an amino acid linker, wherein the first and second monomer units each comprises an FcRn binding motif. The FcRn binding dimer binds FcRn with higher capacity compared to the first monomer unit or second monomer unit alone. The present disclosure also relates to the use of the FcRn binding dimer as an agent for modifying pharmacokinetic and pharmacodynamic properties and as a therapeutic agent.

23 Claims, 38 Drawing Sheets

Specification includes a Sequence Listing.

(56) References Cited

OTHER PUBLICATIONS

J. Jakobsson et al., "Evidence for Disease-Regulated Transgene Expression in the Brain With Use of Lentiviral Vectors," Journal of Neuroscience Research; May 2006, pp. 58-67, vol. 84.
J. Jakobsson et al., "Targeted Transgene Expression in Rat Brain Using Lentiviral Vectors," Journal of Neuroscience Research; 2003, pp. 876-885, vol. 73.
J. Michaelsson et al., "MHC Class 1 Recognition by NK Receptors in the Ly49 Family Is Strongly Influenced by the B2-Microglobulin Subunit," Journal of Immunology; 2001, pp. 7327-7334, vol. 166.
J. Seijsing, et al., "An Engineered Affibody Molecule with pH-dependent Binding to FcRn Mediates Extended Circulatory Half-life of a Fusion Protein," PNAS; Dec. 2014, pp. 17110-17115, vol. 111, No. 48.
J. Thompson et al., "Crustal W: Improving the Sensitivity of Progressive Multiple Sequence Alignment Through Sequence Weighting, Position-specific Gap Penalties and Weight Matrix Choice," Nucleic Acids Research; Sep. 1994, pp. 4673-4680, vol. 22, No. 22.
K. Getman et al., "Pharmacokinetic Effects of 4C9, an Anti-FcRn Antibody, in Rats: Implications for the Use of FcRn Inhibitors for the Treatment of Humoral Autoimmune and Alloimmune Conditions," J Pharm Sci; Apr. 2005, pp. 718-729, vol. 94, No. 4.
K. Tai et al., "Destabilizing Domains Mediate Reversible Transgene Expression in the Brain," PLOS One; Sep. 2012, pp. 1-7, vol. 7:e46269, Issue 9.
N. Simister et al., "An Fc Receptor Structurally Related to MHC Class I Antigens," Nature; Jan. 12, 1989, pp. 184-187, vol. 337.
P. Hinton et al., "Engineered Human IgG Antibodies with Longer Serum Half-lives in Primates," Journal of Biological Chemistry; Feb. 20, 2004, pp. 6213-6216, vol. 279, No. 8.
R. Zufferey et al., "Multiply Attenuated Lentiviral Vector Achieves Efficient Gene Delivery In Vivo," Nature Biotechnology; Sep. 1997, pp. 871-875, vol. 15.
S. Low et al., "Oral and Pulmonary Delivery of FSH-Fc Fusion Proteins via Neonatal Fc receptor-mediated Transcytosis," Human Reproduction; Apr. 2005, pp. 1805-1813, vol. 20, No. 7.
S. Petkova et al., "Enhanced half-life of genetically engineered human IgG1 Antibodies in a humanized FcRn Mouse Model: Potential Application in Humorally Mediated Autoimmune Disease," International Immun.; Sep. 20, 2006, pp. 1759-1769, vol. 18, No. 12.
S. Vallee et al., "Pulmonary Administration of Interferon Beta-1a-Fc Fusion Protein in Non-Human Primates Using an Immunoglobulin Transport Pathway," Journal of Interferon & Cytokine Research; 2012, pp. 178-184, vol. 32, No. 4.
T. Sandalova et al., "Expression, Refolding and Crystallization of Murine MHC Class 1 H-2Db in Complex with Human B2-Microglobulin," Crystallization Communications; Sep. 2005, pp. 1090-1093, vol. F61.
U. Ruther, "pUR 250 Allows Rapid Chemical Sequencing of Both DNA Strands of its Inserts," Nucleic Acids Research; 1982, pp. 5765-5772, vol. 10, No. 19.
V. Schellenberger et al., "A Recombinant Polypeptide Extends the In Vivo Half-life of Peptides and Proteins in a Tunable Manner." Nature Biotechnology; Dec. 2009, pp. 1186-1190, vol. 27, No. 12.
W. Burmeister et al., "Crystal Structure of the Complex of Rat Neonatal Fc Receptor with Fc," Nature; Nov. 24, 1994, pp. 379-383, vol. 372.
Written Opinion; International Application No. PCT/EP2015/071339; International Filing Date: Sep. 17, 2015; dated Jan. 12, 2016; 5 pages.
X. Liu et al., "NF-kB Signaling Regulates Functional Expression of the MHC Class I-Related Neonatal Fc Receptor for IgG via Intronic Binding Sequences," Journal of Immunology; Mar. 2017, pp. 2999-3011, vol. 179.
Challa et al., "Autoantibody depletion ameliorates disease in murine experimental autoimmune encephalomyelitis," mAbs; Oct. 2013, pp. 655-659, vol. 5, No. 5.
Delves, P.J., "Autoimmune Disorders," Merk Manuals, Jun. 2016, downloaded from the internet on Dec. 6, 2016; pp. 1-2.
Deyev, S.M., et al., "Modern Technologies for Creating Synthetic Antibodies for Clinical Application" ACTA Naturae, No. 1, 2009 pp. 32-50.
International Search Report of International Application No. PCT/EP2014/055299, dated May 8, 2014, 5 pages.
Jonsson et al., "Engineering of a Femtomolar Affinity Binding Protein to Human Serum Albumin" Protein Engineering, Design & Selection; vol. 21; No. 8; (2008); pp. 515-527.
Lofblom J. et al., "Affibody molecules: Engineered proteins for thereapeutic, diagnostic and biotechnological applications", FEBS Letters, vol. 584, (2010); pp. 2670-2680.
Mayo Clinic, Dilated cardiomyopathy, Diseases and Conditions. Mayo Clinic Foundation for Medical Education and Research, Aug. 19, 2014, pp. 1-8; downloaded from the internet on Dec. 6, 2016.
Sockolosky, Jonathan T., et al., "Engineering neonatal Fc receptor-mediated recycling and transcytosis in recombinant proteins by short terminal peptide extensions", PNAS, vol. 109, No. 40, Oct. 2, 2012, pp. 16095-16100.
Unverdorben, Felix et al., "Half-life extension of a single-chain diabody by fusion to domain B of staphylococcal protein A", Protein Engineering, Design & Selection, vol. 25, No. 2, 2012, pp. 81-88.
Chen X. et al., "Fusion protein linkers: property, design and functionality", Advanced Drug Delivery Reviews, 65, (2013) pp. 1357-1369.
Gasser, Brigitte, et al., "Antibody production with yeasts and filamentous fungi: on the road to large scale?", Biotechnol Lett (2007) 29: pp. 201-212.
Gavrilova N. A. et al., "The Haemopoietic Activity and Pharmacokinetics of EPO-Fc, EPO-Fcneo and Alb-EPO Fused Proteins, Derivatives of Human Erythropoietin", Biotechnology, 2012, V. 5, pp. 38-49. (English abstract on p. 49).
Maeda Y. et al., Engineering of Functional Chimeric Protein G-Vargula Luciferase, Analytical Biochemistry, 249, p. 147-152, (1997).
Martin, W. Lance, et al., "Crystal Structure at 2.8 A of an FcRn/Heterodimeric Fc Complex: Mechanism of pH-Dependent Binding", Molecular Cell, vol. 7, Apr. 2001; pp. 867-877.

\* cited by examiner

Figure 1A

| Designation | Sequence | SEQ ID NO: |
|---|---|---|
| Z07918 | VDAKYAKEQDAAAHEIRWLPNLTFDQRVAFIHKLADDPSQSSELLSEAKKLNDSQAPK | SEQ ID NO:1 |
| Z10193 | VDAKYAKEWMRAAHEIRWLPNLTFDQRVAFIHKLEDDPSQSSELLSEAKKLNDSQAPK | SEQ ID NO:2 |
| Z10109 | VDAKYAKEANTAAHEIRWLPNLTFDQRVAFIRKLWDDPSQSSELLSEAKKLNDSQAPK | SEQ ID NO:3 |
| Z07960 | VDAKYAKEFESAAHEIRWLPNLTYDQRVAFIHKLSDDPSQSSELLSEAKKLNDSQAPK | SEQ ID NO:4 |
| Z10140 | VDAKYAKERSAAAHEIRWLPNLTFDQRVAFILKLTDDPSQSSELLSEAKKLNDSQAPK | SEQ ID NO:5 |
| Z07930 | VDAKYAKESDSAVHEIRWLPNLTFDQRVAFIHKLLDDPSQSSELLSEAKKLNDSQAPK | SEQ ID NO:6 |
| Z10183 | VDAKYAKEADNAGHEIRWLPNLTWAQRWAFIHKLLDDPSQSSELLSEAKKLNDSQAPK | SEQ ID NO:7 |
| Z10111 | VDAKYAKEDDTAAHEIRWLPNLTYEQRWAFIHKLYDDPSQSSELLSEAKKLNDSQAPK | SEQ ID NO:8 |
| Z10129 | VDAKYAKEQHDAAHEIRWLPNLTYDQRVAFIRKLHDDPSQSSELLSEAKKLNDSQAPK | SEQ ID NO:9 |
| Z10141 | VDAKYAKENQGAAHEIRWLPNLTWDQRVAFIRKLQDDPSQSSELLSEAKKLNDSQAPK | SEQ ID NO:10 |
| Z10156 | VDAKYAKERTQASHEIRWLPNLTYDQRVAFINKLRDDPSQSSELLSEAKKLNDSQAPK | SEQ ID NO:11 |
| Z10127 | VDAKYAKERKDAGHEIRWLPNLTFDQRSAFIKKLEDDPSQSSELLSEAKKLNDSQAPK | SEQ ID NO:12 |
| Z07909 | VDAKYAKERQEAAHEIRWLPNLTFDQRVAFIVKLLDDPSQSSELLSEAKKLNDSQAPK | SEQ ID NO:13 |
| Z10152 | VDAKYAKEEDVAAAHEIRWLPNLTFNQRAAFIDKLLDDPSQSSELLSEAKKLNDSQAPK | SEQ ID NO:14 |
| Z10145 | VDAKYAKENQDAAHEIRWLPNLTYDQRVAFIGKLNDDPSQSSELLSEAKKLNDSQAPK | SEQ ID NO:15 |
| Z10161 | VDAKYAKESGYAVHEIRWLPNLTFDQRVAFINKLQDDPSQSSELLSEAKKLNDSQAPK | SEQ ID NO:16 |
| Z13573 | VDAKYAKESKDAAHEIRWLPNLTFDQRVAFIHKLRDDPSQSSELLSEAKKLNDSQAPK | SEQ ID NO:17 |
| Z13574 | VDAKYAKEKKEAAHEIRWLPNLTFDQRVAFIHKLRDDPSQSSELLSEAKKLNDSQAPK | SEQ ID NO:18 |
| Z13577 | VDAKYAKEWHQAAHEIRWLPNLTFDQRVAFIHKLRDDPSQSSELLSEAKKLNDSQAPK | SEQ ID NO:19 |
| Z13578 | VDAKYAKEWTDAAHEIRWLPNLTFDQRVAFIHKLRDDPSQSSELLSEAKKLNDSQAPK | SEQ ID NO:20 |
| Z13579 | VDAKYAKEISAASHEIRWLPNLTFDQRVAFIHKLRDDPSQSSELLSEAKKLNDSQAPK | SEQ ID NO:21 |
| Z13581 | VDAKYAKEQQAAHEIRWLPNLTFDQRVAFIHKLRDDPSQSSELLSEAKKLNDSQAPK | SEQ ID NO:22 |
| Z13583 | VDAKYAKELEKAGHEIRWLPNLTFDQRVAFIHKLRDDPSQSSELLSEAKKLNDSQAPK | SEQ ID NO:23 |
| Z13585 | VDAKYAKEYLDAAHEIRWLPNLTFDQRVAFIHKLRDDPSQSSELLSEAKKLNDSQAPK | SEQ ID NO:24 |
| Z13586 | VDAKYAKELKDAGHEIRWLPNLTFDQRVAFIHKLRDDPSQSSELLSEAKKLNDSQAPK | SEQ ID NO:25 |
| Z13587 | VDAKYAKEHVDAAHEIRWLPNLTFDQRVAFIHKLRDDPSQSSELLSEAKKLNDSQAPK | SEQ ID NO:26 |
| Z13588 | VDAKYAKEYAAAAHEIRWLPNLTFDQRVAFIHKLRDDPSQSSELLSEAKKLNDSQAPK | SEQ ID NO:27 |
| Z13592 | VDAKYAKEVDIAAHEIRWLPNLTFDQRVAFIHKLRDDPSQSSELLSEAKKLNDSQAPK | SEQ ID NO:28 |

Figure 1B

| Designation | Sequence | SEQ ID NO: |
|---|---|---|
| Z13594 | VDAKYAKEIDEAKHEIRWLPNLTFDQRVAFIHKLDDDPSQSSELLSEAKKLNDSQAPK | SEQ ID NO:29 |
| Z13596 | VDAKYAKELRQAGHEIRWLPNLTFDQRVAFIHKLRDDPSQSSELLSEAKKLNDSQAPK | SEQ ID NO:30 |
| Z13597 | VDAKYAKELQSAAHEIRWLPNLTFDQRVAFIHKLKDDPSQSSELLSEAKKLNDSQAPK | SEQ ID NO:31 |
| Z13598 | VDAKYAKELEKAAHEIRWLPNLTFDQRVAFIHKLRDDPSQSSELLSEAKKLNDSQAPK | SEQ ID NO:32 |
| Z13600 | VDAKYAKEAHELAAHEIRWLPNLTFDQRVAFIHKLRDDPSQSSELLSEAKKLNDSQAPK | SEQ ID NO:33 |
| Z13604 | VDAKYAKELQAASHEIRWLPNLTFDQRVAFIHKLRDDPSQSSELLSEAKKLNDSQAPK | SEQ ID NO:34 |
| Z13605 | VDAKYAKEIESAKHEIRWLPNLTFDQRVAFIHKLNDDPSQSSELLSEAKKLNDSQAPK | SEQ ID NO:35 |
| Z13609 | VDAKYAKEWKVAAHEIRWLPNLTFDQRVAFIHKLRDDPSQSSELLSEAKKLNDSQAPK | SEQ ID NO:36 |
| Z13611 | VDAKYAKEWKAAAHEIRWLPNLTFDQRVAFIHKLDDDPSQSSELLSEAKKLNDSQAPK | SEQ ID NO:37 |
| Z13612 | VDAKYAKEIDLAKHEIRWLPNLTFDQRVAFIHKLRDDPSQSSELLSEAKKLNDSQAPK | SEQ ID NO:38 |
| Z13613 | VDAKYAKELEAARHEIRWLPNLTFDQRVAFIHKLNDDPSQSSELLSEAKKLNDSQAPK | SEQ ID NO:39 |
| Z13615 | VDAKYAKEAATAGHEIRWLPNLTFDQRVAFIHKLRDDPSQSSELLSEAKKLNDSQAPK | SEQ ID NO:40 |
| Z13616 | VDAKYAKEWQQAAHEIRWLPNLTFDQRVAFIHKLRDDPSQSSELLSEAKKLNDSQAPK | SEQ ID NO:41 |
| Z13617 | VDAKYAKEADQAGHEIRWLPNLTFDQRVAFIRKLRDDPSQSSELLSEAKKLNDSQAPK | SEQ ID NO:42 |
| Z13620 | VDAKYAKEQSKAAHEIRWLPNLTFDQRVAFIHKLRDDPSQSSELLSEAKKLNDSQAPK | SEQ ID NO:43 |
| Z13621 | VDAKYAKEADAAGHEIRWLPNLTFDQRVAFIHKLRDDPSQSSELLSEAKKLNDSQAPK | SEQ ID NO:44 |
| Z13622 | VDAKYAKEFMDAGHEIRWLPNLTFDQRVAFIHKLRDDPSQSSELLSEAKKLNDSQAPK | SEQ ID NO:45 |
| Z13624 | VDAKYAKESKQAAHEIRWLPNLTFDQRVAFIHKLRDDPSQSSELLSEAKKLNDSQAPK | SEQ ID NO:46 |
| Z13625 | VDAKYAKEVSDAAHEIRWLPNLTFDQRVAFIHKLRDDPSQSSELLSEAKKLNDSQAPK | SEQ ID NO:47 |
| Z13626 | VDAKYAKEADSASHEIRWLPNLTFDQRVAFIHKLRDDPSQSSELLSEAKKLNDSQAPK | SEQ ID NO:48 |
| Z13627 | VDAKYAKELMEAAHEIRWLPNLTFDQRVAFIHKLRDDPSQSSELLSEAKKLNDSQAPK | SEQ ID NO:49 |
| Z13628 | VDAKYAKELNTAAHEIRWLPNLTFDQRVAFIHKLKDDPSQSSELLSEAKKLNDSQAPK | SEQ ID NO:50 |
| Z13629 | VDAKYAKEVHEAGHEIRWLPNLTFDQRVAFIHKLRDDPSQSSELLSEAKKLNDSQAPK | SEQ ID NO:51 |
| Z13633 | VDAKYAKESTAAAHEIRWLPNLTFDQRVAFIHKLRDDPSQSSELLSEAKKLNDSQAPK | SEQ ID NO:52 |
| Z13634 | VDAKYAKEWYNAAHEIRWLPNLTFDQRVAFIHKLRDDPSQSSELLSEAKKLNDSQAPK | SEQ ID NO:53 |
| Z13635 | VDAKYAKEWNDAAHEIRWLPNLTFDQRVAFIHKLDDDPSQSSELLSEAKKLNDSQAPK | SEQ ID NO:54 |
| Z13637 | VDAKYAKEVEVAKHEIRWLPNLTFDQRVAFIHKLDDDPSQSSELLSEAKKLNDSQAPK | SEQ ID NO:55 |
| Z13638 | VDAKYAKEFNFAAHEIRWLPNLTFDQRVAFIHKLRDDPSQSSELLSEAKKLNDSQAPK | SEQ ID NO:56 |

Figure 1C

| Designation | Sequence | SEQ ID NO: |
|---|---|---|
| Z13639 | VDAKYAKEHDSAAHEIRWLPNLTFDQRVAFIHKLRDDPSQSSELLSEAKKLNDSQAPK | SEQ ID NO:57 |
| Z13640 | VDAKYAKEWMDAAHEIRWLPNLTFDQRVAFIHKLRDDPSQSSELLSEAKKLNDSQAPK | SEQ ID NO:58 |
| Z13641 | VDAKYAKEFSAAGHEIRWLPNLTFDQRVAFIHKLRDDPSQSSELLSEAKKLNDSQAPK | SEQ ID NO:59 |
| Z13644 | VDAKYAKELNSAAHEIRWLPNLTFDQRVAFIHKLRDDPSQSSELLSEAKKLNDSQAPK | SEQ ID NO:60 |
| Z13645 | VDAKYAKEVDTAAHEIRWLPNLTFDQRVAFIHKLRDDPSQSSELLSEAKKLNDSQAPK | SEQ ID NO:61 |
| Z13648 | VDAKYAKESQIAGHEIRWLPNLTFDQRVAFIHKLRDDPSQSSELLSEAKKLNDSQAPK | SEQ ID NO:62 |
| Z13651 | VDAKYAKEVSAASHEIRWLPNLTFDQRVAFIHKLRDDPSQSSELLSEAKKLNDSQAPK | SEQ ID NO:63 |
| Z13652 | VDAKYAKEDQDAAHEIRWLPNLTFDQRVAFIHKLDDDPSQSSELLSEAKKLNDSQAPK | SEQ ID NO:64 |
| Z13654 | VDAKYAKELEAAKHEIRWLPNLTFDQRVAFIHKLRDDPSQSSELLSEAKKLNDSQAPK | SEQ ID NO:65 |
| Z13655 | VDAKYAKESKRAAHEIRWLPNLTFDQRVAFIHKLRDDPSQSSELLSEAKKLNDSQAPK | SEQ ID NO:66 |
| Z13656 | VDAKYAKEYVKAGHEIRWLPNLTFDQRVAFIRKLRDDPSQSSELLSEAKKLNDSQAPK | SEQ ID NO:67 |
| Z13657 | VDAKYAKEFSRAGHEIRWLPNLTFDQRVAFIHKLRDDPSQSSELLSEAKKLNDSQAPK | SEQ ID NO:68 |
| Z13659 | VDAKYAKEWQFAAHEIRWLPNLTFDQRVAFIHKLRDDPSQSSELLSEAKKLNDSQAPK | SEQ ID NO:69 |
| Z13663 | VDAKYAKEWQIAAHEIRWLPNLTFDQRVAFIHKLRDDPSQSSELLSEAKKLNDSQAPK | SEQ ID NO:70 |
| Z13664 | VDAKYAKELQEAAHEIRWLPNLTFDQRVAFIHKLRDDPSQSSELLSEAKKLNDSQAPK | SEQ ID NO:71 |
| Z13667 | VDAKYAKEYRAAAHEIRWLPNLTFDQRVAFIVKLRDDPSQSSELLSEAKKLNDSQAPK | SEQ ID NO:72 |
| Z13669 | VDAKYAKELASAGHEIRWLPNLTFDQRVAFIHKLRDDPSQSSELLSEAKKLNDSQAPK | SEQ ID NO:73 |
| Z13672 | VDAKYAKEVQSASHEIRWLPNLTFDQRVAFIHKLRDDPSQSSELLSEAKKLNDSQAPK | SEQ ID NO:74 |
| Z13674 | VDAKYAKEIEDAGHEIRWLPNLTFDQRVAFIHKLRDDPSQSSELLSEAKKLNDSQAPK | SEQ ID NO:75 |
| Z13675 | VDAKYAKENQAAAHEIRWLPNLTFDQRVAFIHKLRDDPSQSSELLSEAKKLNDSQAPK | SEQ ID NO:76 |
| Z13676 | VDAKYAKEATSAGHEIRWLPNLTFDQRVAFIHKLRDDPSQSSELLSEAKKLNDSQAPK | SEQ ID NO:77 |
| Z13678 | VDAKYAKEDEQAAHEIRWLPNLTFDQRVAFIHKLRDDPSQSSELLSEAKKLNDSQAPK | SEQ ID NO:78 |
| Z13684 | VDAKYAKEQNQAGHEIRWLPNLTFDQRVAFIHKLRDDPSQSSELLSEAKKLNDSQAPK | SEQ ID NO:79 |
| Z13688 | VDAKYAKEYTSAAHEIRWLPNLTFDQRVAFIHKLRDDPSQSSELLSEAKKLNDSQAPK | SEQ ID NO:80 |
| Z13691 | VDAKYAKEWDAAAHEIRWLPNLTFDQRVAFIHKLRDDPSQSSELLSEAKKLNDSQAPK | SEQ ID NO:81 |
| Z13692 | VDAKYAKEEMQAGHEIRWLPNLTFDQRVAFIHKLRDDPSQSSELLSEAKKLNDSQAPK | SEQ ID NO:82 |
| Z13694 | VDAKYAKELSDAAHEIRWLPNLTFDQRVAFIHKLNDDPSQSSELLSEAKKLNDSQAPK | SEQ ID NO:83 |
| Z13695 | VDAKYAKEIDAAKHEIRWLPNLTFDQRVAFIHKLDDDPSQSSELLSEAKKLNDSQAPK | SEQ ID NO:84 |

Figure 1D

| Designation | Sequence | SEQ ID NO: |
|---|---|---|
| Z13697 | VDAKYAKEAERAGHEIRWLPNLTFDQRVAFIRKLRDDPSQSSELLSEAKKLNDSQAPK | SEQ ID NO:85 |
| Z13706 | VDAKYAKEEDSAAHEIRWLPNLTFDQRVAFIHKLKDDPSQSSELLSEAKKLNDSQAPK | SEQ ID NO:86 |
| Z13708 | VDAKYAKEQKAAGHEIRWLPNLTFDQRVAFIHKLRDDPSQSSELLSEAKKLNDSQAPK | SEQ ID NO:87 |
| Z13710 | VDAKYAKEWDQAAHEIRWLPNLTFDQRVAFIHKLRDDPSQSSELLSEAKKLNDSQAPK | SEQ ID NO:88 |
| Z13711 | VDAKYAKEAKAAAHEIRWLPNLTFDQRVAFIHKLRDDPSQSSELLSEAKKLNDSQAPK | SEQ ID NO:89 |
| Z13714 | VDAKYAKELSEAAHEIRWLPNLTFDQRVAFIHKLKDDPSQSSELLSEAKKLNDSQAPK | SEQ ID NO:90 |
| Z13716 | VDAKYAKETEAAKHEIRWLPNLTFDQRVAFIHKLDDDPSQSSELLSEAKKLNDSQAPK | SEQ ID NO:91 |
| Z13719 | VDAKYAKEAKSAAHEIRWLPNLTFDQRVAFIHKLRDDPSQSSELLSEAKKLNDSQAPK | SEQ ID NO:92 |
| Z13720 | VDAKYAKEQSAAAHEIRWLPNLTFDQRVAFIHKLNDDPSQSSELLSEAKKLNDSQAPK | SEQ ID NO:93 |
| Z13721 | VDAKYAKEKERAAHEIRWLPNLTFDQRVAFIHKLRDDPSQSSELLSEAKKLNDSQAPK | SEQ ID NO:94 |
| Z13725 | VDAKYAKEWDEAAHEIRWLPNLTFDQRVAFIHKLRDDPSQSSELLSEAKKLNDSQAPK | SEQ ID NO:95 |
| Z13727 | VDAKYAKEEKDAAHEIRWLPNLTFDQRVAFIHKLRDDPSQSSELLSEAKKLNDSQAPK | SEQ ID NO:96 |
| Z13728 | VDAKYAKEIENAAHEIRWLPNLTFDQRVAFIWKLRDDPSQSSELLSEAKKLNDSQAPK | SEQ ID NO:97 |
| Z13732 | VDAKYAKETKEAAHEIRWLPNLTFDQRVAFIHKLWDDPSQSSELLSEAKKLNDSQAPK | SEQ ID NO:98 |
| Z13735 | VDAKYAKELEAAKHEIRWLPNLTFDQRVAFIHKLNDDPSQSSELLSEAKKLNDSQAPK | SEQ ID NO:99 |
| Z13736 | VDAKYAKEWAEAAHEIRWLPNLTFDQRVAFIHKLRDDPSQSSELLSEAKKLNDSQAPK | SEQ ID NO:100 |
| Z13740 | VDAKYAKESQEAGHEIRWLPNLTFDQRVAFIHKLRDDPSQSSELLSEAKKLNDSQAPK | SEQ ID NO:101 |
| Z13742 | VDAKYAKELSTAAHEIRWLPNLTFDQRVAFIHKLRDDPSQSSELLSEAKKLNDSQAPK | SEQ ID NO:102 |
| Z13747 | VDAKYAKEIEEAGHEIRWLPNLTFDQRVAFIHKLRDDPSQSSELLSEAKKLNDSQAPK | SEQ ID NO:103 |
| Z13749 | VDAKYAKELQTASHEIRWLPNLTFDQRVAFIHKLWDDPSQSSELLSEAKKLNDSQAPK | SEQ ID NO:104 |
| Z13750 | VDAKYAKEQDSAAHEIRWLPNLTFDQRVAFIHKLRDDPSQSSELLSEAKKLNDSQAPK | SEQ ID NO:105 |
| Z13751 | VDAKYAKESASAGHEIRWLPNLTFDQRVAFIHKLRDDPSQSSELLSEAKKLNDSQAPK | SEQ ID NO:106 |
| Z13752 | VDAKYAKEVAKASHEIRWLPNLTFDQRVAFIHKLRDDPSQSSELLSEAKKLNDSQAPK | SEQ ID NO:107 |
| Z13758 | VDAKYAKEVQEAAHEIRWLPNLTFDQRVAFIHKLWDDPSQSSELLSEAKKLNDSQAPK | SEQ ID NO:108 |
| Z13759 | VDAKYAKESYEAAHEIRWLPNLTFDQRVAFIHKLRDDPSQSSELLSEAKKLNDSQAPK | SEQ ID NO:109 |
| Z13760 | VDAKYAKETAEAGHEIRWLPNLTFDQRVAFIHKLRDDPSQSSELLSEAKKLNDSQAPK | SEQ ID NO:110 |
| Z13761 | VDAKYAKELEEAAHEIRWLPNLTFDQRVAFIHKLRDDPSQSSELLSEAKKLNDSQAPK | SEQ ID NO:111 |
| Z13771 | VDAKYAKEAAAAGHEIRWLPNLTFDQRVAFIHKLRDDPSQSSELLSEAKKLNDSQAPK | SEQ ID NO:112 |

Figure 1E

| Designation | Sequence | SEQ ID NO: |
|---|---|---|
| Z13773 | VDAKYAKEYVDAGHEIRWLPNLTFDQRVAFIRKLRDDPSQSSELLSEAKKLNDSQAPK | SEQ ID NO:113 |
| Z13776 | VDAKYAKEIQEAGHEIRWLPNLTFDQRVAFIHKLRDDPSQSSELLSEAKKLNDSQAPK | SEQ ID NO:114 |
| Z13777 | VDAKYAKESATAAHEIRWLPNLTFDQRVAFIHKLRDDPSQSSELLSEAKKLNDSQAPK | SEQ ID NO:115 |
| Z13780 | VDAKYAKEWMSAAHEIRWLPNLTFDQRVAFIHKLRDDPSQSSELLSEAKKLNDSQAPK | SEQ ID NO:116 |
| Z13782 | VDAKYAKEREQASHEIRWLPNLTFDQRVAFIHKLRDDPSQSSELLSEAKKLNDSQAPK | SEQ ID NO:117 |
| Z13783 | VDAKYAKEIEQAGHEIRWLPNLTFDQRVAFIHKLRDDPSQSSELLSEAKKLNDSQAPK | SEQ ID NO:118 |
| Z13786 | VDAKYAKEHNAAAHEIRWLPNLTFDQRVAFIHKLRDDPSQSSELLSEAKKLNDSQAPK | SEQ ID NO:119 |
| Z13792 | VDAKYAKEIEVAAHEIRWLPNLTFDQRVAFIHKLRDDPSQSSELLSEAKKLNDSQAPK | SEQ ID NO:120 |
| Z13796 | VDAKYAKERAEAAHEIRWLPNLTFDQRVAFIHKLRDDPSQSSELLSEAKKLNDSQAPK | SEQ ID NO:121 |
| Z13799 | VDAKYAKESELAAHEIRWLPNLTFDQRVAFIWKLRDDPSQSSELLSEAKKLNDSQAPK | SEQ ID NO:122 |
| Z13806 | VDAKYAKEYRAAGHEIRWLPNLTFDQRVAFIHKLRDDPSQSSELLSEAKKLNDSQAPK | SEQ ID NO:123 |
| Z13808 | VDAKYAKETANAAHEIRWLPNLTFDQRVAFIHKLRDDPSQSSELLSEAKKLNDSQAPK | SEQ ID NO:124 |
| Z13811 | VDAKYAKEWYEAAHEIRWLPNLTFDQRVAFIHKLRDDPSQSSELLSEAKKLNDSQAPK | SEQ ID NO:125 |
| Z13812 | VDAKYAKEEQFAAHEIRWLPNLTFDQRVAFIHKLWDDPSQSSELLSEAKKLNDSQAPK | SEQ ID NO:126 |
| Z13823 | VDAKYAKEHDDAAHEIRWLPNLTFDQRVAFIHKLRDDPSQSSELLSEAKKLNDSQAPK | SEQ ID NO:127 |
| Z13824 | VDAKYAKEWYSAAHEIRWLPNLTFDQRVAFIHKLRDDPSQSSELLSEAKKLNDSQAPK | SEQ ID NO:128 |
| Z13838 | VDAKYAKEISDAAHEIRWLPNLTFDQRVAFIHKLRDDPSQSSELLSEAKKLNDSQAPK | SEQ ID NO:129 |
| Z13840 | VDAKYAKEYTAAHEIRWLPNLTFDQRVAFIHKLRDDPSQSSELLSEAKKLNDSQAPK | SEQ ID NO:130 |
| Z13842 | VDAKYAKEISQAAHEIRWLPNLTFDQRVAFIHKLRDDPSQSSELLSEAKKLNDSQAPK | SEQ ID NO:131 |
| Z13845 | VDAKYAKENDDAAHEIRWLPNLTFDQRVAFIHKLRDDPSQSSELLSEAKKLNDSQAPK | SEQ ID NO:132 |
| Z13846 | VDAKYAKESEIAGHEIRWLPNLTFDQRVAFIRKLRDDPSQSSELLSEAKKLNDSQAPK | SEQ ID NO:133 |
| Z13848 | VDAKYAKEQADAAHEIRWLPNLTFDQRVAFIHKLRDDPSQSSELLSEAKKLNDSQAPK | SEQ ID NO:134 |
| Z13849 | VDAKYAKETESAAHEIRWLPNLTFDQRVAFIHKLRDDPSQSSELLSEAKKLNDSQAPK | SEQ ID NO:135 |
| Z13860 | VDAKYAKEISDAKHEIRWLPNLTFDQRVAFIHKLDDDPSQSSELLSEAKKLNDSQAPK | SEQ ID NO:136 |
| Z13865 | VDAKYAKEHLNAAHEIRWLPNLTFDQRVAFIHKLRDDPSQSSELLSEAKKLNDSQAPK | SEQ ID NO:137 |
| Z13866 | VDAKYAKEWLDAAHEIRWLPNLTFDQRVAFIHKLRDDPSQSSELLSEAKKLNDSQAPK | SEQ ID NO:138 |
| Z13875 | VDAKYAKENAAAAHEIRWLPNLTFDQRVAFIHKLRDDPSQSSELLSEAKKLNDSQAPK | SEQ ID NO:139 |
| Z13879 | VDAKYAKEAELAGHEIRWLPNLTFDQRVAFIRKLRDDPSQSSELLSEAKKLNDSQAPK | SEQ ID NO:140 |

Figure 1F

| Designation | Sequence | SEQ ID NO: |
|---|---|---|
| Z13480 | VDAKYAKEVTDAGHEIRWLPNLTFDQRVAFIEKLKDDPSQSSELLSEAKKLNDSQAPK | SEQ ID NO:141 |
| Z13481 | VDAKYAKELDSASHEIRWLPNLTFDQRVAFINKLLDDPSQSSELLSEAKKLNDSQAPK | SEQ ID NO:142 |
| Z13482 | VDAKYAKEINLAKHEIRWLPNLTFDQRVAFIEKLNDDPSQSSELLSEAKKLNDSQAPK | SEQ ID NO:143 |
| Z13483 | VDAKYAKESEVAKHEIRWLPNLTFDQRVAFIHKLSDDPSQSSELLSEAKKLNDSQAPK | SEQ ID NO:144 |
| Z13484 | VDAKYAKESAEAGHEIRWLPNLTFDQRVAFIHKLQDDPSQSSELLSEAKKLNDSQAPK | SEQ ID NO:145 |
| Z13485 | VDAKYAKEYSNAAHEIRWLPNLTFDQRVAFIDKLSDDPSQSSELLSEAKKLNDSQAPK | SEQ ID NO:146 |
| Z13487 | VDAKYAKETNNAGHEIRWLPNLTFDQRVAFIIKLRDDPSQSSELLSEAKKLNDSQAPK | SEQ ID NO:147 |
| Z13488 | VDAKYAKEVEFAAHEIRWLPNLTFDQRVAFIHKLNDDPSQSSELLSEAKKLNDSQAPK | SEQ ID NO:148 |
| Z13489 | VDAKYAKEVELAGHEIRWLPNLTFDQRVAFIEKLHDDPSQSSELLSEAKKLNDSQAPK | SEQ ID NO:149 |
| Z13490 | VDAKYAKEVLKASHEIRWLPNLTFDQRVAFITKLQDDPSQSSELLSEAKKLNDSQAPK | SEQ ID NO:150 |
| Z13491 | VDAKYAKEIANAGHEIRWLPNLTFDQRVAFIRKLDDDPSQSSELLSEAKKLNDSQAPK | SEQ ID NO:151 |
| Z13493 | VDAKYAKEYMKAGHEIRWLPNLTFDQRVAFIVKLRDDPSQSSELLSEAKKLNDSQAPK | SEQ ID NO:152 |
| Z13495 | VDAKYAKEHANAQHEIRWLPNLTFDQRVAFIHKLQDDPSQSSELLSEAKKLNDSQAPK | SEQ ID NO:153 |
| Z13496 | VDAKYAKEVDIASHEIRWLPNLTYDQRVAFIVKLRDDPSQSSELLSEAKKLNDSQAPK | SEQ ID NO:154 |
| Z13497 | VDAKYAKEEVFAAHEIRWLPNLTFDQRVAFIVKLRDDPSQSSELLSEAKKLNDSQAPK | SEQ ID NO:155 |
| Z13499 | VDAKYAKEFNTAAHEIRWLPNLTFDQRVAFINKLDDDPSQSSELLSEAKKLNDSQAPK | SEQ ID NO:156 |
| Z13501 | VDAKYAKEVDVAGHEIRWLPNLTFDQRVAFIRKLNDDPSQSSELLSEAKKLNDSQAPK | SEQ ID NO:157 |
| Z13502 | VDAKYAKEWSLAAHEIRWLPNLTFDQRVAFIVKLRDDPSQSSELLSEAKKLNDSQAPK | SEQ ID NO:158 |
| Z13503 | VDAKYAKELDDAAHEIRWLPNLTFDQRVAFIQKLNDDPSQSSELLSEAKKLNDSQAPK | SEQ ID NO:159 |
| Z13505 | VDAKYAKERHEAGHEIRWLPNLTFDQRVAFIRKLNDDPSQSSELLSEAKKLNDSQAPK | SEQ ID NO:160 |
| Z13506 | VDAKYAKEISDAIHEIRWLPNLTFDQRVAFIHKLQDDPSQSSELLSEAKKLNDSQAPK | SEQ ID NO:161 |
| Z13507 | VDAKYAKEWETAGHEIRWLPNLTFDQRVAFIVKLSDDPSQSSELLSEAKKLNDSQAPK | SEQ ID NO:162 |
| Z13508 | VDAKYAKERYWASHEIRWLPNLTFDQRVAFIHKLLDDPSQSSELLSEAKKLNDSQAPK | SEQ ID NO:163 |
| Z13512 | VDAKYAKEIDWAGHEIRWLPNLTFDQRVAFIHKLKDDPSQSSELLSEAKKLNDSQAPK | SEQ ID NO:164 |
| Z13515 | VDAKYAKEQSKAGHEIRWLPNLTFDQRVAFIHKLKDDPSQSSELLSEAKKLNDSQAPK | SEQ ID NO:165 |
| Z13518 | VDAKYAKEIEAAQHEIRWLPNLTFDQRVAFIRKLVDDPSQSSELLSEAKKLNDSQAPK | SEQ ID NO:166 |
| Z13519 | VDAKYAKEHEQAAHEIRWLPNLTFDQRVAFIRKLVDDPSQSSELLSEAKKLNDSQAPK | SEQ ID NO:167 |
| Z13520 | VDAKYAKEAEQAGHEIRWLPNLTFDQRVAFINKLQDDPSQSSELLSEAKKLNDSQAPK | SEQ ID NO:168 |

Figure 1G

| Designation | Sequence | SEQ ID NO: |
|---|---|---|
| Z13522 | VDAKYAKEVDYAAHEIRWLPNLTFDQRVAFIHKLWDDPSQSSELLSEAKKLNDSQAPK | SEQ ID NO:169 |
| Z13525 | VDAKYAKEYSAAGHEIRWLPNLTFDQRVAFIEKLRDDPSQSSELLSEAKKLNDSQAPK | SEQ ID NO:170 |
| Z13561 | VDAKYAKELATASHEIRWLPNLTFDQRVAFIHKLRDDPSQSSELLSEAKKLNDSQAPK | SEQ ID NO:171 |
| Z13572 | VDAKYAKEYRVAGHEIRWLPNLTFDQRVAFIQKLRDDPSQSSELLSEAKKLNDSQAPK | SEQ ID NO:172 |
| Z13575 | VDAKYAKEVVSAKHEIRWLPNLTFDQRVAFIHKLDDDPSQSSELLSEAKKLNDSQAPK | SEQ ID NO:173 |
| Z13576 | VDAKYAKESAQAAHEIRWLPNLTFDQRVAFIRKLRDDPSQSSELLSEAKKLNDSQAPK | SEQ ID NO:174 |
| Z13584 | VDAKYAKEYSAAGHEIRWLPNLTFDQRVAFIHKLRDDPSQSSELLSEAKKLNDSQAPK | SEQ ID NO:175 |
| Z13589 | VDAKYAKEQKEAAAEIRWLPNLTFDQRVAFIHKLRDDPSQSSELLSEAKKLNDSQAPK | SEQ ID NO:176 |
| Z13590 | VDAKYAKEAAIAGKEIRWLPNLTFDQRVAFIHKLRDDPSQSSELLSEAKKLNDSQAPK | SEQ ID NO:177 |
| Z13591 | VDAKYAKEISKAKHEIRWLPNLTFDQRVAFIHKLDDDPSQSSELLSEAKKLNDSQAPK | SEQ ID NO:178 |
| Z13593 | VDAKYAKESVAAAHEIRWLPNLTFDQRVAFIWKLDDDPSQSSELLSEAKKLNDSQAPK | SEQ ID NO:179 |
| Z13595 | VDAKYAKEIQQAKHEIRWLPNLTFDQRVAFIHKLDDDPSQSSELLSEAKKLNDSQAPK | SEQ ID NO:180 |
| Z13599 | VDAKYAKEITSAKHEIRWLPNLTFDQRVAFIHKLDDDPSQSSELLSEAKKLNDSQAPK | SEQ ID NO:181 |
| Z13601 | VDAKYAKEQDVAAHEIRWLPNLTFDQRVAFIHKLRDDPSQSSELLSEAKKLNDSQAPK | SEQ ID NO:182 |
| Z13603 | VDAKYAKELERAAHEIRWLPNLTFDQRVAFINKLDDDPSQSSELLSEAKKLNDSQAPK | SEQ ID NO:183 |
| Z13607 | VDAKYAKENQLAAHEIRWLPNLTFDQRVAFIHKLRDDPSQSSELLSEAKKLNDSQAPK | SEQ ID NO:184 |
| Z13608 | VDAKYAKEISQAKHEIRWLPNLTFDQRVAFIYKLRDDPSQSSELLSEAKKLNDSQAPK | SEQ ID NO:185 |
| Z13610 | VDAKYAKEIANASHEIRWLPNLTFDQRVAFIRKLRDDPSQSSELLSEAKKLNDSQAPK | SEQ ID NO:186 |
| Z13614 | VDAKYAKEWQAAAEIRWLPNLTFDQRVAFIHKLDDDPSQSSELLSEAKKLNDSQAPK | SEQ ID NO:187 |
| Z13618 | VDAKYAKERKDAGHEIRWLPNLTFDQRVAFIHKLDDDPSQSSELLSEAKKLNDSQAPK | SEQ ID NO:188 |
| Z13619 | VDAKYAKEITQAKHEIRWLPNLTFDQRVAFIHKLRDDPSQSSELLSEAKKLNDSQAPK | SEQ ID NO:189 |
| Z13623 | VDAKYAKEFIQAGHEIRWLPNLTFDQRVAFIHKLRDDPSQSSELLSEAKKLNDSQAPK | SEQ ID NO:190 |
| Z13630 | VDAKYAKEWNTASHEIRWLPNLTFDQRVAFIHKLDDDPSQSSELLSEAKKLNDSQAPK | SEQ ID NO:191 |
| Z13631 | VDAKYAKEFVAAHEIRWLPNLTFDQRVAFIHKLRDDPSQSSELLSEAKKLNDSQAPK | SEQ ID NO:192 |
| Z13632 | VDAKYAKEADSAGAEIRWLPNLTFDQRVAFIHKLRDDPSQSSELLSEAKKLNDSQAPK | SEQ ID NO:193 |
| Z13636 | VDAKYAKESSVAAAEIRWLPNLTFDQRVAFIHKLDDDPSQSSELLSEAKKLNDSQAPK | SEQ ID NO:194 |
| Z13642 | VDAKYAKEVDLAGREIRWLPNLTFDQRVAFIHKLRDDPSQSSELLSEAKKLNDSQAPK | SEQ ID NO:195 |
| Z13643 | VDAKYAKEQERAAAEIRWLPNLTFDQRVAFIHKLRDDPSQSSELLSEAKKLNDSQAPK | SEQ ID NO:196 |

Figure 1H

| Designation | Sequence | SEQ ID NO: |
|---|---|---|
| Z13646 | VDAKYAKEIWQAKHEIRWLPNLTFDQRVAFIHKLDDDPSQSSELLSEAKKLNDSQAPK | SEQ ID NO:197 |
| Z13647 | VDAKYAKELNQAKHEIRWLPNLTFDQRVAFIHKLEDDPSQSSELLSEAKKLNDSQAPK | SEQ ID NO:198 |
| Z13649 | VDAKYAKELQQASHEIRWLPNLTFDQRVAFIHKLRDDPSQSSELLSEAKKLNDSQAPK | SEQ ID NO:199 |
| Z13650 | VDAKYAKEINQAKHEIRWLPNLTFDQRVAFIHKLDDDPSQSSELLSEAKKLNDSQAPK | SEQ ID NO:200 |
| Z13653 | VDAKYAKELVLAGHEIRWLPNLTFDQRVAFIHKLRDDPSQSSELLSEAKKLNDSQAPK | SEQ ID NO:201 |
| Z13658 | VDAKYAKELTSAAHEIRWLPNLTFDQRVAFIHKLRDDPSQSSELLSEAKKLNDSQAPK | SEQ ID NO:202 |
| Z13661 | VDAKYAKEWNAAAREIRWLPNLTFDQRVAFIHKLRDDPSQSSELLSEAKKLNDSQAPK | SEQ ID NO:203 |
| Z13662 | VDAKYAKEILHAKHEIRWLPNLTFDQRVAFIHKLRDDPSQSSELLSEAKKLNDSQAPK | SEQ ID NO:204 |
| Z13665 | VDAKYAKEVLTAKHEIRWLPNLTFDQRVAFIHKLNDDPSQSSELLSEAKKLNDSQAPK | SEQ ID NO:205 |
| Z13666 | VDAKYAKENSKAAHEIRWLPNLTFDQRVAFIHKLADDPSQSSELLSEAKKLNDSQAPK | SEQ ID NO:206 |
| Z13668 | VDAKYAKEVMTAKHEIRWLPNLTFDQRVAFIHKLDDDPSQSSELLSEAKKLNDSQAPK | SEQ ID NO:207 |
| Z13671 | VDAKYAKEARDAAHEIRWLPNLTFDQRVAFIHKLSDDPSQSSELLSEAKKLNDSQAPK | SEQ ID NO:208 |
| Z13673 | VDAKYAKERSKAAHEIRWLPNLTFDQRVAFIHKLDDPSQSSELLSEAKKLNDSQAPK | SEQ ID NO:209 |
| Z13677 | VDAKYAKEIYSAKHEIRWLPNLTFDQRVAFIHKLDDDPSQSSELLSEAKKLNDSQAPK | SEQ ID NO:210 |
| Z13679 | VDAKYAKEVQSAKHEIRWLPNLTFDQRVAFIHKLDDDPSQSSELLSEAKKLNDSQAPK | SEQ ID NO:211 |
| Z13680 | VDAKYAKETLEAAHEIRWLPNLTFDQRVAFIHKLKDDPSQSSELLSEAKKLNDSQAPK | SEQ ID NO:212 |
| Z13681 | VDAKYAKEQMRAAHEIRWLPNLTFDQRVAFIRKLRDDPSQSSELLSEAKKLNDSQAPK | SEQ ID NO:213 |
| Z13685 | VDAKYAKENKNAAHEIRWLPNLTFDQRVAFIHKLRDDPSQSSELLSEAKKLNDSQAPK | SEQ ID NO:214 |
| Z13687 | VDAKYAKETESAKHEIRWLPNLTFDQRVAFIHKLTDDPSQSSELLSEAKKLNDSQAPK | SEQ ID NO:215 |
| Z13689 | VDAKYAKETVQAKHEIRWLPNLTFDQRVAFIHKLDDDPSQSSELLSEAKKLNDSQAPK | SEQ ID NO:216 |
| Z13693 | VDAKYAKEIASAKHEIRWLPNLTFDQRVAFIHKLRDDPSQSSELLSEAKKLNDSQAPK | SEQ ID NO:217 |
| Z13698 | VDAKYAKEVMDAKHEIRWLPNLTFDQRVAFIHKLRDDPSQSSELLSEAKKLNDSQAPK | SEQ ID NO:218 |
| Z13699 | VDAKYAKETDAAKHEIRWLPNLTFDQRVAFIHKLRDDPSQSSELLSEAKKLNDSQAPK | SEQ ID NO:219 |
| Z13701 | VDAKYAKELQIAKHEIRWLPNLTFDQRVAFIHKLDDDPSQSSELLSEAKKLNDSQAPK | SEQ ID NO:220 |
| Z13702 | VDAKYAKEWKDAAQEIRWLPNLTFDQRVAFIHKLRDDPSQSSELLSEAKKLNDSQAPK | SEQ ID NO:221 |
| Z13703 | VDAKYAKERDSAAHEIRWLPNLTFDQRVAFIRKLRDDPSQSSELLSEAKKLNDSQAPK | SEQ ID NO:222 |
| Z13704 | VDAKYAKEIAAAKHEIRWLPNLTFDQRVAFIHKLDDDPSQSSELLSEAKKLNDSQAPK | SEQ ID NO:223 |
| Z13707 | VDAKYAKESVKAKHEIRWLPNLTFDQRVAFIHKLDDDPSQSSELLSEAKKLNDSQAPK | SEQ ID NO:224 |

Figure 1I

| Designation | Sequence | SEQ ID NO: |
|---|---|---|
| Z13709 | VDAKYAKENERAKHEIRWLPNLTFDQRVAFIHKLDDDPSQSSELLSEAKKLNDSQAPK | SEQ ID NO:225 |
| Z13712 | VDAKYAKEYKRAGHEIRWLPNLTFDQRVAFIRKLRDDPSQSSELLSEAKKLNDSQAPK | SEQ ID NO:226 |
| Z13713 | VDAKYAKEVRAASHEIRWLPNLTFDQRVAFIHKLRDDPSQSSELLSEAKKLNDSQAPK | SEQ ID NO:227 |
| Z13717 | VDAKYAKEDKRAAHEIRWLPNLTFDQRVAFIRKLRDDPSQSSELLSEAKKLNDSQAPK | SEQ ID NO:228 |
| Z13718 | VDAKYAKESEKAGKEIRWLPNLTFDQRVAFIRKLRDDPSQSSELLSEAKKLNDSQAPK | SEQ ID NO:229 |
| Z13722 | VDAKYAKEINRAKHEIRWLPNLTFDQRVAFIHKLDDDPSQSSELLSEAKKLNDSQAPK | SEQ ID NO:230 |
| Z13724 | VDAKYAKETQQASHEIRWLPNLTFDQRVAFIHKLRDDPSQSSELLSEAKKLNDSQAPK | SEQ ID NO:231 |
| Z13729 | VDAKYAKENQSAAHEIRWLPNLTFDQRVAFIRKLRDDPSQSSELLSEAKKLNDSQAPK | SEQ ID NO:232 |
| Z13730 | VDAKYAKEAKQASHEIRWLPNLTFDQRVAFIVKLRDDPSQSSELLSEAKKLNDSQAPK | SEQ ID NO:233 |
| Z13731 | VDAKYAKEAAQAAHEIRWLPNLTFDQRVAFIHKLRDDPSQSSELLSEAKKLNDSQAPK | SEQ ID NO:234 |
| Z13733 | VDAKYAKEVQYASHEIRWLPNLTFDQRVAFIHKLRDDPSQSSELLSEAKKLNDSQAPK | SEQ ID NO:235 |
| Z13734 | VDAKYAKELRNAAHEIRWLPNLTFDQRVAFIHKLRDDPSQSSELLSEAKKLNDSQAPK | SEQ ID NO:236 |
| Z13737 | VDAKYAKEQRAAAHEIRWLPNLTFDQRVAFIHKLRDDPSQSSELLSEAKKLNDSQAPK | SEQ ID NO:237 |
| Z13739 | VDAKYAKEASEAAAEIRWLPNLTFDQRVAFIHKLRDDPSQSSELLSEAKKLNDSQAPK | SEQ ID NO:238 |
| Z13741 | VDAKYAKESVIAAHEIRWLPNLTFDQRVAFIHKLRDDPSQSSELLSEAKKLNDSQAPK | SEQ ID NO:239 |
| Z13744 | VDAKYAKEILRAKHEIRWLPNLTFDQRVAFIHKLDDDPSQSSELLSEAKKLNDSQAPK | SEQ ID NO:240 |
| Z13746 | VDAKYAKESKTAAHEIRWLPNLTFDQRVAFIQKLRDDPSQSSELLSEAKKLNDSQAPK | SEQ ID NO:241 |
| Z13748 | VDAKYAKELAREASHEIRWLPNLTFDQRVAFIRKLRDDPSQSSELLSEAKKLNDSQAPK | SEQ ID NO:242 |
| Z13753 | VDAKYAKEATTAKHEIRWLPNLTFDQRVAFIHKLDDDPSQSSELLSEAKKLNDSQAPK | SEQ ID NO:243 |
| Z13754 | VDAKYAKEIENAAHEIRWLPNLTFDQRVAFIHKLRDDPSQSSELLSEAKKLNDSQAPK | SEQ ID NO:244 |
| Z13755 | VDAKYAKEAKDAAHEIRWLPNLTFDQRVAFIRKLRDDPSQSSELLSEAKKLNDSQAPK | SEQ ID NO:245 |
| Z13757 | VDAKYAKERLEAAAEIRWLPNLTFDQRVAFIHKLRDDPSQSSELLSEAKKLNDSQAPK | SEQ ID NO:246 |
| Z13762 | VDAKYAKEQMEAAAEIRWLPNLTFDQRVAFIHKLRDDPSQSSELLSEAKKLNDSQAPK | SEQ ID NO:247 |
| Z13763 | VDAKYAKEVKTASHEIRWLPNLTFDQRVAFIRKLRDDPSQSSELLSEAKKLNDSQAPK | SEQ ID NO:248 |
| Z13764 | VDAKYAKESFEASHEIRWLPNLTFDQRVAFIQKLRDDPSQSSELLSEAKKLNDSQAPK | SEQ ID NO:249 |
| Z13765 | VDAKYAKEIKSAKHEIRWLPNLTFDQRVAFIHKLDDDPSQSSELLSEAKKLNDSQAPK | SEQ ID NO:250 |
| Z13766 | VDAKYAKEIKNAKHEIRWLPNLTFDQRVAFIHKLDDDPSQSSELLSEAKKLNDSQAPK | SEQ ID NO:251 |
| Z13768 | VDAKYAKELQEAKHEIRWLPNLTFDQRVAFIHKLDDDPSQSSELLSEAKKLNDSQAPK | SEQ ID NO:252 |

Figure 1J

| Designation | Sequence | SEQ ID NO: |
|---|---|---|
| Z13769 | VDAKYAKERQNAAHEIRWLPNLTFDQRVAFIRKLRDDPSQSSELLSEAKKLNDSQAPK | SEQ ID NO:253 |
| Z13770 | VDAKYAKEVLQAKHEIRWLPNLTFDQRVAFIHKLDDDPSQSSELLSEAKKLNDSQAPK | SEQ ID NO:254 |
| Z13772 | VDAKYAKEANVASHEIRWLPNLTFDQRVAFIHKLRDDPSQSSELLSEAKKLNDSQAPK | SEQ ID NO:255 |
| Z13774 | VDAKYAKELDAAKHEIRWLPNLTFDQRVAFIHKLDDDPSQSSELLSEAKKLNDSQAPK | SEQ ID NO:256 |
| Z13775 | VDAKYAKETASAAHEIRWLPNLTFDQRVAFIHKLNDDPSQSSELLSEAKKLNDSQAPK | SEQ ID NO:257 |
| Z13778 | VDAKYAKEWKQAASEIRWLPNLTFDQRVAFIHKLRDDPSQSSELLSEAKKLNDSQAPK | SEQ ID NO:258 |
| Z13779 | VDAKYAKETASASHEIRWLPNLTFDQRVAFIHKLQDDPSQSSELLSEAKKLNDSQAPK | SEQ ID NO:259 |
| Z13781 | VDAKYAKESIVAGHEIRWLPNLTFDQRVAFIHKLRDDPSQSSELLSEAKKLNDSQAPK | SEQ ID NO:260 |
| Z13784 | VDAKYAKEIKQAKHEIRWLPNLTFDQRVAFIHKLDDDPSQSSELLSEAKKLNDSQAPK | SEQ ID NO:261 |
| Z13785 | VDAKYAKEQATASHEIRWLPNLTFDQRVAFIHKLDDDPSQSSELLSEAKKLNDSQAPK | SEQ ID NO:262 |
| Z13787 | VDAKYAKELNAAKHEIRWLPNLTFDQRVAFIHKLDDDPSQSSELLSEAKKLNDSQAPK | SEQ ID NO:263 |
| Z13788 | VDAKYAKEVKRAGHEIRWLPNLTFDQRVAFIRKLRDDPSQSSELLSEAKKLNDSQAPK | SEQ ID NO:264 |
| Z13789 | VDAKYAKESRNAAHEIRWLPNLTFDQRVAFIHKLQDDPSQSSELLSEAKKLNDSQAPK | SEQ ID NO:265 |
| Z13791 | VDAKYAKESITASAEIRWLPNLTFDQRVAFIRKLRDDPSQSSELLSEAKKLNDSQAPK | SEQ ID NO:266 |
| Z13793 | VDAKYAKEAATAAHEIRWLPNLTFDQRVAFIHKLQDDPSQSSELLSEAKKLNDSQAPK | SEQ ID NO:267 |
| Z13794 | VDAKYAKEVYAAKHEIRWLPNLTFDQRVAFIHKLDDDPSQSSELLSEAKKLNDSQAPK | SEQ ID NO:268 |
| Z13795 | VDAKYAKEISRAKHEIRWLPNLTFDQRVAFIHKLDDDPSQSSELLSEAKKLNDSQAPK | SEQ ID NO:269 |
| Z13798 | VDAKYAKEYVTAAHEIRWLPNLTFDQRVAFIHKLRDDPSQSSELLSEAKKLNDSQAPK | SEQ ID NO:270 |
| Z13800 | VDAKYAKEHIDAGHEIRWLPNLTFDQRVAFIHKLNDDPSQSSELLSEAKKLNDSQAPK | SEQ ID NO:271 |
| Z13801 | VDAKYAKEILQAKHEIRWLPNLTFDQRVAFIHKLNDDPSQSSELLSEAKKLNDSQAPK | SEQ ID NO:272 |
| Z13802 | VDAKYAKENSQAKHEIRWLPNLTFDQRVAFIHKLNDDPSQSSELLSEAKKLNDSQAPK | SEQ ID NO:273 |
| Z13803 | VDAKYAKEYRVAAKEIRWLPNLTFDQRVAFIHKLRDDPSQSSELLSEAKKLNDSQAPK | SEQ ID NO:274 |
| Z13804 | VDAKYAKEIYNAGHEIRWLPNLTFDQRVAFIRKLRDDPSQSSELLSEAKKLNDSQAPK | SEQ ID NO:275 |
| Z13805 | VDAKYAKESNEAAAEIRWLPNLTFDQRVAFIHKLRDDPSQSSELLSEAKKLNDSQAPK | SEQ ID NO:276 |
| Z13809 | VDAKYAKESQLAAAEIRWLPNLTFDQRVAFIRKLRDDPSQSSELLSEAKKLNDSQAPK | SEQ ID NO:277 |
| Z13810 | VDAKYAKELKEAGHEIRWLPNLTFDQRVAFIHKLQDDPSQSSELLSEAKKLNDSQAPK | SEQ ID NO:278 |
| Z13813 | VDAKYAKETRVASVEIRWLPNLTFDQRVAFIQKLNDDPSQSSELLSEAKKLNDSQAPK | SEQ ID NO:279 |
| Z13818 | VDAKYAKELRTAAHEIRWLPNLTFDQRVAFIHKLNDDPSQSSELLSEAKKLNDSQAPK | SEQ ID NO:280 |

Figure 1K

| Designation | Sequence | SEQ ID NO: |
|---|---|---|
| Z13820 | VDAKYAKEKTYAHFEIRWLPNLTFDQRVAFISKLWDDPSQSSELLSEAKKLNDSQAPK | SEQ ID NO:281 |
| Z13821 | VDAKYAKEEAQASHEIRWLPNLTFDQRVAFIHKLRDDPSQSSELLSEAKKLNDSQAPK | SEQ ID NO:282 |
| Z13822 | VDAKYAKEITSAAHEIRWLPNLTFDQRVAFIHKLRDDPSQSSELLSEAKKLNDSQAPK | SEQ ID NO:283 |
| Z13825 | VDAKYAKEVKTASHEIRWLPNLTFDQRVAFIHKLKDDPSQSSELLSEAKKLNDSQAPK | SEQ ID NO:284 |
| Z13826 | VDAKYAKETKVAAHEIRWLPNLTFDQRVAFIHKLRDDPSQSSELLSEAKKLNDSQAPK | SEQ ID NO:285 |
| Z13829 | VDAKYAKEDLVAQHEIRWLPNLTFDQRVAFIRKLRDDPSQSSELLSEAKKLNDSQAPK | SEQ ID NO:286 |
| Z13830 | VDAKYAKETQTAFNEIRWLPNLTYDQRAAFILKLWDDPSQSSELLSEAKKLNDSQAPK | SEQ ID NO:287 |
| Z13831 | VDAKYAKEIKDAGHEIRWLPNLTFDQRVAFIRKLRDDPSQSSELLSEAKKLNDSQAPK | SEQ ID NO:288 |
| Z13836 | VDAKYAKEYKEAGHEIRWLPNLTYDQRVAFIVKLRDDPSQSSELLSEAKKLNDSQAPK | SEQ ID NO:289 |
| Z13839 | VDAKYAKEEAALAAHEIRWLPNLTFDQRVAFIHKLRDDPSQSSELLSEAKKLNDSQAPK | SEQ ID NO:290 |
| Z13843 | VDAKYAKEQERAAHEIRWLPNLTFDQRVAFIHKLRDDPSQSSELLSEAKKLNDSQAPK | SEQ ID NO:291 |
| Z13844 | VDAKYAKEWFDAAHEIRWLPNLTFDQRVAFIHKLDDDPSQSSELLSEAKKLNDSQAPK | SEQ ID NO:292 |
| Z13847 | VDAKYAKEIIQAKHEIRWLPNLTFDQRVAFIHKLDDDPSQSSELLSEAKKLNDSQAPK | SEQ ID NO:293 |
| Z13850 | VDAKYAKELTNAKHEIRWLPNLTFDQRVAFIHKLRDDPSQSSELLSEAKKLNDSQAPK | SEQ ID NO:294 |
| Z13851 | VDAKYAKEIQLAKHEIRWLPNLTFDQRVAFIRKLRDDPSQSSELLSEAKKLNDSQAPK | SEQ ID NO:295 |
| Z13854 | VDAKYAKEIHDAKHEIRWLPNLTFDQRVAFIHKLQDDPSQSSELLSEAKKLNDSQAPK | SEQ ID NO:296 |
| Z13869 | VDAKYAKEVKIASHEIRWLPNLTFDQRVAFIHKLRDDPSQSSELLSEAKKLNDSQAPK | SEQ ID NO:297 |
| Z13870 | VDAKYAKEQHSAAHEIRWLPNLTFDQRVAFIRKLRDDPSQSSELLSEAKKLNDSQAPK | SEQ ID NO:298 |
| Z13872 | VDAKYAKEVFAASAEIRWLPNLTFDQRVAFIHKLRDDPSQSSELLSEAKKLNDSQAPK | SEQ ID NO:299 |
| Z13874 | VDAKYAKETDLAGHEIRWLPNLTFDQRVAFIRKLRDDPSQSSELLSEAKKLNDSQAPK | SEQ ID NO:300 |
| Z13877 | VDAKYAKEANFAGHEIRWLPNLTFDQRVAFIRKLRDDPSQSSELLSEAKKLNDSQAPK | SEQ ID NO:301 |
| Z13878 | VDAKYAKEFETAGHEIRWLPNLTFDQRVAFITKLWDDPSQSSELLSEAKKLNDSQAPK | SEQ ID NO:302 |
| Z13880 | VDAKYAKEVNLAKHEIRWLPNLTFDQRVAFIHKLDDDPSQSSELLSEAKKLNDSQAPK | SEQ ID NO:303 |
| Z13881 | VDAKYAKEADTAAHEIRWLPNLTFDQRVAFIYKLRDDPSQSSELLSEAKKLNDSQAPK | SEQ ID NO:304 |
| Z13882 | VDAKYAKEFVDAGHEIRWLPNLTFDQRVAFIQKLRDDPSQSSELLSEAKKLNDSQAPK | SEQ ID NO:305 |
| Z13883 | VDAKYAKEDHKAEHEIRWLPNLTFDQRVAFIHKLRDDPSQSSELLSEAKKLNDSQAPK | SEQ ID NO:306 |
| Z13884 | VDAKYAKETVDAGHEIRWLPNLTFDQRVAFIHKLADDPSQSSELLSEAKKLNDSQAPK | SEQ ID NO:307 |
| Z13885 | VDAKYAKESQRAGHEIRWLPNLTFDQRVAFITKLRDDPSQSSELLSEAKKLNDSQAPK | SEQ ID NO:308 |

Figure 1L

| Designation | Sequence | SEQ ID NO: |
|---|---|---|
| Z13886 | VDAKYAKEWSSAAHEIRWLPNLTFDQRVAFIHKLQDDPSQSSELLSEAKKLNDSQAPK | SEQ ID NO:309 |
| Z13887 | VDAKYAKEVAVAGHEIRWLPNLTYDQRVAFIVKLRDDPSQSSELLSEAKKLNDSQAPK | SEQ ID NO:310 |
| Z13888 | VDAKYAKESAEAGHEIRWLPNLTFDQRVAFTEKLRDDPSQSSELLSEAKKLNDSQAPK | SEQ ID NO:311 |
| Z13889 | VDAKYAKEAVAAGHEIRWLPNLTFDQRVAFIHKLNDDPSQSSELLSEAKKLNDSQAPK | SEQ ID NO:312 |
| Z13890 | VDAKYAKEFQIAGHEIRWLPNLTFDQRVAFINKLRDDPSQSSELLSEAKKLNDSQAPK | SEQ ID NO:313 |
| Z13891 | VDAKYAKELMVAKHEIRWLPNLTFDQRVAFIHKLRDDPSQSSELLSEAKKLNDSQAPK | SEQ ID NO:314 |
| Z13892 | VDAKYAKEYDSAAHEIRWLPNLTYDQRVAFILKLRDDPSQSSELLSEAKKLNDSQAPK | SEQ ID NO:315 |
| Z13893 | VDAKYAKEVLEAKHEIRWLPNLTFDQRVAFIHKLDDDPSQSSELLSEAKKLNDSQAPK | SEQ ID NO:316 |
| Z13894 | VDAKYAKESIAASHEIRWLPNLTFDQRVAFIHKLRDDPSQSSELLSEAKKLNDSQAPK | SEQ ID NO:317 |
| Z13895 | VDAKYAKEVAEAGHEIRWLPNLTFDQRVAFISKLRDDPSQSSELLSEAKKLNDSQAPK | SEQ ID NO:318 |
| Z13896 | VDAKYAKEQAKAAHEIRWLPNLTFDQRVAFIHKLNDDPSQSSELLSEAKKLNDSQAPK | SEQ ID NO:319 |
| Z13897 | VDAKYAKERDDAAHEIRWLPNLTFDQRVAFIEKLRDDPSQSSELLSEAKKLNDSQAPK | SEQ ID NO:320 |
| Z13898 | VDAKYAKEAKDASHEIRWLPNLTFDQRVAFIHKLRDDPSQSSELLSEAKKLNDSQAPK | SEQ ID NO:321 |
| Z13899 | VDAKYAKEASSAAHEIRWLPNLTFDQRVAFIQKLRDDPSQSSELLSEAKKLNDSQAPK | SEQ ID NO:322 |
| Z13900 | VDAKYAKEWMEASHEIRWLPNLTYDQRVAFIVKLRDDPSQSSELLSEAKKLNDSQAPK | SEQ ID NO:323 |
| Z13901 | VDAKYAKEQKNAAHEIRWLPNLTFDQRVAFIEKLRDDPSQSSELLSEAKKLNDSQAPK | SEQ ID NO:324 |
| Z13902 | VDAKYAKEIENAKHEIRWLPNLTFDQRVAFIHKLRDDPSQSSELLSEAKKLNDSQAPK | SEQ ID NO:325 |
| Z13903 | VDAKYAKEVNRASHEIRWLPNLTFDQRVAFIHKLLDDPSQSSELLSEAKKLNDSQAPK | SEQ ID NO:326 |
| Z13904 | VDAKYAKERLLAGHEIRWLPNLTFDQRVAFINKLRDDPSQSSELLSEAKKLNDSQAPK | SEQ ID NO:327 |
| Z13906 | VDAKYAKEVSIAGHEIRWLPNLTFDQRVAFIRKLRDDPSQSSELLSEAKKLNDSQAPK | SEQ ID NO:328 |
| Z13907 | VDAKYAKEKEVAAHEIRWLPNLTFDQRVAFIHKLDDDPSQSSELLSEAKKLNDSQAPK | SEQ ID NO:329 |
| Z13908 | VDAKYAKESERASHEIRWLPNLTFDQRVAFIHKLRDDPSQSSELLSEAKKLNDSQAPK | SEQ ID NO:330 |
| Z13909 | VDAKYAKEWNEAAHEIRWLPNLTFDQRVAFIHKLRDDPSQSSELLSEAKKLNDSQAPK | SEQ ID NO:331 |
| Z13910 | VDAKYAKENVDAAHEIRWLPNLTFDQRVAFIHKLRDDPSQSSELLSEAKKLNDSQAPK | SEQ ID NO:332 |
| Z13911 | VDAKYAKEADAASHEIRWLPNLTFDQRVAFIRKLRDDPSQSSELLSEAKKLNDSQAPK | SEQ ID NO:333 |
| Z13912 | VDAKYAKELESASHEIRWLPNLTFDQRVAFIHKLIDDPSQSSELLSEAKKLNDSQAPK | SEQ ID NO:334 |
| Z13913 | VDAKYAKEEQLAAHEIRWLPNLTFDQRVAFIRKLRDDPSQSSELLSEAKKLNDSQAPK | SEQ ID NO:335 |
| Z13914 | VDAKYAKEFELAGHEIRWLPNLTFDQRVAFIHKLDDDPSQSSELLSEAKKLNDSQAPK | SEQ ID NO:336 |

Figure 1M

| Designation | Sequence | SEQ ID NO: |
|---|---|---|
| Z13915 | VDAKYAKEAFVAQHEIRWLPNLTYDQRVAFIVKLRDDPSQSSELLSEAKKLNDSQAPK | SEQ ID NO:337 |
| Z13916 | VDAKYAKEALKASHEIRWLPNLTFDQRVAFINKLRDDPSQSSELLSEAKKLNDSQAPK | SEQ ID NO:338 |
| Z13917 | VDAKYAKELERAGHEIRWLPNLTFDQRVAFIKKLTDDPSQSSELLSEAKKLNDSQAPK | SEQ ID NO:339 |
| Z13918 | VDAKYAKEVEWAKHEIRWLPNLTFDQRVAFIHKLQDDPSQSSELLSEAKKLNDSQAPK | SEQ ID NO:340 |
| Z13919 | VDAKYAKEKASAQHEIRWLPNLTFDQRVAFIHKLDDDPSQSSELLSEAKKLNDSQAPK | SEQ ID NO:341 |
| Z13920 | VDAKYAKETEIAKHEIRWLPNLTFDQRVAFIHKLDDDPSQSSELLSEAKKLNDSQAPK | SEQ ID NO:342 |
| Z13921 | VDAKYAKEVNLAAHEIRWLPNLTFDQRVAFIHKLTDDPSQSSELLSEAKKLNDSQAPK | SEQ ID NO:343 |
| Z13922 | VDAKYAKEAEEAAHEIRWLPNLTFDQRVAFIHKLRDDPSQSSELLSEAKKLNDSQAPK | SEQ ID NO:344 |
| Z13923 | VDAKYAKETDRAKHEIRWLPNLTFDQRVAFIHKLNDDPSQSSELLSEAKKLNDSQAPK | SEQ ID NO:345 |
| Z13925 | VDAKYAKEFAQAGHEIRWLPNLTFDQRVAFIRKLRDDPSQSSELLSEAKKLNDSQAPK | SEQ ID NO:346 |
| Z13926 | VDAKYAKETDEASHEIRWLPNLTFDQRVAFIHKLRDDPSQSSELLSEAKKLNDSQAPK | SEQ ID NO:347 |
| Z13927 | VDAKYAKENADAGHEIRWLPNLTFDQRVAFIQKLRDDPSQSSELLSEAKKLNDSQAPK | SEQ ID NO:348 |
| Z13928 | VDAKYAKESTQAAHEIRWLPNLTFDQRVAFIHKLQDDPSQSSELLSEAKKLNDSQAPK | SEQ ID NO:349 |
| Z13929 | VDAKYAKEQALAAHEIRWLPNLTFDQRVAFIHKLNDDPSQSSELLSEAKKLNDSQAPK | SEQ ID NO:350 |
| Z13930 | VDAKYAKEAHAASHEIRWLPNLTFDQRVAFIHKLDDDPSQSSELLSEAKKLNDSQAPK | SEQ ID NO:351 |
| Z13932 | VDAKYAKEVDNAGHEIRWLPNLTFDQRVAFIQKLRDDPSQSSELLSEAKKLNDSQAPK | SEQ ID NO:352 |
| Z13993 | VDAKYAKEAGRAAHEIRWLPNLTWDQRVAFIHKLRDDPSQSSELLSEAKKLNDSQAPK | SEQ ID NO:353 |
| Z11948 | AEAKYAKEQDAAAHEIRWLPNLTFDQRVAFIHKLADDPSQSSELLSEAKKLNDSQAPK | SEQ ID NO:354 |
| Z11946 | AEAKYAKEFESAAHEIRWLPNLTFDQRVAFIHKLSDDPSQSSELLSEAKKLNDSQAPK | SEQ ID NO:355 |
| Z11947 | AEAKYAKEWMRAAHEIRWLPNLTFDQRVAFIHKLEDDPSQSSELLSEAKKLNDSQAPK | SEQ ID NO:356 |
| Z17303 | AEAKYAKEADAAGHEIRWLPNLTFDQRVAFIHKLRDDPSQSSELLSEAKKLNDSQAPK | SEQ ID NO:357 |
| Z17347 | AEAKYAKEQDAAAHEIRWLPNLTFDQRVAFIHKLADDPSQSSELLSEAKKLSEQAPK | SEQ ID NO:358 |
| Z17348 | AEAKYAKEQDAAAHEIRWLPNLTFDQRVAFIHKLARQPEQSSELLSEAKKLSESQAPK | SEQ ID NO:359 |
| Z18614 | VDAKYAKELEKAGHEIRWLPNLTFDQRVAFIHKLRDDPSQSSELLSEAKKLSESQAPK | SEQ ID NO:360 |
| Z18615 | VDAKYAKEWTDAAHEIRWLPNLTFDQRVAFIHKLARQPEQSSELLSEAKKLSESQAPK | SEQ ID NO:361 |
| Z18616 | VDAKYAKEWQQAAHEIRWLPNLTFDQRVAFIHKLRDDPSQSSELLSEAKKLSESQAPK | SEQ ID NO:362 |
| Z18617 | VDAKYAKEADAAGHEIRWLPNLTFDQRVAFIHKLRDDPSQSSELLSEAKKLSESQAPK | SEQ ID NO:363 |
| Z18618 | VDAKYAKEIEDAGHEIRWLPNLTFDQRVAFIHKLRDDPSQSSELLSEAKKLSESQAPK | SEQ ID NO:364 |

Figure 1N

| Designation | Sequence | SEQ ID NO: |
|---|---|---|
| Z18632 | AEAKFAKEWTDAAHEIRWLPNLTFDQRVAFIHKLRDDPSQSSELLSEAKKLSESQAPK | SEQ ID NO:365 |
| Z18633 | AEAKFAKEWQQAAHEIRWLPNLTFDQRVAFIHKLRDDPSQSSELLSEAKKLSESQAPK | SEQ ID NO:366 |
| Z18634 | AEAKFAKEADAAGHEIRWLPNLTFDQRVAFIHKLRDDPSQSSELLSEAKKLSESQAPK | SEQ ID NO:367 |
| Z11948-G4S-Z11948 | AEAKYAKEQDAAAHEIRWLPNLTFDQRVAFIHKLADDPSQSSELLSEAKKLNDSQAPKGTGGGGSPRAEAKYAKEQDAAAHEIRWLPNLTFDQRVAFIHKLADDPSQSSELLSEAKKLNDSQAPKLEHHHHHH | SEQ ID NO:368 |
| Z11948-(G4S)3-Z11948 | AEAKYAKEQDAAAHEIRWLPNLTFDQRVAFIHKLADDPSQSSELLSEAKKLNDSQAPKGTGGGGSGGGGSGGGGSAEAKYAKEQDAAAHEIRWLPNLTFDQRVAFIHKLADDPSQSSELLSEAKKLNDSQAPKLEHHHHHH | SEQ ID NO:369 |
| ZZ3556 | GSSHHHHHHLQAEAKYAKEADAAGHEIRWLPNLTFDQRVAFIHKLRDDPSQSSELLSEAKKLNDSQAPKGTGGGGSGGGGSGGGGSAEAKYAKEADAAGHEIRWLPNLTFDQRVAFIHKLRDDPSQSSELLSEAKKLNDSQAPK | SEQ ID NO:370 |
| ZAZ3715 | AEAKYAKEADAAGHEIRWLPNLTFDQRVAFIHKLRDDPSQSSELLSEAKKLNDSQAPKGAPGGGSGGGGSGGGGSTSLAEAKEAANAELDSYGVSDFYKRLIDKAKTVEGVEALKDAILAALPGTGGGCSGGGGSGGGGSPRAEAKYAKEADAAGHEIRWLPNLTFDQRVAFIHKLRDDPSQSSELLSEAKKLNDSQAPK | SEQ ID NO:371 |
| ZZA3716 | AEAKYAKEADAAGHEIRWLPNLTFDQRVAFIHKLRDDPSQSSELLSEAKKLNDSQAPKGAPGGGCSGGGGSCGGGSTSAEAKYAKEADAAGHEIRWLPNLTFDQRVAFIHKLRDDPSQSSELLSEAKKLNDSQAPKGTGGGGSGGGGSGGGGSPRLAEAKEAANAELDSYGVSDFYKRLIDKAKTVEGVEALKDAILAALP | SEQ ID NO:372 |
| ZAZ3824 | AEAKYAKEADAAGHEIRWLPNLTFDQRVAFIHKLRDDPSQSSELLSEAKKLNDSQAPKASGSLAEAKEAANAELDSYGVSDFYKRLIDKAKTVEGVEALKDAILAALPGTGGGGSAEAKYAKEADAAGHEIRWLPNLTFDQRVAFIHKLRDDPSQSSELLSEAKKLNDSQAPK | SEQ ID NO:373 |
| ZAZ3869 | AEAKFAKEWTDAAHEIRWLPNLTFDQRVAFIHKLRDDPSQSSELLSEAKKLSESQAPKASGSLAEAKEAANAELDSYGVSDFYKRLIDKAKTVEGVEALKDAILAALPGTGGGGSAEAKFAKEWTDAAHEIRWLPNLTFDQRVAFIHKLRDDPSQSSELLSEAKKLSESQAPK | SEQ ID NO:374 |
| ZAZ3870 | AEAKFAKEWQQAAHEIRWLPNLTFDQRVAFIHKLRDDPSQSSELLSEAKKLSESQAPKASGSLAEAKEAANAELDSYGVSDFYKRLIDKAKTVEGVEALKDAILAALPGTGGGGSAEAKFAKEWQQAAHEIRWLPNLTFDQRVAFIHKLRDDPSQSSELLSEAKKLSESQAPK | SEQ ID NO:375 |
| ZAZ3871 | AEAKFAKEADAAGHEIRWLPNLTFDQRVAFIHKLRDDPSQSSELLSEAKKLSESQAPKASGSLAEAKEAANAELDSYGVSDFYKRLIDKAKTVEGVEALKDAILAALPGTGGGGSAEAKFAKEADAAGHEIRWLPNLTFDQRVAFIHKLRDDPSQSSELLSEAKKLSESQAPK | SEQ ID NO:376 |
| PP013 | LAEAKEAANAELDSYGVSDFYKRLIDKAKTVEGVEALKDAILAALP | SEQ ID NO:377 |

Figure 10

| Designation | Sequence | SEQ ID NO: |
|---|---|---|
| Z03638 | AEAKYAKELGWATWEIFNLPNLTGVQVKAFIDKLRDDPSQSSELLSEAKKLNDSQAPK | SEQ ID NO:378 |
| Human αFcRn | AESHLSLLYHLTAVSSPAPGTPAFWVSGWLGPQQYLSYNSLRGEAEPCGAWVWENQVSWYWEKE TTDLRIKEKLFLEAFKALGGKGPYTLQGLLGCELGPDNTSVPTAKFALNGEEFMNFDLKQGTWG GDWPEALAISQRWQQQDKAANKELTFLLFSCPHRLREHLERGRGNLEWKEPPSMRLKARPSSPG FSVLTCSAFSFYPPELQLRFLRNGLAAGTGQGDFGPNSDGSFHASSSLTVKSGDEHHYCCIVQH AGLAQPLRVEL | SEQ ID NO:379 |
| Human B2M | IQRTPKIQVYSRHPAENGKSNFLNCYVSGFHPSDIEVDLLKNGERIEKVEHSDLSFSKDWSFYL LYYTEFTPTEKDEYACRVNHVTLSQPKIVKWDRDM | SEQ ID NO:380 |
| Murine B2M | IQKTPQIQVYSRHPPENGKPNILNCYVTQFHPPHIEIQMLKNGKKIPKVEMSDMSFSKDWSFYI LAHTEFTPTETDTYACRVKHASMAEPKTVYWDRDM | SEQ ID NO:381 |
| hFcRn-eGFP | MGVPRPQPWALGLLLFLLPGSLGAESHLSLLYHLTAVSSPAPGTPAFWVSGWLGPQQYLSYNSL RGEAEPCGAWVWENQVSWYWEKETTDLRIKEKLFLEAFKALGGKGPYTLQGLLGCELGPDNTSV PTAKFALNGEEFMNFDLKQGTWGGDWPEALAISQRWQQQDKAANKELTFLLFSCPHRLREHLER GRGNLEWKEPPSMRLKARPSSPGFSVLTCSAFSFYPPELQLRFLRNGLAAGTGQGDFGPNSDGS FHASSSLTVKSGDEHHYCCIVQHAGLAQPLRVELESPAKSSVLVVGIVIGVLLLTAAAVGGALL WRRMRSGLPAPWISLRGDDTGVLLPTPGEAQDADLKDVNVIPATA | SEQ ID NO:382 |
| mFcRn-eGFP | MGMPLPWALSLLLVLLPQTWGSETRPPLMYHLTAVSNPSTGLPSFWATGWLGPQQYLTYNSLRQ EADPCGAWMWENQVSWYWEKETTDLKSKEQLFLEALKTLEKILNGQKRGTYTLQGLLGCELASD NSSVPTAVFALNGEEFMKFNPRIGNWTGEWPETEIVANLWMKQPDAARKESEFLLNSCPERLLG HLERGRRNLEWKEPPSMRLKAPRPGNSGSSVLTCAAFSFYPPELKFRFLRNGLASGSGNCSTGPN GDGSFHAWSLLEVKRGDEHHYQCQVEHEGLAQPLTVDLDSSARSSVPVVGIVLGLLLVVVAIAG GVLLWGRMRSGLPAPWLSLSGDDSGDLLPGGNLPPEAEPQGANAFPATS | SEQ ID NO:383 |
| Murine αFcRn | SETRPPLMYHLTAVSNPSTGLPSFWATGWLGPQQYLTYNSLRQEADPCGAWMWENQVSWYWEKE TTDLKSKEQLFLEALKTLEKILNGQKRGTYTLQGLLGCELASDNSSVPTAVFALNGEEFMKFNP RIGNWTGEWPETEIVANLWMKQPDAARKESEFLLNSCPERLLGHLERGRRNLEWKEPPSMRLKA RPGNSGSSVLTCAAFSFYPPELKFRFLRNGLASGSGNCSTGPNGDGSFHAWSLLEVKRGDEHHY QCQVEHEGLAQPLTVDL | SEQ ID NO:384 |

A
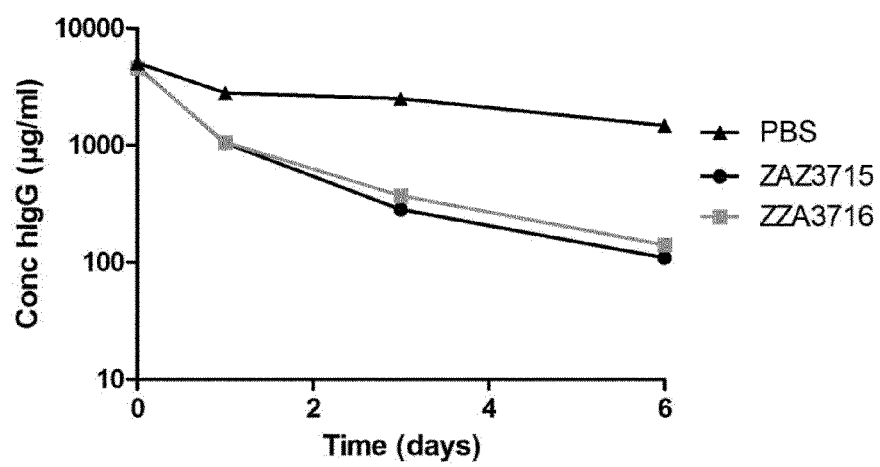
Figure 14
B
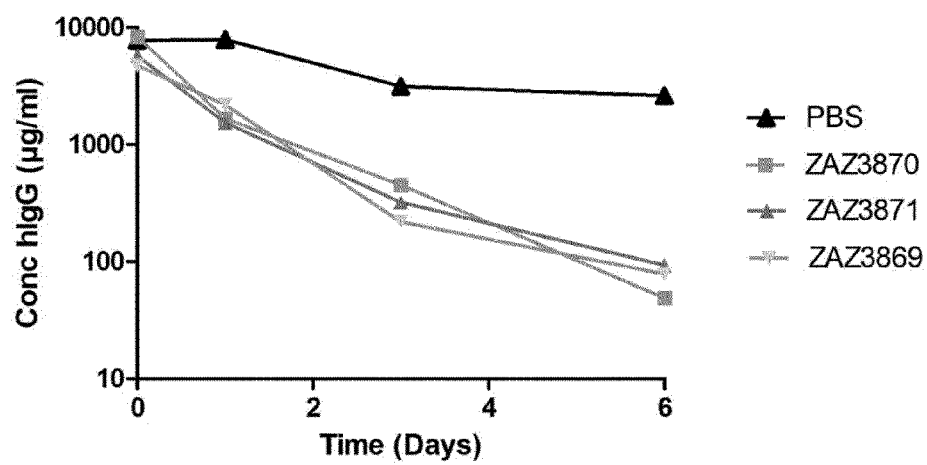

SEQUENCE LISTING

```
<160> NUMBER OF SEQ ID NOS: 470

<210> SEQ ID NO 1
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 1

Val Asp Ala Lys Tyr Ala Lys Glu Gln Asp Ala Ala Ala His Glu Ile
1               5                   10                  15

Arg Trp Leu Pro Asn Leu Thr Phe Asp Gln Arg Val Ala Phe Ile His
```

```
                20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 2

Val Asp Ala Lys Tyr Ala Lys Glu Trp Met Arg Ala Ala His Glu Ile
1               5                   10                  15

Arg Trp Leu Pro Asn Leu Thr Phe Asp Gln Arg Val Ala Phe Ile His
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 3
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 3

Val Asp Ala Lys Tyr Ala Lys Glu Ala Asn Thr Ala Ala His Glu Ile
1               5                   10                  15

Arg Trp Leu Pro Asn Leu Thr Phe Asp Gln Arg Val Ala Phe Ile Arg
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 4
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 4

Val Asp Ala Lys Tyr Ala Lys Glu Phe Glu Ser Ala Ala His Glu Ile
1               5                   10                  15

Arg Trp Leu Pro Asn Leu Thr Tyr Asp Gln Arg Val Ala Phe Ile His
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 5
<211> LENGTH: 58
<212> TYPE: PRT
<213> ORGANISM: Artificial Sequence
```

<220> FEATURE:
<223> OTHER INFORMATION: Engineered FcRn binding polypeptide

<400> SEQUENCE: 5

Val Asp Ala Lys Tyr Ala Lys Glu Arg Ser Ala Ala His Glu Ile
1               5                   10                  15

Arg Trp Leu Pro Asn Leu Thr Phe Asp Gln Arg Val Ala Phe Ile Leu
            20                  25                  30

Lys Leu Thr Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 6

Val Asp Ala Lys Tyr Ala Lys Glu Ser Asp Ser Ala Val His Glu Ile
1               5                   10                  15

Arg Trp Leu Pro Asn Leu Thr Phe Asp Gln Arg Val Ala Phe Ile His
            20                  25                  30

Lys Leu Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 7

Val Asp Ala Lys Tyr Ala Lys Glu Ala Asp Asn Ala Gly His Glu Ile
1               5                   10                  15

Arg Trp Leu Pro Asn Leu Thr Trp Ala Gln Arg Trp Ala Phe Ile His
            20                  25                  30

Lys Leu Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 8

Val Asp Ala Lys Tyr Ala Lys Glu Asp Asp Thr Ala Ala His Glu Ile
1               5                   10                  15

Arg Trp Leu Pro Asn Leu Thr Tyr Glu Gln Arg Trp Ala Phe Ile His
            20                  25                  30

Lys Leu Tyr Asp Asp Pro Ser Gln Ser Ser Glu Leu Leu Ser Glu Ala
        35                  40                  45

```
Lys Lys Leu Asn Asp Ser Gln Ala Pro Lys
    50                  55
```

<210> SEQ ID NO 9
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 9

```
Val Asp Ala Lys Tyr Ala Lys Glu Gln His Asp Ala Ala His Glu Ile
1               5                   10                  15

Arg Trp Leu Pro Asn Leu Thr Tyr Asp Gln Arg Val Ala Phe Ile Arg
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 10
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 10

```
Val Asp Ala Lys Tyr Ala Lys Glu Asn Gln Gly Ala Ala His Glu Ile
1               5                   10                  15

Arg Trp Leu Pro Asn Leu Thr Trp Asp Gln Arg Val Ala Phe Ile Arg
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 11
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 11

```
Val Asp Ala Lys Tyr Ala Lys Glu Arg Thr Gln Ala Ser His Glu Ile
1               5                   10                  15

Arg Trp Leu Pro Asn Leu Thr Tyr Asp Gln Arg Val Ala Phe Ile Asn
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 12
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 12

```
Val Asp Ala Lys Tyr Ala Lys Glu Arg Lys Asp Ala Gly His Glu Ile
1               5                   10                  15

Arg Trp Leu Pro Asn Leu Thr Phe Asp Gln Arg Ser Ala Phe Ile Lys
                20                  25                  30

Lys Leu Glu Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 13
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 13

```
Val Asp Ala Lys Tyr Ala Lys Glu Arg Gln Glu Ala Ala His Glu Ile
1               5                   10                  15

Arg Trp Leu Pro Asn Leu Thr Phe Asp Gln Arg Val Ala Phe Ile Val
                20                  25                  30

Lys Leu Leu Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 14
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 14

```
Val Asp Ala Lys Tyr Ala Lys Glu Glu Asp Val Ala Ala His Glu Ile
1               5                   10                  15

Arg Trp Leu Pro Asn Leu Thr Phe Asn Gln Arg Ala Ala Phe Ile Asp
                20                  25                  30

Lys Leu Leu Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 15
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 15

```
Val Asp Ala Lys Tyr Ala Lys Glu Asn Gln Asp Ala Ala His Glu Ile
1               5                   10                  15

Arg Trp Leu Pro Asn Leu Thr Tyr Asp Gln Arg Val Ala Phe Ile Gly
                20                  25                  30

Lys Leu Asn Asp Asp Pro Ser Gln Ser Ser Glu Leu Leu Ser Glu Ala
            35                  40                  45

Lys Lys Leu Asn Asp Ser Gln Ala Pro Lys
        50                  55
```

```
<210> SEQ ID NO 16
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 16

Val Asp Ala Lys Tyr Ala Lys Glu Ser Gly Tyr Ala Val His Glu Ile
1               5                   10                  15

Arg Trp Leu Pro Asn Leu Thr Phe Asp Gln Arg Val Ala Phe Ile Asn
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 17
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 17

Val Asp Ala Lys Tyr Ala Lys Glu Ser Lys Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 18
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 18

Val Asp Ala Lys Tyr Ala Lys Glu Lys Lys Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 19
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 19

Val Asp Ala Lys Tyr Ala Lys Glu Trp His Gln Ala Ala His Glu Ile
1               5                   10                  15
```

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 20
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 20

Val Asp Ala Lys Tyr Ala Lys Glu Trp Thr Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 21
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 21

Val Asp Ala Lys Tyr Ala Lys Glu Ile Ser Ala Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 22
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 22

Val Asp Ala Lys Tyr Ala Lys Glu Gln Gln Ala Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 23
<211> LENGTH: 58
<212> TYPE: PRT

```
<213> ORGANISM: Artificial Sequence
<220> FEATURE:
<223> OTHER INFORMATION: Engineered FcRn binding polypeptide

<400> SEQUENCE: 23

Val Asp Ala Lys Tyr Ala Lys Glu Leu Glu Lys Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 24
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 24

Val Asp Ala Lys Tyr Ala Lys Glu Tyr Leu Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 25
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 25

Val Asp Ala Lys Tyr Ala Lys Glu Leu Lys Asp Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 26
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 26

Val Asp Ala Lys Tyr Ala Lys Glu His Val Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
```

```
Lys Lys Leu Asn Asp Ser Gln Ala Pro Lys
    50                  55

<210> SEQ ID NO 27
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 27

Val Asp Ala Lys Tyr Ala Lys Glu Tyr Ala Ala Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 28
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 28

Val Asp Ala Lys Tyr Ala Lys Glu Val Asp Ile Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 29
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 29

Val Asp Ala Lys Tyr Ala Lys Glu Ile Asp Glu Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 30
<211> LENGTH: 58
<212> TYPE: PRT
<213> ORGANISM: Artificial Sequence
<220> FEATURE:
<223> OTHER INFORMATION: Engineered FcRn binding polypeptide
```

```
<400> SEQUENCE: 30

Val Asp Ala Lys Tyr Ala Lys Glu Leu Arg Gln Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 31
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 31

Val Asp Ala Lys Tyr Ala Lys Glu Leu Gln Ser Ala Ala His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 32
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 32

Val Asp Ala Lys Tyr Ala Lys Glu Leu Glu Lys Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 33
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 33

Val Asp Ala Lys Tyr Ala Lys Glu Ala His Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 34
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 34

Val Asp Ala Lys Tyr Ala Lys Glu Leu Gln Ala Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 35
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 35

Val Asp Ala Lys Tyr Ala Lys Glu Ile Glu Ser Ala Lys His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 36
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 36

Val Asp Ala Lys Tyr Ala Lys Glu Trp Lys Val Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 37
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 37

Val Asp Ala Lys Tyr Ala Lys Glu Trp Lys Ala Ala Ala His Glu Ile
1               5                   10                  15
```

```
Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 38
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 38

```
Val Asp Ala Lys Tyr Ala Lys Glu Ile Asp Leu Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 39
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 39

```
Val Asp Ala Lys Tyr Ala Lys Glu Leu Glu Ala Ala Arg His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 40
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 40

```
Val Asp Ala Lys Tyr Ala Lys Glu Ala Ala Thr Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 41
<211> LENGTH: 58

```
<212> TYPE: PRT
<213> ORGANISM: Artificial Sequence
<220> FEATURE:
<223> OTHER INFORMATION: Engineered FcRn binding polypeptide

<400> SEQUENCE: 41

Val Asp Ala Lys Tyr Ala Lys Glu Trp Gln Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 42
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 42

Val Asp Ala Lys Tyr Ala Lys Glu Ala Asp Gln Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 43
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 43

Val Asp Ala Lys Tyr Ala Lys Glu Gln Ser Lys Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 44
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 44

Val Asp Ala Lys Tyr Ala Lys Glu Ala Asp Ala Ala Gly His Glu Ile
1               5                   10                  15

Arg Trp Leu Pro Asn Leu Thr Phe Asp Gln Arg Val Ala Phe Ile His
            20                  25                  30
```

-continued

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 45
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 45

Val Asp Ala Lys Tyr Ala Lys Glu Phe Met Asp Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 46
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 46

Val Asp Ala Lys Tyr Ala Lys Glu Ser Lys Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 47
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 47

Val Asp Ala Lys Tyr Ala Lys Glu Val Ser Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 48
<211> LENGTH: 58
<212> TYPE: PRT
<213> ORGANISM: Artificial Sequence
<220> FEATURE:
<223> OTHER INFORMATION: Engineered FcRn binding polypeptide

```
<400> SEQUENCE: 48

Val Asp Ala Lys Tyr Ala Lys Glu Ala Asp Ser Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 49
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 49

Val Asp Ala Lys Tyr Ala Lys Glu Leu Met Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 50
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 50

Val Asp Ala Lys Tyr Ala Lys Glu Leu Asn Thr Ala Ala His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 51
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 51

Val Asp Ala Lys Tyr Ala Lys Glu Val His Glu Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
```

```
                50                  55

<210> SEQ ID NO 52
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 52

Val Asp Ala Lys Tyr Ala Lys Glu Ser Thr Ala Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 53
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 53

Val Asp Ala Lys Tyr Ala Lys Glu Trp Tyr Asn Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 54
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 54

Val Asp Ala Lys Tyr Ala Lys Glu Trp Asn Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 55
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 55

Val Asp Ala Lys Tyr Ala Lys Glu Val Glu Val Ala Lys His Glu Ile
```

```
                1               5                  10                 15
Arg Trp Leu Pro Asn Leu Thr Phe Asp Gln Arg Val Ala Phe Ile His
                20                      25                 30

Lys Leu Asp Asp Pro Ser Gln Ser Ser Glu Leu Leu Ser Glu Ala
        35                      40                 45

Lys Lys Leu Asn Asp Ser Gln Ala Pro Lys
        50                  55

<210> SEQ ID NO 56
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 56

Val Asp Ala Lys Tyr Ala Lys Glu Phe Asn Phe Ala Ala His Glu Ile
1               5                   10                  15

Arg Trp Leu Pro Asn Leu Thr Phe Asp Gln Arg Val Ala Phe Ile His
                20                      25                  30

Lys Leu Arg Asp Asp Pro Ser Gln Ser Ser Glu Leu Leu Ser Glu Ala
        35                      40                  45

Lys Lys Leu Asn Asp Ser Gln Ala Pro Lys
        50                  55

<210> SEQ ID NO 57
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 57

Val Asp Ala Lys Tyr Ala Lys Glu His Asp Ser Ala Ala His Glu Ile
1               5                   10                  15

Arg Trp Leu Pro Asn Leu Thr Phe Asp Gln Arg Val Ala Phe Ile His
                20                      25                  30

Lys Leu Arg Asp Asp Pro Ser Gln Ser Ser Glu Leu Leu Ser Glu Ala
        35                      40                  45

Lys Lys Leu Asn Asp Ser Gln Ala Pro Lys
        50                  55

<210> SEQ ID NO 58
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 58

Val Asp Ala Lys Tyr Ala Lys Glu Trp Met Asp Ala Ala His Glu Ile
1               5                   10                  15

Arg Trp Leu Pro Asn Leu Thr Phe Asp Gln Arg Val Ala Phe Ile His
                20                      25                  30

Lys Leu Arg Asp Asp Pro Ser Gln Ser Ser Glu Leu Leu Ser Glu Ala
        35                      40                  45

Lys Lys Leu Asn Asp Ser Gln Ala Pro Lys
        50                  55

<210> SEQ ID NO 59
```

```
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 59

Val Asp Ala Lys Tyr Ala Lys Glu Phe Ser Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 60
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 60

Val Asp Ala Lys Tyr Ala Lys Glu Leu Asn Ser Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 61
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 61

Val Asp Ala Lys Tyr Ala Lys Glu Val Asp Thr Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 62
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 62

Val Asp Ala Lys Tyr Ala Lys Glu Ser Gln Ile Ala Gly His Glu Ile
1               5                   10                  15

Arg Trp Leu Pro Asn Leu Thr Phe Asp Gln Arg Val Ala Phe Ile His
            20                  25                  30
```

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 63
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 63

Val Asp Ala Lys Tyr Ala Lys Glu Val Ser Ala Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 64
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 64

Val Asp Ala Lys Tyr Ala Lys Glu Asp Gln Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 65
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 65

Val Asp Ala Lys Tyr Ala Lys Glu Leu Glu Ala Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 66
<211> LENGTH: 58
<212> TYPE: PRT
<213> ORGANISM: Artificial Sequence
<220> FEATURE:

<223> OTHER INFORMATION: Engineered FcRn binding polypeptide

<400> SEQUENCE: 66

Val Asp Ala Lys Tyr Ala Lys Glu Ser Lys Arg Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 67
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 67

Val Asp Ala Lys Tyr Ala Lys Glu Tyr Val Lys Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 68
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 68

Val Asp Ala Lys Tyr Ala Lys Glu Phe Ser Arg Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 69
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 69

Val Asp Ala Lys Tyr Ala Lys Glu Trp Gln Phe Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 70
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 70

Val Asp Ala Lys Tyr Ala Lys Glu Trp Gln Ile Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 71
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 71

Val Asp Ala Lys Tyr Ala Lys Glu Leu Gln Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 72
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 72

Val Asp Ala Lys Tyr Ala Lys Glu Tyr Arg Ala Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 73
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 73

```
Val Asp Ala Lys Tyr Ala Lys Glu Leu Ala Ser Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 74
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 74

```
Val Asp Ala Lys Tyr Ala Lys Glu Val Gln Ser Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 75
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 75

```
Val Asp Ala Lys Tyr Ala Lys Glu Ile Glu Asp Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 76
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 76

```
Val Asp Ala Lys Tyr Ala Lys Glu Asn Gln Ala Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 77
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 77

Val Asp Ala Lys Tyr Ala Lys Glu Ala Thr Ser Ala Gly His Glu Ile
1               5                   10                  15

Arg Trp Leu Pro Asn Leu Thr Phe Asp Gln Arg Val Ala Phe Ile Val
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 78
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 78

Val Asp Ala Lys Tyr Ala Lys Glu Asp Glu Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 79
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 79

Val Asp Ala Lys Tyr Ala Lys Glu Gln Asn Gln Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 80
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 80

Val Asp Ala Lys Tyr Ala Lys Glu Tyr Thr Ser Ala Ala His Glu Ile
1               5                   10                  15

Arg Trp Leu Pro Asn Leu Thr Phe Asp Gln Arg Val Ala Phe Ile His
```

```
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 81
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 81

Val Asp Ala Lys Tyr Ala Lys Glu Trp Asp Ala Ala His Glu Ile
1               5                  10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 82
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 82

Val Asp Ala Lys Tyr Ala Lys Glu Glu Met Gln Ala Gly His Glu Ile
1               5                  10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 83
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 83

Val Asp Ala Lys Tyr Ala Lys Glu Leu Ser Asp Ala Ala His Glu Ile
1               5                  10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 84
<211> LENGTH: 58
<212> TYPE: PRT
<213> ORGANISM: Artificial Sequence
```

<220> FEATURE:
<223> OTHER INFORMATION: Engineered FcRn binding polypeptide

<400> SEQUENCE: 84

Val Asp Ala Lys Tyr Ala Lys Glu Ile Asp Ala Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 85
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 85

Val Asp Ala Lys Tyr Ala Lys Glu Ala Glu Arg Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 86
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 86

Val Asp Ala Lys Tyr Ala Lys Glu Glu Asp Ser Ala Ala His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 87
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 87

Val Asp Ala Lys Tyr Ala Lys Glu Gln Lys Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 88
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 88

Val Asp Ala Lys Tyr Ala Lys Glu Trp Asp Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 89
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 89

Val Asp Ala Lys Tyr Ala Lys Glu Ala Lys Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 90
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 90

Val Asp Ala Lys Tyr Ala Lys Glu Leu Ser Glu Ala Ala His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 91
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 91

```
Val Asp Ala Lys Tyr Ala Lys Glu Thr Glu Ala Ala Lys His Glu Ile
1               5                   10                  15

Arg Trp Leu Pro Asn Leu Thr Phe Asp Gln Arg Val Ala Phe Ile His
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 92
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 92

```
Val Asp Ala Lys Tyr Ala Lys Glu Ala Lys Ser Ala Ala His Glu Ile
1               5                   10                  15

Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 93
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 93

```
Val Asp Ala Lys Tyr Ala Lys Glu Gln Ser Ala Ala Ala His Glu Ile
1               5                   10                  15

Arg Trp Leu Pro Asn Leu Thr Phe Asp Gln Arg Val Ala Phe Ile His
                20                  25                  30

Lys Leu Asn Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 94
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 94

```
Val Asp Ala Lys Tyr Ala Lys Glu Lys Glu Arg Ala Ala His Glu Ile
1               5                   10                  15

Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 95
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 95

Val Asp Ala Lys Tyr Ala Lys Glu Trp Asp Glu Ala Ala His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 96
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 96

Val Asp Ala Lys Tyr Ala Lys Glu Glu Lys Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 97
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 97

Val Asp Ala Lys Tyr Ala Lys Glu Ile Glu Asn Ala Ala His Glu Ile
1               5                   10                  15

Arg Trp Leu Pro Asn Leu Thr Phe Asp Gln Arg Val Ala Phe Ile Trp
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 98
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 98

Val Asp Ala Lys Tyr Ala Lys Glu Thr Lys Glu Ala Ala His Glu Ile
1               5                   10                  15

```
Arg Trp Leu Pro Asn Leu Thr Phe Asp Gln Arg Val Ala Phe Ile His
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 99
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 99

```
Val Asp Ala Lys Tyr Ala Lys Glu Leu Glu Ala Ala Lys His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 100
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 100

```
Val Asp Ala Lys Tyr Ala Lys Glu Trp Ala Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 101
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 101

```
Val Asp Ala Lys Tyr Ala Lys Glu Ser Gln Glu Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 102
<211> LENGTH: 58
<212> TYPE: PRT

```
<213> ORGANISM: Artificial Sequence
<220> FEATURE:
<223> OTHER INFORMATION: Engineered FcRn binding polypeptide

<400> SEQUENCE: 102

Val Asp Ala Lys Tyr Ala Lys Glu Leu Ser Thr Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 103
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 103

Val Asp Ala Lys Tyr Ala Lys Glu Ile Glu Glu Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 104
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 104

Val Asp Ala Lys Tyr Ala Lys Glu Leu Gln Thr Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 105
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 105

Val Asp Ala Lys Tyr Ala Lys Glu Gln Asp Ser Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
```

```
                35                  40                  45
Lys Lys Leu Asn Asp Ser Gln Ala Pro Lys
    50                  55

<210> SEQ ID NO 106
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 106

Val Asp Ala Lys Tyr Ala Lys Glu Ser Ala Ser Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 107
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 107

Val Asp Ala Lys Tyr Ala Lys Glu Val Ala Lys Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 108
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 108

Val Asp Ala Lys Tyr Ala Lys Glu Val Gln Glu Ala Ala His Glu Ile
1               5                   10                  15

Arg Trp Leu Pro Asn Leu Thr Phe Asp Gln Arg Val Ala Phe Ile His
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 109
<211> LENGTH: 58
<212> TYPE: PRT
<213> ORGANISM: Artificial Sequence
<220> FEATURE:
<223> OTHER INFORMATION: Engineered FcRn binding polypeptide
```

-continued

```
<400> SEQUENCE: 109

Val Asp Ala Lys Tyr Ala Lys Glu Ser Tyr Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 110
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 110

Val Asp Ala Lys Tyr Ala Lys Glu Thr Ala Glu Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 111
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 111

Val Asp Ala Lys Tyr Ala Lys Glu Leu Glu Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 112
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 112

Val Asp Ala Lys Tyr Ala Lys Glu Ala Ala Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 113
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 113

Val Asp Ala Lys Tyr Ala Lys Glu Tyr Val Asp Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 114
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 114

Val Asp Ala Lys Tyr Ala Lys Glu Ile Gln Glu Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 115
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 115

Val Asp Ala Lys Tyr Ala Lys Glu Ser Ala Thr Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 116
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 116

Val Asp Ala Lys Tyr Ala Lys Glu Trp Met Ser Ala Ala His Glu Ile
1               5                   10                  15

```
Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 117
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 117

```
Val Asp Ala Lys Tyr Ala Lys Glu Arg Glu Gln Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 118
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 118

```
Val Asp Ala Lys Tyr Ala Lys Glu Ile Glu Gln Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 119
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 119

```
Val Asp Ala Lys Tyr Ala Lys Glu His Asn Ala Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 120
<211> LENGTH: 58

```
<212> TYPE: PRT
<213> ORGANISM: Artificial Sequence
<220> FEATURE:
<223> OTHER INFORMATION: Engineered FcRn binding polypeptide

<400> SEQUENCE: 120

Val Asp Ala Lys Tyr Ala Lys Glu Ile Glu Val Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 121
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 121

Val Asp Ala Lys Tyr Ala Lys Glu Arg Ala Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 122
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 122

Val Asp Ala Lys Tyr Ala Lys Glu Ser Glu Leu Ala Ala His Glu Ile
1               5                   10                  15

Arg Trp Leu Pro Asn Leu Thr Phe Asp Gln Arg Val Ala Phe Ile Trp
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 123
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 123

Val Asp Ala Lys Tyr Ala Lys Glu Tyr Arg Ala Ala Gly His Glu Ile
1               5                   10                  15

Arg Trp Leu Pro Asn Leu Thr Phe Asp Gln Arg Val Ala Phe Ile His
            20                  25                  30
```

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 124
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 124

Val Asp Ala Lys Tyr Ala Lys Glu Thr Ala Asn Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 125
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 125

Val Asp Ala Lys Tyr Ala Lys Glu Trp Tyr Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 126
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 126

Val Asp Ala Lys Tyr Ala Lys Glu Glu Gln Glu Ala Ala His Glu Ile
1               5                   10                  15

Arg Trp Leu Pro Asn Leu Thr Phe Asp Gln Arg Val Ala Phe Ile His
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 127
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 127

Val Asp Ala Lys Tyr Ala Lys Glu His Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 128
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 128

Val Asp Ala Lys Tyr Ala Lys Glu Trp Tyr Ser Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 129
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 129

Val Asp Ala Lys Tyr Ala Lys Glu Ile Ser Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 130
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 130

Val Asp Ala Lys Tyr Ala Lys Glu Tyr Thr Thr Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys

<210> SEQ ID NO 131
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 131

Val Asp Ala Lys Tyr Ala Lys Glu Ile Ser Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 132
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 132

Val Asp Ala Lys Tyr Ala Lys Glu Asn Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 133
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 133

Val Asp Ala Lys Tyr Ala Lys Glu Ser Glu Ile Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 134
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 134

Val Asp Ala Lys Tyr Ala Lys Glu Gln Ala Asp Ala Ala His Glu Ile

```
                1               5                  10                  15
Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 135
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 135

Val Asp Ala Lys Tyr Ala Lys Glu Thr Glu Ser Ala Ala His Glu Ile
1               5                  10                  15

Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 136
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 136

Val Asp Ala Lys Tyr Ala Lys Glu Ile Ser Asp Ala Lys His Glu Ile
1               5                  10                  15

Arg Trp Leu Pro Asn Leu Thr Phe Asp Gln Arg Val Ala Phe Ile His
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 137
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 137

Val Asp Ala Lys Tyr Ala Lys Glu His Leu Asn Ala Ala His Glu Ile
1               5                  10                  15

Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 138
```

```
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 138

Val Asp Ala Lys Tyr Ala Lys Glu Trp Leu Asp Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 139
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 139

Val Asp Ala Lys Tyr Ala Lys Glu Asn Ala Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 140
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 140

Val Asp Ala Lys Tyr Ala Lys Glu Ala Glu Leu Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 141
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 141

Val Asp Ala Lys Tyr Ala Lys Glu Val Thr Asp Ala Gly His Glu Ile
1               5                   10                  15

Arg Trp Leu Pro Asn Leu Thr Phe Asp Gln Arg Val Ala Phe Ile Glu
            20                  25                  30
```

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 142
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 142

Val Asp Ala Lys Tyr Ala Lys Glu Leu Asp Ser Ala Ser His Glu Ile
1               5                   10                  15

Arg Trp Leu Pro Asn Leu Thr Phe Asp Gln Arg Val Ala Phe Ile Asn
            20                  25                  30

Lys Leu Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 143
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 143

Val Asp Ala Lys Tyr Ala Lys Glu Ile Asn Leu Ala Lys His Glu Ile
1               5                   10                  15

Arg Trp Leu Pro Asn Leu Thr Phe Asp Gln Arg Val Ala Phe Ile Glu
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 144
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 144

Val Asp Ala Lys Tyr Ala Lys Glu Ser Glu Val Ala Lys His Glu Ile
1               5                   10                  15

Arg Trp Leu Pro Asn Leu Thr Phe Asp Gln Arg Val Ala Phe Ile His
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 145
<211> LENGTH: 58
<212> TYPE: PRT
<213> ORGANISM: Artificial Sequence
<220> FEATURE:

<223> OTHER INFORMATION: Engineered FcRn binding polypeptide

<400> SEQUENCE: 145

Val Asp Ala Lys Tyr Ala Lys Glu Ser Ala Glu Ala Gly His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 146
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 146

Val Asp Ala Lys Tyr Ala Lys Glu Tyr Ser Asn Ala Ala His Glu Ile
1               5                   10                  15

Arg Trp Leu Pro Asn Leu Thr Phe Asp Gln Arg Val Ala Phe Ile Asp
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 147
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 147

Val Asp Ala Lys Tyr Ala Lys Glu Thr Asn Asn Ala Gly His Glu Ile
1               5                   10                  15

Arg Trp Leu Pro Asn Leu Thr Phe Asp Gln Arg Val Ala Phe Ile Ile
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 148
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 148

Val Asp Ala Lys Tyr Ala Lys Glu Val Glu Phe Ala Ala His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 149
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 149

Val Asp Ala Lys Tyr Ala Lys Glu Val Glu Leu Ala Gly His Glu Ile
1               5                   10                  15

Arg Trp Leu Pro Asn Leu Thr Phe Asp Gln Arg Val Ala Phe Ile Glu
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 150
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 150

Val Asp Ala Lys Tyr Ala Lys Glu Val Leu Lys Ala Ser His Glu Ile
1               5                   10                  15

Arg Trp Leu Pro Asn Leu Thr Phe Asp Gln Arg Val Ala Phe Ile Thr
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 151
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 151

Val Asp Ala Lys Tyr Ala Lys Glu Ile Ala Asn Ala Gly His Glu Ile
1               5                   10                  15

Arg Trp Leu Pro Asn Leu Thr Phe Asp Gln Arg Val Ala Phe Ile Arg
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 152
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 152

```
Val Asp Ala Lys Tyr Ala Lys Glu Tyr Met Lys Ala Gly His Glu Ile
1               5                   10                  15

Arg Trp Leu Pro Asn Leu Thr Phe Asp Gln Arg Val Ala Phe Ile Val
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 153
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 153

```
Val Asp Ala Lys Tyr Ala Lys Glu His Ala Asn Ala Gln His Glu Ile
1               5                   10                  15

Arg Trp Leu Pro Asn Leu Thr Phe Asp Gln Arg Val Ala Phe Ile His
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 154
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 154

```
Val Asp Ala Lys Tyr Ala Lys Glu Val Asp Ile Ala Ser His Glu Ile
1               5                   10                  15

Arg Trp Leu Pro Asn Leu Thr Tyr Asp Gln Arg Val Ala Phe Ile Trp
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 155
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 155

```
Val Asp Ala Lys Tyr Ala Lys Glu Glu Val Phe Ala Ala His Glu Ile
1               5                   10                  15

Arg Trp Leu Pro Asn Leu Thr Tyr Asp Gln Arg Val Ala Phe Ile Val
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55
```

```
<210> SEQ ID NO 156
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 156

Val Asp Ala Lys Tyr Ala Lys Glu Phe Asn Thr Ala Ala His Glu Ile
1               5                   10                  15

Arg Trp Leu Pro Asn Leu Thr Phe Asp Gln Arg Val Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 157
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 157

Val Asp Ala Lys Tyr Ala Lys Glu Val Asp Val Ala Gly His Glu Ile
1               5                   10                  15

Arg Trp Leu Pro Asn Leu Thr Phe Asp Gln Arg Val Ala Phe Ile Arg
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 158
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 158

Val Asp Ala Lys Tyr Ala Lys Glu Trp Ser Leu Ala Ala His Glu Ile
1               5                   10                  15

Arg Trp Leu Pro Asn Leu Thr Phe Asp Gln Arg Val Ala Phe Ile Val
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 159
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 159

Val Asp Ala Lys Tyr Ala Lys Glu Leu Asp Ala Ala His Glu Ile
1               5                   10                  15

Arg Trp Leu Pro Asn Leu Thr Phe Asp Gln Arg Val Ala Phe Ile Gln
```

```
                    20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 160
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 160

Val Asp Ala Lys Tyr Ala Lys Glu Arg His Glu Ala Gly His Glu Ile
1               5                   10                  15

Arg Trp Leu Pro Asn Leu Thr Phe Asp Gln Arg Val Ala Phe Ile Arg
                20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 161
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 161

Val Asp Ala Lys Tyr Ala Lys Glu Ile Ser Asp Ala Ile His Glu Ile
1               5                   10                  15

Arg Trp Leu Pro Asn Leu Thr Phe Asp Gln Arg Val Ala Phe Ile His
                20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 162
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 162

Val Asp Ala Lys Tyr Ala Lys Glu Trp Glu Thr Ala Gly His Glu Ile
1               5                   10                  15

Arg Trp Leu Pro Asn Leu Thr Phe Asp Gln Arg Val Ala Phe Ile Val
                20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 163
<211> LENGTH: 58
<212> TYPE: PRT
<213> ORGANISM: Artificial Sequence
```

```
<220> FEATURE:
<223> OTHER INFORMATION: Engineered FcRn binding polypeptide

<400> SEQUENCE: 163

Val Asp Ala Lys Tyr Ala Lys Glu Arg Tyr Trp Ala Ser His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 164
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 164

Val Asp Ala Lys Tyr Ala Lys Glu Ile Asp Trp Ala Gly His Glu Ile
1               5                   10                  15

Arg Trp Leu Pro Asn Leu Thr Phe Asp Gln Arg Val Ala Phe Ile His
            20                  25                  30

Lys Leu Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 165
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 165

Val Asp Ala Lys Tyr Ala Lys Glu Gln Ser Lys Ala Gly His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 166
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 166

Val Asp Ala Lys Tyr Ala Lys Glu Ile Glu Ala Ala Gln His Glu Ile
1               5                   10                  15

Arg Trp Leu Pro Asn Leu Thr Phe Asp Gln Arg Val Ala Phe Ile Asn
            20                  25                  30

Lys Leu Arg Asp Asp Pro Ser Gln Ser Ser Glu Leu Leu Ser Glu Ala
        35                  40                  45
```

Lys Lys Leu Asn Asp Ser Gln Ala Pro Lys
    50                  55

<210> SEQ ID NO 167
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 167

Val Asp Ala Lys Tyr Ala Lys Glu His Glu Gln Ala Ala His Glu Ile
1               5                   10                  15

Arg Trp Leu Pro Asn Leu Thr Phe Asp Gln Arg Val Ala Phe Ile Arg
            20                  25                  30

Lys Leu Val Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 168
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 168

Val Asp Ala Lys Tyr Ala Lys Glu Ala Glu Gln Ala Gly His Glu Ile
1               5                   10                  15

Arg Trp Leu Pro Asn Leu Thr Phe Asp Gln Arg Val Ala Phe Ile Asn
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 169
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 169

Val Asp Ala Lys Tyr Ala Lys Glu Val Asp Tyr Ala Ala His Glu Ile
1               5                   10                  15

Arg Trp Leu Pro Asn Leu Thr Phe Asp Gln Arg Val Ala Phe Ile His
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 170
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 170

-continued

Val Asp Ala Lys Tyr Ala Lys Glu Tyr Ser Ala Ala Gly His Glu Ile
1               5                   10                  15

Arg Trp Leu Pro Asn Leu Thr Phe Asp Gln Arg Val Ala Phe Ile Glu
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 171
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 171

Val Asp Ala Lys Tyr Ala Lys Glu Leu Ala Thr Ala Ser His Glu Ile
1               5                   10                  15

Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 172
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 172

Val Asp Ala Lys Tyr Ala Lys Glu Tyr Arg Val Ala Gly His Glu Ile
1               5                   10                  15

Arg Trp Leu Pro Asn Leu Thr Phe Asp Gln Arg Val Ala Phe Ile Gln
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 173
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 173

Val Asp Ala Lys Tyr Ala Lys Glu Val Val Ser Ala Lys His Glu Ile
1               5                   10                  15

Arg Trp Leu Pro Asn Leu Thr Phe Asp Gln Arg Val Ala Phe Ile His
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 174
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 174

Val Asp Ala Lys Tyr Ala Lys Glu Ser Ala Gln Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 175
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 175

Val Asp Ala Lys Tyr Ala Lys Glu Tyr Ser Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 176
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 176

Val Asp Ala Lys Tyr Ala Lys Glu Gln Lys Glu Ala Ala Ala Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 177
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 177

Val Asp Ala Lys Tyr Ala Lys Glu Ala Ala Ile Ala Gly Lys Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 178
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 178

Val Asp Ala Lys Tyr Ala Lys Glu Ile Ser Lys Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 179
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 179

Val Asp Ala Lys Tyr Ala Lys Glu Ser Val Ala Ala Ala His Glu Ile
1               5                   10                  15

Arg Trp Leu Pro Asn Leu Thr Phe Asp Gln Arg Val Ala Phe Ile Trp
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 180
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 180

Val Asp Ala Lys Tyr Ala Lys Glu Ile Gln Gln Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 181
<211> LENGTH: 58
<212> TYPE: PRT

<213> ORGANISM: Artificial Sequence
<220> FEATURE:
<223> OTHER INFORMATION: Engineered FcRn binding polypeptide

<400> SEQUENCE: 181

Val Asp Ala Lys Tyr Ala Lys Glu Ile Thr Ser Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 182
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 182

Val Asp Ala Lys Tyr Ala Lys Glu Gln Asp Val Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 183
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 183

Val Asp Ala Lys Tyr Ala Lys Glu Leu Glu Arg Ala Ala His Glu Ile
1               5                   10                  15

Arg Trp Leu Pro Asn Leu Thr Phe Asp Gln Arg Val Ala Phe Ile Asn
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 184
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 184

Val Asp Ala Lys Tyr Ala Lys Glu Asn Gln Leu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala 35                  40                  45

Lys Lys Leu Asn Asp Ser Gln Ala Pro Lys
    50                  55

<210> SEQ ID NO 185
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 185

Val Asp Ala Lys Tyr Ala Lys Glu Ile Ser Gln Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 186
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 186

Val Asp Ala Lys Tyr Ala Lys Glu Ile Ala Asn Ala Ser His Glu Ile
1               5                   10                  15

Arg Trp Leu Pro Asn Leu Thr Phe Asp Gln Arg Val Ala Phe Ile Tyr
            20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 187
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 187

Val Asp Ala Lys Tyr Ala Lys Glu Trp Gln Ala Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 188
<211> LENGTH: 58
<212> TYPE: PRT
<213> ORGANISM: Artificial Sequence
<220> FEATURE:
<223> OTHER INFORMATION: Engineered FcRn binding polypeptide -continued

<400> SEQUENCE: 188

Val Asp Ala Lys Tyr Ala Lys Glu Arg Lys Asp Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 189
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 189

Val Asp Ala Lys Tyr Ala Lys Glu Ile Thr Gln Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 190
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 190

Val Asp Ala Lys Tyr Ala Lys Glu Phe Ile Gln Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 191
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 191

Val Asp Ala Lys Tyr Ala Lys Glu Trp Asn Thr Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 192
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 192

Val Asp Ala Lys Tyr Ala Lys Glu Lys Phe Val Ala Ala His Glu Ile
1               5                  10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 193
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 193

Val Asp Ala Lys Tyr Ala Lys Glu Ala Asp Ser Ala Gly Ala Glu Ile
1               5                  10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 194
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 194

Val Asp Ala Lys Tyr Ala Lys Glu Ser Ser Val Ala Ala Ala Glu Ile
1               5                  10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 195
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 195

Val Asp Ala Lys Tyr Ala Lys Glu Val Asp Leu Ala Gly Arg Glu Ile
1               5                  10                  15

-continued

```
Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 196
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 196

Val Asp Ala Lys Tyr Ala Lys Glu Gln Glu Arg Ala Ala Ala Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 197
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 197

Val Asp Ala Lys Tyr Ala Lys Glu Ile Trp Gln Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 198
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 198

Val Asp Ala Lys Tyr Ala Lys Glu Leu Asn Gln Ala Lys His Glu Ile
1               5                   10                  15

Arg Trp Leu Pro Asn Leu Thr Phe Asp Gln Arg Val Ala Phe Ile His
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 199
<211> LENGTH: 58
```

```
<212> TYPE: PRT
<213> ORGANISM: Artificial Sequence
<220> FEATURE:
<223> OTHER INFORMATION: Engineered FcRn binding polypeptide

<400> SEQUENCE: 199

Val Asp Ala Lys Tyr Ala Lys Glu Leu Gln Gln Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 200
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 200

Val Asp Ala Lys Tyr Ala Lys Glu Ile Asn Gln Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 201
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 201

Val Asp Ala Lys Tyr Ala Lys Glu Leu Val Leu Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 202
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 202

Val Asp Ala Lys Tyr Ala Lys Glu Leu Thr Ser Ala Ala His Glu Ile
1               5                   10                  15

Arg Trp Leu Pro Asn Leu Thr Phe Asp Gln Arg Val Ala Phe Ile His
            20                  25                  30
```

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 203
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 203

Val Asp Ala Lys Tyr Ala Lys Glu Trp Asn Ala Ala Arg Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 204
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 204

Val Asp Ala Lys Tyr Ala Lys Glu Ile Leu His Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 205
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 205

Val Asp Ala Lys Tyr Ala Lys Glu Val Leu Thr Ala Lys His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 206
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 206

Val Asp Ala Lys Tyr Ala Lys Glu Asn Ser Lys Ala Ala His Glu Ile
1               5                   10                  15

Arg Trp Leu Pro Asn Leu Thr Phe Asp Gln Arg Val Ala Phe Ile His
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 207
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 207

Val Asp Ala Lys Tyr Ala Lys Glu Val Met Thr Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 208
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 208

Val Asp Ala Lys Tyr Ala Lys Glu Ala Arg Asp Ala Ala His Glu Ile
1               5                   10                  15

Arg Trp Leu Pro Asn Leu Thr Phe Asp Gln Arg Val Ala Phe Ile His
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 209
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 209

Val Asp Ala Lys Tyr Ala Lys Glu Arg Ser Lys Ala Ala His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys

-continued

```
        50                  55

<210> SEQ ID NO 210
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 210

Val Asp Ala Lys Tyr Ala Lys Glu Ile Tyr Ser Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 211
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 211

Val Asp Ala Lys Tyr Ala Lys Glu Val Gln Ser Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 212
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 212

Val Asp Ala Lys Tyr Ala Lys Glu Thr Leu Glu Ala Ala His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 213
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 213

Val Asp Ala Lys Tyr Ala Lys Glu Gln Met Arg Ala Ala His Glu Ile
```

```
                1               5                  10                 15
Arg Trp Leu Pro Asn Leu Thr Phe Asp Gln Arg Val Ala Phe Ile Arg
                20                 25                 30

Lys Leu Arg Asp Asp Pro Ser Gln Ser Ser Glu Leu Leu Ser Glu Ala
        35                 40                 45

Lys Lys Leu Asn Asp Ser Gln Ala Pro Lys
        50                 55
```

<210> SEQ ID NO 214
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 214

```
Val Asp Ala Lys Tyr Ala Lys Glu Asn Lys Asn Ala Ala His Glu Ile
1               5                  10                 15

Arg Trp Leu Pro Asn Leu Thr Phe Asp Gln Arg Val Ala Phe Ile His
                20                 25                 30

Lys Leu Arg Asp Asp Pro Ser Gln Ser Ser Glu Leu Leu Ser Glu Ala
        35                 40                 45

Lys Lys Leu Asn Asp Ser Gln Ala Pro Lys
        50                 55
```

<210> SEQ ID NO 215
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 215

```
Val Asp Ala Lys Tyr Ala Lys Glu Thr Glu Ser Ala Lys His Glu Ile
1               5                  10                 15

Arg Trp Leu Pro Asn Leu Thr Phe Asp Gln Arg Val Ala Phe Ile His
                20                 25                 30

Lys Leu Thr Asp Asp Pro Ser Gln Ser Ser Glu Leu Leu Ser Glu Ala
        35                 40                 45

Lys Lys Leu Asn Asp Ser Gln Ala Pro Lys
        50                 55
```

<210> SEQ ID NO 216
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 216

```
Val Asp Ala Lys Tyr Ala Lys Glu Thr Val Gln Ala Lys His Glu Ile
1               5                  10                 15

Arg Trp Leu Pro Asn Leu Thr Phe Asp Gln Arg Val Ala Phe Ile His
                20                 25                 30

Lys Leu Asp Asp Asp Pro Ser Gln Ser Ser Glu Leu Leu Ser Glu Ala
        35                 40                 45

Lys Lys Leu Asn Asp Ser Gln Ala Pro Lys
        50                 55
```

<210> SEQ ID NO 217

```
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 217

Val Asp Ala Lys Tyr Ala Lys Glu Ile Ala Ser Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 218
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 218

Val Asp Ala Lys Tyr Ala Lys Glu Val Met Asp Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 219
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 219

Val Asp Ala Lys Tyr Ala Lys Glu Thr Asp Ala Ala Lys His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 220
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 220

Val Asp Ala Lys Tyr Ala Lys Glu Leu Gln Ile Ala Lys His Glu Ile
1               5                   10                  15

Arg Trp Leu Pro Asn Leu Thr Phe Asp Gln Arg Val Ala Phe Ile His
            20                  25                  30
```

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 221
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 221

Val Asp Ala Lys Tyr Ala Lys Glu Trp Lys Asp Ala Ala Gln Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 222
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 222

Val Asp Ala Lys Tyr Ala Lys Glu Arg Asp Ser Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 223
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 223

Val Asp Ala Lys Tyr Ala Lys Glu Ile Ala Ala Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 224
<211> LENGTH: 58
<212> TYPE: PRT
<213> ORGANISM: Artificial Sequence
<220> FEATURE:

<223> OTHER INFORMATION: Engineered FcRn binding polypeptide

<400> SEQUENCE: 224

Val Asp Ala Lys Tyr Ala Lys Glu Ser Val Lys Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 225
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 225

Val Asp Ala Lys Tyr Ala Lys Glu Asn Glu Arg Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 226
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 226

Val Asp Ala Lys Tyr Ala Lys Glu Tyr Lys Arg Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 227
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 227

Val Asp Ala Lys Tyr Ala Lys Glu Val Arg Ala Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

```
<210> SEQ ID NO 228
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 228
```

Val Asp Ala Lys Tyr Ala Lys Glu Asp Lys Arg Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 229
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 229
```

Val Asp Ala Lys Tyr Ala Lys Glu Ser Glu Lys Ala Gly Lys Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 230
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 230
```

Val Asp Ala Lys Tyr Ala Lys Glu Ile Asn Arg Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 231
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 231
```

-continued

Val Asp Ala Lys Tyr Ala Lys Glu Thr Gln Gln Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 232
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 232

Val Asp Ala Lys Tyr Ala Lys Glu Asn Gln Ser Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 233
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 233

Val Asp Ala Lys Tyr Ala Lys Glu Ala Lys Gln Ala Ser His Glu Ile
1               5                   10                  15

Arg Trp Leu Pro Asn Leu Thr Phe Asp Gln Arg Val Ala Phe Ile Val
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 234
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 234

Val Asp Ala Lys Tyr Ala Lys Glu Ala Ala Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 235
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 235

Val Asp Ala Lys Tyr Ala Lys Glu Val Gln Tyr Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 236
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 236

Val Asp Ala Lys Tyr Ala Lys Glu Leu Arg Asn Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 237
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 237

Val Asp Ala Lys Tyr Ala Lys Glu Gln Arg Ala Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 238
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 238

Val Asp Ala Lys Tyr Ala Lys Glu Ala Ser Glu Ala Ala Ala Glu Ile
1               5                   10                  15

Arg Trp Leu Pro Asn Leu Thr Phe Asp Gln Arg Val Ala Phe Ile His
```

```
                 20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 239
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 239

Val Asp Ala Lys Tyr Ala Lys Glu Ser Val Ile Ala Ala His Glu Ile
1               5                  10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 240
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 240

Val Asp Ala Lys Tyr Ala Lys Glu Ile Leu Arg Ala Lys His Glu Ile
1               5                  10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 241
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 241

Val Asp Ala Lys Tyr Ala Lys Glu Ser Lys Thr Ala Ala His Glu Ile
1               5                  10                  15

Arg Trp Leu Pro Asn Leu Thr Phe Asp Gln Arg Val Ala Phe Ile Gln
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 242
<211> LENGTH: 58
<212> TYPE: PRT
<213> ORGANISM: Artificial Sequence
```

<220> FEATURE:
<223> OTHER INFORMATION: Engineered FcRn binding polypeptide

<400> SEQUENCE: 242

Val Asp Ala Lys Tyr Ala Lys Glu Leu Ala Glu Ala Ser His Glu Ile
1               5                   10                  15

Arg Trp Leu Pro Asn Leu Thr Phe Asp Gln Arg Val Ala Phe Ile His
            20                  25                  30

Lys Leu Phe Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 243
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 243

Val Asp Ala Lys Tyr Ala Lys Glu Ala Thr Thr Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 244
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 244

Val Asp Ala Lys Tyr Ala Lys Glu Ile Glu Asn Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 245
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 245

Val Asp Ala Lys Tyr Ala Lys Glu Ala Lys Asp Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

```
Lys Lys Leu Asn Asp Ser Gln Ala Pro Lys
    50                  55

<210> SEQ ID NO 246
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 246

Val Asp Ala Lys Tyr Ala Lys Glu Arg Leu Glu Ala Ala Ala Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 247
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 247

Val Asp Ala Lys Tyr Ala Lys Glu Gln Met Glu Ala Ala Ala Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 248
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 248

Val Asp Ala Lys Tyr Ala Lys Glu Val Lys Thr Ala Ser His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 249
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 249
```

Val Asp Ala Lys Tyr Ala Lys Glu Ser Phe Glu Ala Ser His Glu Ile
1               5                   10                  15

Arg Trp Leu Pro Asn Leu Thr Phe Asp Gln Arg Val Ala Phe Ile Gln
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 250
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 250

Val Asp Ala Lys Tyr Ala Lys Glu Ile Lys Ser Ala Lys His Glu Ile
1               5                   10                  15

Arg Trp Leu Pro Asn Leu Thr Phe Asp Gln Arg Val Ala Phe Ile His
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 251
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 251

Val Asp Ala Lys Tyr Ala Lys Glu Ile Lys Asn Ala Lys His Glu Ile
1               5                   10                  15

Arg Trp Leu Pro Asn Leu Thr Phe Asp Gln Arg Val Ala Phe Ile His
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 252
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 252

Val Asp Ala Lys Tyr Ala Lys Glu Leu Gln Glu Ala Lys His Glu Ile
1               5                   10                  15

Arg Trp Leu Pro Asn Leu Thr Phe Asp Gln Arg Val Ala Phe Ile His
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 253
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 253

Val Asp Ala Lys Tyr Ala Lys Glu Arg Gln Asn Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 254
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 254

Val Asp Ala Lys Tyr Ala Lys Glu Val Leu Gln Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 255
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 255

Val Asp Ala Lys Tyr Ala Lys Glu Ala Asn Val Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 256
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 256

Val Asp Ala Lys Tyr Ala Lys Glu Leu Asp Ala Ala Lys His Glu Ile
1               5                   10                  15

```
Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 257
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 257

Val Asp Ala Lys Tyr Ala Lys Glu Thr Ala Ser Ala Ala His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 258
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 258

Val Asp Ala Lys Tyr Ala Lys Glu Trp Lys Gln Ala Ala Ser Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 259
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 259

Val Asp Ala Lys Tyr Ala Lys Glu Thr Ala Ser Ala Ser His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 260
<211> LENGTH: 58
<212> TYPE: PRT
```

<213> ORGANISM: Artificial Sequence
<220> FEATURE:
<223> OTHER INFORMATION: Engineered FcRn binding polypeptide

<400> SEQUENCE: 260

Val Asp Ala Lys Tyr Ala Lys Glu Ser Ile Val Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 261
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 261

Val Asp Ala Lys Tyr Ala Lys Glu Ile Lys Gln Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 262
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 262

Val Asp Ala Lys Tyr Ala Lys Glu Gln Ala Thr Ala Ser His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 263
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 263

Val Asp Ala Lys Tyr Ala Lys Glu Leu Asn Ala Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala

```
                35                  40                  45
Lys Lys Leu Asn Asp Ser Gln Ala Pro Lys
    50                  55

<210> SEQ ID NO 264
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 264

Val Asp Ala Lys Tyr Ala Lys Glu Val Lys Arg Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 265
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 265

Val Asp Ala Lys Tyr Ala Lys Glu Ser Arg Asn Ala Ala His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 266
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 266

Val Asp Ala Lys Tyr Ala Lys Glu Ser Ile Thr Ala Ser Ala Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 267
<211> LENGTH: 58
<212> TYPE: PRT
<213> ORGANISM: Artificial Sequence
<220> FEATURE:
<223> OTHER INFORMATION: Engineered FcRn binding polypeptide
```

-continued

```
<400> SEQUENCE: 267

Val Asp Ala Lys Tyr Ala Lys Glu Ala Ala Thr Ala Ala His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 268
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 268

Val Asp Ala Lys Tyr Ala Lys Glu Val Tyr Ala Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 269
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 269

Val Asp Ala Lys Tyr Ala Lys Glu Ile Ser Arg Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 270
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 270

Val Asp Ala Lys Tyr Ala Lys Glu Tyr Val Thr Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 271
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 271

Val Asp Ala Lys Tyr Ala Lys Glu His Ile Asp Ala Gly His Glu Ile
 1               5                  10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 272
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 272

Val Asp Ala Lys Tyr Ala Lys Glu Ile Leu Gln Ala Lys His Glu Ile
 1               5                  10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 273
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 273

Val Asp Ala Lys Tyr Ala Lys Glu Asn Ser Gln Ala Lys His Glu Ile
 1               5                  10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 274
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 274

Val Asp Ala Lys Tyr Ala Lys Glu Tyr Arg Val Ala Ala Lys Glu Ile
 1               5                  10                  15
```

```
Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 275
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 275

```
Val Asp Ala Lys Tyr Ala Lys Glu Ile Tyr Asn Ala Gly His Glu Ile
1               5                   10                  15

Arg Trp Leu Pro Asn Leu Thr Phe Asp Gln Arg Val Ala Phe Ile Arg
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 276
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 276

```
Val Asp Ala Lys Tyr Ala Lys Glu Ser Asn Glu Ala Ala Ala Glu Ile
1               5                   10                  15

Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 277
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 277

```
Val Asp Ala Lys Tyr Ala Lys Glu Ser Gln Leu Ala Ala Ala Glu Ile
1               5                   10                  15

Arg Trp Leu Pro Asn Leu Thr Phe Asp Gln Arg Val Ala Phe Ile Arg
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 278
<211> LENGTH: 58

```
<212> TYPE: PRT
<213> ORGANISM: Artificial Sequence
<220> FEATURE:
<223> OTHER INFORMATION: Engineered FcRn binding polypeptide

<400> SEQUENCE: 278

Val Asp Ala Lys Tyr Ala Lys Glu Leu Lys Glu Ala Gly His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 279
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 279

Val Asp Ala Lys Tyr Ala Lys Glu Thr Arg Val Ala Ser Val Glu Ile
1               5                   10                  15

Arg Trp Leu Pro Asn Leu Thr Phe Asp Gln Arg Val Ala Phe Ile Gln
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 280
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 280

Val Asp Ala Lys Tyr Ala Lys Glu Leu Arg Thr Ala Ala His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 281
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 281

Val Asp Ala Lys Tyr Ala Lys Glu Lys Thr Tyr Ala His Phe Glu Ile
1               5                   10                  15

Arg Trp Leu Pro Asn Leu Thr Phe Asp Gln Arg Val Ala Phe Ile Ser
            20                  25                  30
```

```
Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 282
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 282

Val Asp Ala Lys Tyr Ala Lys Glu Glu Ala Gln Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 283
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 283

Val Asp Ala Lys Tyr Ala Lys Glu Ile Thr Ser Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 284
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 284

Val Asp Ala Lys Tyr Ala Lys Glu Val Lys Thr Ala Ser His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 285
<211> LENGTH: 58
<212> TYPE: PRT
<213> ORGANISM: Artificial Sequence
<220> FEATURE:
<223> OTHER INFORMATION: Engineered FcRn binding polypeptide
```

```
<400> SEQUENCE: 285

Val Asp Ala Lys Tyr Ala Lys Glu Thr Lys Val Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 286
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 286

Val Asp Ala Lys Tyr Ala Lys Glu Asp Leu Val Ala Gln His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 287
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 287

Val Asp Ala Lys Tyr Ala Lys Glu Thr Gln Thr Ala Phe Asn Glu Ile
1               5                   10                  15

Arg Trp Leu Pro Asn Leu Thr Tyr Asp Gln Arg Ala Ala Phe Ile Leu
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 288
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 288

Val Asp Ala Lys Tyr Ala Lys Glu Ile Lys Asp Ala Gly His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
```

-continued

```
        50                  55

<210> SEQ ID NO 289
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 289

Val Asp Ala Lys Tyr Ala Lys Glu Tyr Lys Glu Ala Gly His Glu Ile
1               5                   10                  15

Arg Trp Leu Pro Asn Leu Thr Tyr Asp Gln Arg Val Ala Phe Ile Val
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 290
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 290

Val Asp Ala Lys Tyr Ala Lys Glu Ala Ala Leu Ala Ala His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 291
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 291

Val Asp Ala Lys Tyr Ala Lys Glu Gln Glu Arg Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 292
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 292

Val Asp Ala Lys Tyr Ala Lys Glu Trp Phe Asp Ala Ala His Glu Ile
```

```
                1               5                   10                  15
Arg Trp Leu Pro Asn Leu Thr Phe Asp Gln Arg Val Ala Phe Ile Arg
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
        50                  55
```

<210> SEQ ID NO 293
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 293

```
Val Asp Ala Lys Tyr Ala Lys Glu Ile Ile Gln Ala Lys His Glu Ile
1               5                   10                  15

Arg Trp Leu Pro Asn Leu Thr Phe Asp Gln Arg Val Ala Phe Ile His
                20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
        50                  55
```

<210> SEQ ID NO 294
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 294

```
Val Asp Ala Lys Tyr Ala Lys Glu Leu Thr Asn Ala Lys His Glu Ile
1               5                   10                  15

Arg Trp Leu Pro Asn Leu Thr Phe Asp Gln Arg Val Ala Phe Ile His
                20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
        50                  55
```

<210> SEQ ID NO 295
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 295

```
Val Asp Ala Lys Tyr Ala Lys Glu Ile Gln Leu Ala Lys His Glu Ile
1               5                   10                  15

Arg Trp Leu Pro Asn Leu Thr Phe Asp Gln Arg Val Ala Phe Ile His
                20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
        50                  55
```

<210> SEQ ID NO 296

```
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 296

Val Asp Ala Lys Tyr Ala Lys Glu Ile His Asp Ala Lys His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 297
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 297

Val Asp Ala Lys Tyr Ala Lys Glu Val Lys Ile Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 298
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 298

Val Asp Ala Lys Tyr Ala Lys Glu Gln His Ser Ala Ala His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 299
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 299

Val Asp Ala Lys Tyr Ala Lys Glu Val Phe Ala Ala Ser Ala Glu Ile
1               5                   10                  15

Arg Trp Leu Pro Asn Leu Thr Phe Asp Gln Arg Val Ala Phe Ile His
            20                  25                  30
```

```
Lys Leu Arg Asp Asp Pro Ser Gln Ser Ser Glu Leu Leu Ser Glu Ala
         35                  40                  45

Lys Lys Leu Asn Asp Ser Gln Ala Pro Lys
 50                  55

<210> SEQ ID NO 300
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 300

Val Asp Ala Lys Tyr Ala Lys Glu Thr Asp Leu Ala Gly His Glu Ile
 1               5                  10                  15

Arg Trp Leu Pro Asn Leu Thr Phe Asp Gln Arg Val Ala Phe Ile Arg
             20                  25                  30

Lys Leu Arg Asp Asp Pro Ser Gln Ser Ser Glu Leu Leu Ser Glu Ala
         35                  40                  45

Lys Lys Leu Asn Asp Ser Gln Ala Pro Lys
 50                  55

<210> SEQ ID NO 301
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 301

Val Asp Ala Lys Tyr Ala Lys Glu Ala Asn Phe Ala Gly His Glu Ile
 1               5                  10                  15

Arg Trp Leu Pro Asn Leu Thr Phe Asp Gln Arg Val Ala Phe Ile Arg
             20                  25                  30

Lys Leu Arg Asp Asp Pro Ser Gln Ser Ser Glu Leu Leu Ser Glu Ala
         35                  40                  45

Lys Lys Leu Asn Asp Ser Gln Ala Pro Lys
 50                  55

<210> SEQ ID NO 302
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 302

Val Asp Ala Lys Tyr Ala Lys Glu Phe Glu Thr Ala Gly His Glu Ile
 1               5                  10                  15

Arg Trp Leu Pro Asn Leu Thr Phe Asp Gln Arg Val Ala Phe Ile Thr
             20                  25                  30

Lys Leu Trp Asp Asp Pro Ser Gln Ser Ser Glu Leu Leu Ser Glu Ala
         35                  40                  45

Lys Lys Leu Asn Asp Ser Gln Ala Pro Lys
 50                  55

<210> SEQ ID NO 303
<211> LENGTH: 58
<212> TYPE: PRT
<213> ORGANISM: Artificial Sequence
<220> FEATURE:
```

<223> OTHER INFORMATION: Engineered FcRn binding polypeptide

<400> SEQUENCE: 303

Val Asp Ala Lys Tyr Ala Lys Glu Val Asn Leu Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 304
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 304

Val Asp Ala Lys Tyr Ala Lys Glu Ala Asp Thr Ala Ala His Glu Ile
1               5                   10                  15

Arg Trp Leu Pro Asn Leu Thr Phe Asp Gln Arg Val Ala Phe Ile Tyr
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 305
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 305

Val Asp Ala Lys Tyr Ala Lys Glu Phe Val Asp Ala Gly His Glu Ile
1               5                   10                  15

Arg Trp Leu Pro Asn Leu Thr Phe Asp Gln Arg Val Ala Phe Ile Gln
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 306
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 306

Val Asp Ala Lys Tyr Ala Lys Glu Asp His Lys Ala Glu His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 307
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 307

Val Asp Ala Lys Tyr Ala Lys Glu Thr Val Asp Ala Gly His Glu Ile
1               5                   10                  15

Arg Trp Leu Pro Asn Leu Thr Phe Asp Gln Arg Val Ala Phe Ile His
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 308
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 308

Val Asp Ala Lys Tyr Ala Lys Glu Ser Gln Arg Ala Gly His Glu Ile
1               5                   10                  15

Arg Trp Leu Pro Asn Leu Thr Phe Asp Gln Arg Val Ala Phe Ile Thr
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 309
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 309

Val Asp Ala Lys Tyr Ala Lys Glu Trp Ser Ser Ala Ala His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 310
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 310

-continued

Val Asp Ala Lys Tyr Ala Lys Glu Val Ala Val Ala Gly His Glu Ile
1               5                   10                  15

Arg Trp Leu Pro Asn Leu Thr Tyr Asp Gln Arg Val Ala Phe Ile Val
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 311
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 311

Val Asp Ala Lys Tyr Ala Lys Glu Ser Ala Glu Ala Gly His Glu Ile
1               5                   10                  15

Arg Trp Leu Pro Asn Leu Thr Phe Asp Gln Arg Val Ala Phe Ile Glu
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 312
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 312

Val Asp Ala Lys Tyr Ala Lys Glu Ala Val Ala Ala Gly His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 313
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 313

Val Asp Ala Lys Tyr Ala Lys Glu Phe Gln Ile Ala Gly His Glu Ile
1               5                   10                  15

Arg Trp Leu Pro Asn Leu Thr Phe Asp Gln Arg Val Ala Phe Ile Asn
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 314
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 314

Val Asp Ala Lys Tyr Ala Lys Glu Leu Met Val Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 315
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 315

Val Asp Ala Lys Tyr Ala Lys Glu Tyr Asp Ser Ala Ala His Glu Ile
1               5                   10                  15

Arg Trp Leu Pro Asn Leu Thr Tyr Asp Gln Arg Val Ala Phe Ile Leu
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 316
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 316

Val Asp Ala Lys Tyr Ala Lys Glu Val Leu Glu Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 317
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 317

Val Asp Ala Lys Tyr Ala Lys Glu Ser Ile Ala Ala Ser His Glu Ile
1               5                   10                  15

Arg Trp Leu Pro Asn Leu Thr Phe Asp Gln Arg Val Ala Phe Ile His
```

```
                    20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 318
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 318

Val Asp Ala Lys Tyr Ala Lys Glu Val Ala Glu Ala Gly His Glu Ile
1               5                   10                  15

Arg Trp Leu Pro Asn Leu Thr Phe Asp Gln Arg Val Ala Phe Ile Ser
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 319
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 319

Val Asp Ala Lys Tyr Ala Lys Glu Gln Ala Lys Ala Ala His Glu Ile
1               5                   10                  15

Arg Trp Leu Pro Asn Leu Thr Phe Asp Gln Arg Val Ala Phe Ile His
                20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 320
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 320

Val Asp Ala Lys Tyr Ala Lys Glu Arg Asp Ala Ala His Glu Ile
1               5                   10                  15

Arg Trp Leu Pro Asn Leu Thr Phe Asp Gln Arg Val Ala Phe Ile Glu
                20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 321
<211> LENGTH: 58
<212> TYPE: PRT
<213> ORGANISM: Artificial Sequence
```

<220> FEATURE:
<223> OTHER INFORMATION: Engineered FcRn binding polypeptide

<400> SEQUENCE: 321

Val Asp Ala Lys Tyr Ala Lys Glu Ala Lys Asp Ala Ser His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 322
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 322

Val Asp Ala Lys Tyr Ala Lys Glu Ala Ser Ser Ala Ala His Glu Ile
1               5                   10                  15

Arg Trp Leu Pro Asn Leu Thr Phe Asp Gln Arg Val Ala Phe Ile Gln
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 323
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 323

Val Asp Ala Lys Tyr Ala Lys Glu Trp Met Glu Ala Ser His Glu Ile
1               5                   10                  15

Arg Trp Leu Pro Asn Leu Thr Tyr Asp Gln Arg Val Ala Phe Ile Val
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 324
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 324

Val Asp Ala Lys Tyr Ala Lys Glu Gln Lys Asn Ala Ala His Glu Ile
1               5                   10                  15

Arg Trp Leu Pro Asn Leu Thr Phe Asp Gln Arg Val Ala Phe Ile Glu
            20                  25                  30

Lys Leu Arg Asp Asp Pro Ser Gln Ser Ser Glu Leu Leu Ser Glu Ala
        35                  40                  45

```
Lys Lys Leu Asn Asp Ser Gln Ala Pro Lys
    50                  55

<210> SEQ ID NO 325
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 325

Val Asp Ala Lys Tyr Ala Lys Glu Ile Glu Asn Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Pro Ser Gln Ser Glu Leu Leu Ser Glu Ala
        35                  40                  45

Lys Lys Leu Asn Asp Ser Gln Ala Pro Lys
    50                  55

<210> SEQ ID NO 326
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 326

Val Asp Ala Lys Tyr Ala Lys Glu Val Asn Arg Ala Ser His Glu Ile
1               5                   10                  15

Arg Trp Leu Pro Asn Leu Thr Phe Asp Gln Arg Val Ala Phe Ile His
            20                  25                  30

Lys Leu Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 327
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 327

Val Asp Ala Lys Tyr Ala Lys Glu Arg Leu Leu Ala Gly His Glu Ile
1               5                   10                  15

Arg Trp Leu Pro Asn Leu Thr Phe Asp Gln Arg Val Ala Phe Ile Asn
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 328
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 328
```

```
Val Asp Ala Lys Tyr Ala Lys Glu Val Ser Ile Ala Gly His Glu Ile
1               5                   10                  15

Arg Trp Leu Pro Asn Leu Thr Phe Asp Gln Arg Val Ala Phe Ile Arg
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 329
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 329

Val Asp Ala Lys Tyr Ala Lys Glu Lys Glu Val Ala Ala His Glu Ile
1               5                   10                  15

Arg Trp Leu Pro Asn Leu Thr Phe Asp Gln Arg Val Ala Phe Ile His
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 330
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 330

Val Asp Ala Lys Tyr Ala Lys Glu Ser Glu Arg Ala Ser His Glu Ile
1               5                   10                  15

Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 331
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 331

Val Asp Ala Lys Tyr Ala Lys Glu Trp Asn Glu Ala Ala His Glu Ile
1               5                   10                  15

Arg Trp Leu Pro Asn Leu Thr Phe Asp Gln Arg Val Ala Phe Ile His
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55
```

<210> SEQ ID NO 332
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 332

Val Asp Ala Lys Tyr Ala Lys Glu Asn Val Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 333
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 333

Val Asp Ala Lys Tyr Ala Lys Glu Ala Asp Ala Ala Ser His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 334
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 334

Val Asp Ala Lys Tyr Ala Lys Glu Leu Glu Ser Ala Ser His Glu Ile
1               5                   10                  15

Arg Trp Leu Pro Asn Leu Thr Phe Asp Gln Arg Val Ala Phe Ile His
            20                  25                  30

Lys Leu Ile Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 335
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 335

Val Asp Ala Lys Tyr Ala Lys Glu Glu Gln Leu Ala Ala His Glu Ile
1               5                   10                  15

-continued

Arg Trp Leu Pro Asn Leu Thr Phe Asp Gln Arg Val Ala Phe Ile Arg
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 336
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 336

Val Asp Ala Lys Tyr Ala Lys Glu Phe Glu Leu Ala Gly His Glu Ile
1               5                   10                  15

Arg Trp Leu Pro Asn Leu Thr Phe Asp Gln Arg Val Ala Phe Ile His
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 337
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 337

Val Asp Ala Lys Tyr Ala Lys Glu Ala Phe Val Ala Gln His Glu Ile
1               5                   10                  15

Arg Trp Leu Pro Asn Leu Thr Tyr Asp Gln Arg Val Ala Phe Ile Val
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 338
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 338

Val Asp Ala Lys Tyr Ala Lys Glu Ala Leu Lys Ala Ser His Glu Ile
1               5                   10                  15

Arg Trp Leu Pro Asn Leu Thr Phe Asp Gln Arg Val Ala Phe Ile Asn
                20                  25                  30

Lys Leu Arg Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 339
<211> LENGTH: 58
<212> TYPE: PRT

```
<213> ORGANISM: Artificial Sequence
<220> FEATURE:
<223> OTHER INFORMATION: Engineered FcRn binding polypeptide

<400> SEQUENCE: 339

Val Asp Ala Lys Tyr Ala Lys Glu Leu Glu Arg Ala Gly His Glu Ile
1               5                   10                  15

Arg Trp Leu Pro Asn Leu Thr Phe Asp Gln Arg Val Ala Phe Ile Lys
            20                  25                  30

Lys Leu Thr Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 340
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 340

Val Asp Ala Lys Tyr Ala Lys Glu Val Glu Trp Ala Lys His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 341
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 341

Val Asp Ala Lys Tyr Ala Lys Glu Lys Ala Ser Ala Gln His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 342
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 342

Val Asp Ala Lys Tyr Ala Lys Glu Thr Glu Ile Ala Lys His Glu Ile
1               5                   10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
```

<210> SEQ ID NO 343
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 343

Val Asp Ala Lys Tyr Ala Lys Glu Val Asn Leu Ala Ala His Glu Ile
1               5                   10                  15

Arg Trp Leu Pro Asn Leu Thr Phe Asp Gln Arg Val Ala Phe Ile His
            20                  25                  30

Lys Leu Thr Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 344
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 344

Val Asp Ala Lys Tyr Ala Lys Glu Ala Glu Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 345
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 345

Val Asp Ala Lys Tyr Ala Lys Glu Thr Asp Arg Ala Lys His Glu Ile
1               5                   10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 346
<211> LENGTH: 58
<212> TYPE: PRT
<213> ORGANISM: Artificial Sequence
<220> FEATURE:
<223> OTHER INFORMATION: Engineered FcRn binding polypeptide

```
<400> SEQUENCE: 346

Val Asp Ala Lys Tyr Ala Lys Glu Phe Ala Gln Ala Gly His Glu Ile
1               5                   10                  15

Arg Trp Leu Pro Asn Leu Thr Phe Asp Gln Arg Val Ala Phe Ile His
            20                  25                  30

Lys Leu Lys Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 347
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 347

Val Asp Ala Lys Tyr Ala Lys Glu Thr Asp Glu Ala Ser His Glu Ile
1               5                   10                  15

Arg Trp Leu Pro Asn Leu Thr Phe Asp Gln Arg Val Ala Phe Ile Arg
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 348
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 348

Val Asp Ala Lys Tyr Ala Lys Glu Asn Ala Asp Ala Gly His Glu Ile
1               5                   10                  15

Arg Trp Leu Pro Asn Leu Thr Phe Asp Gln Arg Val Ala Phe Ile Gln
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 349
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 349

Val Asp Ala Lys Tyr Ala Lys Glu Ser Thr Gln Ala Ala His Glu Ile
1               5                   10                  15

Arg Trp Leu Pro Asn Leu Thr Phe Asp Gln Arg Val Ala Phe Ile His
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 350
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 350

Val Asp Ala Lys Tyr Ala Lys Glu Gln Ala Leu Ala Ala His Glu Ile
1               5                  10                  15

Arg Trp Leu Pro Asn Leu Thr Phe Asp Gln Arg Val Ala Phe Ile His
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 351
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 351

Val Asp Ala Lys Tyr Ala Lys Glu Ala His Ala Ala Ser His Glu Ile
1               5                  10                  15

Arg Trp Leu Pro Asn Leu Thr Phe Asp Gln Arg Val Ala Phe Ile His
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 352
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 352

Val Asp Ala Lys Tyr Ala Lys Glu Val Asp Asn Ala Gly His Glu Ile
1               5                  10                  15

Arg Trp Leu Pro Asn Leu Thr Phe Asp Gln Arg Val Ala Phe Ile Gln
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 353
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 353

Val Asp Ala Lys Tyr Ala Lys Glu Ala Gly Arg Ala Ala His Glu Ile
1               5                  10                  15
```

Arg Trp Leu Pro Asn Leu Thr Trp Asp Gln Arg Val Ala Phe Ile Trp
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 354
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 354

Ala Glu Ala Lys Tyr Ala Lys Glu Gln Asp Ala Ala His Glu Ile
1               5                   10                  15

Arg Trp Leu Pro Asn Leu Thr Phe Asp Gln Arg Val Ala Phe Ile His
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 355
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 355

Ala Glu Ala Lys Tyr Ala Lys Glu Phe Glu Ser Ala Ala His Glu Ile
1               5                   10                  15

Arg Trp Leu Pro Asn Leu Thr Tyr Asp Gln Arg Val Ala Phe Ile His
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 356
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 356

Ala Glu Ala Lys Tyr Ala Lys Glu Trp Met Arg Ala Ala His Glu Ile
1               5                   10                  15

Arg Trp Leu Pro Asn Leu Thr Phe Asp Gln Arg Val Ala Phe Ile His
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 357
<211> LENGTH: 58

```
<212> TYPE: PRT
<213> ORGANISM: Artificial Sequence
<220> FEATURE:
<223> OTHER INFORMATION: Engineered FcRn binding polypeptide

<400> SEQUENCE: 357

Ala Glu Ala Lys Tyr Ala Lys Glu Ala Asp Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 358
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 358

Ala Glu Ala Lys Tyr Ala Lys Glu Gln Asp Ala Ala Ala His Glu Ile
1               5                   10                  15

Arg Trp Leu Pro Asn Leu Thr Phe Asp Gln Arg Val Ala Phe Ile His
            20                  25                  30

Lys Leu Ala Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 359
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 359

Ala Glu Ala Lys Tyr Ala Lys Glu Gln Asp Ala Ala Ala His Glu Ile
1               5                   10                  15

Arg Trp Leu Pro Asn Leu Thr Phe Asp Gln Arg Val Ala Phe Ile His
            20                  25                  30

Lys Leu Ala Arg Gln Pro Glu Gln Ser Ser Glu Leu Leu Ser Glu Ala
        35                  40                  45

Lys Lys Leu Ser Glu Ser Gln Ala Pro Lys
    50                  55

<210> SEQ ID NO 360
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 360

Val Asp Ala Lys Tyr Ala Lys Glu Trp Thr Asp Ala Ala His Glu Ile
1               5                   10                  15

Arg Trp Leu Pro Asn Leu Thr Phe Asp Gln Arg Val Ala Phe Ile His
            20                  25                  30
```

```
Lys Leu Arg Asp Asp Pro Ser Gln Ser Ser Glu Leu Leu Ser Glu Ala
        35                  40                  45

Lys Lys Leu Ser Glu Ser Gln Ala Pro Lys
    50                  55
```

<210> SEQ ID NO 361
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 361

```
Val Asp Ala Lys Tyr Ala Lys Glu Leu Glu Lys Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Ser Glu Ser Gln Ala Pro Lys
    50                  55
```

<210> SEQ ID NO 362
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 362

```
Val Asp Ala Lys Tyr Ala Lys Glu Trp Gln Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Ser Glu Ser Gln Ala Pro Lys
    50                  55
```

<210> SEQ ID NO 363
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 363

```
Val Asp Ala Lys Tyr Ala Lys Glu Ala Asp Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Ser Glu Ser Gln Ala Pro Lys
    50                  55
```

<210> SEQ ID NO 364
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 364

Val Asp Ala Lys Tyr Ala Lys Glu Ile Glu Asp Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 365
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 365

Ala Glu Ala Lys Phe Ala Lys Glu Trp Thr Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 366
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 366

Ala Glu Ala Lys Phe Ala Lys Glu Trp Gln Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 367
<211> LENGTH: 58
<212> TYPE: PRT
<213> ORGANISM: Artificial Sequence
<220> FEATURE:
<223> OTHER INFORMATION: Engineered FcRn binding polypeptide

<400> SEQUENCE: 367

Ala Glu Ala Lys Phe Ala Lys Glu Ala Asp Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Ser Glu Ser Gln Ala Pro Lys

-continued

```
                50                  55

<210> SEQ ID NO 368
<211> LENGTH: 133
<212> TYPE: PRT
<213> ORGANISM: Artificial Sequence
<220> FEATURE:
<223> OTHER INFORMATION: Engineered FcRn binding dimer

<400> SEQUENCE: 368

Ala Glu Ala Lys Tyr Ala Lys Glu Gln Asp Ala Ala His Glu Ile
1               5                   10                  15

Arg Trp Leu Pro Asn Leu Thr Phe Asp Gln Arg Val Ala Phe Ile His
                20                  25                  30

Lys Leu Ala Asp Asp Pro Ser Gln Ser Ser Glu Leu Leu Ser Glu Ala
            35                  40                  45

Lys Lys Leu Asn Asp Ser Gln Ala Pro Lys Gly Thr Gly Gly Gly
        50                  55                  60

Ser Pro Arg Ala Glu Ala Lys Tyr Ala Lys Glu Gln Asp Ala Ala
65                  70                  75                  80

His Glu Ile Arg Trp Leu Pro Asn Leu Thr Phe Asp Gln Arg Val Ala
                85                  90                  95

Phe Ile His Lys Leu Ala Asp Asp Pro Ser Gln Ser Ser Glu Leu Leu
            100                 105                 110

Ser Glu Ala Lys Lys Leu Asn Asp Ser Gln Ala Pro Lys Leu Glu His
            115                 120                 125

His His His His
        130

<210> SEQ ID NO 369
<211> LENGTH: 141
<212> TYPE: PRT
<213> ORGANISM: Artificial Sequence
<220> FEATURE:
<223> OTHER INFORMATION: Engineered FcRn binding dimer

<400> SEQUENCE: 369

Ala Glu Ala Lys Tyr Ala Lys Glu Gln Asp Ala Ala His Glu Ile
1               5                   10                  15

Arg Trp Leu Pro Asn Leu Thr Phe Asp Gln Arg Val Ala Phe Ile His
                20                  25                  30

Lys Leu Ala Asp Asp Pro Ser Gln Ser Ser Glu Leu Leu Ser Glu Ala
            35                  40                  45

Lys Lys Leu Asn Asp Ser Gln Ala Pro Lys Gly Thr Gly Gly Gly
        50                  55                  60

Ser Gly Gly Gly Ser Gly Gly Gly Ser Ala Glu Ala Lys Tyr
65                  70                  75                  80

Ala Lys Glu Gln Asp Ala Ala His Glu Ile Arg Trp Leu Pro Asn
                85                  90                  95

Leu Thr Phe Asp Gln Arg Val Ala Phe Ile His Lys Leu Ala Asp Asp
            100                 105                 110

Pro Ser Gln Ser Ser Glu Leu Leu Ser Glu Ala Lys Lys Leu Asn Asp
            115                 120                 125

Ser Gln Ala Pro Lys Leu Glu His His His His His
        130                 135                 140

<210> SEQ ID NO 370
<211> LENGTH: 144
```

```
<212> TYPE: PRT
<213> ORGANISM: Artificial Sequence
<220> FEATURE:
<223> OTHER INFORMATION: Engineered FcRn binding dimer

<400> SEQUENCE: 370

Gly Ser Ser His His His His His Leu Gln Ala Glu Ala Lys Tyr
1               5                   10                  15

Ala Lys Glu Ala Asp Ala Ala Gly His Glu Ile Arg Trp Leu Pro Asn
            20                  25                  30

Leu Thr Phe Asp Gln Arg Val Ala Phe Ile His Lys Leu Arg Asp Asp
        35                  40                  45

Pro Ser Gln Ser Ser Glu Leu Leu Ser Glu Ala Lys Lys Leu Asn Asp
    50                  55                  60

Ser Gln Ala Pro Lys Gly Thr Gly Gly Gly Ser Gly Gly Gly Gly
65                  70                  75                  80

Ser Gly Gly Gly Gly Ser Ala Glu Ala Lys Tyr Ala Lys Glu Ala Asp
                85                  90                  95

Ala Ala Gly His Glu Ile Arg Trp Leu Pro Asn Leu Thr Phe Asp Gln
                100                 105                 110

Arg Val Ala Phe Ile His Lys Leu Arg Asp Asp Pro Ser Gln Ser Ser
            115                 120                 125

Glu Leu Leu Ser Glu Ala Lys Lys Leu Asn Asp Ser Gln Ala Pro Lys
        130                 135                 140

<210> SEQ ID NO 371
<211> LENGTH: 201
<212> TYPE: PRT
<213> ORGANISM: Artificial Sequence
<220> FEATURE:
<223> OTHER INFORMATION: Engineered FcRn binding dimer

<400> SEQUENCE: 371

Ala Glu Ala Lys Tyr Ala Lys Glu Ala Asp Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys Gly Ala Pro Gly Gly Gly
    50                  55                  60

Gly Ser Gly Gly Gly Gly Ser Gly Gly Gly Ser Thr Ser Leu Ala
65                  70                  75                  80

Glu Ala Lys Glu Ala Ala Asn Ala Glu Leu Asp Ser Tyr Gly Val Ser
                85                  90                  95

Asp Phe Tyr Lys Arg Leu Ile Asp Lys Ala Lys Thr Val Glu Gly Val
                100                 105                 110

Glu Ala Leu Lys Asp Ala Ile Leu Ala Ala Leu Pro Gly Thr Gly Gly
            115                 120                 125

Gly Gly Ser Gly Gly Gly Gly Ser Gly Gly Gly Ser Pro Arg Ala
        130                 135                 140

Glu Ala Lys Tyr Ala Lys Glu Ala Asp Ala Ala Gly His Glu Ile Arg
145                 150                 155                 160

Trp Leu Pro Asn Leu Thr Phe Asp Gln Arg Val Ala Phe Ile His Lys
                165                 170                 175

Leu Arg Asp Asp Pro Ser Gln Ser Ser Glu Leu Leu Ser Glu Ala Lys
            180                 185                 190
```

```
Lys Leu Asn Asp Ser Gln Ala Pro Lys
        195                 200

<210> SEQ ID NO 372
<211> LENGTH: 201
<212> TYPE: PRT
<213> ORGANISM: Artificial Sequence
<220> FEATURE:
<223> OTHER INFORMATION: Engineered FcRn binding dimer

<400> SEQUENCE: 372

Ala Glu Ala Lys Tyr Ala Lys Glu Ala Asp Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys Gly Ala Pro Gly Gly Gly
    50                  55                  60

Gly Ser Gly Gly Gly Gly Ser Gly Gly Gly Gly Ser Thr Ser Ala Glu
65                  70                  75                  80

Ala Lys Tyr Ala Lys Glu Ala Asp Ala Ala Gly His Glu Ile Arg Trp
                85                  90                  95

Leu Pro Asn Leu Thr Phe Asp Gln Arg Val Ala Phe Ile His Lys Leu
            100                 105                 110

Arg Asp Asp Pro Ser Gln Ser Ser Glu Leu Leu Ser Glu Ala Lys Lys
        115                 120                 125

Leu Asn Asp Ser Gln Ala Pro Lys Gly Thr Gly Gly Gly Ser Gly
    130                 135                 140

Gly Gly Gly Ser Gly Gly Gly Ser Pro Arg Leu Ala Glu Ala Lys
145                 150                 155                 160

Glu Ala Ala Asn Ala Glu Leu Asp Ser Tyr Gly Val Ser Asp Phe Tyr
                165                 170                 175

Lys Arg Leu Ile Asp Lys Ala Lys Thr Val Glu Gly Val Glu Ala Leu
            180                 185                 190

Lys Asp Ala Ile Leu Ala Ala Leu Pro
        195                 200

<210> SEQ ID NO 373
<211> LENGTH: 173
<212> TYPE: PRT
<213> ORGANISM: Artificial Sequence
<220> FEATURE:
<223> OTHER INFORMATION: Engineered FcRn binding polypeptide

<400> SEQUENCE: 373

Ala Glu Ala Lys Tyr Ala Lys Glu Ala Asp Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys Ala Ser Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
```

```
                    85                  90                  95

Glu Ala Leu Lys Asp Ala Ile Leu Ala Ala Leu Pro Gly Thr Gly Gly
                100                 105                 110

Gly Gly Ser Ala Glu Ala Lys Tyr Ala Lys Glu Ala Asp Ala Ala Gly
            115                 120                 125

His Glu Ile Arg Trp Leu Pro Asn Leu Thr Phe Asp Gln Arg Val Ala
        130                 135                 140

Phe Ile His Lys Leu Arg Asp Asp Pro Ser Gln Ser Ser Glu Leu Leu
145                 150                 155                 160

Ser Glu Ala Lys Lys Leu Asn Asp Ser Gln Ala Pro Lys
                165                 170

<210> SEQ ID NO 374
<211> LENGTH: 173
<212> TYPE: PRT
<213> ORGANISM: Artificial Sequence
<220> FEATURE:
<223> OTHER INFORMATION: Engineered FcRn binding polypeptide

<400> SEQUENCE: 374

Ala Glu Ala Lys Phe Ala Lys Glu Trp Thr Asp Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45

Lys Lys Leu Ser Glu Ser Gln Ala Pro Lys Ala Ser Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro Gly Thr Gly Gly
                100                 105                 110

Gly Gly Ser Ala Glu Ala Lys Phe Ala Lys Glu Trp Thr Asp Ala Ala
            115                 120                 125

His Glu Ile Arg Trp Leu Pro Asn Leu Thr Phe Asp Gln Arg Val Ala
        130                 135                 140

Phe Ile His Lys Leu Arg Asp Asp Pro Ser Gln Ser Ser Glu Leu Leu
145                 150                 155                 160

Ser Glu Ala Lys Lys Leu Ser Glu Ser Gln Ala Pro Lys
                165                 170

<210> SEQ ID NO 375
<211> LENGTH: 173
<212> TYPE: PRT
<213> ORGANISM: Artificial Sequence
<220> FEATURE:
<223> OTHER INFORMATION: Engineered FcRn binding polypeptide

<400> SEQUENCE: 375

Ala Glu Ala Lys Phe Ala Lys Glu Trp Gln Gln Ala Ala His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
        35                  40                  45
```

```
Lys Lys Leu Ser Glu Ser Gln Ala Pro Lys Ala Ser Gly Ser Leu Ala
    50              55                  60

Glu Ala Lys Glu Ala Ala Asn Ala Glu Leu Asp Ser Tyr Gly Val Ser
65              70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro Gly Thr Gly Gly
            100                 105                 110

Gly Gly Ser Ala Glu Ala Lys Phe Ala Lys Glu Trp Gln Gln Ala Ala
                115                 120                 125

His Glu Ile Arg Trp Leu Pro Asn Leu Thr Phe Asp Gln Arg Val Ala
    130                 135                 140

Phe Ile His Lys Leu Arg Asp Asp Pro Ser Gln Ser Ser Glu Leu Leu
145                 150                 155                 160

Ser Glu Ala Lys Lys Leu Ser Glu Ser Gln Ala Pro Lys
                165                 170
```

<210> SEQ ID NO 376
<211> LENGTH: 173
<212> TYPE: PRT
<213> ORGANISM: Artificial Sequence
<220> FEATURE:
<223> OTHER INFORMATION: Engineered FcRn binding polypeptide

<400> SEQUENCE: 376

```
Ala Glu Ala Lys Phe Ala Lys Glu Ala Asp Ala Ala Gly His Glu Ile
1               5                   10                  15

Arg Trp Leu Pro Asn Leu Thr Phe Asp Gln Arg Val Ala Phe Ile His
            20                  25                  30

Lys Leu Arg Asp Asp Pro Ser Gln Ser Ser Glu Leu Leu Ser Glu Ala
                35                  40                  45

Lys Lys Leu Ser Glu Ser Gln Ala Pro Lys Ala Ser Gly Ser Leu Ala
            50                  55                  60

Glu Ala Lys Glu Ala Ala Asn Ala Glu Leu Asp Ser Tyr Gly Val Ser
65              70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro Gly Thr Gly Gly
            100                 105                 110

Gly Gly Ser Ala Glu Ala Lys Phe Ala Lys Glu Ala Asp Ala Ala Gly
                115                 120                 125

His Glu Ile Arg Trp Leu Pro Asn Leu Thr Phe Asp Gln Arg Val Ala
    130                 135                 140

Phe Ile His Lys Leu Arg Asp Asp Pro Ser Gln Ser Ser Glu Leu Leu
145                 150                 155                 160

Ser Glu Ala Lys Lys Leu Ser Glu Ser Gln Ala Pro Lys
                165                 170
```

<210> SEQ ID NO 377
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 377

```
Leu Ala Glu Ala Lys Glu Ala Ala Asn Ala Glu Leu Asp Ser Tyr Gly
1               5                   10                  15
```

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 378
<211> LENGTH: 58
<212> TYPE: PRT
<213> ORGANISM: Artificial Sequence
<220> FEATURE:
<223> OTHER INFORMATION: Engineered binding polypeptide

<400> SEQUENCE: 378

Ala Glu Ala Lys Tyr Ala Lys Glu Leu Gly Trp Ala Thr Trp Glu Ile
1               5                   10                  15

Phe Asn Leu Pro Asn Leu Thr Gly Val Gln Val Lys Ala Phe Ile Asp
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 379
<211> LENGTH: 267
<212> TYPE: PRT
<213> ORGANISM: Artificial Sequence
<220> FEATURE:
<223> OTHER INFORMATION: Engineered polypeptide

<400> SEQUENCE: 379

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly

```
            210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu
            260                 265
```

<210> SEQ ID NO 380
<211> LENGTH: 99
<212> TYPE: PRT
<213> ORGANISM: Artificial Sequence
<220> FEATURE:
<223> OTHER INFORMATION: Engineered polypeptide

<400> SEQUENCE: 380

```
Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```

<210> SEQ ID NO 381
<211> LENGTH: 99
<212> TYPE: PRT
<213> ORGANISM: Artificial Sequence
<220> FEATURE:
<223> OTHER INFORMATION: Engineered polypeptide

<400> SEQUENCE: 381

```
Ile Gln Lys Thr Pro Gln Ile Gln Val Tyr Ser Arg His Pro Pro Glu
1               5                   10                  15

Asn Gly Lys Pro Asn Ile Leu Asn Cys Tyr Val Thr Gln Phe His Pro
            20                  25                  30

Pro His Ile Glu Ile Gln Met Leu Lys Asn Gly Lys Lys Ile Pro Lys
        35                  40                  45

Val Glu Met Ser Asp Met Ser Phe Ser Lys Asp Trp Ser Phe Tyr Ile
    50                  55                  60

Leu Ala His Thr Glu Phe Thr Pro Thr Glu Thr Asp Thr Tyr Ala Cys
65                  70                  75                  80

Arg Val Lys His Ala Ser Met Ala Glu Pro Lys Thr Val Tyr Trp Asp
                85                  90                  95

Arg Asp Met
```

<210> SEQ ID NO 382
<211> LENGTH: 365
<212> TYPE: PRT
<213> ORGANISM: Artificial Sequence
<220> FEATURE:
<223> OTHER INFORMATION: hFcRn - eGFP fusion protein

<400> SEQUENCE: 382

```
Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
    290                 295                 300

Ile Gly Val Leu Leu Leu Thr Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365
```

<210> SEQ ID NO 383
<211> LENGTH: 369
<212> TYPE: PRT
<213> ORGANISM: Artificial Sequence
<220> FEATURE:
<223> OTHER INFORMATION: mFcRn - eGFP fusion protein

<400> SEQUENCE: 383

```
Met Gly Met Pro Leu Pro Trp Ala Leu Ser Leu Leu Val Leu Leu
1               5                   10                  15

Pro Gln Thr Trp Gly Ser Glu Thr Arg Pro Leu Met Tyr His Leu
            20                  25                  30

Thr Ala Val Ser Asn Pro Ser Thr Gly Leu Pro Ser Phe Trp Ala Thr
        35                  40                  45

Gly Trp Leu Gly Pro Gln Gln Tyr Leu Thr Tyr Asn Ser Leu Arg Gln
50                  55                  60

Glu Ala Asp Pro Cys Gly Ala Trp Met Trp Glu Asn Gln Val Ser Trp
65                  70                  75                  80

Tyr Trp Glu Lys Glu Thr Thr Asp Leu Lys Ser Lys Glu Gln Leu Phe
                85                  90                  95

Leu Glu Ala Leu Lys Thr Leu Glu Lys Ile Leu Asn Gly Gln Lys Arg
            100                 105                 110

Gly Thr Tyr Thr Leu Gln Gly Leu Leu Gly Cys Glu Leu Ala Ser Asp
        115                 120                 125

Asn Ser Ser Val Pro Thr Ala Val Phe Ala Leu Asn Gly Glu Glu Phe
130                 135                 140

Met Lys Phe Asn Pro Arg Ile Gly Asn Trp Thr Gly Glu Trp Pro Glu
145                 150                 155                 160

Thr Glu Ile Val Ala Asn Leu Trp Met Lys Gln Pro Asp Ala Ala Arg
                165                 170                 175

Lys Glu Ser Glu Phe Leu Leu Asn Ser Cys Pro Glu Arg Leu Leu Gly
            180                 185                 190

His Leu Glu Arg Gly Arg Arg Asn Leu Glu Trp Lys Glu Pro Pro Ser
        195                 200                 205

Met Arg Leu Lys Ala Arg Pro Gly Asn Ser Gly Ser Ser Val Leu Thr
210                 215                 220

Cys Ala Ala Phe Ser Phe Tyr Pro Pro Glu Leu Lys Phe Arg Phe Leu
225                 230                 235                 240

Arg Asn Gly Leu Ala Ser Gly Ser Gly Asn Cys Ser Thr Gly Pro Asn
                245                 250                 255

Gly Asp Gly Ser Phe His Ala Trp Ser Leu Leu Glu Val Lys Arg Gly
            260                 265                 270

Asp Glu His His Tyr Gln Cys Gln Val Glu His Glu Gly Leu Ala Gln
        275                 280                 285

Pro Leu Thr Val Asp Leu Asp Ser Ser Ala Arg Ser Ser Val Pro Val
290                 295                 300

Val Gly Ile Val Leu Gly Leu Leu Val Val Ala Ile Ala Gly
305                 310                 315                 320

Gly Val Leu Leu Trp Gly Arg Met Arg Ser Gly Leu Pro Ala Pro Trp
                325                 330                 335

Leu Ser Leu Ser Gly Asp Asp Ser Gly Asp Leu Leu Pro Gly Gly Asn
            340                 345                 350

Leu Pro Pro Glu Ala Glu Pro Gln Gly Ala Asn Ala Phe Pro Ala Thr
        355                 360                 365

Ser
```

<210> SEQ ID NO 384
<211> LENGTH: 273
<212> TYPE: PRT
<213> ORGANISM: Artificial Sequence
<220> FEATURE:

<223> OTHER INFORMATION: Engineered polypeptide

<400> SEQUENCE: 384

```
Ser Glu Thr Arg Pro Leu Met Tyr His Leu Thr Ala Val Ser Asn
1               5                   10                  15
Pro Ser Thr Gly Leu Pro Ser Phe Trp Ala Thr Gly Trp Leu Gly Pro
            20                  25                  30
Gln Gln Tyr Leu Thr Tyr Asn Ser Leu Arg Gln Glu Ala Asp Pro Cys
        35                  40                  45
Gly Ala Trp Met Trp Glu Asn Gln Val Ser Trp Tyr Trp Glu Lys Glu
    50                  55                  60
Thr Thr Asp Leu Lys Ser Lys Glu Gln Leu Phe Leu Glu Ala Leu Lys
65                  70                  75                  80
Thr Leu Glu Lys Ile Leu Asn Gly Gln Lys Arg Gly Thr Tyr Thr Leu
                85                  90                  95
Gln Gly Leu Leu Gly Cys Glu Leu Ala Ser Asp Asn Ser Ser Val Pro
            100                 105                 110
Thr Ala Val Phe Ala Leu Asn Gly Glu Glu Phe Met Lys Phe Asn Pro
        115                 120                 125
Arg Ile Gly Asn Trp Thr Gly Glu Trp Pro Glu Thr Glu Ile Val Ala
    130                 135                 140
Asn Leu Trp Met Lys Gln Pro Asp Ala Ala Arg Lys Glu Ser Glu Phe
145                 150                 155                 160
Leu Leu Asn Ser Cys Pro Glu Arg Leu Leu Gly His Leu Glu Arg Gly
                165                 170                 175
Arg Arg Asn Leu Glu Trp Lys Glu Pro Pro Ser Met Arg Leu Lys Ala
            180                 185                 190
Arg Pro Gly Asn Ser Gly Ser Ser Val Leu Thr Cys Ala Ala Phe Ser
        195                 200                 205
Phe Tyr Pro Pro Glu Leu Lys Phe Arg Phe Leu Arg Asn Gly Leu Ala
    210                 215                 220
Ser Gly Ser Gly Asn Cys Ser Thr Gly Pro Asn Gly Asp Gly Ser Phe
225                 230                 235                 240
His Ala Trp Ser Leu Leu Glu Val Lys Arg Gly Asp Glu His His Tyr
                245                 250                 255
Gln Cys Gln Val Glu His Glu Gly Leu Ala Gln Pro Leu Thr Val Asp
            260                 265                 270
Leu
```

<210> SEQ ID NO 385
<211> LENGTH: 24
<212> TYPE: DNA
<213> ORGANISM: Artificial Sequence
<220> FEATURE:
<223> OTHER INFORMATION: PCR primer

<400> SEQUENCE: 385
tgcttccggc tcgtatgttg tgtg                                    24

<210> SEQ ID NO 386
<211> LENGTH: 21
<212> TYPE: DNA
<213> ORGANISM: Artificial Sequence
<220> FEATURE:
<223> OTHER INFORMATION: PCR primer

<400> SEQUENCE: 386
cggaaccaga gccaccaccg g                                              21

<210> SEQ ID NO 387
<211> LENGTH: 21
<212> TYPE: DNA
<213> ORGANISM: Artificial Sequence
<220> FEATURE:
<223> OTHER INFORMATION: Sequencing primer

<400> SEQUENCE: 387
cggaaccaga gccaccaccg g                                              21

<210> SEQ ID NO 388
<211> LENGTH: 147
<212> TYPE: DNA
<213> ORGANISM: Artificial Sequence
<220> FEATURE:
<223> OTHER INFORMATION: Library polynucleotide
<220> FEATURE:
<221> NAME/KEY: misc_feature
<222> LOCATION: (39)..(47)
<223> OTHER INFORMATION: n is a, c, g, or t
<220> FEATURE:
<221> NAME/KEY: misc_feature
<222> LOCATION: (51)..(56)
<223> OTHER INFORMATION: n is a, c, g, or t
<220> FEATURE:
<221> NAME/KEY: misc_feature
<222> LOCATION: (63)..(68)
<223> OTHER INFORMATION: n is a, c, g, or t
<220> FEATURE:
<221> NAME/KEY: misc_feature
<222> LOCATION: (84)..(89)
<223> OTHER INFORMATION: n is a, c, g, or t
<220> FEATURE:
<221> NAME/KEY: misc_feature
<222> LOCATION: (93)..(98)
<223> OTHER INFORMATION: n is a, c, g, or t
<220> FEATURE:
<221> NAME/KEY: misc_feature
<222> LOCATION: (108)..(110)
<223> OTHER INFORMATION: n is a, c, g, or t
<220> FEATURE:
<221> NAME/KEY: misc_feature
<222> LOCATION: (117)..(119)
<223> OTHER INFORMATION: n is a, c, g, or t

<400> SEQUENCE: 388
aaataaatct cgaggtagat gccaaatacg ccaaagaann nnnnnnngcg nnnnnngaga     60
tcnnnnnntt acctaactta accnnnnnnc aannnnnngc cttcatcnnn aaattannng   120
atgacccaag ccagagctca ttattta                                       147

<210> SEQ ID NO 389
<211> LENGTH: 29
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (2)..(2)
<223> OTHER INFORMATION: Xaa is selected from A, D, E, F, H, I, K, L, N,
      Q, R, S, T, V, W and Y;
<220> FEATURE:
<221> NAME/KEY: MISC_FEATURE
<222> LOCATION: (3)..(3)
<223> OTHER INFORMATION: Xaa is selected from A, D, E, F, G, H, I, K, L,
      M, N, Q, R, S, T, V, W and Y;
<220> FEATURE:
<221> NAME/KEY: MISC_FEATURE
<222> LOCATION: (4)..(4)
<223> OTHER INFORMATION: Xaa is selected from A, D, E, F, G, H, I, K, L,

```
            N, Q, R, S, T, V, W and Y;
<220> FEATURE:
<221> NAME/KEY: MISC_FEATURE
<222> LOCATION: (6)..(6)
<223> OTHER INFORMATION: Xaa is selected from A, D, E, F, G, H, I, K, L,
            N, Q, R, S, T, V, W and Y;
<220> FEATURE:
<221> NAME/KEY: MISC_FEATURE
<222> LOCATION: (7)..(7)
<223> OTHER INFORMATION: Xaa is selected from A, F, H, I, K, L, N, Q, R,
            S, T, V, W and Y
<220> FEATURE:
<221> NAME/KEY: MISC_FEATURE
<222> LOCATION: (16)..(16)
<223> OTHER INFORMATION: Xaa is selected from N and T
<220> FEATURE:
<221> NAME/KEY: MISC_FEATURE
<222> LOCATION: (17)..(17)
<223> OTHER INFORMATION: Xaa is selected from F, W and Y
<220> FEATURE:
<221> NAME/KEY: MISC_FEATURE
<222> LOCATION: (18)..(18)
<223> OTHER INFORMATION: Xaa is selected from A, D, E and N
<220> FEATURE:
<221> NAME/KEY: MISC_FEATURE
<222> LOCATION: (21)..(21)
<223> OTHER INFORMATION: Xaa is selected from A, S, V and W
<220> FEATURE:
<221> NAME/KEY: MISC_FEATURE
<222> LOCATION: (25)..(25)
<223> OTHER INFORMATION: Xaa is selected from A, D, E, F, G, H, I, K, L,
            N, Q, R, S, T, V, W and Y
<220> FEATURE:
<221> NAME/KEY: MISC_FEATURE
<222> LOCATION: (26)..(26)
<223> OTHER INFORMATION: Xaa is selected from K and S
<220> FEATURE:
<221> NAME/KEY: MISC_FEATURE
<222> LOCATION: (28)..(28)
<223> OTHER INFORMATION: Xaa is selected from A, D, E, F, H, I, K, L, N,
            Q, R, S, T, V, W and Y
<220> FEATURE:
<221> NAME/KEY: MISC_FEATURE
<222> LOCATION: (29)..(29)
<223> OTHER INFORMATION: Xaa is selected from is selected from D and R

<400> SEQUENCE: 389

Glu Xaa Xaa Xaa Ala Xaa Xaa Glu Ile Arg Trp Leu Pro Asn Leu Xaa
1               5                   10                  15

Xaa Xaa Gln Arg Xaa Ala Phe Ile Xaa Xaa Leu Xaa Xaa
            20                  25

<210> SEQ ID NO 390
<211> LENGTH: 29
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (2)..(2)
<223> OTHER INFORMATION: Xaa is selected from A, D, E, F, H, I, K, L, N,
            Q, R, S, T, V, W and Y
<220> FEATURE:
<221> NAME/KEY: MISC_FEATURE
<222> LOCATION: (3)..(3)
<223> OTHER INFORMATION: Xaa is selected from A, D, E, F, G, H, I, K, L,
            M, N, Q, R, S, T, V, W and Y
<220> FEATURE:
<221> NAME/KEY: MISC_FEATURE
<222> LOCATION: (4)..(4)
<223> OTHER INFORMATION: Xaa is selected from A, D, E, F, G, H, I, K, L,
            N, Q, R, S, T, V, W and Y
<220> FEATURE:
<221> NAME/KEY: MISC_FEATURE
<222> LOCATION: (6)..(6)
```

```
<223> OTHER INFORMATION: Xaa is selected from A, D, E, F, G, H, I, K, L,
      N, Q, R, S, T, V, W and Y
<220> FEATURE:
<221> NAME/K

```
<223> OTHER INFORMATION: Xaa is selected from D, G, H, K, L, N, R, V and
      W
<220> FEATURE:
<221> NAME/KEY: MISC_FEATURE
<222> LOCATION: (28)..(28)
<223> OTHER INFORMATION: Xaa is selected from A, D, E, H, K, L, N, Q, R,
      S, T, W and Y

<400> SEQUENCE: 391

Glu Xaa Xaa Xaa Ala Xaa His Glu Ile Arg Trp Leu Pro Asn Leu Thr
1               5                   10                  15

Xaa Xaa Gln Arg Xaa Ala Phe Ile Xaa Lys Leu Xaa Asp
            20                  25

<210> SEQ ID NO 392
<211> LENGTH: 49
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (3)..(3)
<223> OTHER INFORMATION: Xaa is selected from A, D, E, F, H, I, K, L, N,
      Q, R, S, T, V, W and Y
<220> FEATURE:
<221> NAME/KEY: MISC_FEATURE
<222> LOCATION: (4)..(4)
<223> OTHER INFORMATION: Xaa is selected from A, D, E, F, G, H, I, K, L,
      M, N, Q, R, S, T, V, W and Y
<220> FEATURE:
<221> NAME/KEY: MISC_FEATURE
<222> LOCATION: (5)..(5)
<223> OTHER INFORMATION: Xaa is selected from A, D, E, F, G, H, I, K, L,
      N, Q, R, S, T, V, W and Y
<220> FEATURE:
<221> NAME/KEY: MISC_FEATURE
<222> LOCATION: (7)..(7)
<223> OTHER INFORMATION: Xaa is selected from A, D, E, F, G, H, I, K, L,
      N, Q, R, S, T, V, W and Y
<220> FEATURE:
<221> NAME/KEY: MISC_FEATURE
<222> LOCATION: (8)..(8)
<223> OTHER INFORMATION: Xaa is selected from A, F, H, I, K, L, N, Q, R,
      S, T, V, W
<220> FEATURE:
<221> NAME/KEY: MISC_FEATURE
<222> LOCATION: (18)..(18)
<223> OTHER INFORMATION: Xaa is selected from F, W and Y
<220> FEATURE:
<221> NAME/KEY: MISC_FEATURE
<222> LOCATION: (19)..(19)
<223> OTHER INFORMATION: Xaa is selected from A, D, E and N
<220> FEATURE:
<221> NAME/KEY: MISC_FEATURE
<222> LOCATION: (19)..(19)
<223> OTHER INFORMATION: Xaa is selected from A and S
<220> FEATURE:
<221> NAME/KEY: MISC_FEATURE
<222> LOCATION: (22)..(22)
<223> OTHER INFORMATION: Xaa is selected from A, S, V and W
<220> FEATURE:
<221> NAME/KEY: MISC_FEATURE
<222> LOCATION: (26)..(26)
<223> OTHER INFORMATION: Xaa is selected from A, D, E, F, G, H, I, K, L,
      N, Q, R, S, T, V, W and Y
<220> FEATURE:
<221> NAME/KEY: MISC_FEATURE
<222> LOCATION: (29)..(29)
<223> OTHER INFORMATION: Xaa is selected from A, D, E, F, H, I, K, L, N,
      Q, R, S, T, V, W and Y
<220> FEATURE:
<221> NAME/KEY: MISC_FEATURE
<222> LOCATION: (36)..(36)
<223> OTHER INFORMATION: Xaa is selected from A and S
<220> FEATURE:
```

```
<221> NAME/KEY: MISC_FEATURE
<222> LOCATION: (37)..(37)
<223> OTHER INFORMATION: Xaa is selected from N and E
<220> FEATURE:
<221> NAME/KEY: MISC_FEATURE
<222> LOCATION: (40)..(40)
<223> OTHER INFORMATION: Xaa is selected from A, S and C
<220> FEATURE:
<221> NAME/KEY: MISC_FEATURE
<222> LOCATION: (46)..(46)
<223> OTHER INFORMATION: Xaa is selected from E, N and S
<220> FEATURE:
<221> NAME/KEY: MISC_FEATURE
<222> LOCATION: (47)..(47)
<223> OTHER INFORMATION: Xaa is selected from D, E and S
<220> FEATURE:
<221> NAME/KEY: MISC_FEATURE
<222> LOCATION: (48)..(48)
<223> OTHER INFORMATION: Xaa is selected from A and S

<400> SEQUENCE: 392

Lys Glu Xaa Xaa Xaa Ala Xaa Xaa Glu Ile Arg Trp Leu Pro Asn Leu
1               5                   10                  15

Thr Xaa Xaa Gln Arg Xaa Ala Phe Ile Xaa Lys Leu Xaa Asp Asp Pro
            20                  25                  30

Ser Gln Ser Xaa Xaa Leu Leu Xaa Glu Ala Lys Lys Leu Xaa Xaa Xaa
        35                  40                  45

Gln

<210> SEQ ID NO 393
<211> LENGTH: 49
<212> TYPE: PRT
<213> ORGANISM: Artificial Sequence
<220> FEATURE:
<223> OTHER INFORMATION: Engineered polypeptide
<220> FEATURE:
<221> NAME/KEY: misc_feature
<222> LOCATION: (3)..(3)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (4)..(4)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (5)..(5)
<223> OTHER INFORMATION: Xaa is selected from A, D, E, F, G, H, I, K, L,
      N, Q, R, S, T, V, W and Y
<220> FEATURE:
<221> NAME/KEY: MISC_FEATURE
<222> LOCATION: (7)..(7)
<223> OTHER INFORMATION: Xaa is selected from A, D, E, F, G, H, I, K, L,
      N, Q, R, S, T, V, W and Y
<220> FEATURE:
<221> NAME/KEY: MISC_FEATURE
<222> LOCATION: (8)..(8)
<223> OTHER INFORMATION: Xaa is selected from A, F, H, I, K, L, N, Q, R,
      S, T, V, W and Y
<220> FEATURE:
<221> NAME/KEY: MISC_FEATURE
<222> LOCATION: (17)..(17)
<223> OTHER INFORMATION: Xaa is selected from N and T
<220> FEATURE:
<221> NAME/KEY: MISC_FEATURE
<222> LOCATION: (18)..(18)
<223> OTHER INFORMATION: Xaa is selected from F, W, and Y
<220> FEATURE:
<221> NAME/KEY: MISC_FEATURE
<222> LOCATION: (19)..(19)
<223> OTHER INFORMATION: Xaa is selected from A, D, E and N
<220> FEATURE:
<221> NAME/KEY: misc_feature
```

```
<222> LOCATION: (22)..(22)
<223> OTHER INFORMATION: Xaa is selected from A, S, V and W
<220> FEATURE:
<221> NAME/KEY: misc_feature
<222> LOCATION: (26)..(26)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (27)..(27)
<223> OTHER INFORMATION: Xaa is selected from K and S
<220> FEATURE:
<221> NAME/KEY: misc_feature
<222> LOCATION: (29)..(29)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (30)..(30)
<223> OTHER INFORMATION: Xaa is R
<220> FEATURE:
<221> NAME/KEY: misc_feature
<222> LOCATION: (36)..(36)
<223> OTHER INFORMATION: Xaa is selected from A and S
<220> FEATURE:
<221> NAME/KEY: misc_feature
<222> LOCATION: (37)..(37)
<223> OTHER INFORMATION: Xaa is selected from N and E
<220> FEATURE:
<221> NAME/KEY: misc_feature
<222> LOCATION: (40)..(40)
<223> OTHER INFORMATION: Xaa is selected from A, S and C
<220> FEATURE:
<221> NAME/KEY: misc_feature
<222> LOCATION: (46)..(46)
<223> OTHER INFORMATION: Xaa is selected from E, N and S
<220> FEATURE:
<221> NAME/KEY: misc_feature
<222> LOCATION: (47)..(47)
<223> OTHER INFORMATION: Xaa is selected from D, E and S
<220> FEATURE:
<221> NAME/KEY: misc_feature
<222> LOCATION: (48)..(48)
<223> OTHER INFORMATION: Xaa is selected from A and S

<400> SEQUENCE: 393

Lys Glu Xaa Xaa Xaa Ala Xaa Xaa Glu Ile Arg Trp Leu Pro Asn Leu
1               5                   10                  15

Xaa Xaa Xaa Gln Arg Xaa Ala Phe Ile Xaa Xaa Leu Xaa Xaa Gln Pro
            20                  25                  30

Glu Gln Ser Xaa Xaa Leu Leu Xaa Glu Ala Lys Lys Leu Xaa Xaa Xaa
        35                  40                  45

Gln

<210> SEQ ID NO 394
<211> LENGTH: 53
<212> TYPE: PRT
<213> ORGANISM: Artificial Sequence
<220> FEATURE:
<223> OTHER INFORMATION: Engineered polypeptide
<220> FEATURE:
<221> NAME/KEY: misc_feature
<222> LOCATION: (5)..(5)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (6)..(6)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (7)..(7)
<223> OTHER INFORMATION: Xaa is selected from A, D, E, F, G, H, I, K, L,
```

```
              N, Q, R, S, T, V, W and Y
<220> FEATURE:
<221> NAME/KEY: misc_feature
<222> LOCATION: (9)..(9)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (10)..(10)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (19)..(19)
<223> OTHER INFORMATION: Xaa is selected from is selected from N and T
<220> FEATURE:
<221> NAME/KEY: misc_feature
<222> LOCATION: (20)..(20)
<223> OTHER INFORMATION: Xaa is selected from is selected from  F, W and
      Y
<220> FEATURE:
<221> NAME/KEY: misc_feature
<222> LOCATION: (21)..(21)
<223> OTHER INFORMATION: Xaa is selected from  A, D, E and N
<220> FEATURE:
<221> NAME/KEY: misc_feature
<222> LOCATION: (24)..(24)
<223> OTHER INFORMATION: Xaa is selected from A, S, V and W
<220> FEATURE:
<221> NAME/KEY: misc_feature
<222> LOCATION: (28)..(28)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (29)..(29)
<223> OTHER INFORMATION: Xaa is selected from K and S
<220> FEATURE:
<221> NAME/KEY: misc_feature
<222> LOCATION: (31)..(31)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (32)..(32)
<223> OTHER INFORMATION: Xaa is selected from D and R
<220> FEATURE:
<221> NAME/KEY: misc_feature
<222> LOCATION: (42)..(42)
<223> OTHER INFORMATION: Xaa is selected from A, S and C

<400> SEQUENCE: 394

Tyr Ala Lys Glu Xaa Xaa Xaa Ala Xaa Xaa Glu Ile Arg Trp Leu Pro
1               5                   10                  15

Asn Leu Xaa Xaa Xaa Gln Arg Xaa Ala Phe Ile Xaa Xaa Leu Xaa Xaa
            20                  25                  30

Asp Pro Ser Gln Ser Ser Glu Leu Leu Xaa Glu Ala Lys Lys Leu Asn
        35                  40                  45

Asp Ser Gln Ala Pro
    50

<210> SEQ ID NO 395
<211> LENGTH: 53
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (5)..(5)
<223> OTHER INFORMATION: Xaa is selected from A, D, E, F, H, I, K, L, N,
      Q, R, S, T, V, W and Y
<220> FEATURE:
<221> NAME/KEY: misc_feature
```

```
<222> LOCATION: (6)..(6)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (7)..(7)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (9)..(9)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (10)..(10)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (19)..(19)
<223> OTHER INFORMATION: Xaa is selected from N and T
<220> FEATURE:
<221> NAME/KEY: misc_feature
<222> LOCATION: (20)..(20)
<223> OTHER INFORMATION: Xaa is selected from F, W and Y
<220> FEATURE:
<221> NAME/KEY: misc_feature
<222> LOCATION: (21)..(21)
<223> OTHER INFORMATION: Xaa is selected from A, D, E and N
<220> FEATURE:
<221> NAME/KEY: misc_feature
<222> LOCATION: (24)..(24)
<223> OTHER INFORMATION: Xaa is selected from A, S, V and W
<220> FEATURE:
<221> NAME/KEY: misc_feature
<222> LOCATION: (28)..(28)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (29)..(29)
<223> OTHER INFORMATION: Xaa is selected from K and S
<220> FEATURE:
<221> NAME/KEY: misc_feature
<222> LOCATION: (31)..(31)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (32)..(32)
<223> OTHER INFORMATION: Xaa is selected from  D and R
<220> FEATURE:
<221> NAME/KEY: misc_feature
<222> LOCATION: (42)..(42)
<223> OTHER INFORMATION: Xaa is selected from A, S and C

<400> SEQUENCE: 395

Phe Ala Lys Glu Xaa Xaa Xaa Ala Xaa Xaa Glu Ile Arg Trp Leu Pro
1               5                   10                  15

Asn Leu Xaa Xaa Xaa Gln Arg Xaa Ala Phe Ile Xaa Xaa Leu Xaa Xaa
            20                  25                  30

Asp Pro Ser Gln Ser Ser Glu Leu Leu Xaa Glu Ala Lys Lys Leu Ser
        35                  40                  45

Glu Ser Gln Ala Pro
    50

<210> SEQ ID NO 396
<211> LENGTH: 58
<212> TYPE: PRT
<213> ORGANISM: Artificial Sequence
<220> FEATURE:
<223> OTHER INFORMATION: Engineered polypeptide
<220> FEATURE:
```

```
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 396

Ala Asp Asn Asn Phe Asn Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ala Asn Leu Leu Ser Glu Ala
            35                  40                  45

Lys Lys Leu Asn Glu Ser Gln Ala Pro Lys
        50                  55

<210> SEQ ID NO 397
<211> LENGTH: 58
<212> TYPE: PRT
<213> ORGANISM: Artificial Sequence
<220> FEATURE:
```

```
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 397

Ala Asp Asn Lys Phe Asn Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 398
<211> LENGTH: 58
<212> TYPE: PRT
```

-continued

```
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 398

Ala Asp Asn Lys Phe Asn Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 399
```

```
<211> LENGTH: 61
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (12)..(12)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (14)..(14)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (16)..(16)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (17)..(17)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (26)..(26)
<223> OTHER INFORMATION: Xaa is selected from N and T
<220> FEATURE:
<221> NAME/KEY: misc_feature
<222> LOCATION: (27)..(27)
<223> OTHER INFORMATION: Xaa is selected from F, W and Y
<220> FEATURE:
<221> NAME/KEY: misc_feature
<222> LOCATION: (28)..(28)
<223> OTHER INFORMATION: Xaa is selected from A, D, E and N
<220> FEATURE:
<221> NAME/KEY: misc_feature
<222> LOCATION: (31)..(31)
<223> OTHER INFORMATION: Xaa is selected from A, S, V and W
<220> FEATURE:
<221> NAME/KEY: misc_feature
<222> LOCATION: (35)..(35)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (36)..(36)
<223> OTHER INFORMATION: Xaa is selected from K and S
<220> FEATURE:
<221> NAME/KEY: misc_feature
<222> LOCATION: (38)..(38)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (39)..(39)
<223> OTHER INFORMATION: Xaa is selected from  D and R

<400> SEQUENCE: 399

Ala Asp Ala Gln Gln Asn Asn Phe Asn Lys Glu Xaa Xaa Xaa Ala Xaa
1               5                   10                  15

Xaa Glu Ile Arg Trp Leu Pro Asn Leu Xaa Xaa Xaa Gln Arg Xaa Ala
            20                  25                  30

Phe Ile Xaa Xaa Leu Xaa Xaa Asp Pro Ser Gln Ser Thr Asn Val Leu
        35                  40                  45

Gly Glu Ala Lys Lys Leu Asn Glu Ser Gln Ala Pro Lys
    50                  55                  60
```

```
<210> SEQ ID NO 400
<211> LENGTH: 56
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (7)..(7)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (8)..(8)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (9)..(9)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (12)..(12)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (21)..(21)
<223> OTHER INFORMATION: Xaa is selected from N and T
<220> FEATURE:
<221> NAME/KEY: misc_feature
<222> LOCATION: (22)..(22)
<223> OTHER INFORMATION: Xaa is selected from F, W and Y
<220> FEATURE:
<221> NAME/KEY: misc_feature
<222> LOCATION: (23)..(23)
<223> OTHER INFORMATION: Xaa is selected from A, D, E and N
<220> FEATURE:
<221> NAME/KEY: misc_feature
<222> LOCATION: (26)..(26)
<223> OTHER INFORMATION: Xaa is selected from A, S, V and W
<220> FEATURE:
<221> NAME/KEY: misc_feature
<222> LOCATION: (30)..(30)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (31)..(31)
<223> OTHER INFORMATION: Xaa is selected from K and S
<220> FEATURE:
<221> NAME/KEY: misc_feature
<222> LOCATION: (33)..(33)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (34)..(34)
<223> OTHER INFORMATION: Xaa is selected from  D and R

<400> SEQUENCE: 400

Ala Gln His Asp Glu Glu Xaa Xaa Xaa Ala Xaa Xaa Glu Ile Arg Trp
1               5                   10                  15

Leu Pro Asn Leu Xaa Xaa Xaa Gln Arg Xaa Ala Phe Ile Xaa Xaa Leu
                20                  25                  30

Xaa Xaa Asp Pro Ser Gln Ser Ala Asn Val Leu Gly Glu Ala Gln Lys
        35                  40                  45

Leu Asn Asp Ser Gln Ala Pro Lys
```

-continued 50                  55

<210> SEQ ID NO 401
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 401

Val Asp Asn Lys Phe Asn Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 402
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 402

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Glu Ser Ser Glu Leu Leu Ser Glu Ala
        35                  40                  45

Lys Lys Leu Asn Lys Ser Gln Ala Pro Lys
    50                  55

<210> SEQ ID NO 403
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 403

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa

```
            20                  25                  30
Xaa Leu Xaa Xaa Asp Pro Ser Gln Ser Ser Glu Leu Leu Ala Glu Ala
         35                  40                  45

Lys Lys Leu Asn Asp Ala Gln Ala Pro Lys
     50                  55
```

<210> SEQ ID NO 404
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
    Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
    M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
    S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
    Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 404

```
Val Asp Ala Lys Tyr Ala Lys Glu Xaa Xaa Xaa Ala Xaa Xaa Glu Ile
1               5                  10                  15
```

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ala Glu Ala
        35                  40                  45

Lys Lys Leu Asn Asp Ser Gln Ala Pro Lys
        50                  55

<210> SEQ ID NO 405
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 405

-continued

```
Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 406
<211> LENGTH: 57
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R
```

<400> SEQUENCE: 406

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Ser Glu Ala
        35                  40                  45

Lys Lys Leu Asn Asp Ser Gln Ala Pro
    50                  55

<210> SEQ ID NO 407
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)

-continued

<223> OTHER INFORMATION: Xaa is selected from D and R

<400> SEQUENCE: 407

Ala Glu Ala Lys Phe Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 408
<211> LENGTH: 57
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:

-continued

```
<221> NAME/KEY: misc_feature
<222> LOCATION: (36)..(36)
<223> OTHER INFORMATION: Xaa is selected from  D and R

<400> SEQUENCE: 408

Ala Glu Ala Lys Phe Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ser Glu Ala
            35                  40                  45

Lys Lys Leu Asn Asp Ser Gln Ala Pro
        50                  55

<210> SEQ ID NO 409
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
```

```
            Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 409

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 410
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
```

```
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 410

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 411
<211> LENGTH: 57
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
```

```
<220> FEATURE:
<221> NAME/KEY: misc_feature
<222> LOCATION: (35)..(35)
<223> OTHER INFORMATION: Xaa is selected from A, D, E, F, H, I, K, L, N,
     Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 411

Ala Glu Ala Lys Tyr Ala Lys Glu Xaa Xaa Xaa Ala Xaa Xaa Glu Ile
1               5                  10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Ser Glu Ser Gln Ala Pro
    50                  55

<210> SEQ ID NO 412
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
     Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
     M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
     N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
     N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
     S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
     N, Q, R, S, T, V, W and Y
<220> FEATURE:
<221> NAME/KEY: misc_feature
```

```
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 412

Ala Glu Ala Lys Phe Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 413
<211> LENGTH: 57
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
```

```
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 413

Ala Glu Ala Lys Phe Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ser Glu Ala
        35                  40                  45

Lys Lys Leu Ser Glu Ser Gln Ala Pro
    50                  55

<210> SEQ ID NO 414
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
```

```
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 414

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ala Glu Ala
        35                  40                  45

Lys Lys Leu Ser Glu Ala Gln Ala Pro Lys
    50                  55

<210> SEQ ID NO 415
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
```

```
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 415

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Gln Pro Glu Gln Ser Ser Glu Leu Leu Ser Glu Ala
        35                  40                  45

Lys Lys Leu Ser Glu Ser Gln Ala Pro Lys
    50                  55

<210> SEQ ID NO 416
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
```

```
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 416

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ser Glu Ala
        35                  40                  45

Lys Lys Leu Glu Ser Ser Gln Ala Pro Lys
    50                  55

<210> SEQ ID NO 417
<211> LENGTH: 57
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
```

-continued

```
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 417

Ala Glu Ala Lys Tyr Ala Lys Glu Xaa Xaa Ala Xaa Xaa Glu Ile
1               5                  10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Glu Ser Ser Gln Ala Pro
    50                  55

<210> SEQ ID NO 418
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
```

<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
    Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 418

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ala Glu Ala
        35                  40                  45

Lys Lys Leu Glu Ser Ala Gln Ala Pro Lys
    50                  55

<210> SEQ ID NO 419
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
    Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
    M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
    S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:

```
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 419

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Gln Pro Glu Gln Ser Ser Glu Leu Leu Ser Glu Ala
        35                  40                  45

Lys Lys Leu Glu Ser Ser Gln Ala Pro Lys
    50                  55

<210> SEQ ID NO 420
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
```

```
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 420

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ser Glu Ala
        35                  40                  45

Lys Lys Leu Ser Asp Ser Gln Ala Pro Lys
    50                  55

<210> SEQ ID NO 421
<211> LENGTH: 57
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
```

```
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 421

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Ser Asp Ser Gln Ala Pro
    50                  55

<210> SEQ ID NO 422
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
```

```
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
     N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
     Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 422

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ala Glu Ala
        35                  40                  45

Lys Lys Leu Ser Asp Ala Gln Ala Pro Lys
    50                  55

<210> SEQ ID NO 423
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
     Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
     M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
     N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
     N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
     S, T, V, W and Y
<220> FEATURE:
```

<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L, N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N, Q, R, S, T, V, W and Y
<220> FEATURE:
<221> NAME/KEY: misc_feature
<222> LOCATION: (36)..(36)
<223> OTHER INFORMATION: Xaa is selected from D and R

<400> SEQUENCE: 423

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Gln Pro Glu Gln Ser Ser Glu Leu Leu Ser Glu Ala
        35                  40                  45

Lys Lys Leu Ser Asp Ser Gln Ala Pro Lys
    50                  55

<210> SEQ ID NO 424
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N, Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L, M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L, N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L, N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,

```
                    S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 424

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 425
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
```

```
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 425

Val Asp Ala Lys Phe Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 426
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
```

```
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 426

Val Asp Ala Lys Tyr Ala Lys Glu Xaa Xaa Xaa Ala Xaa Xaa Glu Ile
1               5                  10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 427
<211> LENGTH: 58
<212> TYPE: PRT
<213> ORGANISM: Artificial Sequence
<220> FEATURE:
<223> OTHER INFORMATION: engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
```

```
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 427

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa

```
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 428

Val Asp Ala Lys Phe Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 429
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
```

```
                N, Q, R, S, T, V, W and Y
<220> FEATURE:
<221> NAME/KEY: misc_feature
<222> LOCATION: (13)..(13)
<223> OTHER INFORM

```
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 430

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg X

```
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 431

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Glu Ser Ser Gln Ala Pro Lys
    50                  55

<210> SEQ ID NO 432
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
```

```
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 432

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ala Glu Ala
        35                  40                  45

Lys Lys Leu Glu Ser Ala Gln Ala Pro Lys
    50                  55

<210> SEQ ID NO 433
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
```

-continued

```
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 433

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe

```
        Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
        M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
        N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
        N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
        S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
        N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
        Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 434

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Ser Asp Ser Gln Ala Pro Lys
    50                  55

<210> SEQ ID NO 435
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
```

```
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 435

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ala Glu Ala
            35                  40                  45

Lys Lys Leu Ser Asp Ala Gln Ala Pro Lys
50                  55

<210> SEQ ID NO 436
<211> LENGTH: 58
<212> TYPE: PRT
<213> ORGANISM: Artificial Sequence
<220> FEATURE:
<223> OTHER INFORMATION: Engineered polypeptide
```

```
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 436

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Gln Pro Glu Gln Ser Ser Glu Leu Leu Ser Glu Ala
        35                  40                  45

Lys Lys Leu Ser Asp Ser Gln Ala Pro Lys
    50                  55

<210> SEQ ID NO 437
<211> LENGTH: 58
<212> TYPE: PRT
<213> ORGANISM: Artificial Sequence
```

```
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 437

Val Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
            20                  25                  30

Xaa Leu Xaa Xaa Asp Pro Ser Gln Ser Ser Glu Leu Leu Ala Glu Ala
        35                  40                  45

Lys Lys Leu Asn Lys Ala Gln Ala Pro Lys
    50                  55

<210> SEQ ID NO 438
<211> LENGTH: 58
```

```
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
    Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
    M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
    S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
    N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
    Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 438

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ala Glu Ala
            35                  40                  45

Lys Lys Leu Asn Lys Ala Gln Ala Pro Lys
    50                  55
```

-continued

```
<210> SEQ ID NO 439
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 439

Ala Asp Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Asp Pro Ser Gln Ser Ser Glu Leu Leu Ser Glu Ala
            35                  40                  45

Lys Lys Leu Asn Asp Ser Gln Ala Pro Lys
        50                  55
```

```
<210> SEQ ID NO 440
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (9)..(9)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (10)..(10)
<223> OTHER INFORMATION: Xaa is selected from A, D, E, F, G, H, I, K, L,
      M, N, Q, R, S, T, V, W and Y
<220> FEATURE:
<221> NAME/KEY: misc_feature
<222> LOCATION: (11)..(11)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (13)..(13)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (14)..(14)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (23)..(23)
<223> OTHER INFORMATION: Xaa is selected from N and T
<220> FEATURE:
<221> NAME/KEY: misc_feature
<222> LOCATION: (24)..(24)
<223> OTHER INFORMATION: Xaa is selected from F, W and Y
<220> FEATURE:
<221> NAME/KEY: misc_feature
<222> LOCATION: (25)..(25)
<223> OTHER INFORMATION: Xaa is selected from A, D, E and N
<220> FEATURE:
<221> NAME/KEY: misc_feature
<222> LOCATION: (28)..(28)
<223> OTHER INFORMATION: Xaa is selected from A, S, V and W
<220> FEATURE:
<221> NAME/KEY: misc_feature
<222> LOCATION: (32)..(32)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (33)..(33)
<223> OTHER INFORMATION: Xaa is selected from K and S
<220> FEATURE:
<221> NAME/KEY: misc_feature
<222> LOCATION: (35)..(35)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (36)..(36)
<223> OTHER INFORMATION: Xaa is selected from  D and R

<400> SEQUENCE: 440

Ala Glu Ala Lys Tyr Ala Lys Glu Xaa Xaa Xaa Ala Xaa Xaa Glu Ile
1               5                   10                  15

Arg Trp Leu Pro Asn Leu Xaa Xaa Xaa Gln Arg Xaa Ala Phe Ile Xaa
                20                  25                  30

Xaa Leu Xaa Xaa Arg Gln Pro Glu Ser Ser Glu Leu Leu Ser Glu Ala
            35                  40                  45
```

```
Lys Lys Leu Ser Glu Ser Gln Ala Pro Lys
        50                  55

<210> SEQ ID NO 441
<211> LENGTH: 5
<212> TYPE: PRT
<213> ORGANISM: Artificial Sequence
<220> FEATURE:
<223> OTHER INFORMATION: Engineered polypeptide

<400> SEQUENCE: 441

Gly Gly Gly Gly Ser
1               5

<210> SEQ ID NO 442
<211> LENGTH: 5
<212> TYPE: PRT
<213> ORGANISM: Artificial Sequence
<220> FEATURE:
<223> OTHER INFORMATION: Engineered polypeptide

<400> SEQUENCE: 442

Ser Ser Ser Ser Gly
1               5

<210> SEQ ID NO 443
<211> LENGTH: 16
<212> TYPE: PRT
<213> ORGANISM: Artificial Sequence
<220> FEATURE:
<223> OTHER INFORMATION: Engineered polypeptide

<400> SEQUENCE: 443

Gly Gly Gly Gly Ser Leu Val Pro Arg Gly Ser Gly Gly Gly Gly Ser
1               5                   10                  15

<210> SEQ ID NO 444
<211> LENGTH: 6
<212> TYPE: PRT
<213> ORGANISM: Artificial Sequence
<220> FEATURE:
<223> OTHER INFORMATION: Engineered polypeptide

<400> SEQUENCE: 444

Gly Ser Gly Ser Gly Ser
1               5

<210> SEQ ID NO 445
<211> LENGTH: 8
<212> TYPE: PRT
<213> ORGANISM: Artificial Sequence
<220> FEATURE:
<223> OTHER INFORMATION: Engineered polypeptide

<400> SEQUENCE: 445

Gly Ser Gly Ser Gly Ser Gly Ser
1               5

<210> SEQ ID NO 446
<211> LENGTH: 16
<212> TYPE: PRT
<213> ORGANISM: Artificial Sequence
<220> FEATURE:
<223> OTHER INFORMATION: Engineered polypeptide

<400> SEQUENCE: 446

Gly Ser Gly Ser Gly Ser Gly Ser Gly Ser Gly Ser Gly Ser Gly Ser
```

```
                1               5                  10                 15

<210> SEQ ID NO 447
<211> LENGTH: 11
<212> TYPE: PRT
<213> ORGANISM: Artificial Sequence
<220> FEATURE:
<223> OTHER INFORMATION: Engineered polypeptide

<400> SEQUENCE: 447

Gly Gly Ser Gly Gly His Met Gly Ser Gly Gly
1               5                   10

<210> SEQ ID NO 448
<211> LENGTH: 11
<212> TYPE: PRT
<213> ORGANISM: Artificial Sequence
<220> FEATURE:
<223> OTHER INFORMATION: Engineered polypeptide

<400> SEQUENCE: 448

Gly Gly Ser Gly Gly Ser Gly Gly Ser Gly Gly
1               5                   10

<210> SEQ ID NO 449
<211> LENGTH: 5
<212> TYPE: PRT
<213> ORGANISM: Artificial Sequence
<220> FEATURE:
<223> OTHER INFORMATION: Engineered polypeptide

<400> SEQUENCE: 449

Gly Gly Ser Gly Gly
1               5

<210> SEQ ID NO 450
<211> LENGTH: 8
<212> TYPE: PRT
<213> ORGANISM: Artificial Sequence
<220> FEATURE:
<223> OTHER INFORMATION: Engineered polypeptide

<400> SEQUENCE: 450

Gly Gly Ser Gly Gly Gly Gly Gly
1               5

<210> SEQ ID NO 451
<211> LENGTH: 18
<212> TYPE: PRT
<213> ORGANISM: Artificial Sequence
<220> FEATURE:
<223> OTHER INFORMATION: Engineered polypeptide

<400> SEQUENCE: 451

Gly Gly Gly Ser Glu Gly Gly Ser Glu Gly Gly Gly Ser Glu Gly
1               5                   10                  15

Gly Gly

<210> SEQ ID NO 452
<211> LENGTH: 8
<212> TYPE: PRT
<213> ORGANISM: Artificial Sequence
<220> FEATURE:
<223> OTHER INFORMATION: Engineered polypeptide

<400> SEQUENCE: 452
```

```
Ala Ala Gly Ala Ala Thr Ala Ala
1               5

<210> SEQ ID NO 453
<211> LENGTH: 5
<212> TYPE: PRT
<213> ORGANISM: Artificial Sequence
<220> FEATURE:
<223> OTHER INFORMATION: Engineered polypeptide

<400> SEQUENCE: 453

Gly Gly Gly Gly Gly
1               5

<210> SEQ ID NO 454
<211> LENGTH: 5
<212> TYPE: PRT
<213> ORGANISM: Artificial Sequence
<220> FEATURE:
<223> OTHER INFORMATION: Engineered polypeptide

<400> SEQUENCE: 454

Gly Gly Ser Ser Gly
1               5

<210> SEQ ID NO 455
<211> LENGTH: 11
<212> TYPE: PRT
<213> ORGANISM: Artificial Sequence
<220> FEATURE:
<223> OTHER INFORMATION: Engineered polypeptide

<400> SEQUENCE: 455

Gly Ser Gly Gly Gly Thr Gly Gly Gly Ser Gly
1               5                   10

<210> SEQ ID NO 456
<211> LENGTH: 11
<212> TYPE: PRT
<213> ORGANISM: Artificial Sequence
<220> FEATURE:
<223> OTHER INFORMATION: Engineered polypeptide

<400> SEQUENCE: 456

Gly Ser Gly Gly Gly Thr Gly Gly Gly Ser Gly
1               5                   10

<210> SEQ ID NO 457
<211> LENGTH: 12
<212> TYPE: PRT
<213> ORGANISM: Artificial Sequence
<220> FEATURE:
<223> OTHER INFORMATION: Engineered polypeptide

<400> SEQUENCE: 457

Gly Ser Gly Ser Gly Ser Gly Ser Gly Gly Ser Gly
1               5                   10

<210> SEQ ID NO 458
<211> LENGTH: 14
<212> TYPE: PRT
<213> ORGANISM: Artificial Sequence
<220> FEATURE:
<223> OTHER INFORMATION: Engineered polypeptide

<400> SEQUENCE: 458

Gly Ser Gly Gly Ser Gly Gly Ser Gly Gly Ser Gly Gly Ser
```

```
1               5                  10
```

<210> SEQ ID NO 459
<211> LENGTH: 14
<212> TYPE: PRT
<213> ORGANISM: Artificial Sequence
<220> FEATURE:
<223> OTHER INFORMATION: Engineered polypeptide

<400> SEQUENCE: 459

```
Gly Ser Gly Gly Ser Gly Ser Gly Gly Ser Gly Gly Ser Gly
1               5                  10
```

<210> SEQ ID NO 460
<211> LENGTH: 15
<212> TYPE: PRT
<213> ORGANISM: Artificial Sequence
<220> FEATURE:
<223> OTHER INFORMATION: Engineered polypeptide

<400> SEQUENCE: 460

```
Ser Ser Ser Ser Gly Ser Ser Ser Ser Gly Ser Ser Ser Ser Gly
1               5                  10                  15
```

<210> SEQ ID NO 461
<211> LENGTH: 20
<212> TYPE: PRT
<213> ORGANISM: Artificial Sequence
<220> FEATURE:
<223> OTHER INFORMATION: Engineered polypeptide

<400> SEQUENCE: 461

```
Ser Ser Ser Ser Gly Ser Ser Ser Ser Gly Ser Ser Ser Ser Gly Ser
1               5                  10                  15

Ser Ser Ser Gly
            20
```

<210> SEQ ID NO 462
<211> LENGTH: 15
<212> TYPE: PRT
<213> ORGANISM: Artificial Sequence
<220> FEATURE:
<223> OTHER INFORMATION: Engineered polypeptide

<400> SEQUENCE: 462

```
Gly Gly Gly Gly Ser Gly Gly Gly Gly Ser Gly Gly Gly Gly Ser
1               5                  10                  15
```

<210> SEQ ID NO 463
<211> LENGTH: 53
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (5)..(5)
<223> OTHER INFORMATION: Xaa is selected from A, D, E, F, H, I, K, L, N,
    Q, R, S, T, V, W and Y
<220> FEATURE:
<221> NAME/KEY: misc_feature
<222> LOCATION: (6)..(6)
<223> OTHER INFORMATION: Xaa is selected from A, D, E, F, G, H, I, K, L,
    M, N, Q, R, S, T, V, W and Y
<220> FEATURE:
<221> NAME/KEY: misc_feature
<222> LOCATION: (7)..(7)
<223> OTHER INFORMATION: Xaa is selected from A, D, E, F, G, H, I, K, L,
    N, Q, R, S, T, V, W and Y

```
<220> FEATURE:
<221> NAME/KEY: misc_feature
<222> LOCATION: (9)..(9)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (10)..(10)
<223> OTHER INFORMATION: Xaa is selected from A, F, H, I, K, L, N, Q, R,
      S, T, V, W and Y
<220> FEATURE:
<221> NAME/KEY: misc_feature
<222> LOCATION: (19)..(19)
<223> OTHER INFORMATION: Xaa is selected from N and T
<220> FEATURE:
<221> NAME/KEY: misc_feature
<222> LOCATION: (20)..(20)
<223> OTHER INFORMATION: Xaa is selected from F, W and Y
<220> FEATURE:
<221> NAME/KEY: misc_feature
<222> LOCATION: (21)..(21)
<223> OTHER INFORMATION: Xaa is selected from A, D, E and N
<220> FEATURE:
<221> NAME/KEY: misc_feature
<222> LOCATION: (24)..(24)
<223> OTHER INFORMATION: Xaa is selected from  A, S, V and W
<220> FEATURE:
<221> NAME/KEY: misc_feature
<222> LOCATION: (28)..(28)
<223> OTHER INFORMATION: Xaa is selected from A, D, E, F, G, H, I, K, L,
      N, Q, R, S, T, V, W and Y
<220> FEATURE:
<221> NAME/KEY: misc_feature
<222> LOCATION: (29)..(29)
<223> OTHER INFORMATION: Xaa is selected from  K and S
<220> FEATURE:
<221> NAME/KEY: misc_feature
<222> LOCATION: (31)..(31)
<223> OTHER INFORMATION: Xaa is selected from A, D, E, F, H, I, K, L, N,
      Q, R, S, T, V, W and Y
<220> FEATURE:
<221> NAME/KEY: misc_feature
<222> LOCATION: (32)..(32)
<223> OTHER INFORMATION: Xaa is selected from D and R
<220> FEATURE:
<221> NAME/KEY: misc_feature
<222> LOCATION: (42)..(42)
<223> OTHER INFORMATION: Xaa is selected from A and C

<400> SEQUENCE: 463

Phe Asn Lys Glu Xaa Xaa Xaa Ala Xaa Xaa Glu Ile Arg Trp Leu Pro
1               5                   10                  15

Asn Leu Xaa Xaa Xaa Gln Arg Xaa Ala Phe Ile Xaa Xaa Leu Xaa Xaa
            20                  25                  30

Asp Pro Ser Gln Ser Ala Asn Leu Leu Xaa Glu Ala Lys Lys Leu Asn
        35                  40                  45

Asp Ala Gln Ala Pro
    50

<210> SEQ ID NO 464
<211> LENGTH: 16
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (8)..(9)
<223> OTHER INFORMATION: Z variant sequence
<220> FEATURE:
<221> NAME/KEY: MISC_FEATURE
<222> LOCATION: (12)..(13)
<223> OTHER INFORMATION: Albumin binding domain
```

```
<400> SEQUENCE: 464

Ala Gln His Asp Glu Ala Leu Glu Val Asp Tyr Val Tyr Val Pro Gly
1               5                   10                  15

<210> SEQ ID NO 465
<211> LENGTH: 154
<212> TYPE: PRT
<213> ORGANISM: Artificial Sequence
<220> FEATURE:
<223> OTHER INFORMATION: Engineered fusion protein
<220> FEATURE:
<221> NAME/KEY: MISC_FEATURE
<222> LOCATION: (1)..(1)
<223> OTHER INFORMATION: X is a Z variant

<400> SEQUENCE: 465

Xaa Gly Ala Pro Gly Gly Gly Ser Gly Gly Gly Ser Gly Gly
1               5                   10                  15

Gly Gly Ser Gly Gly Gly Gly Ser Thr Ser Leu Ala Glu Ala Lys Glu
            20                  25                  30

Ala Ala Asn Ala Glu Leu Asp Ser Tyr Gly Val Ser Asp Phe Tyr Lys
        35                  40                  45

Arg Leu Ile Asp Lys Ala Lys Thr Val Glu Gly Val Glu Ala Leu Lys
    50                  55                  60

Asp Ala Ile Leu Ala Ala Leu Pro Gly Thr Gly Gly Gly Ser Gly
65                  70                  75                  80

Gly Gly Gly Ser Gly Gly Gly Ser Gly Gly Gly Ser Pro Arg
                85                  90                  95

Ala Glu Ala Lys Tyr Ala Lys Glu Leu Gly Trp Ala Thr Trp Glu Ile
                100                 105                 110

Phe Asn Leu Pro Asn Leu Thr Gly Val Gln Val Lys Ala Phe Ile Asp
            115                 120                 125

Lys Leu Arg Asp Asp Pro Ser Gln Ser Ser Glu Leu Leu Ser Glu Ala
        130                 135                 140

Lys Lys Leu Asn Asp Ser Gln Ala Pro Lys
145                 150

<210> SEQ ID NO 466
<211> LENGTH: 129
<212> TYPE: PRT
<213> ORGANISM: Artificial Sequence
<220> FEATURE:
<223> OTHER INFORMATION: engineered negative control fusion protein

<400> SEQUENCE: 466

Ala Glu Ala Lys Tyr Ala Lys Glu Leu Gly Trp Ala Thr Trp Glu Ile
1               5                   10                  15

Phe Asn Leu Pro Asn Leu Thr Gly Val Gln Val Lys Ala Phe Ile Asp
            20                  25                  30

Lys Leu Arg Asp Asp Pro Ser Gln Ser Ser Glu Leu Leu Ser Glu Ala
        35                  40                  45

Lys Lys Leu Asn Asp Ser Gln Ala Pro Lys Gly Ala Pro Gly Gly Gly
    50                  55                  60

Gly Ser Gly Gly Gly Ser Gly Gly Gly Ser Gly Gly Gly
65                  70                  75                  80

Ser Thr Ser Leu Ala Glu Ala Lys Glu Ala Ala Asn Ala Glu Leu Asp
                85                  90                  95

Ser Tyr Gly Val Ser Asp Phe Tyr Lys Arg Leu Ile Asp Lys Ala Lys
                100                 105                 110
```

```
Thr Val Glu Gly Val Glu Ala Leu Lys Asp Ala Ile Leu Ala Ala Leu
        115                 120                 125
Pro

<210> SEQ ID NO 467
<211> LENGTH: 20
<212> TYPE: PRT
<213> ORGANISM: artificial
<220> FEATURE:
<223> OTHER INFORMATION: artificial linker construct

<400> SEQUENCE: 467

Gly Gly Gly Gly Ser Gly Gly Gly Gly Ser Gly Gly Gly Gly Ser Gly
1               5                   10                  15

Gly Gly Gly Ser
            20

<210> SEQ ID NO 468
<211> LENGTH: 15
<212> TYPE: PRT
<213> ORGANISM: Artificial Sequence
<220> FEATURE:
<223> OTHER INFORMATION: artificial construct
<220> FEATURE:
<221> NAME/KEY: MISC_FEATURE
<222> LOCATION: (13)..(13)
<223> OTHER INFORMATION: X is a Z-variant

<400> SEQUENCE: 468

Met Gly Ser Ser His His His His His His Leu Gln Xaa Val Asp
1               5                   10                  15

<210> SEQ ID NO 469
<211> LENGTH: 59
<212> TYPE: PRT
<213> ORGANISM: artificial
<220> FEATURE:
<223> OTHER INFORMATION: Z-dimer fusion construct
<220> FEATURE:
<221> NAME/KEY: MISC_FEATURE
<222> LOCATION: (1)..(1)
<223> OTHER INFORMATION: X is a Z-variant
<220> FEATURE:
<221> NAME/KEY: MISC_FEATURE
<222> LOCATION: (59)..(59)
<223> OTHER INFORMATION: X is a Z-variant

<400> SEQUENCE: 469

Xaa Ala Ser Gly Ser Leu Ala Glu Ala Lys Glu Ala Ala Asn Ala Glu
1               5                   10                  15

Leu Asp Ser Tyr Gly Val Ser Asp Phe Tyr Lys Arg Leu Ile Asp Lys
            20                  25                  30

Ala Lys Thr Val Glu Gly Val Glu Ala Leu Lys Asp Ala Ile Leu Ala
        35                  40                  45

Ala Leu Pro Gly Thr Gly Gly Gly Ser Xaa
    50                  55

<210> SEQ ID NO 470
<211> LENGTH: 13
<212> TYPE: PRT
<213> ORGANISM: artificial
<220> FEATURE:
<223> OTHER INFORMATION: His-tagged fusion construct
<220> FEATURE:
<221> NAME/KEY: MISC_FEATURE
<222> LOCATION: (13)..(13)
```

-continued

```
<223> OTHER INFORMATION: X is a Z-variant

<400> SEQUENCE: 470

Met Gly Ser Ser His His His His His His Leu Gln Xaa
1               5                   10
```

NEONATAL FC RECEPTOR BINDING DIMER AND METHODS OF USE

CROSS REFERENCE TO RELATED APPLICATIONS

This application is a National Stage application of PCT/EP2015/071339, filed Sep. 17, 2015, which claims the benefit of European Patent Application No. 14185140.2, filed Sep. 17, 2014, both of which are incorporated by reference in their entirety herein.

TECHNICAL FIELD OF THE INVENTION

The present disclosure relates to dimers of engineered polypeptides having a binding affinity for the neonatal Fc receptor (in the following referred to as FcRn). The present disclosure also relates to the use of such dimers as agents for modifying pharmacokinetic and pharmacodynamic properties of a biomolecule, e.g. a pharmaceutical, and as therapeutic agents.

BACKGROUND

The neonatal Fc receptor (FcRn) is a heterodimeric protein consisting of a transmembrane MHC class I-like heavy chain (FcRn α-chain) and the β2-microglobulin light chain, the latter also forming a part of MHC class I molecules (Simister and Mostov (1989) Nature 337:184-7; Burmeister et al. (1994) Nature 372:379-83).

FcRn is predominantly located in endosomes and is able to bind to serum albumin and immunoglobulin G (IgG) at pH ≤6.5 and release them at pH ≥7.0 (reviewed in Roopenian (2007) Nat Rev Immunol 7:715-25).

FcRn carries out several distinct tasks in mammals (Roopenian, supra). FcRn is involved in recycling of endocytosed IgG and serum albumin, thus avoiding their degradation in the lysosome, giving them longer half-life and higher availability in the blood than other serum proteins. When IgG, serum albumin and other serum proteins are passively pinocytosed by cells in contact with blood, the pH becomes gradually lower in the formed endosomes, which permits the binding of IgG and serum albumin to FcRn. The receptor is then, together with its bound ligand, transported via recycling endosomes back to the plasma membrane. After returning to the plasma membrane, the pH increases to above 7, at which point the bound ligand is released.

FcRn is also recognized for its ability to transport IgG over barriers such as the placenta, the upper airway epithelium, the blood-brain barrier and the proximal small intestine.

In mammals, the properties of FcRn are used to transcytose IgG from a mother to a fetus via the placenta, and to transcytose IgG from a mother's milk to the blood stream of an infant in the proximal small intestine.

The expression pattern of FcRn differs between species. However, FcRn is widely expressed by cells in the blood brain barrier, upper airway epithelium, kidneys and vascular endothelia, and by antigen presenting cells as well as by other cells of hematopoietic origin in most species (Roopenian (2007), supra).

Antibodies and peptides with affinity towards FcRn (Liu et al. (2007) J Immunol 179:2999-3011, Mezo et al. (2008) Proc Natl Acad Sci USA 105:2337-42) and δ2-microglobulin (Getman and Balthasar (2005) J Pharm Sci 94:718-29) have been developed with a view to inhibit the binding between endogenous IgG and FcRn. Another approach has been to mutate the Fc region of the IgG to get a higher affinity for FcRn (Petkova et al. (2006) Int Immunol 18:1759-69, Vaccaro et al. (2005) Nat Biotechnol 23:1283-8).

Fusion to the Fc domain or to albumin is a widely used strategy to increase the in vivo half-life of proteins. However, the large size of such fusion proteins adversely affects tissue penetration and reduces the specificity to the fusion partner (Valles et al. (2011) J Interferon Cytokine Res 32:178-184). On the other hand, mutations have been made in the Fc fragment of antibodies administered to non human primates to prolong half-life (Hinton et al. (2004) J Biol Chem 279:6213-6). However, this approach is only limited in use to therapeutic antibodies, and cannot be extrapolated to other therapeutic proteins unless the proteins in question are fused to Fc fragments, which also results in large size molecules. A number of chemical and recombinant methods have been devised to improve protein half-life, such as PEGylation and genetic fusions of the protein to the Fc domain of IgG or albumin (reviewed in Schellenberger et al. (2009) Nat Biotechnol 21:1186-1190). PEGylation of proteins has been reported to decrease their potency and contribute to their immunoreactivity.

Fc-fusion proteins have also been used for oral and pulmonary delivery mediated by the FcRn (Low et al., (2005) Human reproduction July; 20(7):1805-13), however similar problems relating to tissue penetration and reduced specificity remain, due to the size of the fusion molecules.

Hence, there is large need in the field for the continued provision of molecules with high affinity for FcRn. In particular, small binding molecules are needed that, when present as a fusion partner, do not adversely affect the properties of the molecules they are fused to and do not contribute to immunoreactivity.

SUMMARY OF THE INVENTION

The present disclosure is based on the unexpected realization that FcRn binding polypeptides in dimeric form exhibit significantly improved FcRn binding properties as compared to corresponding FcRn binding polypeptides in monomeric form. The present inventors have found that the improvement in the binding properties of said FcRn binding polypeptides in dimeric form is greater than anticipated by the mere fusion of two FcRn binding polypeptides.

Thus, it is an object of the present disclosure to provide new FcRn binding agents.

It is also an object of the present disclosure to provide such agents for use in modifying pharmacokinetic and/or pharmacodynamic properties of a biomolecule, e.g. a pharmaceutical.

It is also an object of the present disclosure to provide such agents for use as therapeutic agents in their own right, alone or as combination treatment.

It is an object of the present disclosure to provide a molecule allowing for efficient targeting of FcRn, while alleviating the above-mentioned and other drawbacks of current therapies.

These and other objects which are evident to the skilled person from the present disclosure are met by different aspects of the invention as claimed in the appended claims and as generally disclosed herein.

Thus, in the first aspect of the disclosure, there is provided a neonatal Fc receptor (FcRn) binding polypeptide in dimeric form, i.e. an "FcRn binding dimer", comprising a first monomer unit, a second monomer unit and an amino acid linker, wherein said first and second monomer unit each comprises an FcRn binding motif (BM), which motif consists of the amino acid sequence EX$_2$ X$_3$ X$_4$ AX$_6$ X$_7$ EIR WLPNLX$_{16}$ X$_{17}$ X$_{18}$ QR X$_{21}$ AFIX$_{25}$ X$_{26}$LX$_{28}$ X$_{29}$ (SEQ ID NO:389)

wherein, independently from each other,
X$_2$ is selected from A, D, E, F, H, I, K, L, N, Q, R, S, T, V, W and Y;
X$_3$ is selected from A, D, E, F, G, H, I, K, L, M, N, Q, R, S, T, V, W and Y;
X$_4$ is selected from A, D, E, F, G, H, I, K, L, N, Q, R, S, T, V, W and Y;
X$_6$ is selected from A, D, E, F, G, H, I, K, L, N, Q, R, S, T, V, W and Y;
X$_7$ is selected from A, F, H, I, K, L, N, Q, R, S, T, V, W and Y;
X$_{16}$ is selected from N and T;
X$_{17}$ is selected from F, W and Y;
X$_{18}$ is selected from A, D, E and N;
X$_{21}$ is selected from A, S, V and W;
X$_{25}$ is selected from A, D, E, F, G, H, I, K, L, N, Q, R, S, T, V, W and Y;
X$_{26}$ is selected from K and S;
X$_{28}$ is selected from A, D, E, F, H, I, K, L, N, Q, R, S, T, V, W and Y;
and
X$_{29}$ is selected from D and R, and wherein said FcRn binding dimer binds FcRn with a higher binding capacity compared to said first monomer unit or said second monomer unit alone.

The above definition of a class of sequence related, FcRn binding motifs is based on a statistical analysis of a number of random polypeptide monomer variants of a parent scaffold, that were selected for their interaction with FcRn in several different selection experiments. The identified FcRn binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. In the present disclosure, the random variation of binding surface residues and subsequent selection of variants have replaced the Fc interaction capacity with a capacity for interaction with FcRn.

In one embodiment, the FcRn binding motif of at least one of said first and second monomer units consists of the amino acid sequence $EX_2\ X_3\ X_4\ AX_6\ X_7$ EIR $WLPNLTX_{17}\ X_{18}$ QR $X_{21}$ $AFIX_{25}$ $KLX_{28}$ D (SEQ ID NO:390)

wherein, independently from each other, $X_2$ is selected from A, D, E, F, H, I, K, L, N, Q, R, S, T, V, W and Y;

$X_3$ is selected from A, D, E, F, G, H, I, K, L, M, N, Q, R, S, T, V, W and Y;

$X_4$ is selected from A, D, E, F, G, H, I, K, L, N, Q, R, S, T, V, W and Y;

$X_6$ is selected from A, D, E, F, G, H, I, K, L, N, Q, R, S, T, V, W and Y;

$X_7$ is selected from A, F, H, I, K, L, N, Q, R, S, T, V, W and Y;

$X_{17}$ is selected from F, W and Y;

$X_{18}$ is selected from A, D, E and N;

$X_{21}$ is selected from A, S, V and W;

$X_{25}$ is selected from A, D, E, F, G, H, I, K, L, N, Q, R, S, T, V, W and Y;

and $X_{28}$ is selected from A, D, E, F, H, I, K, L, N, Q, R, S, T, V, W and Y.

In one embodiment of the first aspect of the disclosure, said binding motif of at least one of said first and second monomer units consists of the amino acid sequence $EX_2\ X_3\ X_4\ AX_6\ X_7$ EIR $WLPNLX_{16}X_{17}\ X_{18}$ QR $X_{21}$ $AFIX_{25}\ X_{26}LX_{28}\ X_{29}$ (SEQ ID NO:389)

wherein, independently from each other, $X_2$ is selected from A, D, E, F, H, I, K, L, N, Q, R, S, T, V, W and Y;

$X_3$ is selected from A, D, E, F, G, H, I, K, L, M, N, Q, R, S, T, V, W and Y;

$X_4$ is selected from A, D, E, F, G, H, I, K, L, N, Q, R, S, T, V, W and Y;

$X_6$ is selected from A, E, F, G, H, I, K, Q, R, S and V;

$X_7$ is selected from A, F, H, K, N, Q, R, S and V;

$X_{16}$ is selected from N and T;

$X_{17}$ is selected from F, W and Y;

$X_{18}$ is selected from A, D, E and N;

$X_{21}$ is selected from A, S, V and W;

$X_{25}$ is selected from D, E, G, H, I, K, L, N, Q, R, S, T, V, W and Y;

$X_{26}$ is selected from K and S;

$X_{28}$ is selected from A, D, E, F, H, I, K, L, N, Q, R, S, T, V, W and Y; and $X_{29}$ is selected from D and R.

In another embodiment of the first aspect, said binding motif of at least one of said first and second monomer units consists of such an amino acid sequence wherein, independently from each other, $X_2$ is selected from A, D, E, F, H, I, K, L, N, Q, R, S, T, V, W and Y;

$X_3$ is selected from A, D, E, F, H, I, K, L, M, N, Q, R, S, T, V, W and Y;

$X_4$ is selected from A, D, E, F, H, I, K, L, N, Q, R, S, T, V, W and Y;

$X_6$ is selected from A, E, F, G, H, I, K, Q, R and S;

$X_7$ is selected from A, F, H, K, N, Q, R, S and V;

$X_{16}$ is selected from N and T;

$X_{17}$ is selected from F and Y;

$X_{18}$ is D;

$X_{21}$ is V;

$X_{25}$ is selected from D, E, H, I, K, L, N, Q, R, S, T, V, W and Y;

$X_{26}$ is selected from K and S;

$X_{28}$ is selected from A, D, E, F, H, I, K, L, N, Q, R, S, T, V and W and.

$X_{29}$ is selected from D and R.

In another embodiment of the first aspect, said BM in at least one of said first and second monomer units consists of an amino acid sequence selected from i) $EX_2\ X_3\ X_4\ AX_6$ HEIR $WLPNLTX_{17}\ X_{18}$ QR $X_{21}$ $AFIX_{25}$ $KLX_{28}$ D (SEQ ID NO:391)

wherein, independently from each other, $X_2$ is selected from A, D, E, F, H, I, K, L, N, Q, R, S, T, V, W and Y;

$X_3$ is selected from A, D, E, G, H, K, L, M, N, Q, R, S, T, V and Y;

$X_4$ is selected from A, D, E, F, G, I, K, L, N, Q, R, S, T, V and Y;

$X_6$ is selected from A, G, K, R, S and V;

$X_{17}$ is selected from F, W and Y;

$X_{18}$ is selected from A, D, E and N;

$X_{21}$ is selected from A, S, V and W;

$X_{25}$ is selected from D, G, H, K, L, N, R, V and W;

$X_{28}$ is selected from A, D, E, H, K, L, N, Q, R, S, T, W and Y;

and
   ii) an amino acid sequence which has at least 96% identity to said sequence.

In yet another embodiment of said aspect, said BM in sequence i) consists of an amino acid sequence selected from EX$_2$ X$_3$ X$_4$ AX$_6$ HEIR WLPNLTX$_{17}$ X$_{18}$ QR X$_{21}$ AFIX$_{25}$ KLX$_{28}$ D (SEQ ID NO:391)

wherein, independently from each other,
   X$_2$ is selected from A, D, E, F, N, Q, R, S and W;
   X$_3$ is selected from D, E, G, H, K, M, N, Q, S and T;
   X$_4$ is selected from A, D, E, G, N, Q, R, S, T, V and Y;
   X$_6$ is selected from A, G, S and V;
   X$_{17}$ is selected from F, W and Y;
   X$_{18}$ is selected from A, D, E and N;
   X$_{21}$ is selected from A, S, V and W;
   X$_{25}$ is selected from D, G, H, K, L, N, R and V; and
   X$_{28}$ is selected from A, E, H, L, N, Q, R, S, T, W and Y.

As the skilled person will realize, the function of any polypeptide, including the FcRn binding capacity of the dimer of the present disclosure, is dependent on the tertiary structure of the polypeptide. It is therefore possible to make minor changes to the sequence of amino acids in a polypeptide without affecting the function thereof. Thus, the disclosure encompasses variants of the FcRn binding dimer, for example variants wherein at least one of said first and second monomeric units is modified but the FcRn binding characteristics retained.

Therefore, as described above, also encompassed by the present disclosure is an FcRn binding dimer, wherein at least one of said first and second monomer units comprises an FcRn binding motif (BM) comprising an amino acid sequence with 96% or greater identity to a polypeptide as defined in i).

In some embodiments, such changes may be made in all positions of the sequences of the BM as disclosed herein. In other embodiments, such changes may be made only in the non-variable positions, also denoted as scaffold amino acid residues. In such cases, changes are not allowed in the variable positions, i.e. positions denoted with an "X" in sequence i). For example, it is possible that an amino acid residue belonging to a certain functional grouping of amino acid residues (e.g. hydrophobic, hydrophilic, polar etc) could be exchanged for another amino acid residue from the same functional group.

The term "% identity", as used throughout the specification, may for example be calculated as follows. The query sequence is aligned to the target sequence using the CLUSTAL W algorithm (Thompson et al. (1994) Nucleic Acids Research 22:4673-4680). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared, and the percentage of positions in the query sequence that have identical correspondences in the target sequence is reported as % identity.

As used herein "X$_n$" and "X$_m$" are used to indicate amino acids in positions n and m in the sequence of the BM as defined above, wherein n and m are integers which indicate the position of an amino acid within said sequence as counted from the N-terminal end of said sequence. For example, X$_3$ and X$_7$ indicate the amino acid in position three and seven, respectively, from the N-terminal end of said BM.

In embodiments according to the first aspect, there is provided an FcRn binding dimer, in which at least one of said first and second monomer units comprises an FcRn binding motif, wherein X$_n$ is independently selected from a group of possible residues according to Table 1. The skilled person will appreciate that X$_n$ may be selected from any one of the listed groups of possible residues and that this selection is independent from the selection of amino acids in X$_m$, wherein n≠m. Thus, any of the listed possible residues in position X$_n$ in Table 1 may be independently combined with any of the herein disclosed possible residues in any other variable position in Table 1.

The skilled person will appreciate that Table 1 is to be read as follows: In one embodiment according to the first aspect, there is provided an FcRn binding dimer, wherein said first monomer unit and said second monomer unit each comprise an FcRn binding motif (BM) and wherein amino acid residue "X$_n$" in the BM of at least one of said first monomer unit and said second monomer unit is selected from "Possible residues". The skilled person will appreciate that the amino acid residue "X$_n$" in BM of the first monomer unit is selected independently of the amino acid residue "X$_n$" in BM of the second monomer unit. Thus, Table 1 discloses several specific and individualized variants of the first monomer unit and the second monomer unit of the present disclosure. For example, in one embodiment, there is provided an FcRn binding dimer, comprising at least one first or second monomer unit, wherein X$_2$ in BM is selected from A, I, L, N, Q, S, T, V and W, and in another embodiment, there is provided provided an FcRn binding dimer, comprising at least one first or second monomer unit, wherein X$_2$ in BM is selected from A, I, L and Q. For avoidance of doubt, said first and second monomer units may be freely combined in other embodiments. For example, in one such embodiment, X$_3$ is selected from A, D, E, G, H, K, L, M, N, Q, R, S and T, while X$_7$ is selected from A and H, and X$_{25}$ is selected from H, L, R, V and W.

TABLE 1

Possible residues in variable positions of the FcRn binding motif of the present disclosure.

| X$_n$ | Possible residues |
| --- | --- |
| X$_2$ | A, D, E, F, I, L, N, Q, R, S, T, V, W, Y |
| X$_2$ | A, D, F, I, L, N, Q, R, S, T, V, W, Y |
| X$_2$ | A, D, F, I, L, N, Q, R, S, V, W |
| X$_2$ | A, I, L, N, Q, R, S, T, V, W, Y |
| X$_2$ | A, I, L, N, Q, S, T, V, W |
| X$_2$ | A, I, L, N, Q, V, W |
| X$_2$ | A, I, L, Q, V, W |
| X$_2$ | A, I, L, Q, W |
| X$_2$ | A, I, L, Q |
| X$_2$ | I, L, Q |
| X$_2$ | I, Q |
| X$_2$ | A, W |
| X$_2$ | A |
| X$_2$ | W |
| X$_2$ | I |
| X$_2$ | Q |
| X$_3$ | A, D, E, G, H, K, L, M, N, Q, R, S, T, V, Y |
| X$_3$ | A, D, E, H, K, L, M, N, Q, R, S, T, V, Y |
| X$_3$ | A, D, E, G, H, K, L, M, N, Q, R, S, T |
| X$_3$ | A, D, E, G, H, K, M, N, Q, S, T |
| X$_3$ | A, D, E, G, H, M, N, Q, S, T |

TABLE 1-continued

Possible residues in variable positions of the FcRn binding motif of the present disclosure.

| $X_n$ | Possible residues |
|---|---|
| $X_3$ | A, D, E, K, N, Q, S, T |
| $X_3$ | A, D, E, K, Q, T |
| $X_3$ | A, D, E, Q, T |
| $X_3$ | D, E, T |
| $X_3$ | D, Q, T |
| $X_3$ | D, E |
| $X_3$ | D, Q |
| $X_3$ | D, T |
| $X_3$ | Q, T |
| $X_3$ | D |
| $X_3$ | E |
| $X_3$ | T |
| $X_3$ | Q |
| $X_4$ | A, D, E, F, G, I, K, L, N, Q, R, S, T, V, Y |
| $X_4$ | A, D, E, G, N, Q, R, S, T, V |
| $X_4$ | A, D, E, F, I, K, L, N, Q, R, S, T, V |
| $X_4$ | A, D, E, I, K, N, Q, R, S, T |
| $X_4$ | A, D, E, I, K, Q, S, T |
| $X_4$ | A, D, I, K, Q, S |
| $X_4$ | A, D, E, K, S |
| $X_4$ | A, D, K, S |
| $X_4$ | A, D, E, K |
| $X_4$ | A, D, K, Q |
| $X_4$ | A, D, K |
| $X_4$ | A, D, K, I |
| $X_4$ | A, D |
| $X_4$ | A, E |
| $X_4$ | A, Q |
| $X_4$ | A |
| $X_4$ | D |
| $X_4$ | E |
| $X_4$ | Q |
| $X_6$ | A, G, K, Q, R, S, V |
| $X_6$ | A, G, K, R, S, V |
| $X_6$ | A, G, K, R, S |
| $X_6$ | A, G, K, S, V |
| $X_6$ | A, G, K, V |
| $X_6$ | A, G, K, S |
| $X_6$ | A, G, K |
| $X_6$ | A, G, V |
| $X_6$ | A, G |
| $X_6$ | A |
| $X_6$ | G |
| $X_7$ | A, H, K, R |
| $X_7$ | A, H |
| $X_7$ | H |
| $X_{16}$ | T |
| $X_{16}$ | N |
| $X_{17}$ | F, Y |
| $X_{17}$ | F |
| $X_{18}$ | A, D, E |
| $X_{18}$ | A, D |
| $X_{18}$ | D |
| $X_{21}$ | V, W |
| $X_{21}$ | V |
| $X_{25}$ | D, E, H, K, L, N, Q, R, S, T, V, W, Y |
| $X_{25}$ | D, E, G, H, K, L, N, Q, R, V, W |
| $X_{25}$ | E, H, L, N, Q, R, T, V, W |
| $X_{25}$ | D, G, H, K, L, N, R, V, W |
| $X_{25}$ | H, L, R, V, W |
| $X_{25}$ | H, R, V, W |
| $X_{25}$ | H, R, V |
| $X_{25}$ | H, L, R |
| $X_{25}$ | H, R |
| $X_{25}$ | H, V |
| $X_{25}$ | H |
| $X_{26}$ | K |
| $X_{26}$ | S |
| $X_{28}$ | A, D, E, H, K, L, N, Q, R, S, T, W, Y |
| $X_{28}$ | A, D, E, K, L, N, Q, R, S, T, W, Y |
| $X_{28}$ | A, D, E, L, R, S, T, W, Y |
| $X_{28}$ | A, D, K, L, N, Q, R, S, T, W |
| $X_{28}$ | A, D, K, N, R, W |
| $X_{28}$ | A, D, R |
| $X_{28}$ | A, R |
| $X_{28}$ | D, R |
| $X_{28}$ | A |
| $X_{28}$ | R |
| $X_{28}$ | D |
| $X_{29}$ | D |
| $X_{29}$ | R |

In one embodiment, there is provided an FcRn binding dimer, wherein $X_6X_7$ is selected from AH and GH in at least one of said first and second monomer units. In one embodiment, $X_6X_7$ is AH. In one embodiment, $X_6X_7$ is GH. In one embodiment, $X_{17}X_{18}$ is selected from FD and YD in at least one of said first and second monomer units. In one embodiment, $X_{17}X_{18}$ is FD.

In a more specific embodiment defining a sub-class of FcRn binding dimers, the sequence of the BM of at least one of said first and second monomer units fulfills at least three of the six conditions I-VI:

I. $X_6$ is selected from A, G, K and S, such as in particular A;
II. $X_7$ is H;
III. $X_{17}$ is selected from F and Y, such as in particular F;
IV. $X_{18}$ is D;
V. $X_{21}$ is selected from V and W, such as in particular V;
VI. $X_{25}$ is selected from H and R, such as in particular H.

In some examples of an FcRn binding dimer according to the first aspect, said sequence fulfills at least four of the six conditions I-VI. More specifically, the sequence may fulfill at least five of the six conditions I-VI, such as all of the six conditions I-VI.

In one embodiment, the BM sequences of said first and second monomer units are identical. In another embodiment, the BM sequences of said first and second monomer units are different.

As described in detail in the experimental section to follow, the selection of FcRn binding polypeptide monomer units has led to the identification of a number of individual FcRn binding motif (BM) sequences. These sequences constitute individual variants useful as first and second monomer units as disclosed herein. The sequences of individual FcRn binding motifs (BMs) are presented in FIG. 1 and correspond to the sequence from position 8 to position 36 in a sequence selected from the group consisting of SEQ ID NO:1-353. Hence, in one embodiment of the FcRn binding dimer according to the first aspect, at least one of said first and second monomer units comprises a BM corresponding to the sequence from position 8 to position 36 in a sequence selected from the group consisting of SEQ ID NO:1-353, such as selected from the group consisting of SEQ ID NO:17-352. In one embodiment, said BM sequence corresponds to the sequence from position 8 to position 36 in a sequence selected from the group consisting of SEQ ID NO:1-15, SEQ ID NO:17-140 and SEQ ID NO:353, such as the group consisting of SEQ ID NO:17-140. In one embodiment, said sequence corresponds to the sequence from position 8 to position 36 in a sequence selected from the group consisting of SEQ ID NO:1-2 and SEQ ID NO:17-

140. In one embodiment, said sequence corresponds to the sequence from position 8 to position 36 in a sequence selected from the group consisting of SEQ ID NO:1-2, SEQ ID NO:17-92, SEQ ID NO:94-103, SEQ ID NO:105-125 and SEQ ID NO:127-140, such as the group consisting of SEQ ID NO:17-92, SEQ ID NO:94-103, SEQ ID NO:105-125 and SEQ ID NO:127-140. In one embodiment, said sequence corresponds to the sequence from position 8 to position 36 in a sequence selected from the group consisting of SEQ ID NO:1-8, SEQ ID NO:13, SEQ ID NO:19-20, SEQ ID NO:23, SEQ ID NO:28, SEQ ID NO:41, SEQ ID NO:44, SEQ ID NO:65, SEQ ID NO:70, SEQ ID NO:73, SEQ ID NO:75-77 and SEQ ID NO:353, such as the group consisting of SEQ ID NO:19-20, SEQ ID NO:23, SEQ ID NO:28, SEQ ID NO:41, SEQ ID NO:44, SEQ ID NO:65, SEQ ID NO:70, SEQ ID NO:73 and SEQ ID NO:75-77. In another embodiment, said sequence corresponds to the sequence from position 8 to position 36 in a sequence selected from the group consisting of SEQ ID NO:1, SEQ ID NO:23, SEQ ID NO:28, SEQ ID NO:41, SEQ ID NO:44, SEQ ID NO:65, SEQ ID NO:73 and SEQ ID NO:75-77, such as the group consisting of SEQ ID NO:23, SEQ ID NO:28, SEQ ID NO:41, SEQ ID NO:44, SEQ ID NO:65, SEQ ID NO:73 and SEQ ID NO:75-77. In another embodiment, said sequence corresponds to the sequence from position 8 to position 36 in a sequence selected from the group consisting of SEQ ID NO:1, SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77, such as the group consisting of SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77. In yet another embodiment, said sequence corresponds to the sequence from position 8 to position 36 in a sequence selected from the group consisting of SEQ ID NO:1, SEQ ID NO:23, SEQ ID NO:44, SEQ ID NO:65, SEQ ID NO:75 and SEQ ID NO:77, such as the group consisting of SEQ ID NO:1, SEQ ID NO:23, SEQ ID NO:44, SEQ ID NO:65 and SEQ ID NO:75. In yet another embodiment, said sequence corresponds to the sequence from position 8 to position 36 in a sequence selected from the group consisting of SEQ ID NO:1, SEQ ID NO:20, SEQ ID NO:23, SEQ ID NO:41, SEQ ID NO:44, SEQ ID NO:65, SEQ ID NO:75 and SEQ ID NO:77, such as the group consisting of SEQ ID NO:1, SEQ ID NO:20, SEQ ID NO:23, SEQ ID NO:41, SEQ ID NO:44, SEQ ID NO:65 and SEQ ID NO:75. In yet another embodiment, said sequence corresponds to the sequence from position 8 to position 36 in a sequence selected from the group consisting of SEQ ID NO:23, SEQ ID NO:44, SEQ ID NO:65, SEQ ID NO:75 and SEQ ID NO:77, such as the group consisting of SEQ ID NO:23, SEQ ID NO:44, SEQ ID NO:65 and SEQ ID NO:75. In yet another embodiment, said sequence corresponds to the sequence from position 8 to position 36 in a sequence selected from the group consisting of SEQ ID NO:20, SEQ ID NO:23, SEQ ID NO:41, SEQ ID NO:44, SEQ ID NO:65, SEQ ID NO:75 and SEQ ID NO:77, such as the group consisting of SEQ ID NO:20, SEQ ID NO:23, SEQ ID NO:41, SEQ ID NO:44, SEQ ID NO:65 and SEQ ID NO:75, such as the group consisting of SEQ ID NO:20, SEQ ID NO:23, SEQ ID NO:41, SEQ ID NO:44 and SEQ ID NO:75. In one embodiment, said sequence corresponds to the sequence from position 8 to position 36 in a sequence selected from the group consisting of SEQ ID NO:1, SEQ ID NO:23 and SEQ ID NO:75, such as the group consisting of SEQ ID NO:23 and SEQ ID NO:75. In one embodiment, said sequence corresponds to the sequence from position 8 to position 36 in a sequence selected from the group consisting of SEQ ID NO:20, SEQ ID NO:41 and SEQ ID NO:44, such as the group consisting of SEQ ID NO:20 and SEQ ID NO:41; the group consisting of SEQ ID NO:20 and SEQ ID NO:44; or the group consisting of SEQ ID NO:41 and SEQ ID NO:44. In one embodiment, said sequence corresponds to the sequence from position 8 to position 36 in a sequence selected from the group consisting of SEQ ID NO:1, SEQ ID NO:23 and SEQ ID NO:44, such as the group consisting of SEQ ID NO:23 and SEQ ID NO:44. In one embodiment, said sequence corresponds to the sequence from position 8 to position 36 in SEQ ID NO:1 or SEQ ID NO:23 or SEQ ID NO:44. In one embodiment, said sequence corresponds to the sequence from position 8 to position 36 in SEQ ID NO:20 or SEQ ID NO:41 or SEQ ID NO:44

In one embodiment of the FcRn binding dimer as disclosed herein, both said first and second monomer units comprise a BM corresponding to the sequence from position 8 to position 36 in a sequence selected from one of the groups defined above. In one embodiment, said group consists of SEQ ID NO:1, SEQ ID NO:20, SEQ ID NO:23, SEQ ID NO:41, SEQ ID NO:44, SEQ ID NO:65 and SEQ ID NO:75. In one embodiment, said group consists of SEQ ID NO:20, SEQ ID NO:23, SEQ ID NO:41, SEQ ID NO:44 and SEQ ID NO:75. In one embodiment, said group consists of SEQ ID NO:1, SEQ ID NO:23, SEQ ID NO:44, SEQ ID NO:65 and SEQ ID NO:75. In another embodiment, said group consists of SEQ ID NO:1, SEQ ID NO:23 and SEQ ID NO:44. In yet another embodiment, said group consists of SEQ ID NO:20, SEQ ID NO:41 and SEQ ID NO:44. In one particular embodiment, both said first and second monomer units comprise a BM corresponding to the sequence from position 8 to position 36 in SEQ ID NO:1. In one embodiment, said BM corresponds to the sequence from position 8 to position 36 in SEQ ID NO:20. In one embodiment, said BM corresponds to the sequence from position 8 to position 36 in SEQ ID NO:23. In one embodiment, said BM corresponds to the sequence from position 8 to position 36 in SEQ ID NO:41. In one embodiment, said BM corresponds to the sequence from position 8 to position 36 in SEQ ID NO:44.

In some embodiments of the present disclosure, the BM as defined above "forms part of" a three-helix bundle protein domain. This is understood to mean that the sequence of the BM is "inserted" into or "grafted" onto the sequence of the original three-helix bundle domain, such that the BM replaces a similar structural motif in the original domain. For example, without wishing to be bound by theory, the BM is thought to constitute two of the three helices of a three-helix bundle, and can therefore replace such a two-helix motif within any three-helix bundle. As the skilled person will realize, the replacement of two helices of the three-helix bundle domain by the two BM helices has to be performed so as not to affect the basic structure of the polypeptide. That is, the overall folding of the $C\alpha$ backbone of the polypeptide according to this embodiment of the invention is substantially the same as that of the three-helix bundle protein domain of which it forms a part, e.g. having the same elements of secondary structure in the same order etc. Thus, a BM according to the disclosure "forms part" of a three-helix bundle domain if the polypeptide according to this embodiment of the aspect has the same fold as the original domain, implying that the basic structural properties are shared, those properties e.g. resulting in similar CD spectra. The skilled person is aware of other parameters that are relevant.

In particular embodiments, the FcRn binding motif (BM) in at least one of said first and second monomers thus forms part of a three-helix bundle protein domain. For example, the BM may essentially constitute two alpha helices with an interconnecting loop, within said three-helix bundle protein domain. In particular embodiments, said three-helix bundle protein domain is selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from domain B of staphylococcal Protein A.

In embodiments where the FcRn binding motif as disclosed herein forms part of a three-helix bundle protein domain, at least one of said first and second monomer units of the FcRn binding dimer may comprise a binding module (BMod), which module consists of an amino acid sequence selected from:

iii) K[BM]-DPSQS $X_a X_b LLX_c$ EAKKL $X_d X_e X_f Q$ (SEQ ID NO:392);
wherein
[BM] is an FcRn binding motif as defined herein in SEQ ID NO:389,
provided that $X_{29}$ is D;
$X_a$ is selected from A and S;
$X_b$ is selected from N and E;
$X_c$ is selected from A, S and C;
$X_d$ is selected from E, N and S;
$X_e$ is selected from D, E and S;
$X_f$ is selected from A and S;
and
iv) an amino acid sequence which has at least 93% identity to a sequence defined by iii).

In embodiments where the FcRn binding motif as disclosed herein forms part of a three-helix bundle protein domain, at least one of said first and second monomer units of the FcRn binding dimer may comprise a binding module (BMod), which module consists of an amino acid sequence selected from:

v) K-[BM]-QPEQS $X_a X_b LLX_c$ EAKKL $X_d X_e X_f Q$ (SEQ ID NO:393);
wherein
[BM] is an FcRn binding motif as defined herein in SEQ ID NO:389,
provided that $X_{29}$ is R;
$X_a$ is selected from A and S;
$X_b$ is selected from N and E;
$X_c$ is selected from A, S and C;
$X_d$ is selected from E, N and S;
$X_e$ is selected from D, E and S;
$X_f$ is selected from A and S;
and
vi) an amino acid sequence which has at least 93% identity to a sequence defined by v).

As discussed above, polypeptides comprising minor changes as compared to the above amino acid sequences which do not largely affect the tertiary structure and the function thereof are also within the scope of the present disclosure. Thus, in some embodiments, sequence iv) or sequence vi) has at least 95%, for example at least 97% identity to a sequence defined by iii) and v), respectively.

In one embodiment, there is provided an FcRn binding dimer, wherein at least one of said first and second monomer units comprises sequence iii) or v) wherein $X_a$ is A. In an alternative embodiment, $X_a$ in sequence iii) or v) is S. In one embodiment, $X_a$ in sequence iii) or v) is A. In one embodiment, $X_a$ in sequence iii) or v) is S.

In one embodiment, there is provided an FcRn binding dimer, wherein at least one of said first and second monomer units comprises sequence iii) or v) wherein $X_b$ is N. In one embodiment, $X_b$ in sequence iii) or v) is E.

In one embodiment, there is provided an FcRn binding dimer, wherein at least one of said first and second monomer units comprises sequence iii) or v) wherein $X_c$ is A. In one embodiment, $X_c$ in sequence iii) or v) is S. In one embodiment, $X_c$ in sequence iii) or v) is C.

In one embodiment, there is provided an FcRn binding dimer, wherein at least one of said first and second monomer units comprises sequence iii) or v) wherein $X_d$ is E. In one embodiment, $X_d$ in sequence iii) or v) is N. In one embodiment, $X_d$ in sequence iii) or v) is S.

In one embodiment, there is provided an FcRn binding dimer, wherein at least one of said first and second monomer units comprises sequence iii) or v) wherein $X_e$ is D. In one embodiment, $X_e$ in sequence iii) or v) is E. In one embodiment, $X_e$ in sequence iii) or v) is S.

In one embodiment, there is provided an FcRn binding dimer, wherein at least one of said first and second monomer units comprises sequence iii) or v) wherein $X_d X_e$ is selected from EE, ES, SD, SE and SS. In one embodiment, $X_d X_e$ in sequence iii) or v) is ES. In one embodiment, $X_d X_e$ in sequence iii) or v) is SE. In one embodiment, $X_d X_e$ in sequence iii) or v) is SD.

In one embodiment, there is provided an FcRn binding dimer, wherein at least one of said first and second monomer units comprises sequence iii) or v) wherein $X_f$ is A. In one embodiment, $X_f$ in sequence iii) or v) is S.

In one embodiment, there is provided an FcRn binding dimer, wherein at least one of said first and second monomer units comprises sequence iii) or v), wherein $X_a$ is A; $X_b$ is N; $X_c$ is A and $X_f$ is A.

In one embodiment, in sequence iii) or v), $X_a$ is S; $X_b$ is E; $X_c$ is A and $X_f$ is A.

In one embodiment, in sequence iii) or v), $X_a$ is A; $X_b$ is N; $X_c$ is C and $X_f$ is A.

In one embodiment, in sequence iii) or v), $X_a$ is S; $X_b$ is E; $X_c$ is S and $X_f$ is S.

In one embodiment, in sequence iii) or v), $X_a$ is S; $X_b$ is E; $X_c$ is C and $X_f$ is S.

In one embodiment, in sequence iii) or v), $X_a$ is A; $X_b$ is N; $X_c$ is A; $X_d X_e$ is ND and $X_f$ is A.

In one embodiment, in sequence iii) or v), $X_a$ is S; $X_b$ is E; $X_c$ is A; $X_d X_e$ is ND and $X_f$ is A.

In one embodiment, in sequence iii) or v), $X_a$ is A; $X_b$ is N; $X_c$ is C; $X_d X_e$ is ND and $X_f$ is A.

In one embodiment, in sequence iii) or v), $X_a$ is S; $X_b$ is E; $X_c$ is S; $X_d X_e$ is ND and $X_f$ is S.

In one embodiment, in sequence iii) or v), $X_a$ is S; $X_b$ is E; $X_c$ is C; $X_d X_e$ is ND and $X_f$ is S.

In one embodiment, in sequence iii) or v), $X_a$ is A; $X_b$ is N; $X_c$ is A; $X_d X_e$ is SE and $X_f$ is A.

In one embodiment, in sequence iii) or v), $X_a$ is S; $X_b$ is E; $X_c$ is A; $X_d X_e$ is SE and $X_f$ is A.

In one embodiment, in sequence iii) or v), $X_a$ is A; $X_b$ is N; $X_c$ is C; $X_d X_e$ is SE and $X_f$ is A.

In one embodiment, in sequence iii) or v), $X_a$ is S; $X_b$ is E; $X_c$ is S; $X_d X_e$ is SE and $X_f$ is S.

In one embodiment, in sequence iii) or v), $X_a$ is S; $X_b$ is E; $X_c$ is C; $X_d X_e$ is SE and $X_f$ is S.

In one embodiment, in sequence iii) or v), $X_a$ is A; $X_b$ is N; $X_c$ is A; $X_d X_e$ is ES and $X_f$ is A.

In one embodiment, in sequence iii) or v), $X_a$ is S; $X_b$ is E; $X_c$ is A; $X_dX_e$ is ES and $X_f$ is A.

In one embodiment, in sequence iii) or v), $X_a$ is A; $X_b$ is N; $X_c$ is C; $X_dX_e$ is ES and $X_f$ is A.

In one embodiment, in sequence iii) or v), $X_a$ is S; $X_b$ is E; $X_c$ is S; $X_dX_e$ is ES and $X_f$ is S.

In one embodiment, in sequence iii) or v), $X_a$ is S; $X_b$ is E; $X_c$ is C; $X_dX_e$ is ES and $X_f$ is S.

In one embodiment, in sequence iii) or v), $X_a$ is A; $X_b$ is N; $X_c$ is A; $X_dX_e$ is SD and $X_f$ is A.

In one embodiment, in sequence iii) or v), $X_a$ is S; $X_b$ is E; $X_c$ is A; $X_dX_e$ is SD and $X_f$ is A.

In one embodiment, in sequence iii) or v), $X_a$ is A; $X_b$ is N; $X_c$ is C; $X_dX_e$ is SD and $X_f$ is A.

In one embodiment, in sequence iii) or v), $X_a$ is S; $X_b$ is E; $X_c$ is S; $X_dX_e$ is SD and $X_f$ is S.

In one embodiment, in sequence iii) or v), $X_a$ is S; $X_b$ is E; $X_c$ is C; $X_dX_e$ is SD and $X_f$ is S.

In one embodiment of the FcRn binding dimer according to the first aspect, at least one of said first and second monomer units comprises a BMod according to sequence iii) corresponding to the sequence from position 7 to position 55 in a sequence selected from the group consisting of SEQ ID NO:1-353, SEQ ID NO:358 and SEQ ID NO:360-364. Hence, in one embodiment of the FcRn binding dimer according to the first aspect, at least one of said first and second monomer units comprises a BMod corresponding to the sequence from position 7 to position 55 in a sequence selected from the group consisting of SEQ ID NO:1-353, SEQ ID NO:358 and SEQ ID NO:360-364, such as the group consisting of SEQ ID NO:17-352 and SEQ ID NO:360-364. In one embodiment, said BMod corresponds to the sequence from position 7 to position 55 in a sequence selected from the group consisting of SEQ ID NO:1-15, SEQ ID NO:17-140, SEQ ID NO:353, SEQ ID NO:358 and SEQ ID NO:360-364, such as the group consisting of SEQ ID NO:17-140 and SEQ ID NO:360-364. In one embodiment, said BMod corresponds to the sequence from position 7 to position 55 in a sequence selected from the group consisting of SEQ ID NO:1-2, SEQ ID NO:17-140, SEQ ID NO:358 and SEQ ID NO:360-364. In one embodiment, said BMod corresponds to the sequence from position 7 to position 55 in a sequence selected from the group consisting of SEQ ID NO:1-2, SEQ ID NO:17-92, SEQ ID NO:94-103, SEQ ID NO:105-125, SEQ ID NO:127-140, SEQ ID NO:358 and SEQ ID NO:360-364, such as the group consisting of SEQ ID NO:17-92, SEQ ID NO:94-103, SEQ ID NO:105-125, SEQ ID NO:127-140 and SEQ ID NO:360-364. In one embodiment, said BMod corresponds to the sequence from position 7 to position 55 in a sequence selected from the group consisting of SEQ ID NO:1-8, SEQ ID NO:13, SEQ ID NO:19-20, SEQ ID NO:23, SEQ ID NO:28, SEQ ID NO:41, SEQ ID NO:44, SEQ ID NO:65, SEQ ID NO:70, SEQ ID NO:73, SEQ ID NO:75-77, SEQ ID NO:353, SEQ ID NO:358 and SEQ ID NO:360-364, such as the group consisting of SEQ ID NO:19-20, SEQ ID NO:23, SEQ ID NO:28, SEQ ID NO:41, SEQ ID NO:44, SEQ ID NO:65, SEQ ID NO:70, SEQ ID NO:73, SEQ ID NO:75-77 and SEQ ID NO:360-364. In another embodiment, said BMod corresponds to the sequence from position 7 to position 55 in a sequence selected from the group consisting of SEQ ID NO:1, SEQ ID NO:20, SEQ ID NO:23, SEQ ID NO:28, SEQ ID NO:41, SEQ ID NO:44, SEQ ID NO:65, SEQ ID NO:73, SEQ ID NO:75-77, SEQ ID NO:358 and SEQ ID NO:360-364, such as the group consisting of SEQ ID NO:20, SEQ ID NO:23, SEQ ID NO:28, SEQ ID NO:41, SEQ ID NO:44, SEQ ID NO:65, SEQ ID NO:73, SEQ ID NO:75-77 and SEQ ID NO:360-364. In another embodiment, said BMod corresponds to the sequence from position 7 to position 55 in a sequence selected from the group consisting of SEQ ID NO:1, SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77, such as the group consisting of SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77. In another embodiment, said BMod corresponds to the sequence from position 7 to position 55 in a sequence selected from the group consisting of SEQ ID NO:1, SEQ ID NO:23, SEQ ID NO:28, SEQ ID NO:41, SEQ ID NO:44, SEQ ID NO:65, SEQ ID NO:73 and SEQ ID NO:75-77, such as the group consisting of SEQ ID NO:23, SEQ ID NO:28, SEQ ID NO:41, SEQ ID NO:44, SEQ ID NO:65, SEQ ID NO:73 and SEQ ID NO:75-77. In yet another embodiment, said BMod corresponds to the sequence from position 7 to position 55 in a sequence selected from the group consisting of SEQ ID NO:1, SEQ ID NO:20, SEQ ID NO:23, SEQ ID NO: 41, SEQ ID NO:44, SEQ ID NO:65, SEQ ID NO:75, SEQ ID NO:77, SEQ ID NO:358 and SEQ ID NO:360-364, such as the group consisting of, SEQ ID NO:20, SEQ ID NO:23, SEQ ID NO:41, SEQ ID NO:44, SEQ ID NO:65, SEQ ID NO:75 and SEQ ID NO:360-364. In another embodiment, said BMod corresponds to the sequence from position 7 to position 55 in a sequence selected from the group consisting of SEQ ID NO:20, SEQ ID NO:23, SEQ ID NO:41, SEQ ID NO:44, SEQ ID NO:65, SEQ ID NO:75 and SEQ ID NO:360-364. In yet another embodiment, said BMod corresponds to the sequence from position 7 to position 55 in a sequence selected from the group consisting of SEQ ID NO:1, SEQ ID NO:20, SEQ ID NO:23, SEQ ID NO:41, SEQ ID NO:44, SEQ ID NO:65, SEQ ID NO:75, SEQ ID NO:358 and SEQ ID NO:360-364, such as the group consisting of SEQ ID NO:20, SEQ ID NO:23, SEQ ID NO:41, SEQ ID NO:44, SEQ ID NO:75 and SEQ ID NO:360-364. In yet another embodiment, said BMod corresponds to the sequence from position 7 to position 55 in a sequence selected from the group consisting of SEQ ID NO:1, SEQ ID NO:23, SEQ ID NO:44, SEQ ID NO:65, SEQ ID NO:75 and SEQ ID NO:77, such as the group consisting of SEQ ID NO:1, SEQ ID NO:23, SEQ ID NO:44, SEQ ID NO:65 and SEQ ID NO:75. In another embodiment, said BMod corresponds to the sequence from position 7 to position 55 in a sequence selected from the group consisting of SEQ ID NO:20, SEQ ID NO:23, SEQ ID NO:41, SEQ ID NO:44, SEQ ID NO:65, SEQ ID NO:75 and SEQ ID NO:77, such as the group consisting of SEQ ID NO:20, SEQ ID NO:23, SEQ ID NO:41, SEQ ID NO:44, SEQ ID NO:65 and SEQ ID NO:75, such as the group consisting of SEQ ID NO:20, SEQ ID NO:23, SEQ ID NO:41, SEQ ID NO:44 and SEQ ID NO:75. In yet another embodiment, said BMod corresponds to the sequence from position 7 to position 55 in a sequence selected from the group consisting of SEQ ID NO:23, SEQ ID NO:44, SEQ ID NO:65, SEQ ID NO:75 and SEQ ID NO:77, such as the group consisting of SEQ ID NO:23, SEQ ID NO:44, SEQ ID NO:65 and SEQ ID NO:75. In one embodiment, said BMod corresponds to the sequence from position 7 to position 55 in a sequence selected from the group consisting of SEQ ID NO:1, SEQ ID NO:23 SEQ ID NO:75, SEQ ID NO:358, SEQ ID NO:361 and SEQ ID NO:364, such as the group consisting of SEQ ID NO:23, SEQ ID NO:75, SEQ ID NO:361 and SEQ ID NO:364. In one embodiment, said BMod corresponds to the sequence from position 7 to position 55 in a sequence selected from the group consisting of SEQ ID NO:1, SEQ ID NO:23 and SEQ ID NO:75, such as the group consisting of SEQ ID NO:23 and SEQ ID NO:75.

In one embodiment, said BMod corresponds to the sequence from position 7 to position 55 in a sequence selected from the group consisting of SEQ ID NO:20, SEQ ID NO:41, SEQ ID NO:44, SEQ ID NO:360, SEQ ID NO:362 and SEQ ID NO:363, such as the group consisting of SEQ ID NO:20, SEQ ID NO:41, SEQ ID NO:360 and SEQ ID NO:362; the group consisting of SEQ ID NO:20, SEQ ID NO:44, SEQ ID NO:360 and SEQ ID NO:363; or the group consisting of SEQ ID NO:41, SEQ ID NO:44, SEQ ID NO:362 and SEQ ID NO:363.

In one embodiment, said BMod corresponds to the sequence from position 7 to position 55 in a sequence selected from the group consisting of SEQ ID NO:1, SEQ ID NO:23, SEQ ID NO:44, SEQ ID NO:358, SEQ ID NO:361 and SEQ ID NO:363, such as the group consisting of SEQ ID NO:23, SEQ ID NO:44, SEQ ID NO:361 and SEQ ID NO:363. In one embodiment, said BMod corresponds to the sequence from position 7 to position 55 in a sequence selected from the group consisting of SEQ ID NO:1, SEQ ID NO:23 and SEQ ID NO:44, such as the group consisting of SEQ ID NO:23 and SEQ ID NO:44. In one embodiment, said BMod corresponds to the sequence from position 7 to position 55 in SEQ ID NO:1 or SEQ ID NO:23 or SEQ ID NO:44. In one embodiment, said BMod corresponds to the sequence from position 7 to position 55 in SEQ ID NO:20 or SEQ ID NO:41 or SEQ ID NO:44. In one embodiment, said BMod corresponds to the sequence from position 7 to position 55 in SEQ ID NO:360 or SEQ ID NO:362 or SEQ ID NO:363.

In one embodiment of the FcRn binding dimer as disclosed herein, both of said first and second monomer units comprise a BMod corresponding to the sequence from position 7 to position 55 in a sequence selected from one of the groups defined above. In one embodiment, said group consists of SEQ ID NO:1, SEQ ID NO:20, SEQ ID NO:23, SEQ ID NO:41, SEQ ID NO:44, SEQ ID NO:65, SEQ ID NO:75, SEQ ID NO:358 and SEQ ID NO:360-364. In one embodiment, said group consists of SEQ ID NO:20, SEQ ID NO:23, SEQ ID NO:41, SEQ ID NO:44, SEQ ID NO:75 and SEQ ID NO:360-364. In one embodiment, said group consists of SEQ ID NO:20, SEQ ID NO:23, SEQ ID NO:41, SEQ ID NO:44 and SEQ ID NO:75. In another embodiment, said group consists of SEQ ID NO:360-364. In one embodiment, said group consists of SEQ ID NO:1, SEQ ID NO:23, SEQ ID NO:44, SEQ ID NO:65 and SEQ ID NO:75. In another embodiment, said group consists of SEQ ID NO:1, SEQ ID NO:23 and SEQ ID NO:44. In one embodiment, said group consists of SEQ ID NO:20, SEQ ID NO:41, SEQ ID NO:44, SEQ ID NO:360, SEQ ID NO:362 and SEQ ID NO:363. In another embodiment, said group consists of SEQ ID NO:20, SEQ ID NO:41 and SEQ ID NO:44. In another embodiment, said group consists of SEQ ID NO:360, SEQ ID NO:362 and SEQ ID NO:363. In one particular embodiment, both said first and second monomer units comprise a BMod corresponding to the sequence from position 7 to position 55 in SEQ ID NO:1 or SEQ ID NO:358. In one embodiment, said BMod corresponds to the sequence from position 7 to position 55 in SEQ ID NO:20 or SEQ ID NO:360. In one embodiment, said BMod corresponds to the sequence from position 7 to position 55 in SEQ ID NO:23 or SEQ ID NO:361. In one embodiment, said BMod corresponds to the sequence from position 7 to position 55 in SEQ ID NO:41 or SEQ ID NO:362. In one embodiment, said BMod corresponds to the sequence from position 7 to position 55 in SEQ ID NO:44 or SEQ ID NO:363. In one embodiment, said BMod corresponds to the sequence from position 7 to position 55 in SEQ ID NO:75 or SEQ ID NO:364.

Also, in a further embodiment, there is provided an FcRn binding dimer as defined above, wherein at least one of said first and second monomer units comprises a sequence selected from the group consisting of:
vii) YAK-[BM]-DPSQS SELLX$_c$ EAKKL NDSQA P (SEQ ID NO:394); wherein [BM] is an FcRn binding motif as defined above in SEQ ID NO:389 and X$_c$ is selected from A, S and C; and
viii) an amino acid sequence which has at least 94% identity to a sequence defined by vii).

In another embodiment, there is provided an FcRn binding dimer as defined above, wherein at least one of said first and second monomer units comprises a sequence selected from the group consisting of:
ix) FAK-[BM]-DPSQS SELLX$_c$ EAKKL SESQA P (SEQ ID NO:395); wherein [BM] is an FcRn binding motif as defined above in SEQ ID NO:389 and X$_c$ is selected from A, S and C; and
x) an amino acid sequence which has at least 94% identity to a sequence defined by ix).

In one embodiment, X$_c$ in the sequence defined by ix) is S.

Alternatively, there is provided an FcRn binding dimer as defined above, wherein at least one of said first and second monomer units comprises a sequence selected from the group consisting of:
xi) FNK-[BM]-DPSQS ANLLX$_c$ EAKKL NDAQA P (SEQ ID NO:463); wherein [BM] is an FcRn binding motif as defined above in SEQ ID NO:389 and X$_c$ is selected from A and C; and
xii) an amino acid sequence which has at least 94% identity to a sequence defined by xi).

As discussed above, polypeptides comprising minor changes as compared to the above amino acid sequences that do not largely affect the tertiary structure and the function thereof are also within the scope of the present disclosure. Thus, in some embodiments, the FcRn binding dimer as defined above may comprise a sequence viii), x) or xii) which is at least 96%, such as at least 98% identical to a sequence defined by vii), ix) or xi), respectively.

In some embodiments of the FcRn binding dimer, at least one of said first and second monomer units may comprise an amino acid sequence selected from
ADNNFNK-[BM]-DPSQSANLLSEAKKLNESQAPK (SEQ ID NO:396);
ADNKFNK-[BM]-DPSQSANLLAEAKKLNDAQAPK (SEQ ID NO:397);
ADNKFNK-[BM]-DPSVSKEILAEAKKLNDAQAPK (SEQ ID NO:398);
ADAQQNNFNK-[BM]-DPSQSTNVLGEAKKL-NESQAPK (SEQ ID NO:399);
AQHDE-[BM]-DPSQSANVLGEAQKLNDSQAPK (SEQ ID NO:400);
VDNKFNK-[BM]-DPSQSANLLAEAKKLNDAQAPK (SEQ ID NO:401);
AEAKYAK-[BM]-DPSESSELLSEAKKLNKSQAPK (SEQ ID NO:402);
VDAKYAK-[BM]-DPSQSSELLAEAKKLNDAQAPK (SEQ ID NO:403);
VDAKYAK-[BM]-DPSQSSELLAEAKKLNDSQAPK (SEQ ID NO:404);
AEAKYAK-[BM]-DPSQSSELLSEAKKLNDSQAPK (SEQ ID NO:405);

AEAKYAK-[BM]-DPSQSSELLSEAKKLNDSQAP (SEQ ID NO:406);
AEAKFAK-[BM]-DPSQSSELLSEAKKLNDSQAPK (SEQ ID NO:407);
AEAKFAK-[BM]-DPSQSSELLSEAKKLNDSQAP (SEQ ID NO:408);
AEAKYAK-[BM]-DPSQSSELLAEAKKLNDAQAPK (SEQ ID NO:409);
AEAKYAK-[BM]-DPSQSSELLSEAKKLSESQAPK (SEQ ID NO:410);
AEAKYAK-[BM]-DPSQSSELLSEAKKLSESQAP (SEQ ID NO:411);
AEAKFAK-[BM]-DPSQSSELLSEAKKLSESQAPK (SEQ ID NO:412);
AEAKFAK-[BM]-DPSQSSELLSEAKKLSESQAP (SEQ ID NO:413);
AEAKYAK-[BM]-DPSQSSELLAEAKKLSEAQAPK (SEQ ID NO:414);
AEAKYAK-[BM]-QPEQSSELLSEAKKLSESQAPK (SEQ ID NO:415);
AEAKYAK-[BM]-DPSQSSELLSEAKKLESSQAPK (SEQ ID NO:416);
AEAKYAK-[BM]-DPSQSSELLSEAKKLESSQAP (SEQ ID NO:417);
AEAKYAK-[BM]-DPSQSSELLAEAKKLESAQAPK (SEQ ID NO:418);
AEAKYAK-[BM]-QPEQSSELLSEAKKLESSQAPK (SEQ ID NO:419);
AEAKYAK-[BM]-DPSQSSELLSEAKKLSDSQAPK (SEQ ID NO:420);
AEAKYAK-[BM]-DPSQSSELLSEAKKLSDSQAP (SEQ ID NO:421);
AEAKYAK-[BM]-DPSQSSELLAEAKKLSDAQAPK (SEQ ID NO:422);
AEAKYAK-[BM]-QPEQSSELLSEAKKLSDSQAPK (SEQ ID NO:423);
VDAKYAK-[BM]-DPSQSSELLSEAKKLNDSQAPK (SEQ ID NO:424);
VDAKFAK-[BM]-DPSQSSELLSEAKKLNDSQAPK (SEQ ID NO:425);
VDAKYAK-[BM]-DPSQSSELLAEAKKLNDAQAPK (SEQ ID NO:426);
VDAKYAK-[BM]-DPSQSSELLSEAKKLSESQAPK (SEQ ID NO:427);
VDAKFAK-[BM]-DPSQSSELLSEAKKLSESQAPK (SEQ ID NO:428);
VDAKYAK-[BM]-DPSQSSELLAEAKKLSEAQAPK (SEQ ID NO:429);
VDAKYAK-[BM]-QPEQSSELLSEAKKLSESQAPK (SEQ ID NO:430);
VDAKYAK-[BM]-DPSQSSELLSEAKKLESSQAPK (SEQ ID NO:431);
VDAKYAK-[BM]-DPSQSSELLAEAKKLESAQAPK (SEQ ID NO:432);
VDAKYAK-[BM]-QPEQSSELLSEAKKLESSQAPK (SEQ ID NO:433);
VDAKYAK-[BM]-DPSQSSELLSEAKKLSDSQAPK (SEQ ID NO:434);
VDAKYAK-[BM]-DPSQSSELLAEAKKLSDAQAPK (SEQ ID NO:435);
VDAKYAK-[BM]-QPEQSSELLSEAKKLSDSQAPK (SEQ ID NO:436);
VDAKYAK-[BM]-DPSQSSELLAEAKKLNKAQAPK (SEQ ID NO:437);
AEAKYAK-[BM]-DPSQSSELLAEAKKLNKAQAPK (SEQ ID NO:438);
and
ADAKYAK-[BM]-DPSQSSELLSEAKKLNDSQAPK (SEQ ID NO:439); wherein [BM] is an FcRn binding motif as defined above in SEQ ID NO:389.

In one embodiment, at least one of said first and second monomer units of the FcRn binding dimer may comprise an amino acid sequence selected from:
xiii) AEAKYAK-[BM]-DPSQSSELLSEAKKLND-SQAPK (SEQ ID NO:405); wherein [BM] is an FcRn binding motif as defined above in SEQ ID NO:389; and
xiv) an amino acid sequence which has at least 94% identity to the sequence defined in xiii).

In one embodiment, sequence xiii) is selected from the group consisting of SEQ ID NO:354-357, such as in particular selected from the group consisting of SEQ ID NO:354 and 357.

In one embodiment, both said first and second monomer units comprise a sequence xiii) selected from the group consisting of SEQ ID NO:354-357, such as in particular selected from the group consisting of SEQ ID NO:354 and 357. In one embodiment, said sequence xiii) is SEQ ID NO:354 in both said first and second monomer units. In one embodiment, said sequence xiii) is SEQ ID NO:357 in both said first and second monomer units.

In one embodiment, at least one of said first and second monomer units of the FcRn binding dimer may comprise an amino acid sequence selected from:
xv) AEAKFAK-[BM]-DPSQSSELLSEAKKLSESQAPK (SEQ ID NO:412);
wherein [BM] is an FcRn binding motif as defined above in SEQ ID NO:389; and
xvi) an amino acid sequence which has at least 94% identity to the sequence defined in xv).

In one embodiment, sequence xv) is selected from the group consisting of SEQ ID NO:365-367. In one embodiment, sequence xv) is SEQ ID NO:365, SEQ ID NO:366 or SEQ ID NO:367.

In one embodiment, at least one of said first and second monomer units of the FcRn binding dimer may comprise an amino acid sequence selected from:
xvii) VDAKYAK-[BM]-DPSQSSELLSEAKKLS-ESQAPK (SEQ ID NO:427);
wherein [BM] is an FcRn binding motif as defined above in SEQ ID NO:389; and
xviii) an amino acid sequence which has at least 94% identity to the sequence defined in xvii).

In one embodiment, sequence xvii) is selected from the group consisting of SEQ ID NO:360-364. In one embodiment, sequence xvii) is SEQ ID NO:360, SEQ ID NO:361. SEQ ID NO:362, SEQ ID NO:363 or SEQ ID NO:364.

In one embodiment, at least one of said first and second monomer units of the FcRn binding dimer may comprise an amino acid sequence selected from:
xix) AEAKYAK-[BM]-RQPESSELLSEAKKLS-ESQAPK (SEQ ID NO:440);
wherein [BM] is an FcRn binding motif as defined above in SEQ ID NO:389; and
xx) an amino acid sequence which has at least 94% identity to the sequence defined in xix).

In one embodiment, sequence xix) is SEQ ID NO:359.

In one embodiment, at least one of said first and second monomer units of the FcRn binding dimer may comprise an amino acid sequence selected from:
xxi) VDAKYAK-[BM]-DPSQSSELLSEAKKLND-SQAPK (SEQ ID NO:424); wherein [BM] is an FcRn binding motif as defined above in SEQ ID NO:389; and
xxii) an amino acid sequence which has at least 94% identity to the sequence defined in xxi).

Again, polypeptides comprising minor changes as compared to the above amino acid sequences which do not largely affect the tertiary structure and the function thereof are also within the scope of the present disclosure. Thus, in some embodiments, the FcRn binding dimer as defined above may comprise a sequence xiv), xvi), xviii), xx) or xxii) which is at least 96%, such as at least 98% identical to a sequence defined by xiii), xv), xvii), xix) or xxi), respectively.

In one embodiment of the FcRn binding dimer according to the first aspect, at least one of said first and second monomer units comprises a sequence xxi) selected from the group consisting of SEQ ID NO:1-353, such as the group consisting of SEQ ID NO:17-352. In one embodiment, said sequence xxi) is a sequence selected from the group consisting of SEQ ID NO:1-15, SEQ ID NO:17-140 and SEQ ID NO:353, such as the group consisting of SEQ ID NO:17-140. In one embodiment, said sequence xxi) is a sequence selected from the group consisting of SEQ ID NO:1-2 and SEQ ID NO:17-140. In one embodiment, said sequence xxi) is a sequence selected from the group consisting of SEQ ID NO:1-2, SEQ ID NO:17-92, SEQ ID NO:94-103, SEQ ID NO:105-125 and SEQ ID NO:127-140, such as the group consisting of SEQ ID NO:17-92, SEQ ID NO:94-103, SEQ ID NO:105-125 and SEQ ID NO:127-140. In one embodiment, said sequence xxi) is a sequence selected from the group consisting of SEQ ID NO:1-8, SEQ ID NO:13, SEQ ID NO:19-20, SEQ ID NO:23, SEQ ID NO:28, SEQ ID NO:41, SEQ ID NO:44, SEQ ID NO:65, SEQ ID NO:70, SEQ ID NO:73, SEQ ID NO:75-77 and SEQ ID NO:353, such as the group consisting of SEQ ID NO:19-20, SEQ ID NO:23, SEQ ID NO:28, SEQ ID NO:41, SEQ ID NO:44, SEQ ID NO:65, SEQ ID NO:70, SEQ ID NO:73 and SEQ ID NO:75-77. In another embodiment, said sequence xxi) is a sequence selected from the group consisting of SEQ ID NO:1, SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77, such as the group consisting of SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77. In another embodiment, said sequence xxi) is a sequence selected from the group consisting of SEQ ID NO:1, SEQ ID NO:23, SEQ ID NO:28, SEQ ID NO:41, SEQ ID NO:44, SEQ ID NO:65, SEQ ID NO:73 and SEQ ID NO:75-77, such as the group consisting of SEQ ID NO:23, SEQ ID NO:28, SEQ ID NO:41, SEQ ID NO:44, SEQ ID NO:65, SEQ ID NO:73 and SEQ ID NO:75-77. In yet another embodiment, said sequence xxi) is a sequence selected from the group consisting of SEQ ID NO:1, SEQ ID NO:20, SEQ ID NO:23, SEQ ID NO:41, SEQ ID NO:44, SEQ ID NO:65, SEQ ID NO:75 and SEQ ID NO:77, such as the group consisting of SEQ ID NO:1, SEQ ID NO:20, SEQ ID NO:23, SEQ ID NO:41, SEQ ID NO:44, SEQ ID NO:65, SEQ ID NO:75 and SEQ ID NO:77. In yet another embodiment, said sequence xxi) is a sequence selected from the group consisting of SEQ ID NO:1, SEQ ID NO:23, SEQ ID NO:44, SEQ ID NO:65, SEQ ID NO:75 and SEQ ID NO:77, such as the group consisting of SEQ ID NO:1, SEQ ID NO:23, SEQ ID NO:44, SEQ ID NO:65 and SEQ ID NO:75. In yet another embodiment, said sequence xxi) is a sequence selected from the group consisting of SEQ ID NO:20, SEQ ID NO:23, SEQ ID NO:41, SEQ ID NO:44, SEQ ID NO:65, SEQ ID NO:75 and SEQ ID NO:77, such as the group consisting of SEQ ID NO:20, SEQ ID NO:23, SEQ ID NO:41, SEQ ID NO:44, SEQ ID NO:65 and SEQ ID NO:75. In yet another embodiment, said sequence xxi) is a sequence selected from the group consisting of SEQ ID NO:23, SEQ ID NO:44, SEQ ID NO:65, SEQ ID NO:75 and SEQ ID NO:77, such as the group consisting of SEQ ID NO:23, SEQ ID NO:44, SEQ ID NO:65 and SEQ ID NO:75. In one embodiment, said sequence xiii) is a sequence selected from the group consisting of SEQ ID NO:1, SEQ ID NO:23 and SEQ ID NO:75, such as the group consisting of SEQ ID NO:23 and SEQ ID NO:75. In one embodiment, said sequence xxi) is a sequence selected from the group consisting of SEQ ID NO:20, SEQ ID NO:41 and SEQ ID NO:44, such as the group consisting of SEQ ID NO:20 and SEQ ID NO:41; the group consisting of SEQ ID NO:20 and SEQ ID NO:44; or the group consisting of SEQ ID NO:41 and SEQ ID NO:44. In one embodiment, said sequence xxi) is a sequence selected from the group consisting of SEQ ID NO:1, SEQ ID NO:23 and SEQ ID NO:44, such as the group consisting of SEQ ID NO:23 and SEQ ID NO:44. In one embodiment, said sequence xxi) is SEQ ID NO:1, or is SEQ ID NO:20, or is SEQ ID NO:23, or is SEQ ID NO:41, or is SEQ ID NO:44.

In one embodiment of the FcRn binding dimer as disclosed herein, both said first and second monomer units comprise a sequence xxi) or xiii) selected from one of the groups defined above. In one embodiment, said group consists of SEQ ID NO:1, SEQ ID NO:23, SEQ ID NO:44, SEQ ID NO:65, SEQ ID NO:75, SEQ ID NO:354 and SEQ ID NO:357, such as the group consisting of SEQ ID NO:1, SEQ ID NO:23, SEQ ID NO:44, SEQ ID NO:354 and SEQ ID NO:357, such as the group consisting of SEQ ID NO:1, SEQ ID NO:23 and SEQ ID NO:44 or the group consisting of SEQ ID NO:23, SEQ ID NO:44, SEQ ID NO:354 and SEQ ID NO:357.

In one embodiment of the FcRn binding dimer as disclosed herein, both said first and second monomer units comprise a sequence xiii), xv), xvii), xix) or xxi) selected from one of the groups defined above.

In one embodiment, said group consists of SEQ ID NO:1, SEQ ID NO:20; SEQ ID NO:23, SEQ ID:41; SEQ ID NO:44, SEQ ID NO:65, SEQ ID NO:75, SEQ ID NO:354, SEQ ID NO:357 and SEQ ID NO:360-367, such as the group consisting of SEQ ID NO:20; SEQ ID NO:23, SEQ ID:41; SEQ ID NO:44, SEQ ID NO:75, SEQ ID NO:357 and SEQ ID NO:360-367, such as the group consisting of SEQ ID NO:20, SEQ ID NO:41, SEQ ID NO:44, SEQ ID NO:357, SEQ ID NO:360, SEQ ID NO:362, SEQ ID NO:363, SEQ ID NO:365, SEQ ID NO:366 and SEQ ID NO:367, such as the group consisting of SEQ ID NO:357, SEQ ID NO:360, SEQ ID NO:362, SEQ ID NO:363, SEQ ID NO:365, SEQ ID NO:366 and SEQ ID NO:367. In one particular embodiment, both said first and second monomer units comprise a sequence xxi) selected from the group consisting of SEQ ID NO:1, SEQ ID NO:23, SEQ ID NO:44, SEQ ID NO:65 and SEQ ID NO:75, such as the group consisting of SEQ ID NO:23, SEQ ID NO:44, SEQ ID NO:65 and SEQ ID NO:75, such as the group consisting of SEQ ID NO:23 and SEQ ID NO:44. In one particular embodiment, both said first and second monomer units comprise a sequence xxi) corresponding to SEQ ID NO:1. In one embodiment, said sequence xxi) is SEQ ID NO:20. In one embodiment, said sequence xxi) is SEQ ID NO:23. In one embodiment, said sequence xxi) is SEQ ID NO:41. In one embodiment, said sequence xxi) is SEQ ID NO:44. In one embodiment, said sequence xxi) is SEQ ID NO:75.

In another embodiment, both said first and second monomer units comprise a sequence xiii) corresponding to SEQ ID NO:354.

In one particular embodiment, both said first and second monomer units comprise a sequence xix) corresponding to SEQ ID NO:360. In one embodiment, said sequence xix) is SEQ ID NO:361. In one embodiment, said sequence xix) is SEQ ID NO:362. In one embodiment, said sequence xix) is SEQ ID NO:363. In one embodiment, said sequence xix) is SEQ ID NO:364. In another particular embodiment, both said first and second monomer units comprise a sequence xv) corresponding to SEQ ID NO:365. In one embodiment, said sequence xv) is SEQ ID NO:366. In one embodiment, said sequence xv) is SEQ ID NO:367.

In a specific embodiment of the FcRn binding dimer, the first and second monomer units comprise SEQ ID NO:1 and SEQ ID NO:1; SEQ ID NO:1 and SEQ ID NO:23; SEQ ID NO:1 and SEQ ID NO:44; SEQ ID NO:1 and SEQ ID NO:65; SEQ ID NO:1 and SEQ ID NO:75; SEQ ID NO:1 and SEQ ID NO:354; SEQ ID NO:1 and SEQ ID NO:357; SEQ ID NO:23 and SEQ ID NO:23; SEQ ID NO:23 and SEQ ID NO:44; SEQ ID NO:23 and SEQ ID NO:65; SEQ ID NO:23 and SEQ ID NO:75; SEQ ID NO:23 and SEQ ID NO:354; SEQ ID NO:23 and SEQ ID NO:357; SEQ ID NO:44 and SEQ ID NO:44; SEQ ID NO:44 and SEQ ID NO:65; SEQ ID NO:44 and SEQ ID NO:75; SEQ ID NO:44 and SEQ ID NO:354; SEQ ID NO:44 and SEQ ID NO:357; SEQ ID NO:65 and SEQ ID NO:65; SEQ ID NO:65 and SEQ ID NO:75; SEQ ID NO:65 and SEQ ID NO:354; SEQ ID NO:65 and SEQ ID NO:357; SEQ ID NO:75 and SEQ ID NO:354; SEQ ID NO:75 and SEQ ID NO:357; SEQ ID NO:354 and SEQ ID NO:354; SEQ ID NO:354 and SEQ ID NO:357; or SEQ ID NO:357 and SEQ ID NO:357, respectively. In one embodiment, the first and second monomer units comprise SEQ ID NO:1 and SEQ ID NO:1; SEQ ID NO:1 and SEQ ID NO:23; SEQ ID NO:1 and SEQ ID NO:44; SEQ ID NO:1 and SEQ ID NO:354; SEQ ID NO:1 and SEQ ID NO:357; SEQ ID NO:23 and SEQ ID NO:23; SEQ ID NO:23 and SEQ ID NO:44; SEQ ID NO:23 and SEQ ID NO:354; SEQ ID NO:23 and SEQ ID NO:357; SEQ ID NO:44 and SEQ ID NO:44; SEQ ID NO:44 and SEQ ID NO:354; SEQ ID NO:44 and SEQ ID NO:357; SEQ ID NO:354 and SEQ ID NO:354; SEQ ID NO:354 and SEQ ID NO:357; or SEQ ID NO:357 and SEQ ID NO:357, respectively. In another embodiment, the first and second monomer units comprise SEQ ID NO:1 and SEQ ID NO:1; SEQ ID NO:23 and SEQ ID NO:23; SEQ ID NO:44 and SEQ ID NO:44; SEQ ID NO:354 and SEQ ID NO:354; or SEQ ID NO:357 and SEQ ID NO:357, respectively. In yet another embodiment, the first and second monomer units comprise SEQ ID NO:44 and SEQ ID NO:44; or SEQ ID NO:357 and SEQ ID NO:357, respectively.

In a specific embodiment of the FcRn binding dimer, the first and second monomer units comprise SEQ ID NO:1 and SEQ ID NO:1; SEQ ID NO:1 and SEQ ID NO:20; SEQ ID NO:1 and SEQ ID NO:23; SEQ ID NO:1 and SEQ ID NO:41; SEQ ID NO:1 and SEQ ID NO:44; SEQ ID NO:1 and SEQ ID NO:65; SEQ ID NO:1 and SEQ ID NO:75; SEQ ID NO:1 and SEQ ID NO:354; SEQ ID NO:1 and SEQ ID NO:357; SEQ ID NO:1 and SEQ ID NO:365; SEQ ID NO:1 and SEQ ID NO:366; SEQ ID NO:1 and SEQ ID NO:367; SEQ ID NO:20 and SEQ ID NO:20; SEQ ID NO:20 and SEQ ID NO:23; SEQ ID NO:20 and SEQ ID NO:41; SEQ ID NO:20 and SEQ ID NO:44; SEQ ID NO:20 and SEQ ID NO:357; SEQ ID NO:20 and SEQ ID NO:365; SEQ ID NO:20 and SEQ ID NO:366; SEQ ID NO:20 and SEQ ID NO:367; SEQ ID NO:23 and SEQ ID NO:23; SEQ ID NO:23 and SEQ ID NO:41; SEQ ID NO:23 and SEQ ID NO:44; SEQ ID NO:23 and SEQ ID NO:65; SEQ ID NO:23 and SEQ ID NO:75; SEQ ID NO:23 and SEQ ID NO:354; SEQ ID NO:23 and SEQ ID NO:357; SEQ ID NO:23 and SEQ ID NO:365; SEQ ID NO:23 and SEQ ID NO:366; SEQ ID NO:23 and SEQ ID NO:367; SEQ ID NO:41 and SEQ ID NO:41; SEQ ID NO:41 and SEQ ID NO:44; SEQ ID NO:41 and SEQ ID NO:357; SEQ ID NO:41 and SEQ ID NO:357; SEQ ID NO:41 and SEQ ID NO:365; SEQ ID NO:41 and SEQ ID NO:366; SEQ ID NO:41 and SEQ ID NO:367; SEQ ID NO:44 and SEQ ID NO:44; SEQ ID NO:44 and SEQ ID NO:65; SEQ ID NO:44 and SEQ ID NO:75; SEQ ID NO:44 and SEQ ID NO:354; SEQ ID NO:44 and SEQ ID NO:357; SEQ ID NO:44 and SEQ ID NO:365; SEQ ID NO:44 and SEQ ID NO:366; SEQ ID NO:44 and SEQ ID NO:367; SEQ ID NO:65 and SEQ ID NO:65; SEQ ID NO:65 and SEQ ID NO:75; SEQ ID NO:65 and SEQ ID NO:354; SEQ ID NO:65 and SEQ ID NO:357; SEQ ID NO:75 and SEQ ID NO:354; SEQ ID NO:75 and SEQ ID NO:357; SEQ ID NO:354 and SEQ ID NO:354; SEQ ID NO:354 and SEQ ID NO:357; SEQ ID NO:357 and SEQ ID NO:357; SEQ ID NO:357 and SEQ ID NO:365; SEQ ID NO:357 and SEQ ID NO:366; SEQ ID NO:357 and SEQ ID NO:367; SEQ ID NO:365 and SEQ ID NO:365; SEQ ID NO:365 and SEQ ID NO:366; SEQ ID NO:365 and SEQ ID NO:367; SEQ ID NO:366 and SEQ ID NO:366; SEQ ID NO:366 and SEQ ID NO:367; or SEQ ID NO:367 and SEQ ID NO:367, respectively. In one embodiment, the first and second monomer units comprise SEQ ID NO:1 and SEQ ID NO:1; SEQ ID NO:1 and SEQ ID NO:20; SEQ ID NO:1 and SEQ ID NO:23; SEQ ID NO:1 and SEQ ID NO:41; SEQ ID NO:1 and SEQ ID NO:44; SEQ ID NO:1 and SEQ ID NO:354; SEQ ID NO:1 and SEQ ID NO:357; SEQ ID NO:1 and SEQ ID NO:365; SEQ ID NO:1 and SEQ ID NO:366; SEQ ID NO:1 and SEQ ID NO:367; SEQ ID NO:20 and SEQ ID NO:20; SEQ ID NO:20 and SEQ ID NO:23; SEQ ID NO:20 and SEQ ID NO:41; SEQ ID NO:20 and SEQ ID NO:44; SEQ ID NO:20 and SEQ ID NO:357; SEQ ID NO:20 and SEQ ID NO:365; SEQ ID NO:20 and SEQ ID NO:366; SEQ ID NO:20 and SEQ ID NO:367; SEQ ID NO:23 and SEQ ID NO:23; SEQ ID NO:23 and SEQ ID NO:41; SEQ ID NO:23 and SEQ ID NO:44; SEQ ID NO:23 and SEQ ID NO:354; SEQ ID NO:23 and SEQ ID NO:357; SEQ ID NO:23 and SEQ ID NO:365; SEQ ID NO:23 and SEQ ID NO:366; SEQ ID NO:23 and SEQ ID NO:367; SEQ ID NO:41 and SEQ ID NO:41; SEQ ID NO:41 and SEQ ID NO:44; SEQ ID NO:41 and SEQ ID NO:357; SEQ ID NO:41 and SEQ ID NO:41 and SEQ ID NO:365; SEQ ID NO:41 and SEQ ID NO:366; SEQ ID NO:41 and SEQ ID NO:367; SEQ ID NO:44 and SEQ ID NO:44; SEQ ID NO:44 and SEQ ID NO:354; SEQ ID NO:44 and SEQ ID NO:357; SEQ ID NO:44 and SEQ ID NO:365; SEQ ID NO:44 and SEQ ID NO:366; SEQ ID NO:44 and SEQ ID NO:367; SEQ ID NO:354 and SEQ ID NO:354; SEQ ID NO:354 and SEQ ID NO:357; SEQ ID NO:357 and SEQ ID NO:357; SEQ ID NO:357 and SEQ ID NO:365; SEQ ID NO:357 and SEQ ID NO:366; SEQ ID NO:357 and SEQ ID NO:367; SEQ ID NO:365 and SEQ ID NO:365; SEQ ID NO:365 and SEQ ID NO:366; SEQ ID NO:365 and SEQ ID NO:367; SEQ ID NO:366 and SEQ ID NO:366; SEQ ID NO:366 and SEQ ID NO:367; or SEQ ID NO:367 and SEQ ID NO:367, respectively. In another embodiment, the first and second monomer units comprise SEQ ID NO:1 and SEQ ID NO:1; SEQ ID NO:20 and SEQ ID NO:20; SEQ ID NO:23 and SEQ ID NO:23; SEQ ID NO:41 and SEQ ID NO:41; SEQ ID NO:44 and SEQ ID NO:44; SEQ ID NO:354 and SEQ ID NO:354; SEQ ID NO:357 and SEQ ID NO:357; SEQ ID NO:365 and SEQ ID NO:365; SEQ ID NO:366 and SEQ ID NO:366; or SEQ ID NO:367 and SEQ ID NO:367, respectively. In yet another embodiment, the first and second monomer units comprise SEQ ID NO:20 and SEQ ID NO:20; SEQ ID NO:41 and SEQ ID NO:41; SEQ ID NO:44 and SEQ ID NO:44; SEQ ID NO:357 and SEQ ID NO:357; SEQ ID NO:365 and SEQ ID NO:365; SEQ ID NO:366 and SEQ ID NO:366; or SEQ ID NO:367 and SEQ ID NO:367, respectively.

In yet another embodiment, the first and second monomer units comprise SEQ ID NO:365 and SEQ ID NO:365; SEQ ID NO:366 and SEQ ID NO:366; or SEQ ID NO:367 and SEQ ID NO:367, respectively.

For the sake of clarity, the designation of first and second monomer units as used throughout the present disclosure is made for clarity reasons to distinguish between them, and is not intended to refer to the actual order of the monomer units in the polypeptide chain of the FcRn binding dimer. Thus, for example, said first monomer unit may appear N-terminally or C-terminally in a polypeptide chain, with respect to said second monomer unit.

As the skilled person understands, the construction of a fusion protein often involves using linkers between functional moieties to be fused. The skilled person is aware of different kinds of linkers with different properties, such as flexible amino acid linkers, rigid amino acid linkers and cleavable amino acid linkers. Linkers have been used to for example increase stability or improve folding of fusion proteins, to increase expression, improve biological activity, enable targeting and alter pharmacokinetics of fusion proteins.

Thus, in one embodiment of the first aspect, there is provided an FcRn binding dimer as defined herein, wherein said linker is selected from the group consisting of flexible amino acid linkers, rigid amino acid linkers and cleavable amino acid linkers. In one embodiment of an FcRn binding dimer as defined herein, said linker is arranged between the first monomeric unit and the second monomeric unit. The skilled person will appreciate that the presence of a linker arranged between the first monomeric unit and the second monomeric unit does not exclude the presence of additional linkers.

Flexible linkers are often used in the art when the joined domains require a certain degree of movement or interaction, and may be particularly useful in some embodiments of the FcRn binding dimer. Such linkers are generally composed of small, non-polar (for example G) or polar (for example S or T) amino acids. Some flexible linkers primarily consist of stretches of G and S residues, for example (GGGGS (SEQ ID NO:441))$_p$ and (SSSSG (SEQ ID NO:442))$_p$. Adjusting the copy number "p" allows for optimization of the linker in order to achieve appropriate separation between the functional moieties or to maintain necessary inter-moiety interaction. Apart from G and S linkers, other flexible linkers are known in the art, such as G and S linkers containing additional amino acid residues, such as T, A, K and E, to maintain flexibility, as well as polar amino acid residues to improve solubility.

Additional non-limiting examples of linkers include GGGGSLVPRGSGGGGS (SEQ ID NO:443), (GS)$_3$ (SEQ ID NO:444), (GS)$_4$ (SEQ ID NO:445), (GS)$_8$ (SEQ ID NO:446), GGSGGHMGSGG (SEQ ID NO:447), GGSGGSGGSGG (SEQ ID NO:448), GGSGG (SEQ ID NO:449), GGSGGGGG (SEQ ID NO:450), GGGSEGGGSEGGGSEGGG (SEQ ID NO:451), AAGAATAA (SEQ ID NO:452), GGGGG (SEQ ID NO:453), GGSSG (SEQ ID NO:454), GSGGGTGGGSG (SEQ ID NO:455), GSGGGTGGGSG (SEQ ID NO:456), GT, GSGSGSGSGGSG (SEQ ID NO:457), GSGGSGGSGGSGGS (SEQ ID NO:458) and GSGGSGSGGSGGSG (SEQ ID NO:459). The skilled person is aware of other suitable linkers.

In one embodiment, said linker is a flexible linker comprising glycine (G), serine (S) and/or threonine (T) residues. In one embodiment, said linker has a general formula selected from $(G_nS_m)_p$ and $(S_nG_m)_p$, wherein, independently, n=1-7, m=0-7, n+m 8 and p=1-7. In one embodiment, n=1-5. In one embodiment, m=0-5. In one embodiment, p=1-5. In a more specific embodiment, n=4, m=1 and p=1-4. In one embodiment, said linker is selected from the group consisting of S$_4$G (SEQ ID NO:442), (S$_4$G)$_3$ (SEQ ID NO:460) and (S$_4$G)$_4$ (SEQ ID NO:461). In one embodiment, said linker is selected from the group consisting of GS, G$_4$S (SEQ ID NO:441) and (G$_4$S)$_3$ (SEQ ID NO:462). In one particular embodiment, said linker is G$_4$S (SEQ ID NO:441) and in another embodiment said linker is (G$_4$S)$_3$ (SEQ ID NO:462).

The terms "FcRn binding" and "binding affinity for FcRn" as used in this specification refer to a property of a polypeptide which may be tested for example by the use of surface plasmon resonance (SPR) technology or ELISA.

For example as described in the examples below, FcRn binding affinity may be tested in an experiment in which FcRn, or a correctly folded fragment thereof, is immobilized on a sensor chip of the instrument, and the sample containing the polypeptide to be tested is passed over the chip. Alternatively, the polypeptide to be tested is immobilized on a sensor chip of the instrument, and a sample containing FcRn, or a correctly folded fragment thereof, is passed over the chip. The skilled person may then interpret the results obtained by such experiments to establish at least a qualitative measure of the binding affinity of the polypeptide for FcRn. If a quantitative measure is desired, for example to determine a K$_D$ value for the interaction, surface plasmon resonance methods may also be used. Binding values may for example be defined in a Biacore (GE Healthcare) or ProteOn XPR 36 (Bio-Rad) instrument. FcRn is suitably immobilized on a sensor chip of the instrument, and samples of the polypeptide whose affinity is to be determined are prepared by serial dilution and injected in random order. K$_D$ values may then be calculated from the results using for example the 1:1 Langmuir binding model of the BIAevaluation 4.1 software, or other suitable software, provided by the instrument manufacturer.

Alternatively, as described in the examples below, FcRn binding affinity may be tested in an experiment in which samples of the polypeptide are captured on antibody coated ELISA plates, and biotinylated FcRn is added followed by streptavidin conjugated HRP. TMB substrate is added and the absorbance at 450 nm is measured using a multi-well plate reader, such as Victor$^3$ (Perkin Elmer). The skilled person may then interpret the results obtained by such experiments to establish at least a qualitative measure of the binding affinity of the polypeptide for FcRn. If a quantitative measure is desired, for example to determine the K$_D$ value (the half maximal effective concentration) for the interaction, ELISA may also be used. The response of the polypeptides against a dilution series of biotinylated FcRn are measured using ELISA as described above. The skilled person may then interpret the results obtained by such experiments and K$_D$ values may be calculated from the results using for example Graph Pad Prism 5 and non-linear regression.

Alternatively, affinity for FcRn may also be studied indirectly by looking at the ability of an FcRn binding polypeptide to block binding of IgG to FcRn. Thus, a skilled person would appreciate that the ability of an FcRn binding polypeptide to block said binding correlates with the binding capacity of the FcRn binding polypeptide to FcRn, provided that the FcRn binding dimer interacts with FcRn at the same, or an at least partially overlapping, region of FcRn as IgG. Thus, the higher the capacity of binding of the polypeptide to FcRn, the better the ability to block IgG binding to FcRn.

The skilled person would also appreciate that interaction of an FcRn binding polypeptide and FcRn can be evaluated by FACS (Fluorescence-activated cell sorting) analysis, wherein the obtained mean fluorescence intensity (MFI) value is an indirect readout of the strength of binding of a tested polypeptide relative to other tested polypeptides in the same experiment. Thus, a higher MFI-value correlates to a higher relative affinity and a lower MFI-value correlates to a lower relative affinity.

As used herein, the term "higher binding capacity" in the context of binding affinity for FcRn or binding of FcRn is to be interpreted in the context of any one or more of the above-mentioned assays for direct or indirect evaluation of affinity.

As defined herein, the FcRn binding dimer binds FcRn with a higher binding capacity compared to said first or second monomer unit alone. In one embodiment, the FcRn binding dimer may bind to FcRn with at least 2 times, such as at least 3 times, such as at least 4 times, such as at least 5 times, such as at least 6 times, such as at least 7 times, such as at least 8 times, such as at least 9 times, such as at least 10 times, such as at least 25 times, such as at least 50 times, such as at least 100 times higher capacity than the corresponding first monomer unit or second monomer unit alone. This relationship may be true at both pH 6.0 and pH 7.4, or at pH 6.0 only, or at pH 7.4 only.

In some In some embodiments, explained further below, the FcRn binding dimer inhibits binding of IgG to FcRn. In such embodiments, said FcRn binding dimer may bind FcRn such that the ability of the FcRn binding dimer to block IgG binding to FcRn is at least 2 times higher, such as at least 3 times higher, such as at least 4 times higher, such as at least 5 times higher, such as at least 10 times, such as at least 15 times, such as at least 20 times, such as at least 25 times higher compared to the blocking ability of the corresponding first or second monomer unit alone.

In some embodiments, said FcRn binding dimer may bind FcRn such that the MFI value of the interaction between FcRn and the FcRn binding dimer is at least 2 times higher, such as at least 3 times higher, such as at least 4 times higher, such as at least 5 times higher, such as at least 10 times higher compared to MFI value of the interaction between FcRn and the corresponding first or second monomer unit alone.

In some embodiments, said FcRn binding dimer may bind FcRn such that the $K_D$ value of the interaction between FcRn and the FcRn binding dimer is at least 2 times lower, such as at least 3 times lower, such as at least 4 times lower, such as at least 5 times lower, such as at least 10 times lower, such as at least 25 times lower, such as at least 50 times lower, such as at least 100 times lower, such as at least 1000 times lower compared to the $K_D$ value of the interaction between FcRn and the corresponding first monomer unit or second monomer unit alone.

In one embodiment, there is provided an FcRn binding dimer, which is capable of binding to FcRn at pH 6.0 such that the $K_D$ value of the interaction is at most $1 \times 10^{-7}$ M, such as at most $1 \times 10^{-8}$ M, such as at most $1 \times 10^{-9}$ M, such as at most $1 \times 10^{-10}$ M, such as at most $1 \times 10^{-11}$ M, such as at most $1 \times 10^{-12}$ M. An FcRn binding dimer according to this embodiment would bind, or remain bound, to FcRn in acidic pH conditions, such as pH 6.0, for example in an endosome. If such a polypeptide were to enter an increasingly acidic intracellular environment, it would be recycled to the plasma membrane through its interaction with FcRn, and thus avoid degradation.

In one embodiment, the $K_D$ value of the interaction between an FcRn binding dimer and FcRn at pH 7.4 is higher than the $K_D$ value of said interaction at pH 6.0. Thus, the FcRn binding polypeptide would bind to FcRn with higher affinity at pH 6.0 than at pH 7.4. In one embodiment, the $K_D$ value of said interaction at pH 7.4 is at least 2 times higher, such as at least 5 times higher, such as at least 10 times higher, such at least 25 times, such as at least 50 times higher, such as at least 100 times, such as at least 1000 times higher than the $K_D$ value of said interaction at pH 6.0.

As mentioned above, FACS analysis may be used to analyze the interaction of between an FcRn binding dimer and FcRn. Hence, the interaction of between an FcRn binding dimer and FcRn at pH 6.0 and pH 7.4 can be evaluated and the MFI value at pH 6.0 and pH 7.4 may be compared as disclosed in the experimental section to follow. An obtained higher relative MFI value corresponds to a higher affinity and a lower relative MFI value corresponds to a lower affinity, provided that said MFI values are compared within the same experimental set up. Thus, in one embodiment, the FcRn binding dimer binds to FcRn with a higher affinity at pH 6.0 than at pH 7.4, such as at least 10% higher, such as at least 20% higher, such as at least 35% higher, such as at least 50% higher, such as least 100% higher.

In one embodiment, the $K_D$ value of the interaction between FcRn binding dimer and FcRn at pH 7.4 is at least $1 \times 10^{-10}$ M, such as at least $1 \times 10^{-9}$ M, such as at least $1 \times 10^{-8}$ M, such as at least $1 \times 10^{-7}$ M, such as at least $1 \times 10^{-6}$ M, such as at least $1 \times 10^{-5}$ M. In some embodiments, the only criterion for the interaction between FcRn binding dimer and FcRn at pH 7.4 is that any FcRn binding dimer which has bound to FcRn during more acidic conditions is released more rapidly from FcRn when the pH value increases.

In an alternative embodiment, there is provided an FcRn binding dimer, for which the $K_D$ of said interaction at pH 7.4 is the same as or lower than the $K_D$ of said interaction at pH 6.0. An FcRn binding dimer according to this embodiment would bind or remain bound to FcRn in acidic pH conditions (i.e. would have an off-rate at pH 6.0 which is sufficiently slow to avoid release), for example in the endosome, as well as in neutral or slightly basic pH conditions, for example on the plasma membrane. In a more specific embodiment, the $K_D$ value of said interaction at pH 7.4 is at least 2 times lower, such as at least 5 times lower, such as at least 10 times lower, such as at least 50 times lower, such as at least 100 times lower than the $K_D$ value of said interaction at pH 6.0.

In another embodiment, there is provided an FcRn binding dimer, which is capable of binding to FcRn at pH 7.4 such that the $K_D$ value of the interaction is at most $1 \times 10^{-7}$ M, such as at most $1 \times 10^{-8}$ M, such as at most $1 \times 10^{-9}$ M, such as at most $1 \times 10^{-10}$ M, such as at most $1 \times 10^{-11}$ M, such as at most $1 \times 10^{-12}$ M. An FcRn binding dimer according to this embodiment would bind or remain bound for an extended time to FcRn in neutral or slightly basic pH conditions, such as pH 7.4, for example on the plasma membrane. The term "remain bound" should be understood to mean an interaction having a slow off-rate at given conditions.

In general, the skilled person knows that the $K_D$ value of an interaction is defined as the ratio between the off-rate ($k_{off}$) and the on-rate ($k_{on}$). Thus, a high $K_D$ value may be due to either a high $k_{off}$, a low $k_{on}$ or both, and conversely, a low $K_D$ value may be due to either a low $k_{off}$, a high $k_{on}$ or both.

The skilled person will understand that various modifications and/or additions can be made to an FcRn binding dimer according to any aspect disclosed herein in order to tailor the polypeptide to a specific application without departing from the scope of the present disclosure.

For example, in one embodiment there is provided an FcRn binding dimer as described herein, wherein at least one of said first and second monomer units comprises at least one additional amino acid at the C-terminal and/or N-terminal end. Such a polypeptide should be understood as a polypeptide having one or more additional amino acid residues at the very first and/or the very last position in the polypeptide chain of at least one of said first and second monomer units. Thus, said at least one of said monomer units of the FcRn binding dimer as defined herein may comprise any suitable number of additional amino acid residues, for example at least one additional amino acid residue. Each additional amino acid residue may individually or collectively be added in order to, for example, improve or simplify production, purification, stabilization in vivo or in vitro, coupling, or detection of the polypeptide. Such additional amino acid residues may comprise one or more amino acid residues added for the purpose of chemical coupling. One example of this is the addition of a cysteine residue. Such additional amino acid residues may also provide a "tag" for purification or detection of the polypeptide, such as a $His_6$ tag or a "myc" (c-myc) tag or a "FLAG" tag for interaction with antibodies specific to the tag or immobilized metal affinity chromatography (IMAC) in the case of the hexahistidine tag.

The further amino acids as discussed above may be coupled to the FcRn binding dimer or to any one or both of said first and second monomeric units by means of chemical conjugation (using known organic chemistry methods) or by any other means, such as expression of the FcRn binding dimer as a fusion protein or joined in any other fashion, either directly or via a linker, for example an amino acid linker as described above.

The further amino acids as discussed above may for example comprise one or more polypeptide domain(s). A further polypeptide domain may provide the FcRn binding dimer with another function, such as for example another binding function, or an enzymatic function, or a toxic function or a fluorescent signaling function, or combinations thereof.

Thus, in a second aspect of the present disclosure, there is provided a fusion protein or a conjugate, comprising a first moiety consisting of an FcRn binding dimer according to the first aspect, and a second moiety consisting of a polypeptide having a desired biological activity. In another embodiment, said fusion protein or conjugate may additionally comprise further moieties, comprising desired biological activities that can be either the same or different from the biological activity of the second moiety.

In one embodiment of said fusion protein or conjugate, the total size of the molecule is below the threshold for efficient renal clearance upon administration to a mammalian subject.

In another embodiment of said fusion protein or conjugate, the total size of the molecule is above the threshold for efficient renal clearance upon administration to a mammalian subject.

In one embodiment of said fusion protein or conjugate, the in vivo half-life of said fusion protein or conjugate is longer than the in vivo half-life of the polypeptide having the desired biological activity per se.

Non-limiting examples of a desired biological activity comprise a therapeutic activity, a binding activity, and an enzymatic activity.

In one embodiment, said desired biological activity is a binding activity to a selected target.

One example of such a binding activity is a binding activity, which increases the in vivo half-life of a fusion protein or conjugate. This fusion protein or conjugate may comprise at least one further moiety. In one particular embodiment, said target is albumin, binding to which increases the in vivo half-life of said fusion protein or conjugate. In one embodiment, said albumin binding activity is provided by an albumin binding domain (ABD) of streptococcal protein G or a derivative thereof. For example, said fusion protein or conjugate, comprising at least one further moiety, may comprise [FcRn binding dimer]-[albumin binding moiety]-[moiety with affinity for selected target]. Furthermore, it will be appreciated that said fusion protein or conjugate may comprise an albumin binding moiety or other target binding moiety interspaced between two FcRn binding monomer units making up the FcRn binding dimer as described herein, and may thus, as non-limiting examples, be arranged according to [FcRn binding monomer moiety]-[albumin binding moiety]-[FcRn binding monomer moiety]-[moiety with affinity for selected target] or according to [FcRn binding monomer moiety]-[moiety with affinity for selected target]-[FcRn binding monomer moiety]-[albumin binding moiety]. It is to be understood that the moieties in the fusion protein or conjugate may be freely arranged in any order from the N- to the C-terminal of the polypeptide. In one embodiment, said in vivo half-life is increased at least 10 times, such as at least 25 times, such as at least 50 times, such as at least 75 times, such as at least 100 times compared the in vivo half-life of the fusion protein or conjugate per se.

In one embodiment, when a complex between a target and the fusion protein or conjugate as described herein is formed (or maintained) at acidic pH, such as pH 6.0, the target is rescued from elimination by lysosomal degradation. Thus, target half-life is extended. Half-life extension implies that the elimination rate of a target is lower when interacting with said fusion protein or conjugate than the elimination rate of the target molecule in the absence of said fusion protein or conjugate. Furthermore, it is desirable in this embodiment that the binding of target by the fusion protein or conjugate should not interfere substantially with the function of the target.

On the other hand, when a complex between the target and the fusion protein or conjugate as described herein is not maintained or not formed at acidic pH, the target is directed to the subcellular lysosomes where it is degraded.

In one embodiment, there is provided a fusion protein or conjugate, wherein the rate of elimination of a selected, undesirable target from the subject is increased. Increased elimination of an undesirable target implies increased elimination rate of the target from the body of the multicellular organism, as compared to a "normal" elimination rate of the target molecule per se, i.e. without previous interaction with the fusion protein or conjugate.

In another embodiment, binding of a selected undesirable target could inactivate the function of the target, thereby blocking its biological activity in situations where this is desirable. Such biological activity may for example be activation or blocking of receptors or an enzymatic or otherwise toxic or undesirable activity. Such undesirable target may be an endogenous hormone, enzyme, cytokine, chemokine or a target having some other biological activity. By using an inactivating target binding, the biological activity is blocked until the target is delivered for degradation and released at a low pH value, and the target binding fusion protein is recycled to circulation. This recycling of the target binding fusion protein (via its FcRn binding moiety) enables it to "catalyze" the removal of more than one molecule of the selected undesirable target.

Undesirable targets may for example be foreign proteins and compounds, or naturally expressed proteins that display elevated levels in plasma following a medical condition and where a therapeutic effect may be achieved by elimination of said protein. The undesired target is not necessarily evenly distributed in the plasma but may be concentrated in certain regions, for example around a tumor or at sites of inflammation.

Non-limiting examples of targets are targets selected from the group consisting of allergens, amyloids, antibodies, auto-antigens, blood clotting factors, hormones, tumor cells, drug molecules, cytokines, chemokines, proteases, hypersensitivity mediators, proinflammatory factors, toxins such as bacterial toxins and snake venoms; pollutants, metals and anti-oxidants.

Under certain conditions, such as in certain cancer diseases, it is desired to remove endogenous molecules, for example VEGF, PDGF, HGF and other growth stimulatory hormones. Such molecules could also be targeted by a binding function in said fusion protein or conjugate.

Under other conditions, such as in certain immunological diseases, it may be desirable to remove endogenous molecules transiently, such as selected interleukins or TNF. Such molecules could also be targeted by a binding function in said fusion protein or conjugate.

In one embodiment, the second moiety having a desired biological activity is a therapeutically active polypeptide. Non-limiting examples of therapeutically active polypeptides are biomolecules, such as molecules selected from the group consisting of enzymes, for example algasidase α and β, glucocerebrosidase, laronidase, arylsulphatase, aglucosidase-α, asparaginase, Factor VII, Factor VIII, Factor IX and Factor $X_a$; hormones and growth factors, for example growth hormone, transforming growth factor-β2, erythropoietin, insulin, insulin-like growth factor-1, myostatin, bone-derived growth factor and glucagon-like peptide-1; chemokines, for example CCL17, CCL19, CCL20, CCL21, CCL22, CCL27, XCL1 and CXC3CL1, and cytokines, for example interleukin (IL)-2, IL-4, IL-7, IL-10, IL-12, IL-15, IL-18, IL-22, IL-27, interferon (IFN)-α, IFN-β, IFN-γ, tumor necrosis factor (TNF), granulocyte-colony stimulating factor (G-CSF), macrophage-CSF, and granulocyte/macrophage-CSF.

As the skilled person understands, the FcRn binding dimer according to the first aspect may be useful in a fusion protein or as a conjugate partner to any other moiety. Therefore, the above lists of therapeutically active polypeptides should not be construed as limiting in any way.

Other possibilities for the creation of fusion polypeptides or conjugates are also contemplated. Thus, an FcRn binding dimer according to the first aspect of the invention may be covalently coupled to a second or further moiety or moieties, which, in addition to or instead of target binding, exhibit other functions. One example is a fusion between one or more FcRn binding dimer and an enzymatically active polypeptide serving as a reporter or effector moiety.

With regard to the description above of fusion proteins or conjugates incorporating an FcRn binding dimer according to the disclosure, it is to be noted that the designation of first, second and further moieties is made for clarity reasons to distinguish between FcRn binding dimer according to the disclosure on the one hand, and moieties exhibiting other functions on the other hand. These designations are not intended to refer to the actual order of the different domains in the polypeptide chain of the fusion protein or conjugate. Thus, for example, said first moiety may without restriction appear at the N-terminal end, in the middle, or at the C-terminal end of the fusion protein or conjugate. Furthermore, the FcRn binding dimer as disclosed herein may comprise a second moiety interspaced between the two FcRn binding monomer units of the FcRn binding dimer.

The half maximal inhibitory concentration (IC50) is a measure of the effectiveness of a substance for inhibiting a specific quantifiable biological or biochemical function. This quantitative measure indicates how much of a particular substance is needed to inhibit a specific biological function by 50% and is commonly used in the art. In one particular embodiment, there is provided an FcRn binding dimer, fusion protein or conjugate as defined herein capable of blocking IgG binding to FcRn such that the half maximal inhibitory concentration (IC50) of the blocking is at most $1\times10^{-8}$ M, such as at most $6\times10^{-9}$ M, such as at most $4\times10^{-9}$ M, such as at most $1\times10^{-9}$ M, such as at most $1\times10^{-10}$ M, such as at most $1\times10^{-11}$ M. In one embodiment, there is provided an FcRn binding dimer, fusion protein or conjugate as defined herein capable of blocking IgG binding to FcRn such that the half maximal inhibitory concentration (IC50) of the blocking is at least 10 times lower, such as at least 100 times lower, such as at least 1000 times lower compared to the IC50 of the blocking by the corresponding first or second monomer unit alone.

The inhibition may be due to binding of the FcRn binding dimer, fusion protein or conjugate to the same, or an at least partially overlapping, region of FcRn as IgG. Alternatively, the FcRn binding dimer, fusion protein or conjugate may bind to a different region of FcRn than IgG but sterically hinder the binding of IgG to FcRn. Thus, the rate of elimination or clearance of IgG from the circulatory system would increase due to increased lysosomal degradation of IgG, because the FcRn mediated recycling of IgG would be wholly or partially unavailable due to the occupation of FcRn binding sites by the FcRn binding dimer according to the present disclosure. In other words, administration of FcRn binding dimer, fusion protein or conjugate according to the present disclosure will act to increase the catabolism of circulating IgG antibodies.

In one embodiment, the $K_D$ value of the interaction between the FcRn binding dimer, fusion protein or conjugate and FcRn is lower than the $K_D$ of the interaction between IgG and FcRn. This relationship may be true at both pH 6.0 and pH 7.4, or at pH 6.0 only.

The above aspects furthermore encompass polypeptides in which the FcRn binding dimer according to the first aspect, or the FcRn binding dimer as comprised in a fusion protein or conjugate according to the second aspect, further comprises a label, such as a label selected from the group consisting of fluorescent dyes and metals, chromophoric dyes, chemiluminescent compounds and bioluminescent proteins, enzymes, radionuclides and radioactive particles. Such labels may for example be used for detection of the polypeptide.

In other embodiments, the labeled FcRn binding dimer is present as a moiety in a fusion protein or conjugate also comprising a second moiety having a desired biological activity and/or comprising a binding function as described above. The label may in some instances be coupled only to the FcRn binding dimer (for example to one, two or both of said first and second monomeric units), and in some instances both to the FcRn binding dimer and to the second moiety of the conjugate or fusion protein. Furthermore, it is also possible that the label may be coupled to a second moiety only and not to the FcRn binding moiety. Hence, in yet another embodiment there is provided an FcRn binding dimer comprising a second moiety, wherein said label is coupled to the second moiety only.

When reference is made to a labeled polypeptide, this should be understood as a reference to all aspects of the FcRn binding dimer as described herein, including fusion proteins and conjugates comprising an FcRn binding dimer and a second and optionally further moieties. Thus, a labeled polypeptide may contain only the FcRn binding dimer and e.g. a therapeutic radionuclide, which may be chelated or covalently coupled to the FcRn binding dimer, or contain the FcRn binding dimer, a therapeutic radionuclide and a second moiety such as a small molecule having a desired biological activity, for example resulting in a therapeutic efficacy.

In embodiments where the FcRn binding dimer, fusion protein or conjugate is radiolabeled, such a radiolabeled polypeptide may comprise a radionuclide. A majority of radionuclides have a metallic nature, are used in the ionic form, and are typically incapable of forming stable covalent bonds with elements presented in proteins and peptides. For this reason, labeling of proteins and peptides with radioactive metals is performed with the use of chelators, i.e. multidentate ligands, which form non-covalent compounds, called chelates, with the metal ions. In an embodiment of the FcRn binding dimer, fusion protein or conjugate, the incorporation of a radionuclide is enabled through the provision of a chelating environment, through which the radionuclide may be coordinated, chelated or complexed to the polypeptide.

One example of a chelator is the polyaminopolycarboxylate type of chelator. Two classes of such polyaminopolycarboxylate chelators can be distinguished: macrocyclic and acyclic chelators.

In one embodiment, the FcRn binding dimer, fusion protein or conjugate comprises a chelating environment provided by a polyaminopolycarboxylate chelator coupled to the FcRn binding dimer via a thiol group of a cysteine residue or an epsilon amine group of a lysine residue. Alternatively, the polyaminopolycarboxylate chelator may be coupled to any part of the fusion protein or conjugate as disclosed herein, such as to the second or further moiety of said fusion protein or conjugate.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7,10-tetraacetic acid). In one embodiment, a chelating environment of the FcRn binding dimer, fusion protein or conjugate is provided by DOTA or a derivative thereof. More specifically, in one embodiment, the chelating polypeptides encompassed by the present disclosure are obtained by reacting the DOTA derivative 1,4,7,10-tetraazacyclododecane-1,4,7-tris-acetic acid-10-maleimidoethylacetamide (maleimidomonoamide-DOTA) with said polypeptide.

Additionally, 1,4,7-triazacyclononane-1,4,7-triacetic acid (NOTA) and derivatives thereof may be used as chelators. Hence, in one embodiment, there is provided an FcRn binding dimer, fusion protein or conjugate, wherein the polyaminopolycarboxylate chelator is 1,4,7-triazacyclononane-1,4,7-triacetic acid or a derivative thereof.

The most commonly used acyclic polyaminopolycarboxylate chelators are different derivatives of DTPA (diethylenetriamine-pentaacetic acid). Hence, polypeptides having a chelating environment provided by diethylenetriaminepentaacetic acid or derivatives thereof are also encompassed by the present disclosure.

In a further embodiment, the FcRn binding dimer, produced recombinantly through expression of a polynucleotide or synthetically, is conjugated to one or more synthetic polymers, in order for example to increase its hydrodynamic radius. Polyethylene glycol (PEG) is commonly used for this purpose, but other polymers have also been used in the art. Such "PEGylation" may be used to increase the size of the FcRn binding dimer, fusion protein or conjugate as described herein to a size above the threshold for effective renal excretion.

In one embodiment, a synthetic polymer is conjugated to one or more chemically synthesized FcRn binding dimer(s). Other functionalities may also be conjugated to the same synthetic polymer. If the FcRn binding dimer and other components are chemically synthesized, none of the components will have to be made in a biological system if this is not desired.

In a preferred embodiment, one or more synthetically or biologically manufactured FcRn binding dimers are conjugated to a synthetic polymer, to achieve a size exceeding the size associated with efficient renal clearance and used for blocking binding of IgG to FcRn. A unique cysteine in the monomer units of the FcRn binding dimer may be used for site specific conjugation, for example a C-terminally located cysteine introduced for this purpose. With a branched synthetic polymer, more than two FcRn binding moieties may be conjugated to the same polymer, to enhance the avidity and therefore the blocking potency.

In a third aspect of the present disclosure, there is provided a polynucleotide encoding an FcRn binding dimer or a fusion protein as described herein. Also encompassed by this disclosure is a method of producing an FcRn binding dimer or fusion protein as described above comprising expressing the polynucleotide; an expression vector comprising the polynucleotide; and a host cell comprising the expression vector.

Also encompassed is a method of producing FcRn binding dimer or a fusion protein, comprising culturing said host cell under conditions permissive of expression of said polypeptide from its expression vector, and isolating the polypeptide.

The FcRn binding dimer or fusion protein of the present disclosure may alternatively be produced by non-biological peptide synthesis using amino acids and/or amino acid derivatives having protected reactive side-chains, the non-biological peptide synthesis comprising
    step-wise coupling of the amino acids and/or the amino acid derivatives to form an FcRn binding dimer or a fusion protein having protected reactive side-chains,
    removal of the protecting groups from the reactive side-chains of the FcRn binding dimer or fusion protein, and
    folding of the FcRn binding dimer or fusion protein in aqueous solution.

In a fourth aspect of the disclosure, there is provided a composition comprising an FcRn binding dimer, fusion protein or conjugate as described herein and at least one pharmaceutically acceptable excipient or carrier. In one embodiment thereof, said composition further comprises at least one additional active agent, such as at least two additional active agents, such as at least three additional active agents. Non-limiting examples of additional active agents that may prove useful in such a combination are immunosuppressing agents, anti-inflammatory agents, antimicrobial agents and enzymes.

In one embodiment of this aspect, said composition is adapted for administration by a route selected from the group consisting of oral administration, intranasal administration, pulmonar administration, vaginal administration, rectal administration, intravenous injection, intraperitoneal injection, intramuscular injection, subcutaneous injection and intradermal injection.

As used herein, the term "systemic administration" refers to a route of administration such that the substance of interest enters into the circulatory system so that the entire body is affected. The skilled person is aware that systemic administration can take place via enteral administration (absorption of the drug through the gastrointestinal tract) or parenteral administration (generally injection, infusion or implantation).

In one embodiment, said composition is adapted for administration systemically or locally. In certain embodiments, systemic administration of said composition may be used. In another embodiment, said composition is adapted for administration by a local route. For example, local administration may be topical in an ointment, paste, foam or cream. In another embodiment, said composition is adapted for administration across an endothelial or epithelial layer. Here, the composition may be transcytosed across said layer.

In one embodiment, the rate of uptake of a composition comprising a fusion protein or conjugate as described herein is higher than the rate of uptake of polypeptides corresponding to second or further moieties per se. In one embodiment, the rate of uptake is at least 2 times higher, such as at least 5 times higher, such as at least 10 times higher, such as at least 25 times higher than the rate of uptake of the at second or further moieties per se.

It should be understood from the above disclosure that the FcRn binding dimer, fusion protein or conjugate or the composition as described herein may for example be useful as a therapeutic agent, and/or as a means for extending the in vivo half-life of a fusion partner, and/or as a means for increasing the rate of elimination of undesirable targets.

Hence, in a fifth aspect of the present disclosure, there is provided an FcRn binding dimer, fusion protein, conjugate or composition as disclosed herein for use as a medicament.

In a related, sixth, aspect of the present disclosure, there is provided a method of treatment or prophylaxis of a subject in need thereof, comprising the step of administrating a therapeutically or prophylactically active amount of an FcRn binding dimer, fusion protein, conjugate or composition as disclosed herein.

In one embodiment of any one of these two latter aspects, the medicament or method is intended for reduction of an IgG level in a subject in need thereof.

In one embodiment of any one of these two latter aspects, the medicament or method is intended for treatment or prophylaxis in which the capacity of the FcRn binding dimer to at least partially block binding of IgG to FcRn is exploited, for example treatment or prophylaxis in which increased catabolism of IgG antibodies is desired.

In another embodiment wherein the IgG blocking capacity is used, the administration of FcRn binding dimers as described herein has the effect of improving the efficacy of a drug, by blocking antibodies that exhibit anti-drug properties. In particular, the action of drugs that are cleared by antibodies or for which neutralizing antibodies are induced may be improved in this way, by administration of FcRn binding dimers prior to administration of the drug in question.

In another embodiment wherein the IgG blocking capacity is used, the administration of FcRn binding dimers as described herein has the effect of reducing harmful effects of antibodies by removing them or reducing their circulation time in the bloodstream of a subject. For example, radiolabelled or toxin-conjugated antibodies may be removed by the subsequent administration of FcRn binding dimers as disclosed herein. Alternatively, in cases where toxic adverse effects occur as a reaction against a therapeutic antibody drug, such adverse effect may be ameliorated or neutralized by the subsequent administration of an FcRn binding dimer to remove such antibodies or limit their circulation time.

In one embodiment, a condition in which such treatment or prophylaxis may be indicated is an auto-immune condition. As non-limiting examples of indicated conditions, mention is made of acute disseminated encephalomyelitis (ADEM), acute necrotizing hemorrhagic leukoencephalitis, Addison's disease, agammaglobulinemia, alopecia areata, amyloidosis, ANCA-associated vasculitis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune limbic encephalitis, autoimmune myocarditis, autoimmune pancreatitis, autoimmune retinopathy, autoimmune thrombocytopenic purpura (ATP), autoimmune thyroid disease, autoimmune urticarial, axonal & anal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), dilated cardiomyopathy, discoid lupus, Dressler's syndrome, endometriosis, eosinophilic angiocentric fibrosis, eosinophilic fasciitis, epidermolysis bullosa acquisita, erythema nodosum, experimental allergic encephalomyelitis, Evans syndrome, fibrosing alveolitis, giant cell arteritis (temporal arteritis), glomerulonephritis, Goodpasture's syndrome, granulomatosis with polyangiitis (GPA; Wegener's), Graves' disease, Guillain-Barré syndrome, Hashimoto's encephalitis, Hashimoto's thyroiditis, hemolytic anemia, Henoch-Schonlein purpura, herpes gestationis, hypogammaglobulinemia, idiopathic hypocomplementemic tubulointestitial nephritis, idiopathic membranous nephropathy, idiopathic thrombocytopenic purpura (ITP), IgA nephropathy, IgG4-related disease, IgG4-related sclerosing disease, immunoregulatory lipoproteins, inflammatory aortic aneurysm, inflammatory pseudotumor, inclusion body myositis, insulin-dependent diabetes (type 1), interstitial cystitis, juvenile arthritis, juvenile diabetes, Kawasaki syndrome, Kuttner's tumor, Lambert-Eaton syndrome, leukocytoclastic vasculitis, lichen planus, lichen sclerosus, ligneous conjunctivitis, linear IgA disease (LAD), lyme disease, chronic mediastinal fibrosis, Meniere's disease, microscopic polyangiitis, Mikulicz's syndrome, mixed connective tissue disease (MCTD), Mooren's ulcer, morvan syndrome, Mucha-Habermann disease, mucus membrane pemphigoid, multifocal fibrosclerosis, multiple sclerosis, myasthenia gravis, myositis, narcolepsy, neuromyelitis optica (Devic's), neuromyotonia (Isaac's syndrome), neutropenia, ocular cicatricial pemphigoid, optic neuritis, Ormond's disease (retroperitoneal fibrosis), palindromic rheumatism, PANDAS (pediatric autoimmune neuropsychiatric disorders associated with *streptococcus*), paraneoplastic cerebellar degeneration, paraproteinemic polyneuropathies, paroxysmal nocturnal hemoglobinuria (PNH), Parry Romberg syndrome, Parsonnage-Turner syndrome, pars planitis (peripheral uveitis), pemphigoid gestationis, pemphigus vulgaris, periaortitis, periarteritis, peripheral neuropathy, perivenous encephalomyelitis, pernicious anemia, POEMS syndrome, polyarteritis *nodosa*, polyarthritis, Type I, II, & III autoimmune polyglandular syndromes, polymyalgia rheumatic, polymyositis, postmyocardial infarction syndrome, post-pericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reflex sympathetic dystrophy, Reiter's syndrome, relapsing polychondritis, restless legs syndrome, retroperitoneal fibrosis (Ormond's disease), rheumatic fever, rheumatoid arthritis, Riedel's thyroiditis, sarcoidosis, Schmidt syndrome, scleritis, scleroderma, Sjögren's syndrome, sperm & testicular autoimmunity, stiff person syndrome, subacute bacterial endocarditis (SBE), Susac's syndrome, sympathetic ophthalmia, Takayasu's arteritis, systemic lupus erythematosus (SLE), temporal arteritis/giant cell arteritis, thrombotic thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenström macroglobulinaemia and warm idiopathic hemolytic anemia.

In another embodiment of the fifth and sixth aspects, a condition in which such treatment or prophylaxis may be indicated is an allo-immune condition. As non-limiting examples of indicated conditions, mention is made of transplantation donor mismatch due to anti-HLA antibodies; foetal and neonatal alloimmune thrombocytopenia, FNAIT (or neonatal alloimmune thrombocytopenia, NAITP or NAIT or NAT, or foeto-maternal alloimmune thrombocytopenia, FMAITP or FMAIT).

In another embodiment of the fifth and sixth aspects, a condition in which such treatment or prophylaxis may be indicated is selected from the group consisting of autoimmune polyendocrine syndrome types 1 (APECED or Whitaker's Syndrome) and 2 (Schmidt's Syndrome); alopecia universalis; myasthenic crisis; thyroid crisis; thyroid associated eye disease; thyroid ophthalmopathy; autoimmune diabetes; autoantibody associated encephalitis and/or encephalopathy; pemphigus *foliaceus*; epidermolysis bullosa; dermatitis herpetiformis; Sydenham's chorea; acute motor axonal neuropathy (AMAN); Miller-Fisher syndrome; multifocal motor neuropathy (MMN); opsoclonus; inflammatory myopathy; Isaac's syndrome (autoimmune neuromyotonia), paraneoplastic syndromes and limbic encephalitis.

In another embodiment of the fifth and sixth aspects, a condition in which such treatment or prophylaxis may be indicated is selected from epilepsy and seizures.

In another embodiment, there is provided an FcRn binding dimer, fusion protein, conjugate or composition as described herein for use in blocking or removal of an undesirable target from the circulation. In one embodiment, said undesirable target is selected from the group comprising allergens, amyloids, antibodies, auto-antigens, blood clotting factors, hormones, tumor cells, drug molecules, cytokines, chemokines, hypersensitivity mediators, pro-inflammatory factors, toxins such as bacterial toxins and snake venoms, pollutants, metals and anti-oxidants.

While the invention has been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated, but that the invention will include all embodiments falling within the scope of the appended claims.

BRIEF DESCRIPTION OF THE FIGURES

FIG. 1 is a listing of the amino acid sequences of examples of FcRn binding polypeptides in monomeric form (SEQ ID NO:1-367) and FcRn binding polypeptides in dimeric form (SEQ ID NO:368-376), as well as the amino acid sequences of the albumin binding polypeptide variant PP013 (SEQ ID NO:377), Taq polymerase binding Z variant Z03638 (SEQ ID NO:378), human αFcRn (SEQ ID NO:379), murine αFcRn (SEQ ID NO:384), human δ2-microglobulin (SEQ ID NO:380), murine δ2-microglobulin (SEQ ID NO:381), human αFcRn (SEQ ID NO:382) when in human FcRn-eGFP and murine αFcRn (SEQ ID NO:383) when in murine FcRn-eGFP. The deduced FcRn binding motifs (BMs) of the FcRn binding polypeptides disclosed herein extend from residue 8 to residue 36 in sequences with SEQ ID NO:1-367. The amino acid sequences of the 49 amino acid residues long polypeptides (BMod) predicted to constitute the complete three-helix bundle within each of these Z variants extend from residue 7 to residue 55.

FIG. 14 shows reduction of hIgG levels in FcRn transgenic mice treated with dimeric polypeptides as described in Example 20. (A) Reduction of hIgG levels was equally efficient with the albumin binding domain PP013 (SEQ ID NO:377) situated between the two Z moieties (ZAZ3715; SEQ ID NO:371) as with PP013 situated at the C-terminus of the polypeptide (ZZA3716; SEQ ID NO:372). (B) Equal reduction of hIgG levels was obtained with the polypeptides ZAZ3869 (SEQ ID NO:374), ZAZ3870 (SEQ ID NO:375) and ZAZ3871 (SEQ ID NO:376).

EXAMPLES

Summary

Figure 2A:
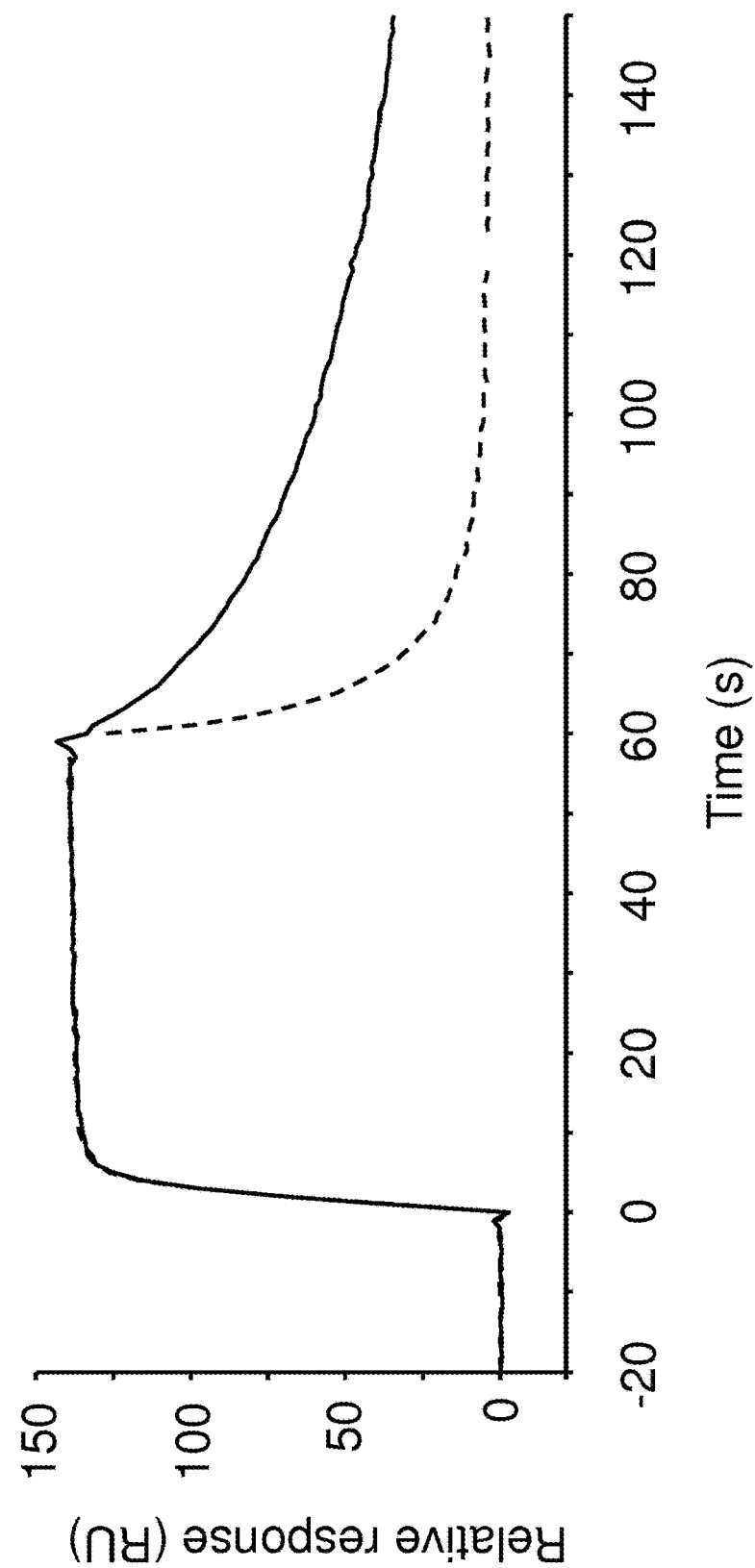
FIGS. 2A-2E show the binding to human FcRn at pH 6.0 and dissociations at pH 6.0 and 7.4 for $His_6$-tagged Z variants and for IgG as described in Example 3. Overlays of sensorgrams obtained from a Biacore instrument representing injection at pH 6.0 followed by dissociation at pH 6.0 (solid line) and injection at pH 6.0 followed by dissociation at pH 7.4 (dashed line) are displayed for (A) Z07918 (SEQ ID NO:1), (B) Z07960 (SEQ ID NO:4), (C) Z10109 (SEQ ID NO:3), (D) Z10193 (SEQ ID NO:2) and (E) IgG.
Figure 2B:
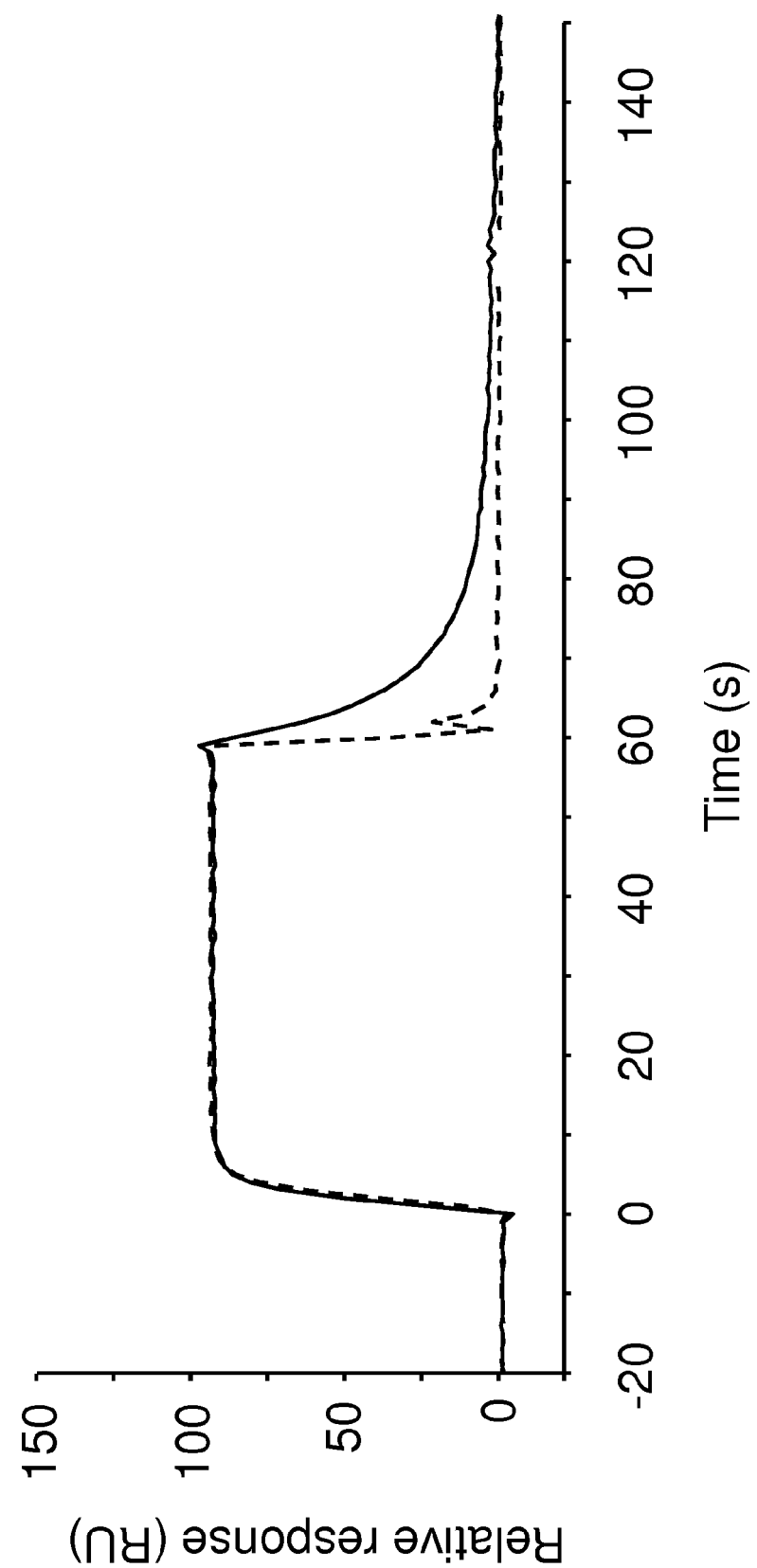
Figure 2C:
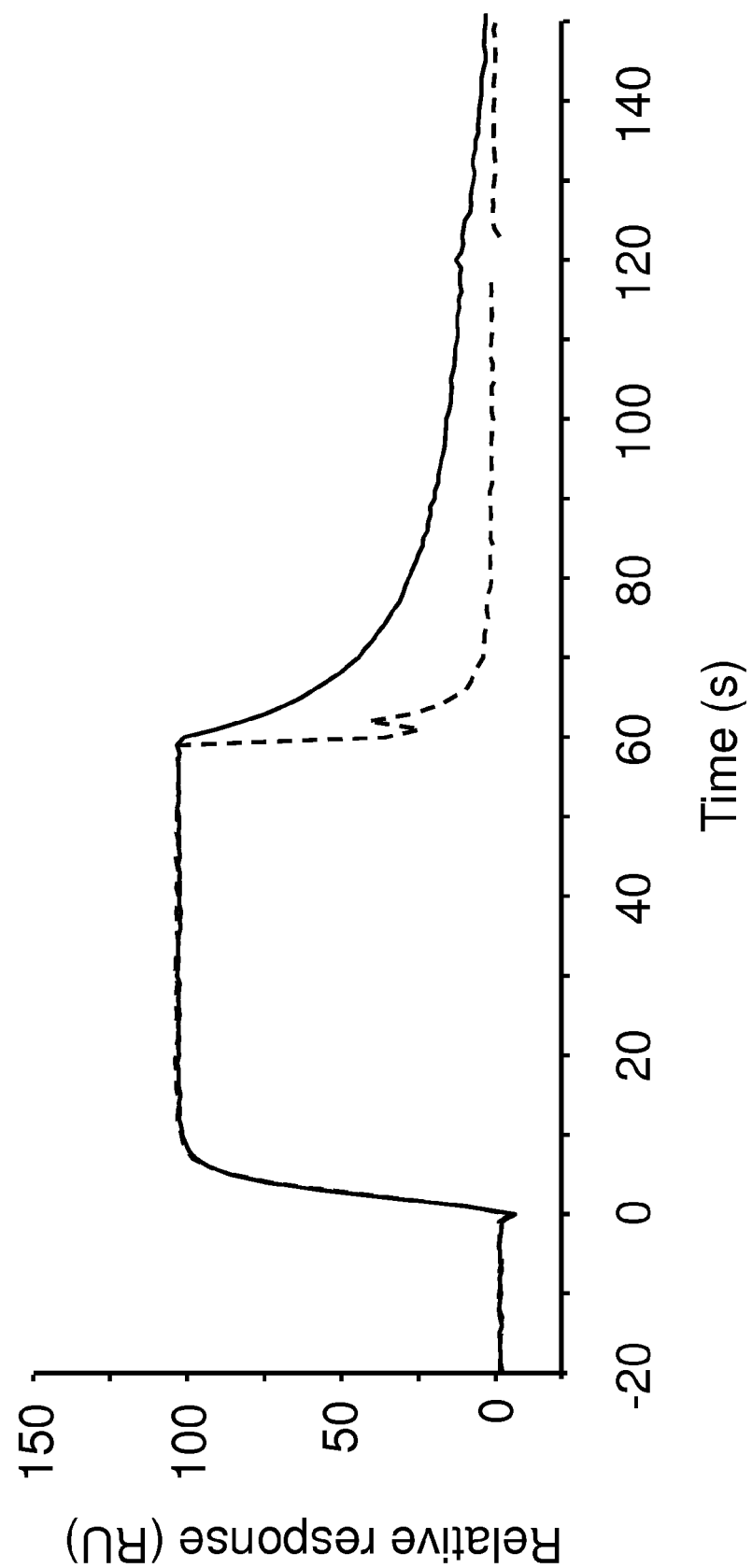
Figure 2D:
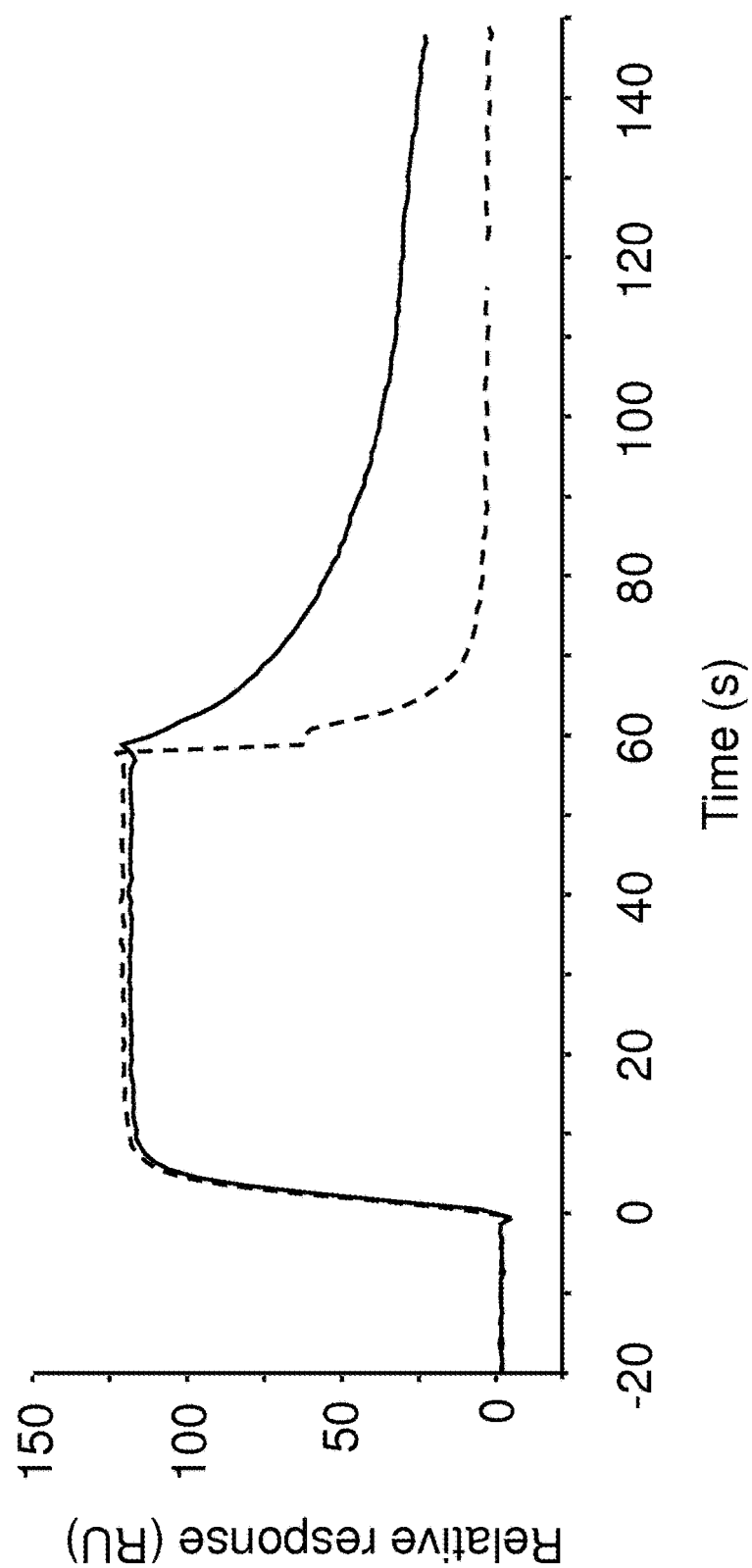
Figure 2E:
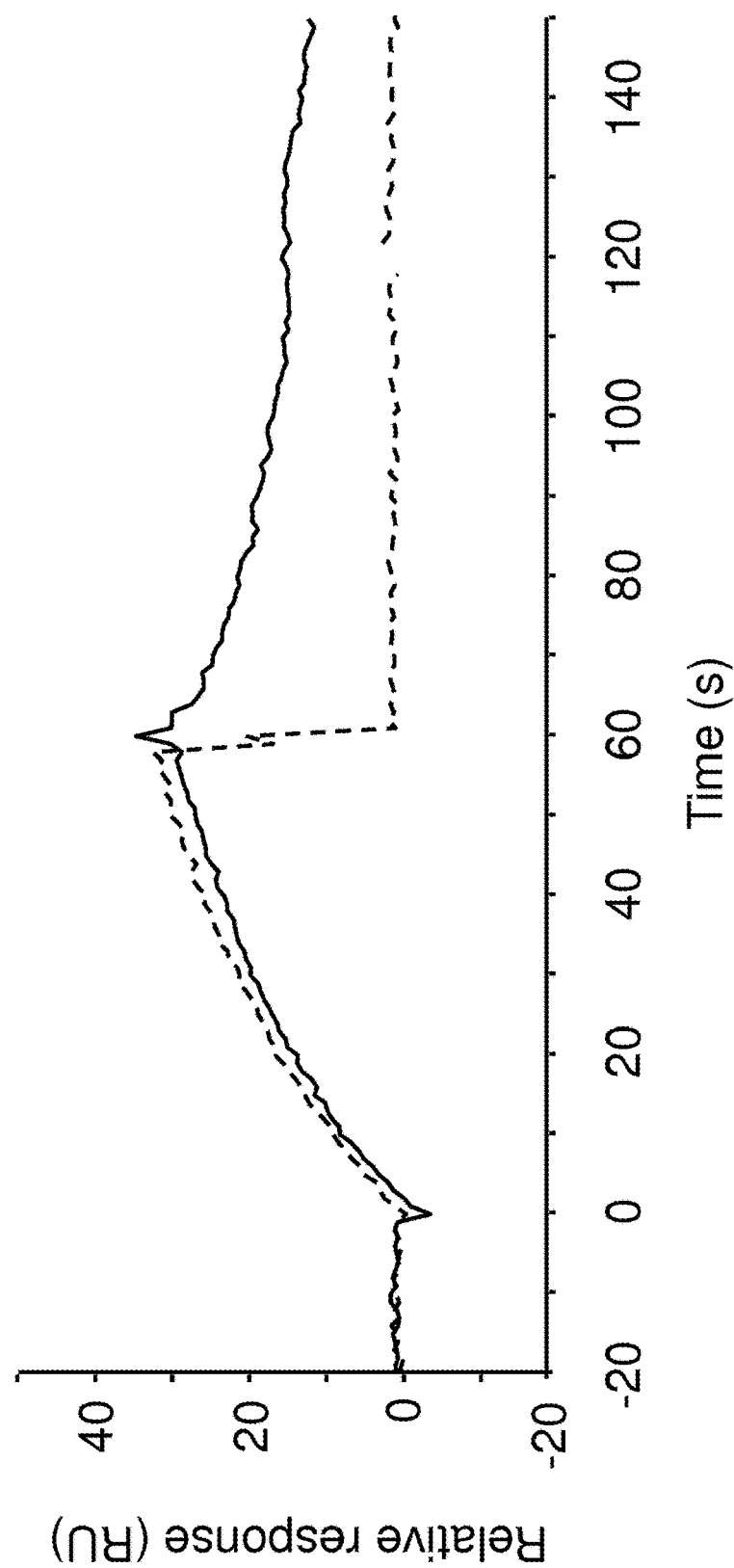

The following Examples disclose the development of novel Z variant molecules targeting the neonatal Fc receptor (FcRn). The Z variants were obtained using phage display technology. The genes encoding FcRn binding polypeptides described herein were sequenced, and the corresponding amino acid sequences are listed in FIG. 1, and denoted by the identifiers SEQ ID NO:1-353. The deduced FcRn binding motifs (BMs) of the FcRn binding polypeptides disclosed herein extend from residue 8 to residue 36 in sequences with SEQ ID NO:1-353. Furthermore, the FcRn binding properties and ability to block IgG binding to FcRn of said polypeptides in dimeric form were investigated.

Example 1

Production of Human αFcRn and Human β2-Microglobulin (B2M)

In this Example, the extracellular domain (ECD) of human αFcRn (SEQ ID NO:379) in complex with human δ2-microglobulin (SEQ ID NO:380) (complex denoted FcRn) and human δ2-microglobulin in non-complexed form (denoted B2M) were produced as soluble proteins. Human FcRn and B2M produced in this Example were used for phage selection, ELISA and Biacore assays in Examples 2 and 3.

Materials and Methods

Construction of Plasmids Containing the Genes for Human αFcRn and Human β2-Microglobulin to be Used for Co-Expression:

The genes encoding human αFcRn (Genbank BC008734.2) and human δ2-microglobulin (B2M) (Genbank BC032589.1) were obtained from OpenBiosystems. Using PCR overlap extension, a gene fragment encoding amino acids 24-290 of human αFcRn (αFcRn$_{ECD}$) (SEQ ID NO:379) was amplified to a construct consisting of attB1-site/Kozak sequence followed by a gene encoding: an Ig kappa chain leader sequence, hFcRn$_{ECD}$, a GS-linker and a flag tag, followed by an attB2 site. A similar construct was made containing a gene fragment encoding amino acids 21-119 of human B2M (SEQ ID NO:380), except that a Hiss tag replaced the flag tag. The constructs were inserted into the plasmid pDONOR221 (Invitrogen, cat. no. 12536-017) by recombination using the Gateway system (Invitrogen, cat. no. 11789020, Gateway® BP Clonase® II Enzyme mix), according to the manufacturer's recommendations. After verification of correct sequences, the human αFcRn$_{ECD}$ construct was inserted into 2K7$_{bsd}$ (Suter et al. (2006) Stem Cells 24:615-623) using multi-site gateway cloning together with the promoter-containing plasmid pENTR-CMV (Tai et al. (2012) PLoS One 7(9):e46269), resulting in the vector 2K7$_{bsd}$-CMV-hFcRn$_{ECD}$. The human B2M gene construct was similarly inserted into 2K7$_{neo}$ (Suter et al., supra), giving the vector 2K7$_{neo}$-CMV-hB2M.

Cell Culture, Preparation of Recombinant Lentiviral Vectors and Gene Insertions into SKOV-3 Cell Line:

The HEK293T and SKOV-3 cell lines were obtained from ATCC. Cells were grown at 37° C. in a humidified incubator in the presence of 5% CO$_2$. Complete medium for the HEK293T cell line was Dulbeccos modified eagle medium (DMEM) supplemented with 10% fetal bovine serum (FBS), 1% Antibiotic Antimycotic Solution (AA) and 1% MEM Non-essential Amino Acid Solution (NEAA). Complete medium for the SKOV-3 cell line was McCoy's 5A medium supplemented with 10% FBS and 1% AA.

The plasmids 2K7$_{bsd}$-CMV-hFcRn$_{ECD}$ and 2K7$_{neo}$-CMV-hB2M were separately co-transfected together with VSV-G envelope and gag/pol packaging plasmid into HEK293T cells using calcium chloride transfection (Zufferey et al. (1997) Nat Biotechnol 15(9):871-5, Jakobsson et al. (2006) J Neurosci Res 84:58-67). HEK293 culture supernatants containing formed lentiviral particles with human αFcRnE$_{ECD}$ and human B2M transgenes, respectively, were cleared from cell debris by centrifugation and filtration. The two types of lentiviral particles were used to sequentially transduce SKOV-3 cells. Successful double integrants containing both the human αFcRn$_{ECD}$ and the B2M genes were selected for by the addition of blasticidin (Invitrogen) and G418 sulfate (Invitrogen) to culture medium while passaging the cells for two weeks. The resulting, stably transduced SKOV-3 cell line was denoted SKOV-3 hFcRn$_{ECD}$/hB2M.

Expression of Recombinant Human FcRn:

SKOV-3 cells, co-expressing human αFcRn$_{ECD}$ and B2M resulting in human FcRn, were expanded and $1.5 \times 10^7$ cells were seeded in a HYPERFlask (Corning) in 560 ml complete growth medium. After five days, when the cells had settled and multiplied, the medium was changed to complete growth medium without FBS. After five days, the culture was terminated and the supernatant was collected, passed through a 45 μm filter and frozen at −80° C.

Purification of Recombinant Human FcRn Using Human IgG Chromatography:

Protein purification was carried out in an ÄKTA Explorer system (GE Healthcare). Human IgG (Pharmacia), 1 ml in 0.2 M NaHCO$_3$, 0.5 M NaCl pH 8.3 at a concentration of 10 mg/ml, was coupled to a 1 ml HiTrap NHS-activated HP column (GE Healthcare) according to the manufacturer's instruction. The supernatant containing recombinant human FcRn from SKOV-3 cells was thawed and the pH was adjusted to 5.8 with HCl. The supernatant was subsequently loaded in batches of 100 ml onto the column previously equilibrated with 20 mM Bis-Tris pH 5.8. The column was washed with 20 ml of 20 mM Bis-Tris pH 5.8 and eluted in fractions of 1 ml using 50 mM Tris, pH 8.1. Buffer exchange to PBS (phosphate buffered saline, 10 mM phosphate, 137 mM NaCl, 2.68 mM KCl, pH 7.4) was performed using dialysis.

SDS-PAGE and Western Blot:

The purity of the eluted fractions from the protein purification was analyzed by SDS-PAGE and staining with GelCode Blue Stain Reagent (Pierce) and SilverXpress® Silver Staining Kit (Invitrogen). Western blotting was carried out using an Amersham Hybond™-C Extra nitrocellulose membrane (GE Healthcare). The membrane was blocked with 5% non-fat dry milk (Semper) in TBS+T (50 mM Trizma base, 150 mM NaCl, 0.05% Tween-20, pH 8) for 1 hour, then probed with a mixture of rabbit anti-FCGRT polyclonal antibody (Atlas Antibodies) at a concentration of 0.15 μg/ml and rabbit anti-B2M polyclonal antibody (Atlas Antibodies) at a concentration of 0.23 μg/ml in TBS+T. The membrane was subsequently incubated with stabilized goat anti-rabbit antibody conjugated with horse radish peroxidase (Pierce) diluted 1:10,000 in TBS+T. After addition of TMB Substrate (Pierce), an image of the membrane was acquired on Amersham Hyperfilm ECL (GE Healthcare). The Hyperfilm was processed using GBX developer and GBX fixer (Sigma-Aldrich).

Production of a Non-Complexed Form of Human B2M:

Human B2M was produced in E. coli. The expression and purification was performed essentially as described in Sandalova et al. (2005) Acta Chryst F61:1090-1093 and Michaelsson et al. (2001) J Immunol 166:7327-7334. The purified protein, consisting of amino acids 21-119 of human B2M, in urea was subjected to arginine refolding as follows; 0.5 mg of B2M was rapidly added to 2 ml refolding buffer (20 ml 1 M Tris-HCl pH 8.0, 16.87 g L-Arginine (buffered with HCl), 0.8 ml 0.5 M EDTA, 61 mg GSSG, 307 mg GSH and milli-Q water to a final volume of 200 ml, pH 8.0, and supplemented with protease inhibitor (Roche, cat. no. 11 873 580 001)). The refolding procedure was performed at 4° C. during 4 hours. Refolded B2M protein was buffer exchanged to PBS using a PD-10 column (GE Healthcare).

Results

Construction of Plasmids Containing the Genes for Human αFcRn and Human β2-Microglobulin to be Used for Co-Expression:

Genes encoding the extracellular domain of the α-chain of human FcRn (αFcRn$_{ECD}$) and human B2M were inserted into the lentiviral transfer plasmids 2K7$_{bsd}$ and 2K7$_{neo}$, respectively. In both cases, the inserted gene is under the control of a CMV promoter. The genes were extended so that the resulting proteins would have an Ig kappa chain leader sequence in the N-terminus to target the protein for export through the endoplasmic reticulum to the culture medium (the signal sequence was cleaved upon secretion). In addition, αFcRn$_{ECD}$ had a C-terminal spacer sequence followed by a FLAG-tag for potential detection. Human B2M had a C-terminal spacer sequence followed by a His$_6$ tag for potential detection. The spacer sequence was added to enhance accessibility of the tag. The lentiviral transfer plasmids also contained two different antibiotic resistance genes to allow selection of cells where both constructs had been inserted.

Expression and Purification of Recombinant Human FcRn:

The genes encoding αFcRn$_{ECD}$ and B2M were inserted into the genome of SKOV-3 by lentiviruses, and the resulting FcRn protein was secreted into the culture medium. To capture only FcRn having retained pH-dependent IgG binding, affinity chromatography using immobilized IgG was used where the receptor was captured at pH 5.8 and eluted at pH 8.1. Captured protein was eluted in three fractions.

SDS-PAGE and Western Blot:

To investigate the presence of two peptide chains (αFcRn$_{ECD}$ and B2M) of the produced FcRn protein, and to analyze the purity of the eluted material, an SDS-PAGE analysis was performed on the eluted fractions. For the gel stained with GelCode Blue Stain, two bands were detected with molecular weights of 12 and 36 kDa, respectively. This corresponds approximately to the theoretical molecular weights of the non-glycosylated peptide chains of 12 kDa for B2M and 31 kDa for αFcRn$_{ECD}$. The αFcRn$_{ECD}$ part of the protein contains one glycosylation site and it was therefore expected that its molecular mass would be higher than 31 kDa. The gel was also silver stained to increase sensitivity and possibly detect impurities. A band of approximately 66 kDa was detected in the first eluted fraction, which could correspond to BSA (bovine serum albumin) originating from cell attachment. The total amount of protein recovered in fraction 2 and 3 corresponded to 1.4 mg/l culture medium. A western blot analysis on the pooled material was carried out, which showed essentially only the two major bands and in addition a very weak band below 12 kDa which might correspond to a degradation product.

Example 2

Selection and ELISA Binding of FcRn Binding Z Variants

In this Example, human FcRn was used as target in phage display selections using a phage library of Z variants. Selected clones were DNA sequenced, produced in *E. coli* periplasmic fractions and assayed against FcRn in ELISA (enzyme-linked immunosorbent assay).

Materials and Methods

Biotinylation of Target Protein FcRn and of B2M:

Human FcRn and human B2M, produced as described in Example 1, were biotinylated using No-Weigh EZ-Link Sulfo-NHS-LC-Biotin (Pierce, cat. no. 21327) at a 31× (FcRn) and 10× (B2M) molar excess, respectively, according to the manufacturer's recommendations. The reactions were performed at room temperature (RT) for 30 min. Subsequent buffer exchange to PBS was performed using Slide-a-lyzer dialysis cassettes (FcRn; Pierce, cat. no. 66380, 10,000 MWCO and B2M; Pierce, cat. no. 66333, 3,500 MWCO), according to the manufacturer's instructions.

Phage Display Selection of FcRn Binding Z Variants:

A library of random variants of protein Z displayed on bacteriophage, constructed in phagemid pAY02592 essentially as described in Grönwall et al. (2007) J Biotechnol, 128:162-183, was used to select FcRn binding Z variants. In this library, an albumin binding domain (ABD, GA3 of protein G from *Streptococcus* strain G148) is used as fusion partner to the Z variants. The library is denoted Zlib006Naive.II and has a size of $1.5 \times 10^{10}$ library members (Z variants). *E. coli* RRIΔM15 cells (Ruther et al., (1982) Nucleic Acids Res 10:5765-5772) from a glycerol stock containing the phagemid library Zlib006Naive.II, were inoculated in 20 l of a defined proline free medium [dipotassium hydrogenphosphate 7 g/l, trisodium citrate dihydrate 1 g/l, uracil 0.02 g/l, YNB (Difco™ Yeast Nitrogen Base w/o amino acids, Becton Dickinson) 6.7 g/l, glucose monohydrate 5.5 g/l, L-alanine 0.3 g/l, L-arginine monohydrochloride 0.24 g/l, L-asparagine monohydrate 0.11 g/l, L-cysteine 0.1 g/l, L-glutamic acid 0.3 g/l, L-glutamine 0.1 g/l, glycine 0.2 g/l, L-histidine 0.05 g/l, L-isoleucine 0.1 g/l, L-leucine 0.1 g/l, L-lysine monohydrochloride 0.25 g/l, L-methionine 0.1 g/l, L-phenylalanine 0.2 g/l, L-serine 0.3 g/l, L-threonine 0.2 g/l, L-tryptophane 0.1 g/l, L-tyrosine 0.05 g/l, L-valine 0.1 g/l], supplemented with 100 µg/ml ampicillin. The cultivations were grown at 37° C. in a fermenter (Belach Bioteknik, BR20). When the cells reached an optical density at 600 nm (OD600) of 0.75, approximately 2.6 l of the cultivation was infected using a 10× molar excess of M13K07 helper phage (New England Biolabs, cat. no. N0315S). The cells were incubated for 30 minutes, whereupon the fermenter was filled up to 20 l with TSB-YE (Tryptic Soy Broth-Yeast Extract; 30 g/l TSB, 5 g/l yeast extract) supplemented with 100 µM isopropyl-β-D-1-thiogalactopyranoside (IPTG) for induction of expression and with 25 µg/ml kanamycin and 12.5 µg/ml carbenicillin and grown at 30° C. for 22 h. The cells in the cultivation were pelleted by centrifugation at 15,900 g. The phage particles were precipitated from the supernatant twice in PEG/NaCl (polyethylene glycol/sodium chloride), filtered and dissolved in PBS and glycerol as described in Grönwall et al., supra. Phage stocks were stored at −80° C. before use.

Selections against biotinylated human FcRn were performed in four cycles divided in two different tracks. Phage stock preparation and selection procedure were performed essentially as described for selection against another biotinylated target in WO2009/077175. The amplification of phage between the selection cycles was performed by infecting *E. coli* RRIΔM15 with phage, then performing cultivation in solution as follows. Eluted phage and 10× excess of M13K07 helper phage compared to bacteria were allowed to simultaneously infect log phase bacteria at 37° C. for 30 min without rotation, followed by 30 min with slow rotation. Prior to infection, bacteria were grown to log phase in the defined proline free medium described above. Infected bacteria were pelleted by centrifugation at 4,300 g for 10 min and resuspended in 200 ml TSB+YE medium supplemented with 0.1 mM IPTG, 25 μg/ml kanamycin and 100 μg/ml ampicillin and cultivated at 30° C. overnight for phage production.

The selection buffer consisted of 100 mM sodium phosphate and 150 mM sodium chloride adjusted to pH 5.5 with hydrogen chloride and supplemented with 0.1% gelatin and 0.1% Tween-20. At selection, human serum albumin (HSA, Albucult, Novozymes) was added to the selection buffer to a final concentration of 1.5 μM. In order to reduce the amount of background binders, pre-selection was performed by incubation of phage stock with Dynabeads® M-280 Streptavidin (SA-beads, Dynal, cat. no. 112.06) for 1 hour at RT. A second pre-selection was performed during 30 min at RT against human B2M immobilized in immunotubes (Nunc, cat. no. 444474). 5 μg/ml of human B2M in carbonate buffer (Sigma, cat. no. 068K8214) was immobilized in the tube at 7° C. for >1 h. After washing twice with tap water, the tubes were blocked with PBS+0.5% casein (Sigma, cat. no. C8654) for 30 min at RT before use. All tubes and beads used in the selection were pre-blocked with PBS+0.1% gelatin. Selection was performed in solution at RT, followed by capture of target-phage complexes on SA-beads where 1 mg beads per 2.9 μg biotinylated FcRn were used. In cycle 1 of the selections, 100 nM biotinylated FcRn was used and two washes of two min each were performed using selection buffer. An increased stringency, using a lowered target concentration and an increased number of washes, was applied in the subsequent cycles: 50 nM/5 washes, 25 nM/8 washes and 10 nM/12 washes were applied in cycle 2, 3 and 4, respectively. After the washes, bound phage was eluted from the two selection tracks using two different procedures; 1) 500 μl 0.1 M glycine-HCl, pH 2.2, followed by immediate neutralization with 50 μl 1 M Tris-HCl, pH 8.0, and 450 μl PBS, or; 2) 500 μl of 100 mM sodium phosphate and 150 mM sodium chloride, pH 8.0 and neutralization with 500 μl PBS.

Sequencing:

PCR fragments were amplified from single colonies using a standard PCR program and the primers AFFI-21 (5'-tgcttccggctcgtatgttgtgtg (SEQ ID NO:385)) and AFFI-22 (5'-cggaaccagagccaccaccgg (SEQ ID NO:386)). Sequencing of amplified fragments was performed using the biotinylated oligonucleotide AFFI-72 (5'-biotin-cggaaccagagccaccaccgg (SEQ ID NO:387)) and a BigDye® Terminator v3.1 Cycle Sequencing Kit (Applied Biosystems), used in accordance with the manufacturer's protocol. The sequencing reactions were purified by binding to magnetic streptavidin coated beads (Detach Streptavidin Beads, Nordiag, cat. no. 2012-01) using a Magnatrix 8000 (Magnetic Biosolution), and analyzed on ABI PRISM® 3130xl Genetic Analyzer (PE Applied Biosystems).

Production of Z Variants for ELISA:

Sequenced Z variants were produced by inoculating single colonies from the selections into 10 ml TSB-YE medium supplemented with 100 μg/ml ampicillin and 0.1 mM IPTG and incubating for 24 h at 37° C. Cells were pelleted by centrifugation, re-suspended in 2 ml PBST (PBS supplemented with 0.05% Tween-20), frozen at −80° C. and thawed in a water bath, to release the periplasmic fraction of the cells. The freeze-thawing procedure was repeated seven times and cells were then pelleted by centrifugation. The supernatant of the periplasmic extract contained the Z variants as fusions to ABD, expressed as AQHDEALE-[Z#####]-VDYV-[ABD]YVPG (SEQ ID NO:464) (Grönwall et al., supra). Z##### refers to individual, 58 amino acid residue Z variants.

ELISA $K_D$ Analysis of Z Variants:

The binding of Z variants to FcRn was analyzed in ELISA assays. Half-area 96-well ELISA plates were coated with 2 μg/ml of an anti-ABD goat antibody (produced in-house) diluted in coating buffer (50 mM sodium carbonate, pH 9.6) at 4° C. overnight. The antibody solution was poured off and the wells were blocked with 100 μl of PBSC (PBS supplemented with 0.5% casein) for 1.5 h at RT. The blocking solution was discarded and 50 μl periplasmic solution, diluted 1:4, was added to the wells and incubated for 1.5 h at RT under slow shaking. The solutions were poured off and the wells were washed four times with either 0.05% PCT buffer, pH 6.0 (McIlvaines phosphate-citrate buffer, pH 6.0, supplemented with 0.05% Tween-20) or 0.05% PCT buffer, pH 7.4 (McIlvaines phosphate-citrate buffer, pH 7.4, supplemented with 0.05% Tween-20). The target protein, biotinylated human FcRn, was added to the wells in a 1:3 diluted concentration series from 2 μg/ml (45 nM) to 0.3 ng/ml (6.9 pM) diluted in PCC buffer, pH 6.0 or pH 7.4, (McIlvaines phosphate-citrate buffer, pH 6.0 or pH 7.4, supplemented with 0.5% casein), respectively. The plates were incubated for 1.5 h at RT followed by washes as described above. Streptavidin conjugated HRP (Thermo Scientific, cat. no. N100) was diluted 1:30 000 in PCC buffer, pH 6.0 or pH 7.4, respectively, and added to the wells followed by 45 min incubation. After washing as described above, 50 μl ImmunoPure TMB substrate (Thermo Scientific, cat. no. 34021) was added to the wells and the plates were treated according to the manufacturer's recommendations. Absorbance was measured at 450 nm using a multi-well plate reader, Victor$^3$ (Perkin Elmer). A Z variant binding an irrelevant protein was used as negative control and a blank was created by omitting the periplasmic step. A Z variant which bound to FcRn in a pre-experiment (Z07918, SEQ ID NO:1) was used as positive control. Measured values were analyzed using GraphPad Prism 5 (GraphPad Software, Inc.) and non-linear regression in order to determine the affinities ($K_D$) of the interactions.

ELISA Specificity Analysis of Z Variants:

In another ELISA experiment, the specificities of the Z variants were tested by assaying them against 2 μg/ml biotinylated human proteins B2M, PSMA (produced in-house) and IgG (polyclonal, Pharmacia) and against PCC buffer pH 6.0 or pH 7.4, respectively. The assay was performed at pH 6.0 and at pH 7.4, respectively, as described above. The biotinylated proteins or buffer were added to the wells instead of FcRn in the target protein step.

Results

Phage Display Selection of FcRn Binding Z Variants:

Individual clones were obtained after four cycles of phage display selections against biotinylated human FcRn.

Sequencing:

Sequencing was performed on clones picked at random from selection round four. Each Z variant was given a unique identification number ##### and individual variants are referred to as Z#####. The amino acid sequences of the 58 amino acid residues long Z variants are listed in FIG. 1 as SEQ ID NO:1-16 and SEQ ID NO:353.

The deduced FcRn binding motifs of these Z variants extend from residue 8 to residue 36 in sequences with SEQ ID NO:1-16 and SEQ ID NO:353 in FIG. 1. The amino acid sequences of the 49 amino acid residues long polypeptides (BMod) predicted to constitute the complete three-helix bundle within each of these Z variants extend from residue 7 to residue 55.

ELISA Assays with Z Variants:

Sixteen clones were produced as ABD fusion proteins in E. coli. The periplasmic fractions were used in an ELISA against a dilution series of human FcRn. The clones were: Z07909 (SEQ ID NO:13), Z07918 (SEQ ID NO:1), Z07930 (SEQ ID NO:6), Z07960 (SEQ ID NO:4), Z10109 (SEQ ID NO:3), Z10111 (SEQ ID NO:8), Z10127 (SEQ ID NO:12), Z10129 (SEQ ID NO:9), Z10140 (SEQ ID NO:5), Z10141 (SEQ ID NO:10), Z10145 (SEQ ID NO:15), Z10152 (SEQ ID NO:14), Z10156 (SEQ ID NO:11), Z10161 (SEQ ID NO:16), Z10183 (SEQ ID NO:7) and Z10193 (SEQ ID NO:2). $K_D$ values were determined for all variants at pH 6.0 and for three variants at pH 7.4 (Table 2). For thirteen variants, data was not obtained for a $K_D$ analysis at pH 7.4. None of the sixteen variants displayed non-specific binding when assayed against human B2M, IgG or PSMA.

TABLE 2

ELISA KD analysis of Z-ABD variants in E. coli periplasmic fractions.

| Z variant | SEQ ID NO: | $K_D$ pH 6.0 (M) | $K_D$ pH 7.4 (M) |
|---|---|---|---|
| Z07909 | 13 | $24.5 \times 10^{-9}$ | n.d. |
| Z07918 | 1 | $2.0 \times 10^{-9}$ | $10.9 \times 10^{-9}$ |
| Z07930 | 6 | $10.4 \times 10^{-9}$ | n.d. |
| Z07960 | 4 | $6.0 \times 10^{-9}$ | n.d. |
| Z10109 | 3 | $3.9 \times 10^{-9}$ | $23.9 \times 10^{-9}$ |
| Z10111 | 8 | $11.4 \times 10^{-9}$ | n.d. |
| Z10127 | 12 | $21.3 \times 10^{-9}$ | n.d. |
| Z10129 | 9 | $17.6 \times 10^{-9}$ | n.d. |
| Z10140 | 5 | $8.8 \times 10^{-9}$ | n.d. |
| Z10141 | 10 | $21.2 \times 10^{-9}$ | n.d. |
| Z10145 | 15 | $42.0 \times 10^{-9}$ | n.d. |
| Z10152 | 14 | $24.6 \times 10^{-9}$ | n.d. |
| Z10156 | 11 | $21.3 \times 10^{-9}$ | n.d. |
| Z10161 | 16 | $163.0 \times 10^{-9}$ | n.d. |
| Z10183 | 7 | $10.9 \times 10^{-9}$ | n.d. |
| Z10193 | 2 | $2.3 \times 10^{-9}$ | $25.9 \times 10^{-9}$ | n.d. = not determinable

Example 3

Production and Characterization of FcRn Binding Z Variants

In this Example, seventeen Z variants were produced in *E. coli*, purified and assayed against human FcRn in Biacore. A subset of said variants was also assayed against mouse FcRn. Circular dichroism (CD) spectroscopy was performed for a subset of Z variants for investigation of their secondary structure.

Materials and Methods

Subcloning of Z Variants:

The DNA of seventeen FcRn binding Z variants (SEQ ID NO:1-16 and SEQ ID NO:353) was amplified from the library vector pAY02592. A subcloning strategy for construction of monomeric Z variant molecules with N-terminal $His_6$ tag was applied using standard molecular biology techniques (essentially as described in detail in WO2009/077175 for Z variants binding another target). The Z gene fragments were subcloned into the expression vector pAY01448 resulting in the encoded sequence MGSSHHH-HHHLQ-[Z#####]-VD (SEQ ID NO:468.

In addition, the FcRn binding variant Z07918 (SEQ ID NO:1), but starting with the amino acids AE instead of VD and denoted Z11948 (SEQ ID NO:354), was cloned as homodimeric constructs with two different linkers between the Z variants and followed by a C-terminal $His_6$ tag. This was performed using conventional molecular biology methods including DNA amplification, restriction with suitable restriction enzymes and ligation of the DNA. The two linkers were obtained from Thermo Fisher Scientific. The Z gene fragments were subcloned into the expression vector (pET-26 origin, Novagen) resulting in the encoded sequence [Z#####]-GT-(G$_4$S)-PR-[Z###]-LEHHHHHH and [Z#####]-GT-(G$_4$S)$_3$-[Z#####]-LEHHHHHH, respectively.

Cultivation and Purification:

*E. coli* BL21(DE3) cells (Novagen) were transformed with plasmids containing the gene fragment of each respective FcRn binding Z variant and cultivated at 37° C. in 800 or 1000 ml of TSB-YE medium supplemented with 50 μg/ml kanamycin. At OD600=2, IPTG was added to induce expression at a final concentration of 0.17 or 0.2 mM and the culture was incubated at 37° C. for another 5 h. The cells were harvested by centrifugation.

Approximately 2-5 g of each cell pellet was resuspended in 10-25 ml binding buffer (20 mM sodium phosphate, 0.5 M NaCl, 20 mM imidazole, pH 7.4) supplemented with Benzonase® (Merck, cat. no. 1.01654.0001) to a concentration of 15 U/ml and Lysozyme (Sigma, cat. no. L-7651) to a concentration of 0.5 mg/ml. After cell disruption by three freeze-thawing cycles or sonication, cell debris was removed by centrifugation and each supernatant was applied on a 1 ml His GraviTrap IMAC column (GE Healthcare, cat. no. 11-0033-99). Contaminants were removed by washing with wash buffer (20 mM sodium phosphate, 0.5 M NaCl, 20 or 60 mM imidazole, pH 7.4), and the FcRn binding Z variants were subsequently eluted with elution buffer 1 (20 mM sodium phosphate, 0.5 M sodium chloride, 250 mM imidazole, pH 7.4) or elution buffer 2 (0.1 M acetic acid, 0.5 M sodium chloride, pH 4.5). Purified Z variants were buffer exchanged to PBS using PD-10 columns (GE Healthcare), according to the manufacturer's protocol. Protein concentrations were determined by measuring the absorbance at 280 nm, using a NanoDrop® ND-1000 spectrophotometer, and using the extinction coefficient of the respective protein. The purity of the FcRn binding Z variants was analyzed by SDS-PAGE stained with Coomassie Blue. The identity of each purified FcRn binding Z variant was confirmed using LC/MS analysis.

CD Analysis:

Purified $His_6$-tagged Z variants were diluted to 0.5 mg/ml in PBS. For each diluted Z variant, a CD spectrum at 250-195 nm or 250-190 nm was obtained at 20° C. In addition, a variable temperature measurement (VTM) was performed to determine the melting temperature (Tm). In the VTM, the absorbance was measured at 221 nm while the temperature was raised from 20 to 90° C., with a temperature slope of 5° C./min. A new CD spectrum was obtained at 20° C. after the heating procedure in order to study the refolding ability of the Z variants. The CD measurements were performed on a Jasco J-810 spectropolarimeter (Jasco Scandinavia AB) using a cell with an optical path-length of 1 mm.

Biacore Binding and Kinetic Analysis:

The interaction of FcRn binding $His_6$-tagged Z variants with human FcRn was analyzed in a Biacore 2000 instrument (GE Healthcare). Human FcRn was immobilized in a flow cell on the carboxylated dextran layer of a CM5 chip surface (GE Healthcare). The immobilization was performed using amine coupling chemistry according to the manufacturer's protocol and using HBS-EP (GE Healthcare) as running buffer. One flow cell surface on the chip was activated and deactivated for use as blank during analyte injections. In the two binding experiments presented below, McIlvaines phosphate-citrate buffer pH 6.0 supplemented with 0.005% Tween-20 (0.005% PCT) was used as running buffer. In all experiments, a flow rate of 50 μl/min was used.

In one experiment, the dissociation at pH 6.0 was compared to the dissociation at pH 7.4. $His_6$-tagged Z variants and a human monoclonal IgG1 were diluted in running buffer to a final concentration of 250 nM or 2.5 nM, respectively, and injected over the FcRn chip for 1 minute using the co-inject procedure. The second injection of the co-inject procedure, representing the dissociation phase of the interactions, contained either running buffer (pH 6.0) or 0.005% PCT pH 7.4. The Z variants were allowed to dissociate for 1 minute, except for Z07918 and Z10193, which were allowed to dissociate for 4 minutes, before a surface equilibration during 5 minutes in running buffer. IgG was allowed to dissociate for 4 minutes before equilibration. Buffer injections were performed in a similar way; co-injection of buffer pH 6.0 followed by pH 6.0 or co-injection of buffer pH 6.0 followed by pH 7.4. The results were analyzed in BiaEvaluation software 4.1 (GE Healthcare). Curves of the blank surface were subtracted from the curves of the ligand surface. In addition, curves of buffer injections were subtracted from the Z variant curves and from the IgG curves to adjust for the buffer effects.

In another experiment, approximate kinetic constants ($k_{on}$ and $k_{off}$) and affinities ($K_D$) were determined for a subset of His$_6$-tagged Z variants. Three concentrations of the Z variants were injected for 1 minute followed by dissociation in running buffer for 1 minute. The surfaces were equilibrated with running buffer during 7.5 minutes before the start of next cycle. Injected concentrations were either 675 nM, 225 nM and 75 nM (Z10140, Z10156 and Z10183) or 225 nM, 75 nM and 25 nM (Z07918 and Z10193). Kinetic constants were calculated from the sensorgrams using the Langmuir 1:1 model of BiaEvaluation software 4.1 (GE Healthcare).

In a separate experiment, the affinity of the interactions of Z variants to hFcRn (SEQ ID NO:379) and mFcRn (SEQ ID NO:384), respectively, was measured at both pH 6.0 and pH 7.4 on a Biacore 3000 instrument (GE Healthcare). hFcRn and mFcRn were produced essentially as described in Example 1 but using mouse 3T3 cells instead of human SKOV-3 cells for production of mFcRn, and immobilized on separate flow cells on a CM5 chip in acetate buffer at pH 4.65. The immobilization level was approximately 1000 RU for both receptors. A reference flow cell was created by activation and deactivation. 0.005% PCT pH 6.0 or 7.4 was used as running buffer and for dilution of the analytes. All analyses were performed at 25° C. The affinity constants for the His$_6$-tagged Z variants Z07918 (SEQ ID NO:1), Z07960 (SEQ ID NO:4) and Z10193 (SEQ ID NO:2) were determined by injecting a dilution series from 1024 nM to 0.5 nM (pH 6.0) or from 10240 nM to 5 nM (pH 7.4). The affinities were derived using GraphPad Prism 5 software, using a one site binding saturation model.

AlphaLISA Blocking Assay:

The potential of Z variants to inhibit binding of IgG to FcRn was analyzed in an AlphaLISA assay with an EnSpire multiplate reader 2300 (Perkin Elmer). Human IgG (Roactemra) was immobilized on AlphaLISA acceptor beads (Perkin Elmer, cat. no. 6772002) according to the manufacturer's recommendations. Stepwise serial dilutions 1:3 of His-tagged Z variants to final concentrations of 250 nM to 38 pM were made in a 384-well plate (Perkin Elmer, cat. no. G6005350) and incubated for 45 min with 10 nM biotinylated human FcRn (Biorbyt, cat. no. orb84388, biotinylated essentially as described in Example 2) in AlphaLISA buffer (Perkin Elmer, cat. no. AL000F) adjusted to pH 6.0 using HCl. IgG-coated Acceptor beads were added to a final concentration of 10 µM and incubated for 45 min. Finally, streptavidin coated Donor beads (Perkin Elmer, cat. no. 6772002) were added to a final concentration of 40 µg/ml and incubated for 30 min. All incubations were performed at RT in the dark. The plate was analyzed in the EnSpire instrument and the IC50 values were calculated using GraphPad Prism 5.

Results

Cultivation and Purification:

The seventeen FcRn binding Z variants (SEQ ID NO:1-16 and SEQ ID NO:353), constructed with an N-terminal Hiss tag, were produced in *E. coli*. The amount of IMAC-purified protein from approximately 2-5 g bacterial pellets, determined spectrophotometrically by measuring the absorbance at 280 nm, ranged from approximately 10 mg to 20 mg for the different FcRn binding Z variants. SDS-PAGE analysis of each final protein preparation showed that these predominantly contained the FcRn binding Z variant. The correct identity and molecular weight of each FcRn binding Z variant was confirmed by HPLC-MS analysis.

CD Analysis:

The CD spectra determined for six Z variants showed that each had an α-helical structure at 20° C. This result was also verified in the variable temperature measurements, wherein melting temperatures (Tm) were determined (Table 3). A reversible folding was seen for the six Z variants when overlaying spectra measured before and after heating to 90° C.

TABLE 3

Melting temperatures for a selection of Z variants.

| Z variant | SEQ ID NO: | Tm (°C.) |
|---|---|---|
| Z07909 | 13 | 56 |
| Z07918 | 1 | 49 |
| Z07930 | 6 | 56 |
| Z07960 | 4 | 58 |
| Z10109 | 3 | 61 |
| Z10193 | 2 | 59 |

Biacore Binding and Kinetic Analyses:

The binding of seventeen His$_6$-tagged Z variants to human FcRn and the dissociation at different pH were tested in a Biacore instrument by sequentially injecting each of the Z variants at pH 6.0 and either buffer pH 6.0 or pH 7.4 over a chip surface containing FcRn. The ligand immobilization level of the surface was 1668 RU human FcRn. The seventeen Z variants showed binding to FcRn at pH 6.0, and for all variants, faster off-rates were seen at pH 7.4 compared to pH 6.0. The result for IgG was similar, displaying a faster off-rate at pH 7.4. The variants Z07918 and Z10193 showed the slowest dissociation curves. Sensorgrams for a subset of variants and IgG are displayed in FIG. 2 A-E.

TABLE 4

Biacore kinetic constants and affinities for hFcRn binding at pH 6.0.

| Z variant | SEQ ID NO: | $k_{on}$ (M$^{-1}$s$^{-1}$) | $k_{off}$ (s$^{-1}$) | $K_D$ (M) |
|---|---|---|---|---|
| Z07918 | 1 | $1.4 \times 10^6$ | 0.022 | $1.6 \times 10^{-8}$ |
| Z10140 | 5 | $1.4 \times 10^6$ | 0.12 | $8.6 \times 10^{-8}$ |
| Z10156 | 11 | $7.6 \times 10^5$ | 0.28 | $3.7 \times 10^{-7}$ |
| Z10183 | 7 | $1.0 \times 10^6$ | 0.13 | $1.3 \times 10^{-7}$ |
| Z10193 | 2 | $1.5 \times 10^6$ | 0.033 | $2.2 \times 10^{-8}$ |

The kinetic constants of five Z variants interacting with FcRn at pH 6.0 were determined (see Table 4). The immobilization level of the surface was 2015 RU human FcRn. For each Z variant, kinetic constants were calculated using a curve set of three injected concentrations.

Affinity ($K_D$) constants were also determined for $His_6$-tagged Z variants Z07918 (SEQ ID NO:1), Z07960 (SEQ ID NO:4) and Z10193 (SEQ ID NO:2) interacting with human and mouse FcRn at pH 6.0 and pH 7.4 (Table 5). For all three variants, $K_D$ values were lower at pH 6.0 compared to pH 7.4.

TABLE 5

Biacore affinities for hFcRn and mFcRn at pH 6.0 and pH 7.4.

| Z variant | SEQ ID NO: | $K_D$ (M) hFcRn | | $K_D$ (M) mFcRn | |
|---|---|---|---|---|---|
| | | pH 6.0 | pH 7.4 | pH 6.0 | pH 7.4 |
| Z07918 | 1 | $1.2 \times 10^{-8}$ | $>5 \times 10^{-7}$ | $9.0 \times 10^{-8}$ | $>5 \times 10^{-7}$ |
| Z07960 | 4 | $5.0 \times 10^{-8}$ | $>1 \times 10^{-6}$ | $3.5 \times 10^{-7}$ | $>5 \times 10^{-6}$ |
| Z10193 | 2 | $1.4 \times 10^{-8}$ | $>5 \times 10^{-7}$ | $9.5 \times 10^{-8}$ | $>5 \times 10^{-7}$ |

TABLE 6

Calculated IC50 values from AlphaLISA blocking assay.

| Z variant | SEQ ID NO | IC50 (M) |
|---|---|---|
| Z07909 | 13 | $4.6 \times 10^{-8}$ |
| Z07918 | 1 | $2.1 \times 10^{-9}$ |
| Z07930 | 6 | $4.2 \times 10^{-8}$ |
| Z07960 | 4 | $4.2 \times 10^{-8}$ |
| Z10109 | 3 | $5.7 \times 10^{-8}$ |
| Z10111 | 8 | $4.6 \times 10^{-8}$ |
| Z10140 | 5 | $5.6 \times 10^{-8}$ |
| Z10183 | 7 | $3.9 \times 10^{-8}$ |
| Z10193 | 2 | $1.2 \times 10^{-8}$ |
| Z13993 | 353 | $1.3 \times 10^{-7}$ |
| Z11948-($G_4$S)-Z11948 | 368 | $3.8 \times 10^{-10}$ |
| Z11948-($G_4$S)$_3$-Z11948 | 369 | $4.1 \times 10^{-10}$ |

AlphaLISA blocking assay: The ability of seventeen $His_6$-tagged monomeric Z variants (SEQ ID NO:1-16 and SEQ ID NO:353) and two dimeric variant, Z11948-$G_4$S-Z11948 and Z11948-($G_4$S)$_3$-Z11948 to inhibit IgG binding to FcRn was tested in an AlphaLISA blocking assay. Serial dilutions of the Z variants were incubated with biotinylated human FcRn and the blocking ability of each respective variant was measured after addition of IgG coated Acceptor beads and subsequently streptavidin coated Donor beads. Inhibition could be measured as a decrease in AlphaLISA counts for positive Z variants. The calculated IC50 values for the ten monomeric variants and the two dimeric variants that were shown to block IgG binding to FcRn in this assay are shown in Table 6.

Example 4

Binding of FcRn Binding Z Variants to Human or Mouse FcRn/eGFP Transfected HeLa Cells In this Example, the binding ability of FcRn binding Z variants was investigated. The production of HeLa cells expressing human and murine FcRn-eGFP gene transgene and the use of these cells for flow cytometry analysis with Alexa Fluor® 647 labeled Z variants is described.

Materials and Methods

Cloning of FcRn-eGFP and B2M Viral Vectors:

The genes encoding murine FcRn (mFcRn, Genbank BC003786.1, OpenBiosystems) and murine B2M (mB2M, Genbank BC085164.1, OpenBiosystems) were amplified in a similar way as the genes for human FcRn and human B2M as described in Example 1. Human and murine FcRn and B2M genes were amplified as follows: for hFcRn, the sequence encoding amino acids 1-365 (SEQ ID NO:382) was amplified; for hB2M, the sequence encoding amino acids 21-119 (SEQ ID NO:380) was amplified; for mFcRn, the sequence encoding amino acids 1-369 (SEQ ID NO:383) was amplified; and for mB2M, the sequence encoding amino acids 21-119 (SEQ ID NO:381) was amplified. The vector pHR-cPPT-CMV-EGFP (Jakobsson et al. (2003) J Neurosci Res 73:876-85) and FcRn PCR amplicons (human and murine) were cut using the restriction enzymes BamHI (human) or BclI (murine) and MluI (New England Biolabs, cat. nos. R0136M, R0160L and R0198L, respectively), and ligated using T4 DNA Ligase (New England Biolabs, cat. no. M0202M). The ligation mix was chemically transformed into *E. coli* RRIΔM15 and spread on ampicillin plates. Colonies were picked and screened with suitable primer pairs. The construct encoding the original signal peptide, human or murine FcRn and eGFP at the cytoplasmic tail were verified by sequencing and denoted pHR-cPPT-CMV-hFcRn-eGFP and pHR-cPPT-CMV-mFcRn-eGFP, respectively.

The human and murine B2M PCR amplicons were inserted into the plasmid pDONOR221 (Invitrogen, cat. no. 12536-017) by recombination using the Gateway system (Invitrogen, cat. no. 11789020, Gateway® BP Clonase® II Enzyme mix) according to the manufacturer's recommendations. After verification of correct sequences, human or murine B2M was inserted into p2k7_gtc (Suter et al., supra) using a multi-site gateway cloning system (Invitrogen, cat. no. 11791020, Gateway® LR Clonase® II Enzyme mix) together with the promoter containing plasmid pENTR-CMV (Tai et al. supra), resulting in the vectors $2k7_{neo}$-CMV-hB2M and $2k7_{neo}$-CMV-mB2M, respectively.

Lentiviral Transduction of HeLa Cells:

The vector pairs $2k7_{neo}$-CMV-hB2M and pHR-cPPT-CMV-hFcRn-eGFP or $2k7_{neo}$-CMV-mB2M and pHR-cPPT-CMV-mFcRn-eGFP were co-transfected together with VSV-G envelope and gag/pol packaging plasmid into HEK293T cells using calcium chloride transfection (Zufferey et al., supra; Jakobsson et al. (2006) supra). HEK293T culture supernatants containing formed lentiviral particles with FcRn and B2M transgenes respectively were used to sequentially transduce HeLa Cervix adenocarcinoma cells (Cell Line Service) at low passage number. The resulting two stably transduced HeLa cell lines are in the following denoted hFcRn-eGFP (transduced with genes for human FcRn-eGFP and hB2M) and mFcRn-eGFP (transduced with genes for mouse FcRn-eGFP and mB2M).

Alexa Fluor® 647 Labeling of FcRn Binding Z Variants:

The three $His_6$-tagged Z variants Z07918, Z07930 and Z07960 were labeled with Alexa Fluor® 647 Carboxylic Acid Succinimidyl Ester (Invitrogen, cat. no. A20106). Before labeling, buffer was exchanged to 0.2 M carbonate buffer, pH 8.3, using Vivaspin500 centrifugal filter units (10 kDa MWCO, Vivaproducts cat. no. 512-2838) spun at 10,000 g. The labeling was performed in the Vivaspin500 and 1 µl of Alexa Fluor® 647 Succinimidyl Ester dye (40 µg/µl in DMSO corresponding to 1.3× molar excess) was added to 200 µg/25 µl Z variant. The mixes were incubated at RT in the dark for 40 minutes in a wiggling rota mixer. The reaction mixes were subsequently put on ice for 3.5 hours and free dye was removed by washing with 15×100 µl PBS in the Vivaspin500.

Immunofluorescence Staining of Human and Mouse FcRn-eGFP Transfected HeLa-Cells with FcRn Binding Z Variants:

hFcRn-eGFP and mFcRn-eGFP HeLa cells were harvested by trypsination and washed twice in PBS at pH 6.0 before counting. 100,000 cells were pipetted per well of a v-bottomed 96 well plate (Nunc, cat no 277143) and the cells in the plate were subsequently pelleted at 1,700 rpm for 4 min at 4° C. The supernatants were removed and the cells were fixed with 50 µl of 2% formaldehyde (Sigma Aldrich, cat. no. F8775) in PBS at pH 6.0 for 10 min at RT. Cells were thereafter washed with 2×100 µl PBS, pH 6.0, saturated with casein (PBSC), and resuspended in PBSC with 0.1% saponin (AppliChem, cat no A4518.0100) containing 620 nM of Alexa Fluor® 647 labeled His$_6$-tagged Z variants; Z07960, Z07930 and Z07918. Transduced HeLa cells, incubated with buffer alone, were used as control. The cells were incubated for 1 h at 8° C. on a shaker in the dark, washed with 2×100 µl PBSC and resuspended in 180 µl of PBS, pH 6.0, containing 1% BSA (fraction V, Merck, cat. no. 1.12018.0100). 10,000 cells/well were analyzed in a Gallios Flow Cytometer (Beckman Coulter) and the data was analyzed using Kaluza software (Beckman Coulter).

Results

Figure 3:
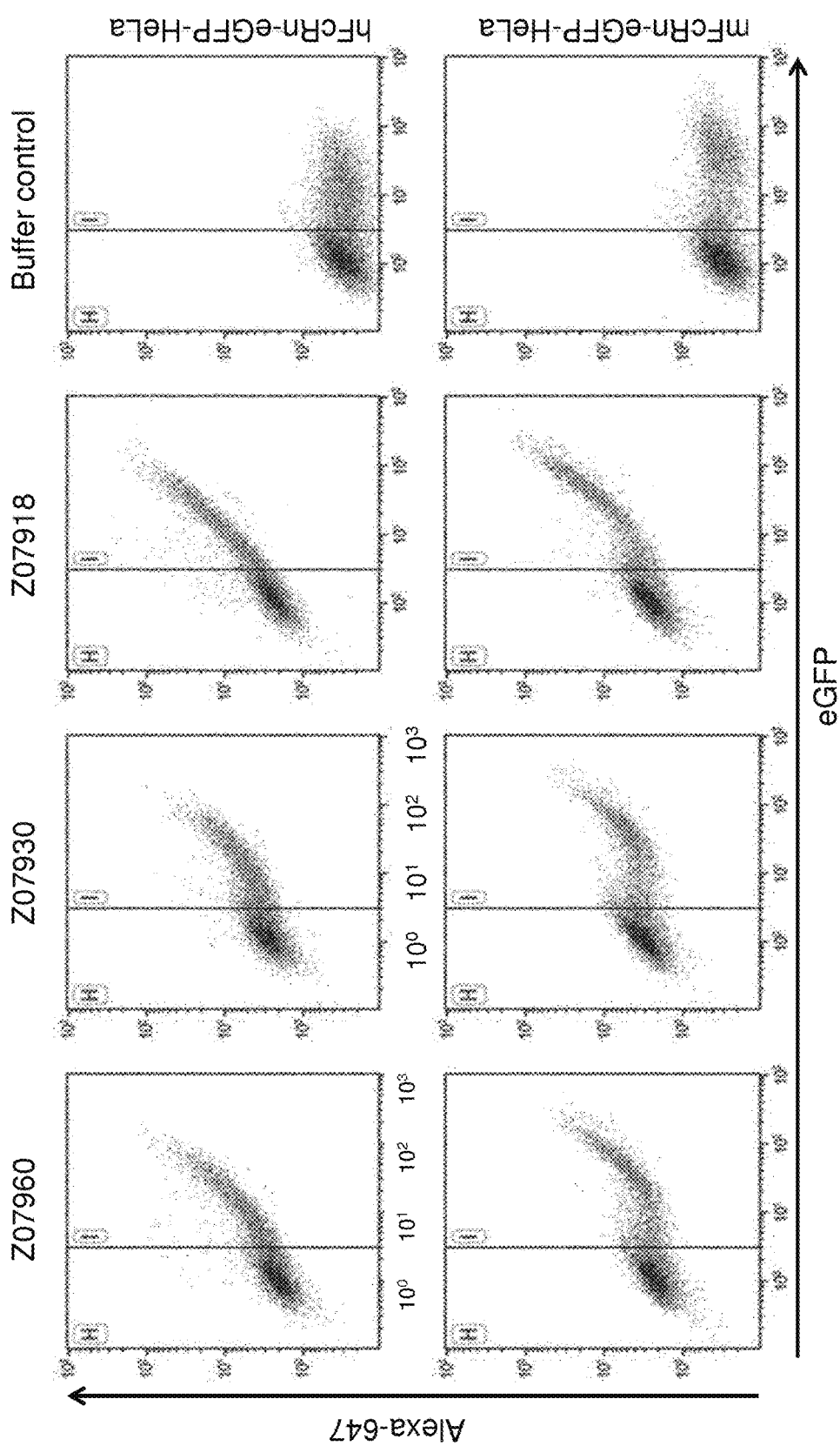
FIG. 3 shows dot plots from a flow cytometry analysis of binding of FcRn binding Z variant to human (upper panel) and mouse (lower panel) FcRn-eGFP HeLa cells, as described in Example 4. Due to heterogeneous expression of FcRn-eGFP by HeLa cells, cells were gated according to FcRn-eGFP expression level. Cells in gate H are considered to be FcRn-eGFP negative and cells in gate I are considered to be positive. Incubation with Alexa Fluor® 647 labeled Z variants resulted in a population positive both for Alexa Fluor® 647 and eGFP, whereas incubation with buffer (buffer control) did not. The figure shows that the three variants Z07960 (SEQ ID NO:4), Z07930 (SEQ ID NO:6) and Z07918 (SEQ ID NO:1) bind to human FcRn and mouse FcRn. The y-axis shows Alexa Fluor® 647 intensity and the x-axis shows eGFP activity.
Figure 4:
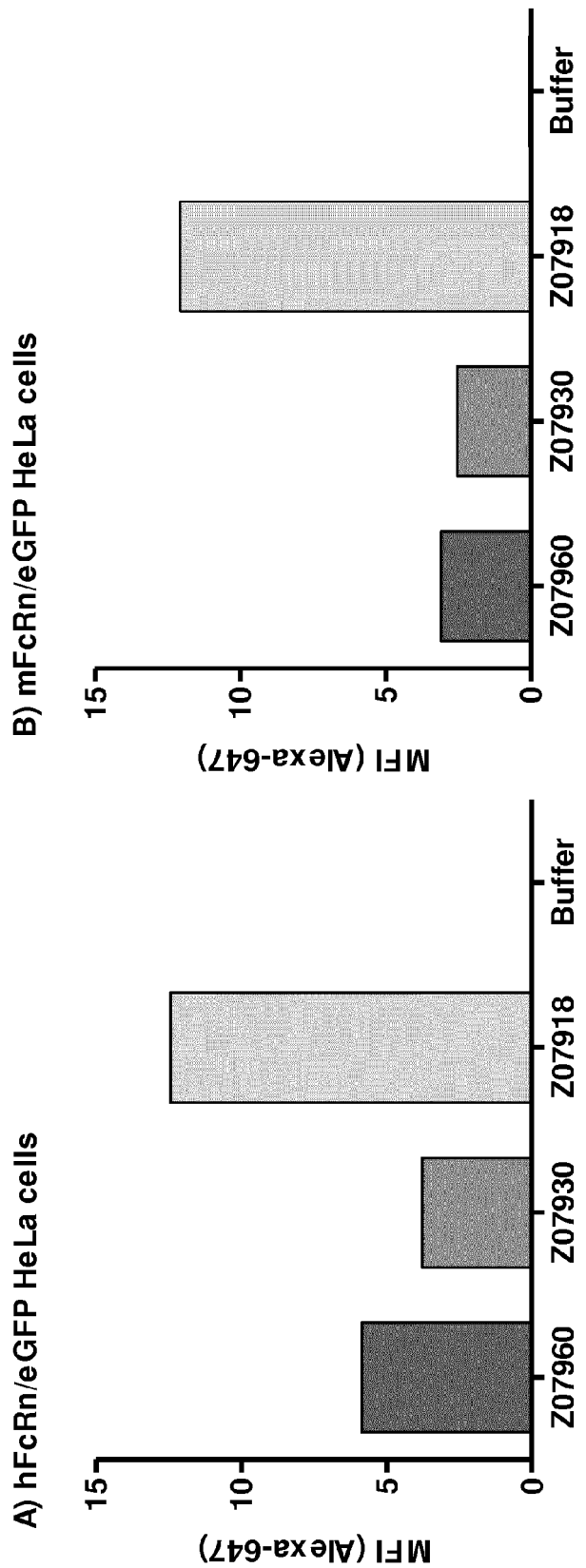
FIG. 4 shows mean fluorescence intensity (MFI) values of Alexa Fluor® 647 labeled Z07960 (SEQ ID NO:4), Z07930 (SEQ ID NO:6) and Z07918 (SEQ ID NO:1), measured in the cell binding assay described in Example 4. Diagram (A) shows MFI from HeLa cells transduced with human FcRneGFP and diagram (B) shows MFI from HeLa cells transduced with mouse FcRn-eGFP.

Flow cytometry analysis was utilized to determine whether the FcRn binding Z variants could bind to human and/or mouse FcRn on human or mouse FcRn/eGFP transduced HeLa cells. The experiment was performed at pH 6.0 with Alexa Fluor® 647 labeled Z07960, Z07930 and Z07918 (SEQ ID NO:4, 6 and 1, respectively). Dot plot analysis (y-axis: Alexa Fluor® 647, x-axis: eGFP) showed that the transduced cell population could be divided into FcRn-eGFP negative and positive population (FIG. 3, gate H and I, respectively) indicating heterogeneous expression of the FcRn-eGFP fusion protein by HeLa cells (FIG. 3). Accordingly, the mean fluorescence intensity (MFI) values for Alexa Fluor® 647 in gate I were subtracted by background MFI values of Alexa Fluor® 647 in gate H. The calculated MFI values are presented in FIG. 4. The results show that Z07960, Z07930 and Z07918 are capable of binding HeLa cells displaying human (FIG. 4A) or murine (FIG. 4B) FcRn-eGFP.

Example 5

Blocking of IgG Binding to FcRn with the FcRn Binding Z Variant Z07918

In this Example, the potential competition of FcRn binding Z variants with IgG for binding to FcRn was investigated in a cell based assay. Such binding will result in blocking of the IgG-FcRn interaction.

Materials and Methods

Blocking of IgG-FcRn Immunofluorescence Staining:

Human or murine FcRn-eGFP transduced HeLa cells were prepared as described in Example 4. Fixed cells were resuspended in 50 µl of a mix of either 100 nM Alexa Fluor® 647-conjugated human or mouse IgG (Jackson laboratories, cat. no. 009-600-003 and 015-600-003, respectively) and 1000, 100, 10, 1 or 0 (buffer control) nM His$_6$-tagged Z07918 diluted in PBS-casein, pH 6.0, containing 0.1% saponin (AppliChem). The cells were incubated for 1 h at 37° C. on a shaker in the dark, washed with 2×100 µl PBS-casein pH 6.0 and re-suspended in 180 µl of PBS, pH 6.0, containing 1% BSA. Data from 10,000 cells/well (except somewhat fewer cells for mouse 100 nM mIgG-Alexa Fluor® 647) were obtained using a Gallios Flow Cytometer (Beckman Coulter) and the data was analyzed using Kaluza software (Beckman Coulter).

Results

Figure 5:
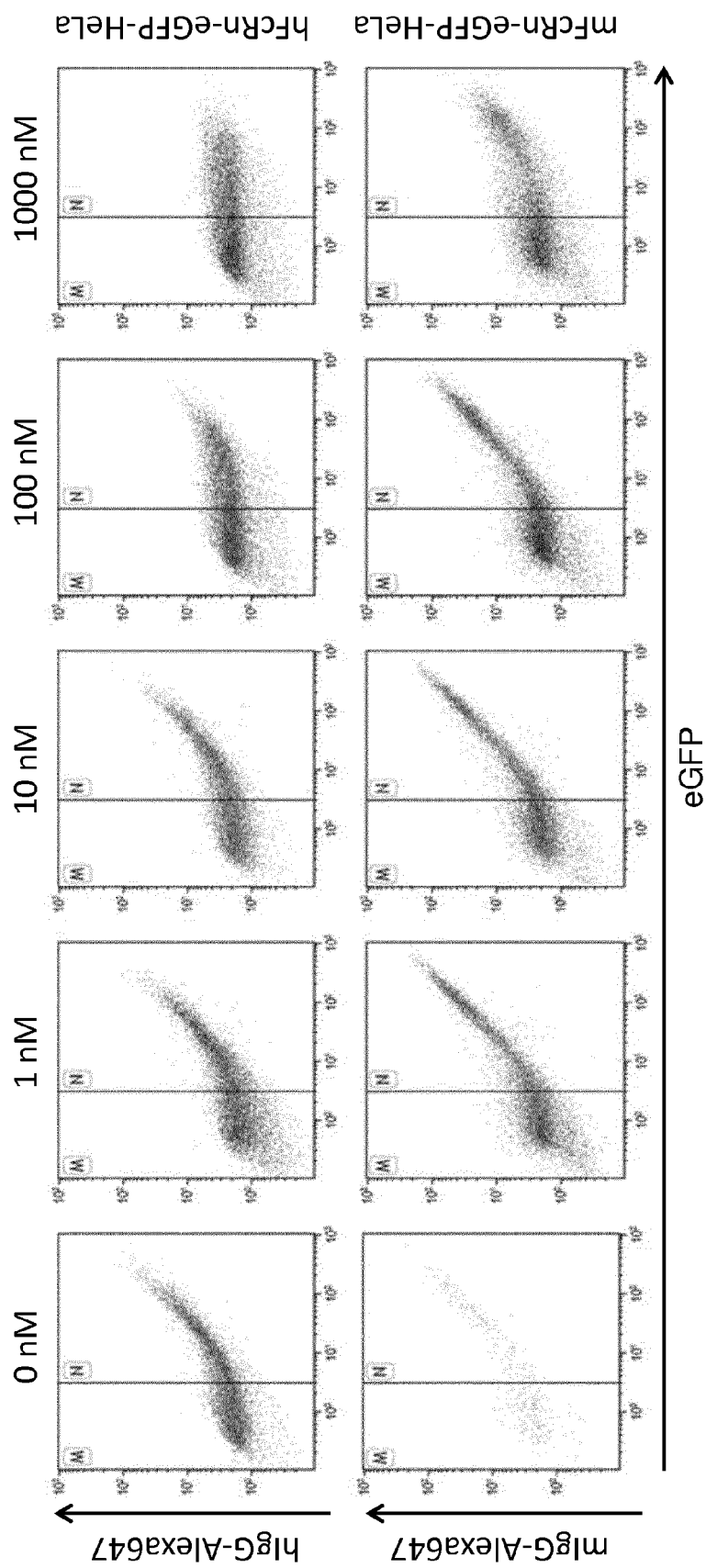
FIG. 5 shows dot plots from flow cytometry analysis of human or mouse IgG Alexa Fluor® 647 binding to human (upper panel) and mouse (lower panel) FcRn-eGFP HeLa cells, as described in Example 5. Due to heterogeneous expression of FcRn-eGFP by HeLa cells, cells were gated according to the abundance of FcRn-eGFP on the cell surface. Cells in gate M are considered to be FcRn-eGFP negative and cells in gate N are considered to be positive. Binding of 100 nM human or mouse IgG-Alexa Fluor® 647 to FcRn transduced HeLa cells are shown in the left panel (0 nM). The figure shows that IgG binding was blocked by $His_6$-tagged Z07918 (SEQ ID NO:1) in a dose dependent manner (1, 10, 100 and 1000 nM). The y-axis shows Alexa Fluor® 647 intensity and the x-axis shows eGFP activity.
Figure 6:
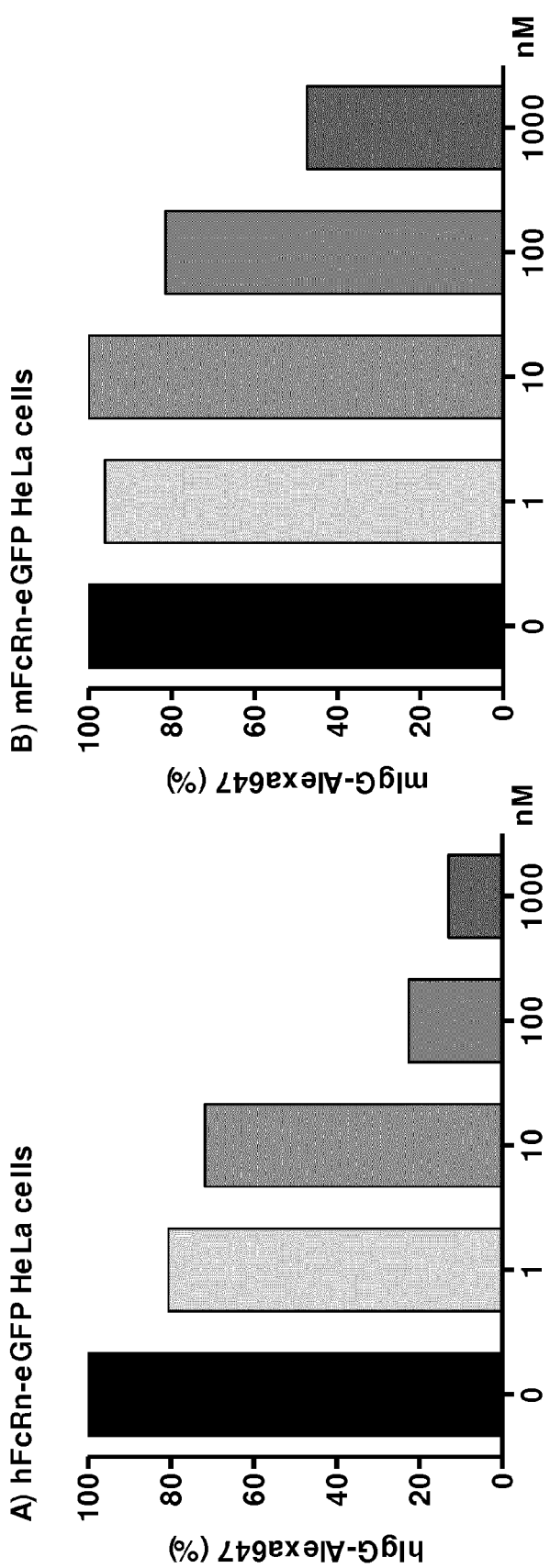
FIG. 6 shows mean fluorescence intensity (MFI) values resulting from FcRn binding of IgG Alexa Fluor® 647 in the presence of different concentrations of $His_6$-tagged Z07918 (SEQ ID NO:1) on (A) human FcRn-eGFP transduced HeLa cells and (B) mouse FcRn-eGFP transduced HeLa cells, as described in Example 5. The figure shows dose dependent blocking of the IgG-FcRn binding by the Z variant.

The experiment was performed to determine if the FcRn binding Z variant Z07918 (SEQ ID NO:1) blocks the IgG-FcRn interaction. Human or murine FcRn-eGFP transduced HeLa cells were incubated with human or mouse Alexa Fluor® 647-conjugated IgG. The binding was blocked with unlabeled Z07918 at different concentrations. Due to the heterogeneous expression of FcRn by the transduced HeLa cells (described in Example 4), the MFI values for Alexa Fluor® 647 in gate N of each sample was subtracted by the corresponding MFI values in gate M (FIG. 5). The percent IgG Alexa Fluor® 647 binding was calculated by dividing the different MFI values with the MFI for the blank control. The results showed that Z07918 effectively blocked hIgG binding to hFcRn (FIG. 6A) in a dose dependent manner. Furthermore, Z07918 also blocked mIgG binding to mFcRn (FIG. 6B) although less efficiently compared to hIgG-binding.

Example 6

Pharmacokinetic Study of Three FcRn Binding Z Variants

In this Example, the ability of FcRn binding Z variants to prolong serum half-life of a non-specific Z variant was investigated by a pharmacokinetic study performed in mice.

Materials and Methods

Subcloning of Z Variants:

A subset of Z variants (Z07918, Z07960 and Z10193) was submitted to a second subcloning. DNA from the subcloned His$_6$-tagged variants in Example 3 was used as template. First, PCR amplification using suitable primer pairs was performed to create genes encoding Z variants starting with the amino acids AE instead of VD. The mutated Z variants are listed in FIG. 1 and were denoted Z11948 (SEQ ID NO:354), Z11946 (SEQ ID NO:355) and Z11947 (SEQ ID NO:356), corresponding to mutated Z07918, Z07960 and Z10193, respectively. Genes encoding the new Z variants were restriction cleaved and ligated into a vector harboring the genes encoding albumin binding variant PP013 (SEQ ID NO:377) and Z03638 (SEQ ID NO:378) with spacer sequences resulting in a gene fusion encoding [Z#####]GAP(G$_4$S)$_4$TS-[PP013]-GT(G$_4$S)$_4$PR-[Z03638] (SEQ ID NO:465) (also denoted "Z#####-PP013-Z03638" or "Z variant in fusion with PP013-Z03638"). The negative control molecule [Z03638]-GAP(G$_4$S)$_4$TS-[PP013] (SEQ ID NO:466) was subcloned in a similar way by ligating Z03638 into a vector containing a (G$_4$S)$_4$ (SEQ ID NO:467) linker and the sequence for PP013. The subsequent steps for vector transformation into *E. coli* were performed as in Example 3.

Cultivation and Purification:

Z variants in fusion with PP013-Z03638 were produced in *E. coli* as described in Example 3. Approximately 3 g of each cell pellet was re-suspended in 30 ml TST-buffer (25 mM Tris-HCl, 1 mM EDTA, 200 mM NaCl, 0.05% Tween20, pH 8.0) supplemented with Benzonase® (Merck). After cell disruption by sonication and clarification by centrifugation, each supernatant was applied on a gravity flow column with 5 ml agarose immobilized with an anti-ABD ligand (see WO2014/064237). After washing with TST-buffer and 5 mM NH$_4$Ac buffer, pH 5.5, the Z variants were eluted with 0.1 M HAc. Acetonitrile (ACN) was added to a final concentration of 10% to the eluted fractions from the anti-ABD agarose affinity chromatography purification step and the samples were loaded on a 3 ml Resource 15RPC column (GE Healthcare), previously equilibrated with RPC solvent A (0.1% trifluoroacetic acid (TFA), 10% ACN, 90% water). After column wash with RPC solvent A, bound protein was eluted with a linear gradient 0-50% RPC solvent B (0.1% TFA, 80% ACN, 20% water) during 60 ml. Fractions containing pure Z variant were identified by SDS-PAGE analysis and pooled. After the RPC purification, the buffer of the pools was exchanged to PBS using a HiPrep 26/10 Desalting column (GE Healthcare). Finally, the Z variants were purified on 1 ml EndoTrap red columns (Hyglos, cat. no. 321063) to ensure low endotoxin content.

Protein concentrations, purities and the identity of each purified Z variant were analyzed as described in Example 3.

Biacore Analysis:

Expressed and purified Z variants fused to PP013-Z03638 were assayed against human FcRn at pH 6.0 essentially as described for the kinetic analysis in Example 3. The Z variants and the negative control Z03638-PP013 were injected at 40 nM, 160 nM and 640 nM during 1 minute followed by dissociation for 2.5 minutes and equilibration for 1 minute. Kinetic constants and affinities were determined for the Z variants using the BiaEvaluation software.

Pharmacokinetic Study:

Z11947, Z11946 and Z11948 fused to PP013-Z03638 were administered intravenously (i.v.) to male NMRI mice (Charles River, Germany) at a dose of 92 nmol/kg body weight. Sera from groups of three mice were obtained at 0.08, 6, 18, 78, 120, 168 and 240 hours. The concentration of respective Z variant was determined by ELISA.

ELISA:

Half-area 96-well ELISA plates were coated at 4° C. overnight with 50 µl/well of an Z specific goat antibody (produced in-house) diluted to 4 µg/ml in coating buffer (50 mM sodium carbonate, pH 9.6). The antibody solution was poured off and the wells were blocked with 100 µl of PBSC for 1.5 h at RT. The sera were diluted in PBSC containing 1% mouse serum (matrix) from 1:100 to 1:51,200 in a two-fold dilution series in a dilutions plate. A standard titration for respective Z variant and four quality controls (very low, low, medium and high control) diluted in matrix were included on each plate. 50 µl of the dilutions were transferred per well and the ELISA plates were incubated for 1.5 h at RT. The plates were washed four times with PBST. Bound Z variants were detected with 50 µl/well of rabbit anti-PP013 Ig (produced in-house) diluted to 4 µg/ml in PBSC. The plates were subsequently incubated for 1.5 h at RT followed by washes as described above. HRP conjugated donkey anti-rabbit HRP obtained from Jackson laboratories (cat. no. 711-035-152), diluted 1:20,000 in PBSC, was added and the plates were incubated for 1 hour. After washing as described above, 50 µl of ImmunoPure TMB substrate was added to the wells and the plates were developed according to the manufacturer's recommendations. After 15 minutes of development, the absorbance was measured at 450 nm using a multi-well plate reader (Victor³). The absorbance values were analyzed using GraphPad Prism 5 to determine the concentrations (cubic-spline curve fit) and area under curve (AUC). The concentrations were then plotted as their natural logarithms against time. The resulting curves followed a two compartment model and the terminal half-life was calculated as In2 divided by the slope based on the last three time points.

Results

Cultivation and Purification:

The three FcRn binding Z variants Z11947, Z11946 and Z11948 (SEQ ID NO:356, 355 and 354), constructed as Z#####-PP013-Z03638, and the negative control Z03638-PP013, were produced in *E. coli*. The amount of purified protein from approximately 3 g bacterial pellets, determined spectrophotometrically by measuring the absorbance at 280 nm, ranged from approximately 10 to 25 mg for the different FcRn binding Z variants. SDS-PAGE analysis of each final protein preparation showed that they predominantly contained respective FcRn binding Z variant. The correct molecular weight of each FcRn binding Z variant was confirmed by LC/MS analysis.

TABLE 7

Kinetic constants and affinities for FcRn at pH 6.0 of Z variants produced as fusions to PP013-Z03638.

| Z variant | SEQ ID NO: | $k_{on}$ (M⁻¹s⁻¹) | $k_{off}$ (s⁻¹) | $K_D$ (M) |
|---|---|---|---|---|
| Z11948 | 354 | $7.73 \times 10^5$ | 0.047 | $6.2 \times 10^{-8}$ |
| Z11946 | 355 | $3.35 \times 10^5$ | 0.275 | $8.2 \times 10^{-7}$ |
| Z11947 | 356 | $6.54 \times 10^5$ | 0.064 | $9.8 \times 10^{-8}$ |

Figure 7A:
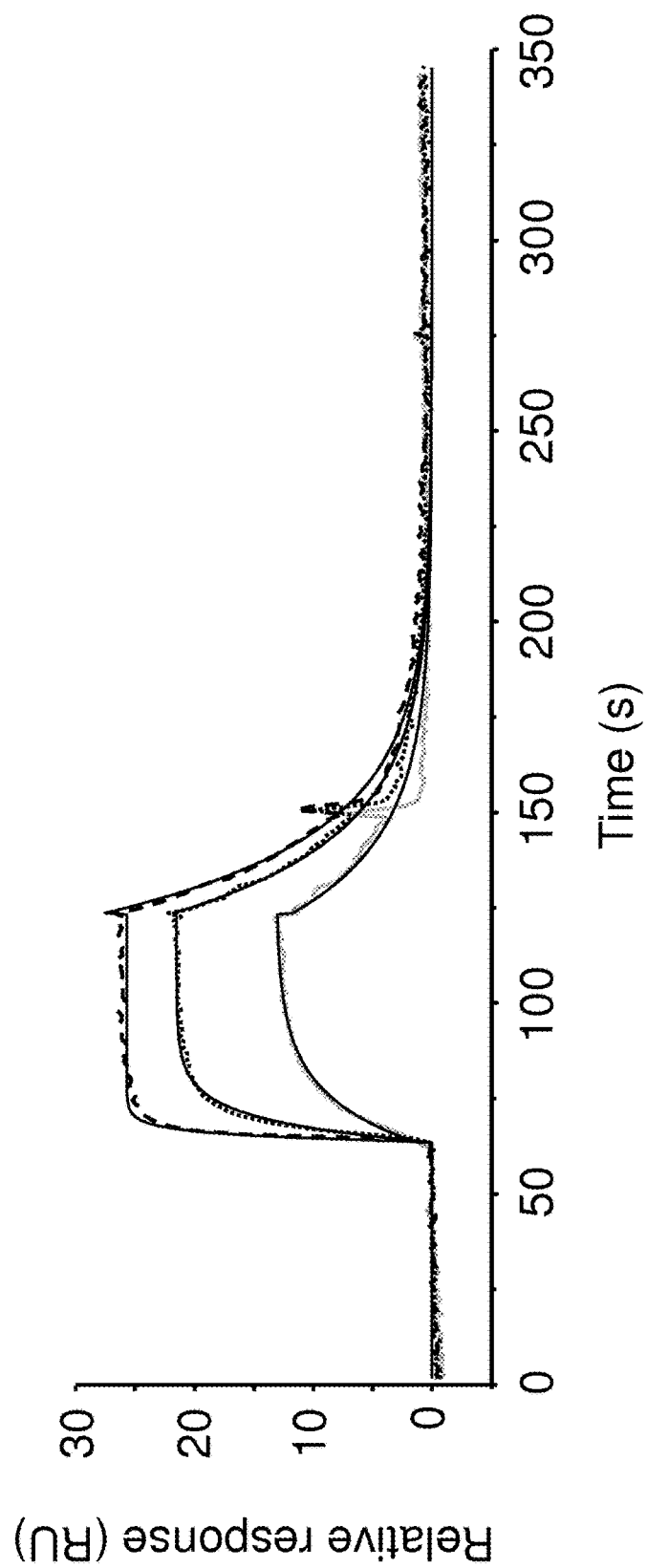
FIGS. 7A-7C show kinetics of binding of three Z variants to human FcRn at pH 6.0, as described in Example 6, using a Biacore instrument. Sensorgrams for a concentration series of (A) Z11948 (SEQ ID NO:354), (B) Z11946 (SEQ ID NO:355) and (C) Z11947 (SEQ ID NO:356), respectively, in fusion with the albumin binding polypeptide PP013 (SEQ ID NO:377) and the control Z variant molecule Z03638 (SEQ ID NO:378; not specific for FcRn), are displayed. Curves from 640 nM (dashed line), 160 nM (dotted line) and 40 nM (solid grey line) were subjected to kinetic analysis using the Langmuir 1:1 binding model. Kinetic parameters and affinities were calculated from fitted curves (solid black lines) and are shown in Table 6.
Figure 7B:
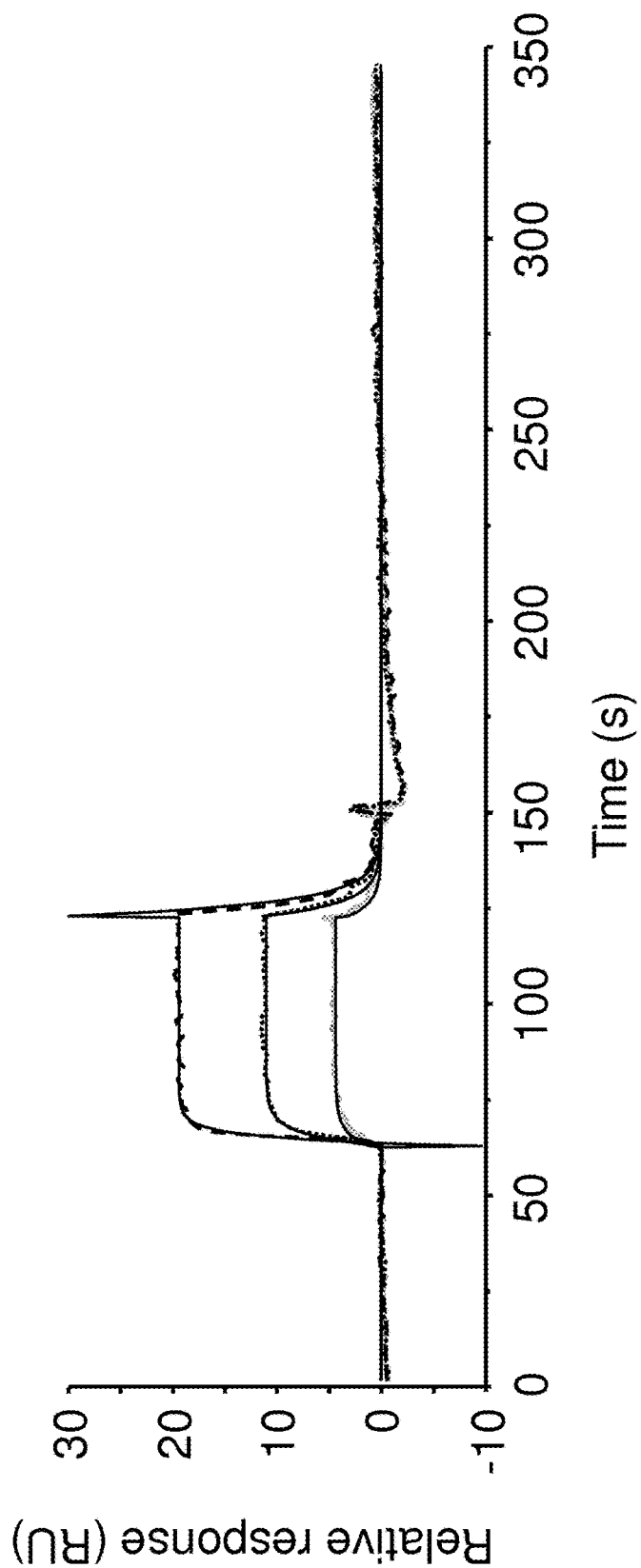
Figure 7C:
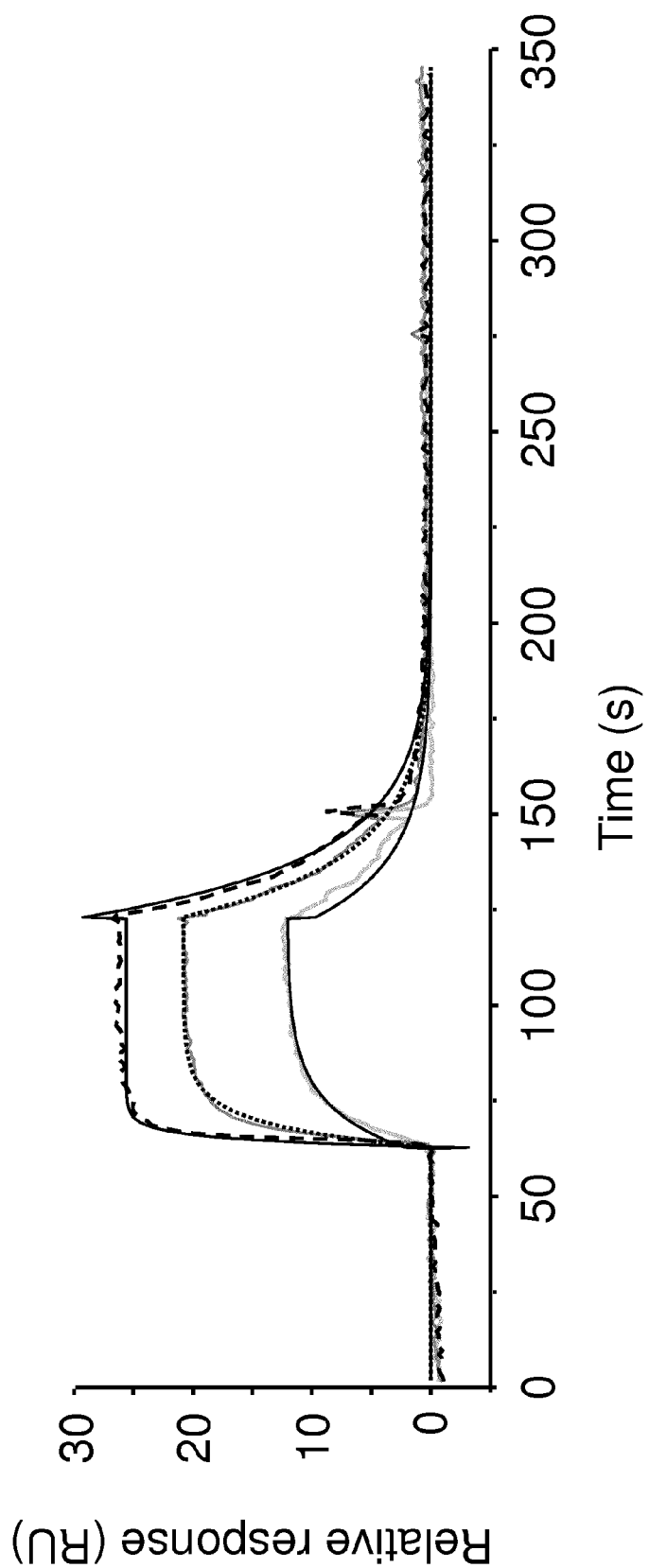

Biacore Analysis:

The binding to FcRn was analyzed for the three PP013-Z03638 fused Z variants. The immobilization level of the surface was 548 RU of human FcRn. The resulting rough kinetic constants and affinities for the target binding at pH 6.0 are displayed in Table 7. Fitted curves are displayed in FIG. 7A-C. The negative control Z03638-PP013 was negative against FcRn.

Figure 8:
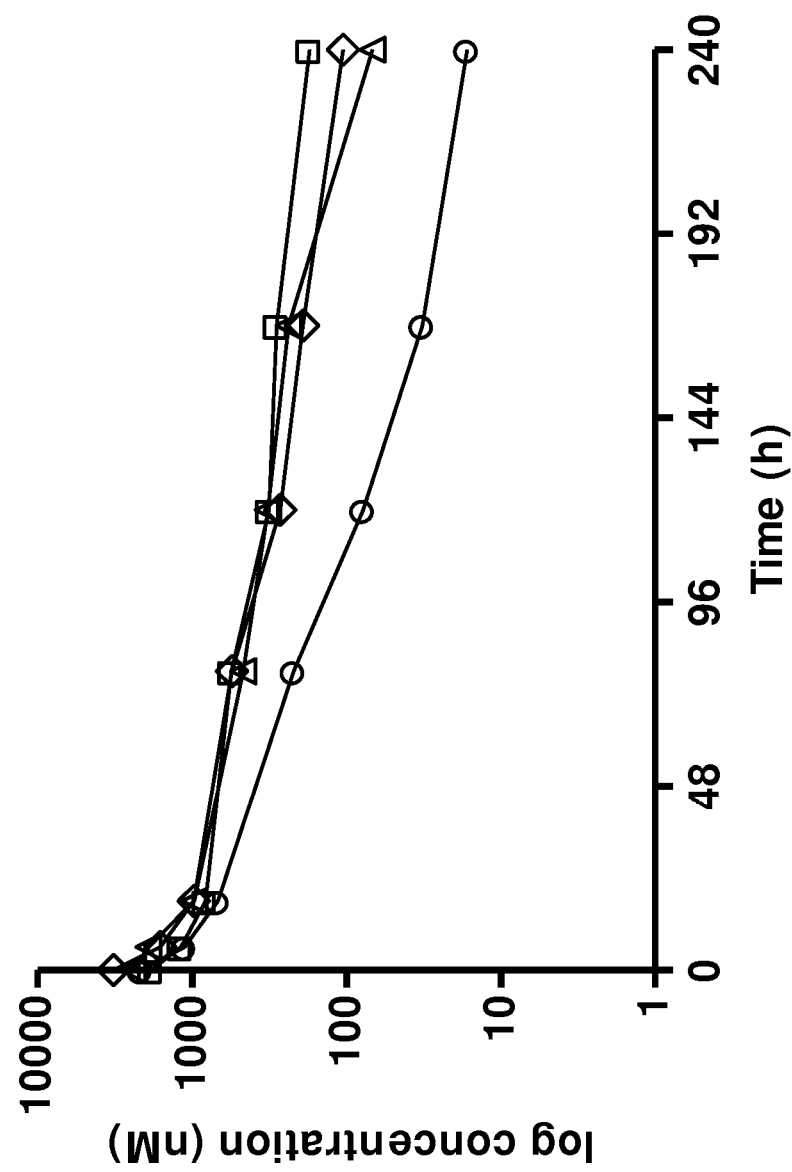
FIG. 8 shows the pharmacokinetic profiles for three FcRn binding Z variants fused to the albumin binding polypeptide PP013 obtained as described in Example 6. The Z variants Z11947 (SEQ ID NO:356, open squares), Z11946 (SEQ ID NO:355, open triangles) and Z11948 (SEQ ID NO:354, open diamonds) all displayed prolonged half-life compared to the negative control Z03638-PP013 (open circles).

Pharmacokinetic Study:

The pharmacokinetic profiles of the above-mentioned constructs of Z variants fused to PP013-Z03638 were compared to the negative control Z03638-PP013 in a mouse pharmacokinetic study. In previous work, e.g. as described in PCT application WO2009/016043, it is shown that ABD fusion proteins have a long half-life in serum, caused by ABD binding to serum albumin. In accordance with the previous results, terminal half-life of ABD-fused Z variant molecule (Z03638-PP013) was approximately 43 hours, which is comparable to half-life of mouse albumin (35 hours). The terminal half-lives of the constructs containing FcRn binding Z variant molecule in addition to ABD were two- to three-fold longer (FIG. 8). The calculated terminal half-lives were 99 hours (Z11947), 69 hours (Z11946) and 58 hours (Z11948), suggesting that FcRn binding of the Z variants contributed to the prolonged half-life.

Example 7

Design and Construction of a Maturation Library of FcRn Binding Z Variants

In this Example, a maturated library was constructed. The library was used for selections of FcRn binding Z variants. Selections from maturated libraries are usually expected to result in binders with increased affinity (Orlova et al., (2006) Cancer Res 66(8):4339-48). In this study, randomized single stranded linkers were generated using split-pool synthesis enabling incorporation of defined codons in desired positions in the synthesis.

Materials and Methods

Library Design:

The library was based on the sixteen sequences of the human FcRn binding Z variants in Table 1 and further described in Examples 2-6. In the new library, 13 variable positions in the Z molecule scaffold were biased towards certain amino acid residues, according to a strategy mainly based on the binding motifs of the Z variants defined in SEQ ID NO:1-16. A DNA linker was generated using split-pool synthesis containing the 147 bp partially randomized helix 1 and 2 of the amino acid sequence: 5'-AA ATA AAT CTC GAG GTA GAT GCC AAA TAC GCC AAA GAA NNN NNN NNN GCG NNN NNN GAG ATC NNN NNN TTA CCT AAC TTA ACC NNN NNN CAA NNN NNN GCC TTC ATC NNN AAA TTA NNN GAT GAC CCA AGC CAG AGC TCA TTA TTT A-3' (SEQ ID NO:388; randomized codons are illustrated as NNN) flanked by restriction sites XhoI and SacI, was ordered from DNA 2.0 (Menlo Park, Calif., USA). The theoretical distributions of amino acid residues in the new library, including eight variable amino acid positions (9, 10, 11, 13, 14, 24, 32 and 35) and five constant amino acid positions (17, 18, 25, 27 and 28) in the Z molecule scaffold are given in Table 8. The resulting theoretical library size is $5.3 \times 10^8$ variants.

TABLE 8

Design of library for maturation.

| Amino acid position in the Z variant | Randomization (amino acid abbreviations) | No of amino acids | Proportion |
|---|---|---|---|
| 9 | A, D, E, F, H, I, K, L, N, Q, R, S, T, V, W, Y | 16 | 1/16 |
| 10 | A, D, E, F, H, I, K, L, M, N, Q, R, S, T, V, W, Y | 17 | 1/17 |
| 11 | A, D, E, F, H, I, K, L, N, Q, R, S, T, V, W, Y | 16 | 1/16 |
| 13 | A, D, E, F, G, H, I, K, L, N, Q, R, S, T, V, W, Y | 17 | 1/17 |
| 14 | A, F, H (25%), I, K, L, N, Q, R, S, T, V, W, Y | 14 | 3/52, 13/52 (H) |
| 17 | R | 1 | 1 |
| 18 | W | 1 | 1 |
| 24 | F, Y | 2 | 1/2 |
| 25 | D | 1 | 1 |
| 27 | R | 1 | 1 |
| 28 | V | 1 | 1 |
| 32 | A, D, E, F, H, I, K, L, N, Q, R, S, T, V, W, Y | 16 | 1/16 |
| 35 | A, D, E, F, H, I, K, L, N, Q, R, S, T, V, W, Y | 16 | 1/16 |

Library Construction:

The library was amplified using AmpliTaq Gold polymerase (Applied Biosystems, cat. no. 4311816) during 12 cycles of PCR and pooled products were purified with QIAquick PCR Purification Kit (QIAGEN, cat. no. 28106) according to the supplier's recommendations. The purified pool of randomized library fragments was digested with restriction enzymes XhoI and SacI-HF (New England Biolabs, cat. no. R0146L, and cat. no. R3156M) and concentrated using a PCR Purification Kit. Subsequently, the product was subjected to preparative 2.5% agarose (Nuisieve GTC agarose, Cambrex, Invitrogen) gel electrophoresis and purified using QIAGEN gel extraction Kit (QIAGEN, cat. no. 28706) according to the supplier's recommendations.

The phagemid vector pAY02592 (essentially as pAffi1 described in Grönwall et al., supra) was restricted with the same enzymes, purified using phenol/chloroform extraction and ethanol precipitation. The restricted fragments and the restricted vector were ligated in a molar ratio of 5:1 with T4 DNA ligase (Fermentas, cat. no. EL0011) for 2 hours at RT, followed by overnight incubation at 4° C. The ligated DNA was recovered by phenol/chloroform extraction and ethanol precipitation, followed by dissolution in 10 mM Tris-HCl, pH 8.5. Thus, the resulting library in vector pAY02592 encoded Z variants, each fused to an albumin binding domain (ABD) derived from streptococcal protein G.

The ligation reactions (approximately 160 ng DNA/transformation) were electroporated into electrocompetent E. coli ER2738 cells (50 µl, Lucigen, Middleton, Wis., USA). Immediately after electroporation, approximately 1 ml of recovery medium (supplied with the ER2738 cells) was added. The transformed cells were incubated at 37° C. for 60 min. Samples were taken for titration and for determination of the number of transformants. The cells were thereafter pooled and cultivated overnight at 37° C. in 1 l of TSB-YE medium, supplemented with 2% glucose, 10 µg/ml tetracycline and 100 µg/ml ampicillin. The cells were pelleted for 7 min at 4,000 g and resuspended in a PBS/glycerol solution (approximately 40% glycerol). The cells were aliquoted and stored at −80° C. Clones from the library of Z variants were sequenced in order to verify the content and to evaluate the outcome of the constructed library vis-à-vis the library design. Sequencing was performed as described in Example 1 and the amino acid distribution was verified.

Preparation of Phage Stock:

Phage stock containing the phagemid library was prepared in a 20 l fermenter (Belach Bioteknik). Cells from a glycerol stock containing the phagemid library were inoculated in 10 l of TSB-YE (Tryptic Soy Broth-Yeast Extract; 30 g/l TSB, 5 g/l yeast extract) supplemented with 1 g/l glucose, 100 mg/l ampicillin and 10 mg/l tetracycline. When the cells reached an optical density at 600 nm (OD600) of 0.6, approximately 1.5 l of the cultivation was infected using a 5× molar excess of M13K07 helper phage. The cells were incubated for 30 min, whereupon the fermenter was filled up to 10 l with complex fermentation medium [2.5 g/l $(NH_4)_2SO_4$, 5.0 g/l yeast extract; 30 g/l tryptone, 2 g/l $K_2HPO_4$; 3 g/l $KH_2PO_4$, 1.25 g/l, $Na_3CeH_5O_7.2 H_2O$; Breox FMT30 antifoaming agent 0.1 ml/l]. The following components were added: 10 ml carbenicillin 25 mg/ml; 5 ml kanamycin 50 mg/ml; 1 ml 1 M isopropyl-8-D-1-thiogalactopyranoside (IPTG); 17.5 ml/l of 300 g/l $MgSO_4$, and 5 ml of a trace element solution [35 g/l $FeCl_3$. 6 $H_2O$; 10.56 g/l $ZnSO_4.7 H_2O$; 2.64 g/l $CuSO_4.5 H_2O$; 13.2 g/l $MnSO_4. H_2O$; 13.84 g/l $CaCl_2.2 H_2O$, dissolved in 1.2 M HCl]. A glucose limited fed-batch cultivation was started where a 600 g/l glucose solution was fed to the reactor (3.5 g/h in the start, 37.5 g/h after 20 h and until the end of the cultivation). pH was controlled at pH 7 through the automatic addition of 25% $NH_4OH$, air was supplemented (5 l/min), and the stirrer was set at 500 rpm. After 24 h of fed-batch cultivation the OD600 was 33.2. The cells in the cultivation were pelleted by centrifugation at 15,900 g. The phage particles were precipitated from the supernatant twice in PEG/NaCl, filtered and dissolved in PBS and glycerol as in Example 2. Phage stocks were stored at −80° C. until use in selection.

Results

Library Construction:

The new library was designed based on a set of 16 FcRn binding Z variants with verified binding properties (Example 2-6). The theoretical size of the designed library was 5.3× $10^8$ Z variants. The actual size of the library, determined by titration after transformation to *E. coli* ER2738 cells, was $4.5×10^9$ transformants.

The library quality was tested by sequencing of 96 transformants and by comparing their actual sequences with the theoretical design. The contents of the actual library compared to the designed library were shown to be satisfying. A maturated library of potential binders to FcRn was thus successfully constructed.

Example 8

Selection and Screening of Z Variants from a Maturated Library

Materials and Methods
Phage Display Selection of Matured FcRn Binding Z Variants:

The target proteins human FcRn (Biorbyt, cat. no. orb84388) and murine FcRn (Biorbyt, cat. no. orb99076) were biotinylated essentially as described in Example 2 using biotin at 10× molar excess. Phage display selections, using the new library of Z variant molecules described in Example 7, were performed in four cycles against human FcRn or murine FcRn essentially as in Example 2 but with the following exceptions. Selection buffers were 0.1% PCTG buffer, pH 5.5 (McIlvaines phosphate-citrate buffer, pH 5.5, supplemented with 0.1% Tween-20 and 0.1% gelatin) or 0.1% PCTG buffer, pH 7.4, (McIlvaines phosphate-citrate buffer, pH 7.4, supplemented with 0.1% Tween-20 and 0.1% gelatin) respectively. Prior to selection, HSA was added to the selection buffers to a final concentration of 1.5 µM. All tubes and beads used in the selection were pre-blocked with either of the two different selections buffers. A pre-selection step, by incubation of phage stock with SA-beads for 45 min, was performed in cycle 1. For capture of phage-target complexes, 1 mg beads per 1.1 µg biotinylated human FcRn or 1.6 µg biotinylated murine FcRn was used. Washes were performed with 0.1% PCT buffer pH 5.5 or pH 7.4 except for tracks 2-1-2-1 and 2-1-2-2 where 0.1% PCT supplemented with 25 nM IgG (Herceptin®) or 10 nM IgG, respectively, was used as outlined in Table 9.

The five tracks (1-5) in cycle 1 were divided in the second to fourth cycles, resulting in totally seven tracks (1-1 to 5-1) in cycle 2, eleven tracks (1-1-1 to 5-1-1) in cycle 3 and fourteen tracks (1-1-1-1 to 5-1-1-1) in cycle 4. The bound phage particles were eluted as described in Example 2.

An overview of the selection strategy, describing an increased stringency in subsequent cycles, using a lowered target concentration and an increased number of washes, is shown in Table 9.

Amplification of Phage Particles:
Amplification of phage particles between selection cycle 1 and 2 was performed essentially as described in Example 2, with the following exceptions. *E. coli* ER2738 was used for phage amplification and M13K07 helper phage was used in 5× excess. The amplification of phage particles between the selection cycles 2 and 4 was done by performing infection of bacteria in solution as follows. After infection of log phase *E. coli* ER2738 with phage particles, TSB supplemented with 2% glucose, 10 µg/ml tetracycline and 100 µg/ml ampicillin was added, followed by incubation with rotation for 30 min at 37° C. Thereafter, the bacteria were infected with M13K07 helper phage in 5× excess. The infected bacteria were pelleted by centrifugation, re-suspended in TSB-YE medium supplemented with 100 µM IPTG, 25 µg/ml kanamycin and 100 µg/ml ampicillin, and grown overnight at 30° C. The overnight cultures were pelleted in a centrifuge, and phage particles in the supernatant were precipitated twice with PEG/NaCl buffer. Finally, the phage particles were re-suspended in selection buffer before entering the next selection cycle.

In the final selection cycle, log phase bacteria were infected with eluate and diluted before spreading onto TBAB plates (30 g/l tryptose blood agar base, Oxoid cat. no. CM0233B) supplemented with 0.2 g/l ampicillin in order to form single colonies to be used in ELISA screening.

TABLE 9

Overview of the maturation selection data.

| Cycle | Selection track | Phage stock from library or selection track | Target species | Target conc. (nM) | Selection pH | Wash pH | Number of washes |
|---|---|---|---|---|---|---|---|
| 1 | 1 | Zlib006FcRn.l | human | 100 | 7.4 | 7.4 | 2 |
| 1 | 2 | Zlib006FcRn.l | human | 100 | 7.4 | 5.5 | 2 |
| 1 | 3 | Zlib006FcRn.l | human | 25 | 5.5 | 5.5 | 4 |
| 1 | 4 | Zlib006FcRn.l | murine | 100 | 7.4 | 7.4 | 2 |
| 1 | 5 | Zlib006FcRn.l | murine | 100 | 5.5 | 5.5 | 2 |
| 2 | 1-1 | 1 | human | 50 | 7.4 | 7.4 | 4 |
| 2 | 2-1 | 2 | human | 50 | 7.4 | 5.5 | 4 |
| 2 | 2-2 | 2 | human | 25 | 5.5 | 7.4 | 6 |
| 2 | 3-1 | 3 | human | 5 | 5.5 | 7.4 | 4 |
| 2 | 3-2 | 3 | human | 5 | 5.5 | 5.5 | 8 |
| 2 | 4-1 | 4 | murine | 50 | 7.4 | 5.5 | 2 |
| 2 | 5-1 | 5 | murine | 100 | 5.5 | 5.5 | 2 |
| 3 | 1-1-1 | 1-1 | human | 10 | 7.4 | 7.4 | 8 |
| 3 | 1-1-2 | 1-1 | human | 5 | 5.5 | 7.4 | 8 |
| 3 | 2-1-1 | 2-1 | human | 10 | 7.4 | 5.5 | 8 |
| 3 | 2-1-2 | 2-1 | human | 5 | 7.4 | 5.5 | 12 |
| 3 | 2-2-1 | 2-2 | human | 10 | 7.4 | 5.5 | 12 |
| 3 | 2-2-2 | 2-2 | human | 5 | 7.4 | 5.5 | 15 |
| 3 | 3-1-1 | 3-1 | human | 1 | 5.5 | 7.4 | 8 |
| 3 | 3-2-1 | 3-2 | human | 0.5 | 5.5 | 5.5 | 12 |
| 3 | 3-2-2 | 3-2 | human | 0.25 | 5.5 | 5.5 | 16 |
| 3 | 4-1-1 | 4-1 | murine | 10 | 7.4 | 5.5 | 6 |
| 3 | 5-1-1 | 5-1 | murine | 5 | 5.5 | 5.5 | 8 |
| 4 | 1-1-1-1 | 1-1-1 | human | 1 | 7.4 | 7.4 | 12 |

TABLE 9-continued

Overview of the maturation selection data.

| Cycle | Selection track | Phage stock from library or selection track | Target species | Target conc. (nM) | Selection pH | Wash pH | Number of washes |
|---|---|---|---|---|---|---|---|
| 4 | 1-1-1-2 | 1-1-1 | human | 0.25 | 7.4 | 7.4 | 15 |
| 4 | 1-1-2-1 | 1-1-2 | human | 0.5 | 7.4 | 5.5 | 15 |
| 4 | 1-1-2-2 | 1-1-2 | human | 0.1 | 5.5 | 7.4 | 15 |
| 4 | 2-1-1-1 | 2-1-1 | human | 1 | 7.4 | 5.5 | 15 |
| 4 | 2-1-1-2 | 2-1-1 | human | 0.5 | 7.4 | 5.5 | 15 |
| 4 | 2-1-2-1 | 2-1-2 | human | 0.25 | 7.4 | 5.5 | 20 (+IgG) |
| 4 | 2-1-2-2 | 2-1-2 | human | 0.1 | 7.4 | 5.5 | 20 (+IgG) |
| 4 | 2-2-1-1 | 2-2-1 and 2-2-2 | human | 0.5 | 5.5 | 7.4 | 15 |
| 4 | 2-2-2-1 | 2-2-1 and 2-2-2 | human | 0.5 | 7.4 | 5.5 | 20 |
| 4 | 3-1-1-1 | 3-1-1 | human | 1 | 5.5 | 7.4 | 12 |
| 4 | 3-2-1-1 | 3-2-1 and 3-2-2 | human | 0.5 | 5.5 | 5.5 | 16 |
| 4 | 4-1-1-1 | 4-1-1 | murine | 1 | 7.4 | 5.5 | 12 |
| 4 | 5-1-1-1 | 5-1-1 | murine | 0.5 | 5.5 | 5.5 | 15 |

Sequencing of Potential Binders:

Individual clones from the different selection tracks were picked for sequencing. All clones run in the ELISA screening were sequenced. Amplification of gene fragments and sequence analysis of gene fragments were performed essentially as described in Example 2.

ELISA Screening of Z Variants:

Single colonies containing Z variants (expressed as Z variant ABD fusion proteins as described in Example 2) were randomly picked from the selected clones of the FcRn maturated library and grown in 1 ml cultivations essentially as described in Example 2. Preparation of the periplasmic supernatants was performed as in Example 2 with eight freeze thawing cycles and the periplasmic fractions were used undiluted in the ELISA screening. ELISA screenings were performed at both pH 6.0 and pH 7.4 essentially as described in Example 2 using biotinylated human FcRn at a concentration of 2 nM in each well. The periplasmic fraction of the primary FcRn binder Z10193 (SEQ ID NO:2; assayed in above experiments) was used as a positive control. Periplasm containing the ABD moiety only was used as a negative control.

ELISA $K_D$ Analysis of FcRn Binding Z Variants:

A selection of FcRn binders was subjected to an analysis of the response against a dilution series of biotinylated human FcRn using ELISA at both pH 6.0 and pH 7.4 as described above. Biotinylated human FcRn was added at a concentration of 30 nM and diluted stepwise 1:3 down to 14 pM. As a background control, all Z variants were also assayed with no target protein added. Periplasm samples containing the primary FcRn binder Z07918 (SEQ ID.NO:1) was included and analyzed as a positive control. Periplasm containing the ABD moiety only was used as a negative control. Data were analyzed using GraphPad Prism 5 and non-linear regression and $K_D$ values (the half maximal effective concentration) were calculated.

Results

Phage Display Selection of Maturated FcRn Binding Z Variants:

Selection was performed in totally 14 parallel tracks containing four cycles each. The different selection tracks differed in target concentration, target type (human FcRn or murine FcRn), selection time, and wash conditions.

Sequencing of Potential Binders:

Randomly picked clones were sequenced. Each individual Z variant was given an identification number, Z#####, as described in Example 2. In total, 445 new unique Z variant molecules were identified.

The amino acid sequences of a subset of the 58 amino acid residues long Z variants are listed in FIG. 1 and in the sequence listing as SEQ ID NO:17-352. The deduced FcRn binding motifs of these Z variants extend from residue 8 to residue 36 in sequences with SEQ ID NO:17-352. The amino acid sequences of the 49 amino acid residues long polypeptides (BMod) predicted to constitute the complete three-helix bundle within each of these Z variants extend from residue 7 to residue 55.

ELISA Screening of Z Variants:

Clones obtained after four selection cycles were produced in 96-well plates and screened for FcRn binding activity using ELISA. All randomly picked clones were analyzed. At pH 6.0, 333 of the 445 unique Z variants were found to give a response of 0.3 AU or higher (corresponding to at least 3× the negative control) against human FcRn at a concentration of 2 nM. At pH 7.4, 278 of the 445 unique Z variants were found to give a response of 0.3 AU or higher (corresponding to at least 3× the negative control) against human FcRn at a concentration of 2 nM. Clones with a positive signal against human FcRn were found in all tracks (including those with murine target) except 1-1-1-1. The negative controls had absorbances of 0.070-0.096 AU (pH 6.0) and 0.060-0.112 AU (pH 7.4), respectively. The average response of the blank controls was 0.070 AU (pH 6.0) and 0.062 (pH 7.4).

ELISA $K_D$ Analysis of FcRn Binding Z Variants:

A subset of Z variants was selected based on the result in the ELISA experiment described above (highest ELISA value at pH 6.0 and/or pH 7.4) and subjected to a target titration in ELISA format. Periplasm samples were incubated with a serial dilution of biotinylated human FcRn. A periplasm sample with the primary binder Z07918 (SEQ ID NO:1) was also assayed as a positive control. Obtained values were analyzed and their respective $K_D$ values were calculated (Table 10).

TABLE 10

Calculated $K_D$ values from ELISA titration analysis of Z-ABD variants from the maturation.

| Z variant | SEQ ID NO: | $K_D$ pH 6.0 (M) | $K_D$ pH 7.4 (M) |
|---|---|---|---|
| Z13573 | 17 | $1.1 \times 10^{-9}$ | $3.8 \times 10^{-9}$ |
| Z13574 | 18 | $1.2 \times 10^{-9}$ | $5.0 \times 10^{-9}$ |
| Z13577 | 19 | $9.9 \times 10^{-10}$ | $1.4 \times 10^{-9}$ |
| Z13578 | 20 | $1.0 \times 10^{-9}$ | $2.5 \times 10^{-9}$ |
| Z13579 | 21 | $1.2 \times 10^{-9}$ | $5.3 \times 10^{-9}$ |
| Z13581 | 22 | $1.1 \times 10^{-9}$ | $3.3 \times 10^{-9}$ |
| Z13583 | 23 | $8.0 \times 10^{-10}$ | $1.5 \times 10^{-9}$ |
| Z13585 | 24 | $1.2 \times 10^{-9}$ | $1.7 \times 10^{-9}$ |
| Z13586 | 25 | $1.2 \times 10^{-9}$ | $2.3 \times 10^{-9}$ |
| Z13587 | 26 | $1.4 \times 10^{-9}$ | $6.9 \times 10^{-9}$ |
| Z13588 | 27 | $1.0 \times 10^{-9}$ | $2.3 \times 10^{-9}$ |
| Z13592 | 28 | $9.5 \times 10^{-10}$ | $1.8 \times 10^{-9}$ |
| Z13594 | 29 | $1.3 \times 10^{-9}$ | $6.3 \times 10^{-9}$ |
| Z13596 | 30 | $1.5 \times 10^{-9}$ | $3.6 \times 10^{-9}$ |
| Z13597 | 31 | $1.4 \times 10^{-9}$ | $6.0 \times 10^{-9}$ |
| Z13598 | 32 | $1.1 \times 10^{-9}$ | $1.7 \times 10^{-9}$ |
| Z13600 | 33 | $1.4 \times 10^{-9}$ | $4.0 \times 10^{-9}$ |
| Z13604 | 43 | $1.3 \times 10^{-9}$ | $4.1 \times 10^{-9}$ |
| Z13605 | 35 | $1.3 \times 10^{-9}$ | $3.8 \times 10^{-9}$ |
| Z13609 | 36 | $1.3 \times 10^{-9}$ | $2.7 \times 10^{-9}$ |
| Z13611 | 37 | $1.3 \times 10^{-9}$ | $2.5 \times 10^{-9}$ |
| Z13612 | 38 | $1.2 \times 10^{-9}$ | $8.6 \times 10^{-9}$ |
| Z13613 | 39 | $1.2 \times 10^{-9}$ | $4.3 \times 10^{-9}$ |
| Z13615 | 40 | $1.2 \times 10^{-9}$ | $3.1 \times 10^{-9}$ |
| Z13616 | 41 | $9.6 \times 10^{-10}$ | $1.7 \times 10^{-9}$ |
| Z13617 | 42 | $1.2 \times 10^{-9}$ | $1.9 \times 10^{-9}$ |
| Z13620 | 43 | $1.4 \times 10^{-9}$ | $3.3 \times 10^{-9}$ |
| Z13621 | 44 | $8.6 \times 10^{-10}$ | $1.4 \times 10^{-9}$ |
| Z13622 | 45 | $1.1 \times 10^{-9}$ | $2.1 \times 10^{-9}$ |
| Z13624 | 46 | $1.3 \times 10^{-9}$ | $3.4 \times 10^{-9}$ |
| Z13625 | 47 | $1.3 \times 10^{-9}$ | $2.8 \times 10^{-9}$ |
| Z13626 | 48 | $1.2 \times 10^{-9}$ | $2.7 \times 10^{-9}$ |
| Z13627 | 49 | $1.2 \times 10^{-9}$ | $2.9 \times 10^{-9}$ |
| Z13628 | 50 | $1.3 \times 10^{-9}$ | $5.5 \times 10^{-9}$ |
| Z13629 | 51 | $1.2 \times 10^{-9}$ | $8.5 \times 10^{-9}$ |
| Z13633 | 52 | $1.5 \times 10^{-9}$ | $6.2 \times 10^{-9}$ |
| Z13634 | 53 | $1.1 \times 10^{-9}$ | $2.3 \times 10^{-9}$ |
| Z13635 | 54 | $1.0 \times 10^{-9}$ | $1.7 \times 10^{-9}$ |
| Z13637 | 55 | $1.3 \times 10^{-9}$ | $4.8 \times 10^{-9}$ |
| Z13638 | 56 | $1.2 \times 10^{-9}$ | $2.9 \times 10^{-9}$ |
| Z13639 | 57 | $1.3 \times 10^{-9}$ | $3.0 \times 10^{-9}$ |
| Z13640 | 58 | $1.1 \times 10^{-9}$ | $1.9 \times 10^{-9}$ |
| Z13641 | 59 | $1.1 \times 10^{-9}$ | $1.8 \times 10^{-9}$ |
| Z13644 | 60 | $1.3 \times 10{-9}$ | $2.8 \times 10{-9}$ |
| Z13645 | 61 | $1.2 \times 10^{-9}$ | $2.5 \times 10^{-9}$ |
| Z13648 | 62 | $1.6 \times 10^{-9}$ | $3.3 \times 10^{-9}$ |
| Z13651 | 63 | $1.2 \times 10^{-9}$ | $2.7 \times 10^{-9}$ |
| Z13652 | 64 | $1.4 \times 10^{-9}$ | $2.9 \times 10^{-9}$ |
| Z13654 | 65 | $9.5 \times 10^{-10}$ | $2.9 \times 10^{-9}$ |
| Z13655 | 66 | $1.1 \times 10^{-9}$ | $2.4 \times 10^{-9}$ |
| Z13656 | 67 | $1.1 \times 10^{-9}$ | $3.7 \times 10^{-9}$ |
| Z13657 | 68 | $2.1 \times 10^{-9}$ | $3.9 \times 10^{-9}$ |
| Z13659 | 69 | $2.2 \times 10^{-9}$ | $3.1 \times 10^{-9}$ |
| Z13663 | 70 | $9.3 \times 10^{-10}$ | $1.5 \times 10^{-9}$ |
| Z13664 | 71 | $2.4 \times 10^{-9}$ | $4.2 \times 10^{-9}$ |
| Z13667 | 72 | $1.2 \times 10^{-9}$ | $2.3 \times 10^{-9}$ |
| Z13669 | 73 | $9.2 \times 10^{-10}$ | $1.7 \times 10^{-9}$ |
| Z13672 | 74 | $2.5 \times 10^{-9}$ | $5.6 \times 10^{-9}$ |
| Z13674 | 75 | $9.2 \times 10^{-10}$ | $1.3 \times 10^{-9}$ |
| Z13675 | 76 | $9.6 \times 10^{-10}$ | $2.2 \times 10^{-9}$ |
| Z13676 | 77 | $9.4 \times 10^{-10}$ | $3.1 \times 10^{-9}$ |
| Z13678 | 78 | $2.0 \times 10^{-9}$ | $3.3 \times 10^{-9}$ |
| Z13684 | 79 | $1.0 \times 10^{-9}$ | $2.2 \times 10^{-9}$ |
| Z13688 | 80 | $1.3 \times 10^{-9}$ | $2.1 \times 10^{-9}$ |
| Z13691 | 81 | $1.8 \times 10^{-9}$ | $2.7 \times 10^{-9}$ |
| Z13692 | 82 | $1.3 \times 10^{-9}$ | $3.7 \times 10^{-9}$ |
| Z13694 | 83 | $9.8 \times 10^{-10}$ | $3.6 \times 10^{-9}$ |
| Z13695 | 84 | $1.8 \times 10^{-9}$ | $5.3 \times 10^{-9}$ |
| Z13697 | 85 | $1.2 \times 10^{-9}$ | $2.4 \times 10^{-9}$ |
| Z13706 | 86 | $2.0 \times 10^{-9}$ | $6.4 \times 10^{-9}$ |
| Z13708 | 87 | $1.9 \times 10^{-9}$ | $4.4 \times 10^{-9}$ |
| Z13710 | 88 | $1.6 \times 10^{-9}$ | $2.6 \times 10^{-9}$ |
| Z13711 | 89 | $2.1 \times 10^{-9}$ | $4.9 \times 10^{-9}$ |
| Z13714 | 90 | $2.1 \times 10^{-9}$ | $6.0 \times 10^{-9}$ |
| Z13716 | 91 | $1.8 \times 10^{-9}$ | $5.8 \times 10^{-9}$ |
| Z13719 | 92 | $2.6 \times 10^{-9}$ | $7.3 \times 10^{-9}$ |
| Z13720 | 93 | $2.5 \times 10^{-9}$ | $4.5 \times 10^{-7}$ |
| Z13721 | 94 | $1.9 \times 10^{-9}$ | $2.9 \times 10^{-9}$ |
| Z13725 | 95 | $1.8 \times 10^{-9}$ | $4.9 \times 10^{-9}$ |
| Z13727 | 96 | $2.1 \times 10^{-9}$ | $5.9 \times 10^{-9}$ |
| Z13728 | 97 | $2.6 \times 10^{-9}$ | $6.7 \times 10^{-9}$ |
| Z13732 | 98 | $2.1 \times 10^{-9}$ | $9.4 \times 10^{-9}$ |
| Z13735 | 99 | $1.6 \times 10^{-9}$ | $9.1 \times 10^{-9}$ |
| Z13736 | 100 | $1.7 \times 10^{-9}$ | $3.0 \times 10^{-9}$ |
| Z13740 | 101 | $2.0 \times 10^{-9}$ | $5.0 \times 10^{-9}$ |
| Z13742 | 102 | $2.4 \times 10^{-9}$ | $7.6 \times 10^{-9}$ |
| Z13747 | 103 | $1.3 \times 10^{-9}$ | $2.3 \times 10^{-9}$ |
| Z13749 | 104 | $2.8 \times 10^{-9}$ | $1.2 \times 10^{-8}$ |
| Z13750 | 105 | $2.7 \times 10^{-9}$ | $8.4 \times 10^{-9}$ |
| Z13751 | 106 | $2.0 \times 10^{-9}$ | $3.8 \times 10^{-9}$ |
| Z13752 | 107 | $2.0 \times 10^{-9}$ | $5.8 \times 10^{-9}$ |
| Z13758 | 108 | $1.9 \times 10^{-9}$ | $6.5 \times 10^{-9}$ |
| Z13759 | 109 | $2.1 \times 10^{-9}$ | $5.6 \times 10^{-9}$ |
| Z13760 | 110 | $2.1 \times 10^{-9}$ | $5.8 \times 10^{-9}$ |
| Z13761 | 111 | $1.9 \times 10^{-9}$ | $3.7 \times 10^{-9}$ |
| Z13771 | 112 | $1.5 \times 10^{-9}$ | $2.0 \times 10^{-9}$ |
| Z13773 | 113 | $2.5 \times 10^{-9}$ | $4.9 \times 10^{-9}$ |
| Z13776 | 114 | $2.2 \times 10^{-9}$ | $5.5 \times 10^{-9}$ |
| Z13777 | 115 | $2.4 \times 10^{-9}$ | $4.6 \times 10^{-9}$ |
| Z13780 | 116 | $2.1 \times 10^{-9}$ | $4.0 \times 10^{-9}$ |
| Z13782 | 117 | $2.2 \times 10^{-9}$ | $4.2 \times 10^{-9}$ |
| Z13783 | 118 | $1.4 \times 10^{-9}$ | $2.2 \times 10^{-9}$ |
| Z13786 | 119 | $2.3 \times 10^{-9}$ | $4.7 \times 10^{-9}$ |
| Z13792 | 120 | $2.0 \times 10^{-9}$ | $2.9 \times 10^{-9}$ |
| Z13796 | 121 | $2.3 \times 10^{-9}$ | $4.2 \times 10^{-9}$ |
| Z13799 | 122 | $1.9 \times 10^{-9}$ | $5.6 \times 10^{-9}$ |
| Z13806 | 123 | $1.6 \times 10^{-9}$ | $3.1 \times 10^{-9}$ |
| Z13808 | 124 | $2.4 \times 10^{-9}$ | $5.5 \times 10^{-9}$ |
| Z13811 | 125 | $2.0 \times 10^{-9}$ | $3.1 \times 10^{-9}$ |
| Z13812 | 126 | $2.3 \times 10^{-9}$ | $1.1 \times 10^{-8}$ |
| Z13823 | 127 | $2.9 \times 10^{-9}$ | $3.8 \times 10^{-9}$ |
| Z13824 | 128 | $1.9 \times 10^{-9}$ | $3.8 \times 10^{-9}$ |
| Z13838 | 129 | $2.6 \times 10^{-9}$ | $5.4 \times 10^{-9}$ |
| Z13840 | 130 | $2.2 \times 10^{-9}$ | $4.1 \times 10^{-9}$ |
| Z13842 | 131 | $2.2 \times 10^{-9}$ | $5.5 \times 10^{-9}$ |
| Z13845 | 132 | $2.6 \times 10^{-9}$ | $4.2 \times 10^{-9}$ |
| Z13846 | 133 | $2.3 \times 10^{-9}$ | $4.3 \times 10^{-9}$ |
| Z13848 | 134 | $2.1 \times 10^{-9}$ | $3.1 \times 10^{-9}$ |
| Z13849 | 135 | $2.1 \times 10^{-9}$ | $3.0 \times 10^{-9}$ |
| Z13860 | 136 | $2.3 \times 10^{-9}$ | $8.7 \times 10^{-9}$ |
| Z13865 | 137 | $2.5 \times 10^{-9}$ | $5.6 \times 10^{-9}$ |
| Z13866 | 138 | $2.0 \times 10^{-9}$ | $2.8 \times 10^{-9}$ |
| Z13875 | 139 | $2.0 \times 10^{-9}$ | $3.4 \times 10^{-9}$ |
| Z13879 | 140 | $2.1 \times 10^{-9}$ | $3.0 \times 10^{-9}$ |

Example 9

Production and Characterization of Z Variants from a Maturated Library

In this Example, twelve Z variants were produced in *E. coli*, purified and assayed for stability, for binding to FcRn as well as for inhibition of IgG binding to FcRn.

Materials and Methods

Subcloning of Z Variants into Expression Vectors:

The DNA of twelve FcRn binding Z variants (Z13577 (SEQ ID NO:19), Z13578 (SEQ ID NO:20), Z13583 (SEQ ID NO:23), Z13592 (SEQ ID NO:28), Z13616 (SEQ ID NO:41), Z13621 (SEQ ID NO:44), Z13654 (SEQ ID NO:65), Z13663 (SEQ ID NO:70), Z13669 (SEQ ID NO:73), Z13674 (SEQ ID NO:75), Z13675 (SEQ ID NO:76) and Z13676 (SEQ ID NO:77)) was amplified from the library vector pAY02592. The subcloning was performed as described in Example 3. The Z gene fragments were subcloned into the expression vector pAY01448 resulting in the encoded sequence MGSSHHHHHHLQ-[Z#####]-VD (SEQ ID NO:468).

Production of Z Variants:

Cultivation and purification of the $His_6$-tagged Z variants were performed essentially as described in Example 3. In order to obtain higher purity, a reversed phase chromatography (RPC) step was added after the IMAC purification of a second batch of the twelve matured variants and the primary Z variant Z07918. Samples from this batch were used where indicated.

CD Analysis:

In order to determine the melting temperatures (Tm) and assess the secondary structure of the Z variants (RPC purified batch), CD analysis was carried out as described in Example 3.

Biacore Binding and Kinetic Analyses:

The interaction of FcRn binding $His_6$-tagged Z variants with human FcRn was analyzed in a Biacore 2000 instrument essentially as described in Example 3. Human FcRn (hFcRn) or cynomolgus FcRn (cFcRn) purchased from Biorbyt (cat. no. orb84388 and orb99075, respectively) were used as target protein. In a first set of experiments, 100 nM of the Z variants was injected at pH 6.0 during 2 min at 30 µl/min over immobilized hFcRn followed by dissociation in buffers of pH 6.0 or pH 7.4 using the co-inject procedure. The dissociation phase was 4 min and the equilibration time between the analyte injections was 30 min. In a second set of experiments, approximate kinetic constants ($k_{on}$ and $k_{off}$) and affinities ($K_D$) were determined for a subset of Z variants injected at concentrations of 540 nM, 180 nM, 60 nM, 20 nM and 6.7 nM over immobilized hFcRn. As above, the analytes were injected during 2 min at 30 µl/min, the dissociation phase was 4 min and the equilibration time between the analyte injections was 30 min.

In a third set of experiments, a kinetic analysis of the twelve matured Z variants and the primary Z variant Z07918 (SEQ ID NO:1) (RPC purified batches) binding to hFcRn and cFcRn was performed at pH 6. A concentration series of $His_6$-tagged Z variants (270, 90, 30 and 10 nM) were injected during 4 min at 30 µl/min over hFcRn and cFcRn, immobilized in different flow cells of a CM5 chip surface. 0.005% PCT pH 6.0 was used as running buffer and for dilutions of the $His_6$-tagged Z variants. Dissociation in running buffer was allowed for 20 min, followed by surface regeneration by injection of 3×30 second pulses of 0.005% PCT pH 7.4 and equilibration ten minutes before the start of next cycle.

AlphaLISA Blocking Assay:

The potential of Z variants to inhibit binding of IgG to FcRn was analyzed in the AlphaLISA assay described in Example 3.

Results

Production of Z Variants:

The twelve FcRn binding Z variants constructed with an N-terminal $His_6$ tag were produced in *E. coli*. SDS-PAGE analysis of each final protein preparation showed that these predominantly contained the FcRn binding Z variant. The correct identity and molecular weight of each FcRn binding Z variant was confirmed by HPLC-MS analysis.

CD Analysis:

Determined melting temperatures are shown in Table 11. Reversible folding was seen for all FcRn binding Z variants when overlaying spectra measured before and after heating to 90° C.

Biacore Binding and Kinetic Analyses:

In a first set of experiments, the binding of the twelve Z variants to human FcRn and the dissociation at different pH were tested in a Biacore instrument by sequentially injecting each of the Z variants at pH 6.0 and either buffer pH 6.0 or buffer pH 7.4 over a chip surface containing FcRn. The ligand immobilization level of the surface was 890 RU human FcRn. The twelve Z variants showed binding to FcRn at pH 6.0, and for all variants, faster off-rates were seen at pH 7.4 compared to pH 6.0.

The kinetic constants of the Z variants Z13577 (SEQ ID NO:19) and Z13621 (SEQ ID NO:44) interacting with FcRn at pH 6.0 were determined in a second set of experiments (see Table 12). Kinetic constants were calculated using curve sets of two or four injected concentrations of Z13577 and Z13621, respectively.

TABLE 11

Melting temperatures for a set of matured FcRn binding Z variants.

| Z variant | SEQ ID NO: | Tm (°C.) |
|---|---|---|
| Z13577 | 19 | 61 |
| Z13578 | 20 | 57 |
| Z13583 | 23 | 51 |
| Z13592 | 28 | 58 |
| Z13616 | 41 | 60 |
| Z13621 | 44 | 49 |
| Z13654 | 65 | 58 |
| Z13663 | 70 | 60 |
| Z13669 | 73 | 45 |
| Z13674 | 75 | 50 |
| Z13675 | 76 | 48 |
| Z13676 | 77 | 45 |
| Z07918 | 1 | 49 |

TABLE 12

Biacore kinetic constants and affinities for FcRn binding at pH 6.0.

| Z variant | SEQ ID NO: | $k_{on}$ ($M^{-1}s^{-1}$) | $k_{off}$ ($s^{-1}$) | $K_D$ (M) |
|---|---|---|---|---|
| Z13577 | 19 | $3.0 \times 10^5$ | $4.0 \times 10^{-3}$ | $13 \times 10^{-9}$ |
| Z13621 | 44 | $6.4 \times 10^5$ | $3.7 \times 10^{-3}$ | $6 \times 10^{-9}$ |

In a third set of experiments, the kinetic constants of thirteen $His_6$-tagged Z variants interacting with human or cynomolgus FcRn at pH 6.0 were determined (Table 13). The FcRn immobilization levels of the chip surfaces were 1196 RU (human) and 788 RU (cynomolgus), respectively. For each Z variant, kinetic constants were calculated using a curve set of four injected concentrations.

TABLE 13

Biacore kinetic constants and affinities for human and cynomolgus FcRn binding at pH 6.0.

| | | hFcRn | | | cFcRn | | |
|---|---|---|---|---|---|---|---|
| Z variant | SEQ ID NO: | $k_{on}$ $(M^{-1}s^{-1})$ | $k_{off}$ $(s^{-1})$ | $K_D$ (M) | $k_{on}$ $(M^{-1}s^{-1})$ | $k_{off}$ $(s^{-1})$ | $K_D$ (M) |
| Z13577 | 19 | $7.2 \times 10^5$ | $2.9 \times 10^{-3}$ | $4.1 \times 10^{-9}$ | $8.2 \times 10^5$ | $4.4 \times 10^{-3}$ | $5.4 \times 10^{-9}$ |
| Z13578 | 20 | $4.1 \times 10^5$ | $7.3 \times 10^{-3}$ | $1.8 \times 10^{-8}$ | $5.6 \times 10^5$ | $1.1 \times 10^{-2}$ | $2.1 \times 10^{-8}$ |
| Z13583 | 23 | $4.5 \times 10^5$ | $2.6 \times 10^{-3}$ | $5.8 \times 10^{-9}$ | $6.7 \times 10^5$ | $4.4 \times 10^{-3}$ | $6.6 \times 10^{-9}$ |
| Z13592 | 28 | $5.9 \times 10^5$ | $7.2 \times 10^{-3}$ | $1.2 \times 10^{-8}$ | $7.5 \times 10^5$ | $1.1 \times 10^{-2}$ | $1.5 \times 10^{-8}$ |
| Z13616 | 41 | $2.9 \times 10^5$ | $3.1 \times 10^{-3}$ | $1.0 \times 10^{-8}$ | $4.3 \times 10^5$ | $4.8 \times 10^{-3}$ | $1.1 \times 10^{-8}$ |
| Z13621 | 44 | $4.1 \times 10^5$ | $2.8 \times 10^{-3}$ | $6.8 \times 10^{-9}$ | $6.1 \times 10^5$ | $4.6 \times 10^{-3}$ | $7.6 \times 10^{-9}$ |
| Z13654 | 65 | $6.0 \times 10^5$ | $9.5 \times 10^{-3}$ | $1.6 \times 10^{-8}$ | $8.4 \times 10^5$ | $1.3 \times 10^{-2}$ | $1.5 \times 10^{-8}$ |
| Z13663 | 70 | $3.9 \times 10^5$ | $3.4 \times 10^{-3}$ | $8.7 \times 10^{-9}$ | $5.2 \times 10^5$ | $5.3 \times 10^{-3}$ | $1.0 \times 10^{-8}$ |
| Z13669 | 73 | $5.6 \times 10^5$ | $2.8 \times 10^{-3}$ | $4.9 \times 10^{-9}$ | $8.2 \times 10^5$ | $4.6 \times 10^{-3}$ | $5.6 \times 10^{-9}$ |
| Z13674 | 75 | $5.3 \times 10^5$ | $3.7 \times 10^{-3}$ | $7.0 \times 10^{-9}$ | $8.3 \times 10^5$ | $5.9 \times 10^{-3}$ | $7.1 \times 10^{-9}$ |
| Z13675 | 76 | $4.9 \times 10^5$ | $5.1 \times 10^{-3}$ | $1.0 \times 10^{-8}$ | $7.5 \times 10^5$ | $8.0 \times 10^{-3}$ | $1.1 \times 10^{-8}$ |
| Z13676 | 77 | $6.5 \times 10^5$ | $3.6 \times 10^{-3}$ | $5.5 \times 10^{-9}$ | $9.6 \times 10^5$ | $5.9 \times 10^{-3}$ | $6.2 \times 10^{-9}$ |
| Z07918 | 1 | $2.6 \times 10^5$ | $4.2 \times 10^{-3}$ | $1.6 \times 10^{-8}$ | $3.8 \times 10^5$ | $7.0 \times 10^{-3}$ | $1.9 \times 10^{-8}$ |

TABLE 14

Calculated IC50 values from AlphaLISA blocking assay.

| Z variant | SEQ ID NO: | IC50 (M) |
|---|---|---|
| Z13577 | 19 | $1.2 \times 10^{-8}$ |
| Z13578 | 20 | $1.2 \times 10^{-8}$ |
| Z13583 | 23 | $2.7 \times 10^{-9}$ |
| Z13592 | 28 | $6.4 \times 10^{-9}$ |
| Z13616 | 41 | $7.4 \times 10^{-9}$ |
| Z13621 | 44 | $3.2 \times 10^{-9}$ |
| Z13654 | 65 | $3.5 \times 10^{-9}$ |
| Z13663 | 70 | $1.1 \times 10^{-8}$ |
| Z13669 | 73 | $5.2 \times 10^{-9}$ |
| Z13674 | 75 | $2.5 \times 10^{-9}$ |
| Z13675 | 76 | $8.2 \times 10^{-9}$ |
| Z13676 | 77 | $3.9 \times 10^{-9}$ |

AlphaLISA Blocking Analysis:

The ability of twelve maturated $His_6$-tagged monomeric Z variants to inhibit IgG binding to FcRn was tested in an AlphaLISA blocking assay. Serial dilutions of the Z variants were incubated with biotinylated human FcRn and the blocking ability of each respective variant was measured after addition of IgG coated Acceptor beads and subsequently streptavidin coated Donor beads. Inhibition could be measured as a decrease in AlphaLISA counts for positive Z variants. All twelve tested Z variants were shown to block IgG binding to FcRn and the calculated IC50 values are shown in Table 14.

Example 10

Comparison of Blocking Capacity of IgG Binding to FcRn

In this Example, the IgG blocking capacity of the FcRn binding Z variant $His_6$-Z07918 (SEQ ID NO:1) was compared to Intravenous immunoglobulin (IVIg) and Subcutaneous immunoglobulin (SCIg) currently used in the treatment of some autoimmune disorders.

Materials and Methods

Blocking of IgG-FcRn Immunofluorescence Staining:

Human or murine FcRn-eGFP transduced HeLa cells were prepared as described in Example 4. Fixed cells were resuspended in 50 μl of a mix of 50 nM Alexa Fluor® 647-conjugated human IgG (Jackson laboratories, cat. no. 009-600-003) and Hise-tagged Z07918, IVIg (Octagam®, Octapharma) or SCIg (Gammanorm®, Octapharma), respectively, diluted at concentrations of 1000, 100, 10, 1, 0.1 or 0 (buffer control) nM in McIlvanes buffer pH 6.0, containing 2.5% FBS Ultra low IgG (Life Technologies) and 0.1% saponin (AppliChem). The cells were incubated for 1 h at 37° C. in the dark, washed with 2×100 μl McIlvanes, pH 6.0, containing 2.5% FBS Ultra low IgG and re-suspended in 180 μl of McIlvanes, pH 6.0, containing 1% BSA. Data from 10,000 GFP/FcRn positive cells were obtained using a FACS Calibur (Beckman Coulter) and the data was analyzed using Flowing software 2.5.0 (Turku University).

Results

Figure 9:
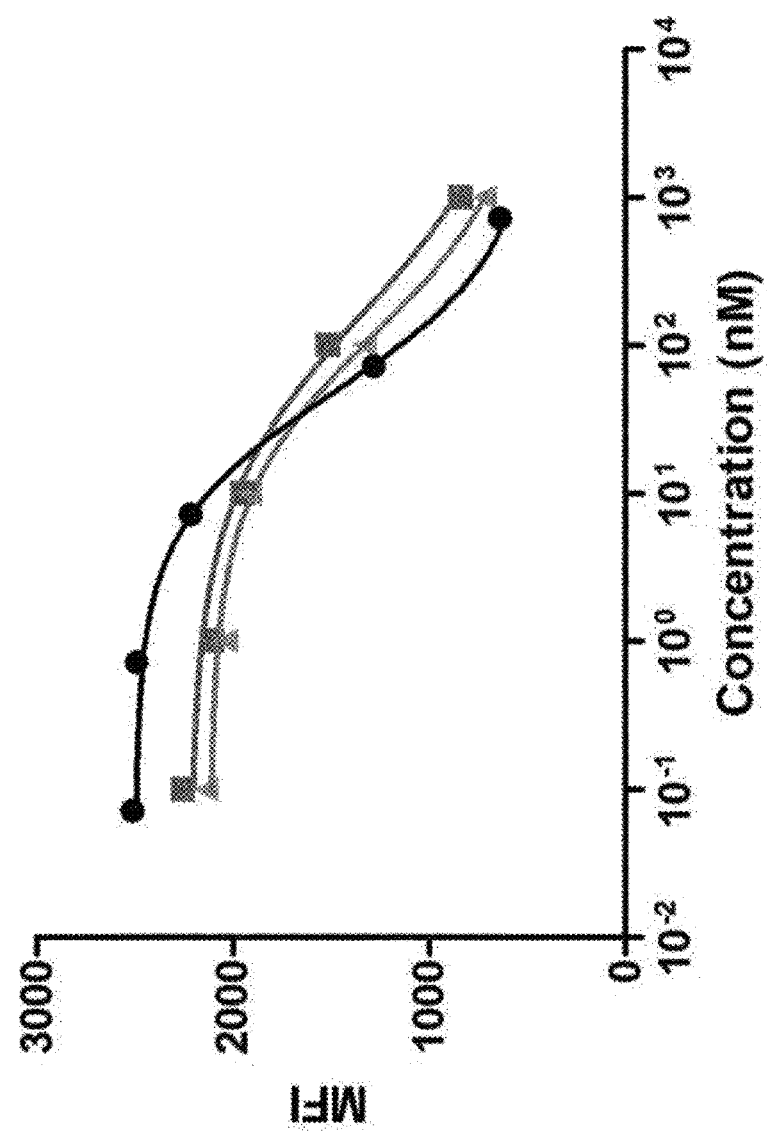
FIG. 9 shows the blocking of human IgG to human FcRn by $His_6$-Z07918 (SEQ ID NO:1; black circles), IVIg (grey squares) and SCIg (grey triangles), respectively, assayed as described in Example 10.

The experiment was performed to determine if the FcRn binding Z variant $His_6$-Z07918 (SEQ ID NO:1) blocks the IgG-FcRn interaction and compare the blocking effect to IVIg and SCIg. Human or murine FcRn-eGFP transduced HeLa cells were incubated with human Alexa Fluor® 647-conjugated IgG. The binding was blocked with unlabeled $His_6$-Z07918, IVIg or SCIg at different concentrations. The results showed that $His_6$-Z07918 effectively blocked hIgG binding to hFcRn to a similar extent as IVIg or SCIg (FIG. 9).

Example 11

Increased IgG Catabolism by FcRn Binding Z Variants in Mice

The ability of the FcRn binding Z variant Z07918 to block IgG binding to FcRn in vitro was shown in Example 10. In this example, the blocking ability of the same Z variant was evaluated in vivo. Blocking of IgG-FcRn interactions in vivo will lead to increased IgG catabolism and concomitant reduced levels of IgG (Mezo 2008, supra).

Materials and Methods

Animal Study:

The FcRn-binding Z variants Z11948 (SEQ ID NO:354) and Z07918-PP013 (Z07918 (SEQ ID NO:1) identical to Z11948 but with the N-terminus starting with the amino acids VD instead of AE, in fusion with the ABD variant PP013 (SEQ ID NO:377)) or vehicle (PBS buffer), were administered to male NMRI (Charles River), at a dose of 16.3 μmol/kg. The mice were treated with five intravenous injections given at 0, 24, 48, 72 and 96 h. Serum samples were taken at 0, 72, 120 and 168 h (termination of study) and stored at −20° C. The concentration of mouse IgG in serum was quantified by ELISA.

Mouse IgG ELISA:

The concentration of mouse IgG in mouse serum samples was analyzed by a mouse IgG ELISA kit (Mabtech 3825-1AD-6) and performed as described by the manufacturer. The concentration of mIgG was calculated from a standard curve provided and GraphPad Prism 5 using a non-linear regression formula. The concentration of IgG in individual mice at 24, 72, 120 and 168 h were related to the level at 0 h and the results are therefore presented as percentage of IgG (0 h).

Results

The results showed a reduction of mouse IgG concentration in mice treated with FcRn-specific Z variants. Both Z11948 and the ABD-fused variant Z07918-PP013 lowered the concentration of endogenous IgG in mice in vivo. Most pronounced effects were obtained with the ABD-fused variant and after 120 hours. Thus, the results indicates that the FcRn-specific Z variants blocked recycling of IgG resulting in increased IgG catabolism and subsequent lower levels of IgG in mice.

Example 12

In Vitro Transcytosis of FcRn Binding Z Variants

In this Example, the FcRn binding Z variants are tested for their ability to be transported through epithelial or endothelial cells or recycled by FcRn in vitro. A drug containing a Z variant with the power of transcytosis will facilitate drug uptake after for example oral or pulmonary administration.

Materials and Methods

Cells, for example T84, MDCK, HeLa, CaCo2, CaLu-1 and/or CaLu-3 cells, with or without endogenous or recombinant expression of FcRn, are grown in respective growth medium on a membrane in a transwell to form a monolayer. The integrity of monolayers can be evaluated by measuring the electrical resistance or adding a probe that is not able to penetrate or being actively transported over the cell monolayer. A defined monolayer of cells is pulsed from the apical or basolateral side with ligand such as FcRn binding Z variants, HSA or IgG in a buffer such as HBSS (Hanks' Balanced Salt Solution, SigmaAldrich, cat. no. H9269) or growth medium at a suitable pH and temperature, and chased with buffers such as HBSS or growth medium at a suitable pH and temperature on the opposite side.

In a variant of this assay, ligands can be chased with buffers such as HBSS or growth medium at suitable pH and temperature on the same side as administration to measure recycled ligand as well. This can be done in a transwell or in a cell culture dish. Cells are seeded into transwell or cell culture dishes and pulsed with ligands such as FcRn binding Z variants, HSA or IgG. Endocytosed ligands will bind to FcRn and return to the cell surface at the same or opposite side as they were loaded. After pulsing, free ligands are removed by washing the cells with cold buffer. To chase ligands, warm buffer or medium is added to the cells and, after a period in the range from 10 minutes to several hours, the buffer or medium is removed and assayed for the presence of ligands.

In a variant of this assay, ligands such as FcRn binding Z variants, HSA or IgG can be used to block the binding to FcRn by ligands such as other FcRn binding Z variants, HSA or IgG by administering them at the same time or sequentially to the cells.

The amount of ligand can be quantified by methods such as ELISA, HPLC-MS, fluorescent dye or radio labeling.

The results of the experiment described above are expected to show that the FcRn-specific Z variants can be transcytosed and/or recycled in vitro.

Example 13

Binding of Homodimeric FcRn Binding Polypeptides to Human FcRn/eGFP Transfected HeLa Cells In this Example, the binding ability of homodimeric FcRn binding polypeptides was investigated and compared to the binding ability of monomeric primary and maturated Z variants. The production of HeLa cells expressing human FcRn-eGFP gene transgene was performed as described in Example 4 and the use of these cells for flow cytometry analysis with Alexa Fluor® 647 labeled Z variants is described.

Materials and Methods

Alexa Fluor® 647 Labeling of FcRn Binding Polypeptides:

The two homodimeric $His_6$-tagged polypeptides Z11948-$(G_4S)_3$-Z11948 (SEQ ID NO:369) and Z11948-$(G_4S)$-Z11948 (SEQ ID NO:368), the primary monomeric $His_6$-tagged Z variant Z07918 (SEQ ID NO:1) and the maturated monomeric $His_6$-tagged Z-variants Z13583 (SEQ ID NO:23), Z13621 (SEQ ID NO:44), Z13654 (SEQ ID NO:65) and Z13674 (SEQ ID NO:75) were labeled with Alexa Fluor® 647 Carboxylic Acid Succinimidyl Ester (Invitrogen cat. no. A20106). Before labeling, the pH in the sample suspensions (in PBS pH 7.4) was adjusted to 8.3 by addition of 10 µl of 0.1 M sodium bicarbonate buffer, pH 8.3, to 90 µl sample suspension. 10 µl of Alexa Fluor® 647 Succinimidyl Ester dye (10 mg/ml in DMSO corresponding to 4× molar excess) was added to 100 µl of each sample suspension. The mixes were incubated at RT in the dark for 1 h in a wiggling rota mixer. The reaction mixes were immediately transferred to dialysis cassettes (3500 MWCO) (Thermo Scientific cat. no. 66333) and free dye was removed by dialysis in PBS pH 7.4.

Immunofluorescence Staining of Human FcRn-eGFP Transfected HeLa-Cells with FcRn Binding Polypeptides:

hFcRn-eGFP HeLa cells were harvested by trypsination and washed twice in McIlvanes buffer, pH 6.0 before counting. 100,000 cells were pipetted per well of a v-bottomed 96 well plate (Nunc, cat no 277143) and the cells in the plate were subsequently pelleted at 1,700 rpm for 4 min at 4° C. The supernatants were removed and the cells were fixed with 50 µl of 2% formaldehyde (Sigma Aldrich, cat. no. F8775) in McIlvanes buffer for 10 min at RT. Cells were thereafter washed with 2×100 µl McIlvanes buffer, pH 6.0, containing 2.5% FBS Ultra low IgG (Life Technologies), and resuspended in McIlvanes buffer, pH 6.0, containing 2.5% FBS Ultra low IgG and 0.1% saponin (AppliChem, cat no A4518.0100) containing 640 nM of Alexa Fluor® 647 labeled $His_6$-tagged polypeptides; Z11948-$(G_4S)_3$-Z11948 and Z11948-$(G_4S)$-Z11948 and Z07918. Transduced HeLa cells, incubated with buffer alone, were used as control. The cells were incubated for 1 h at 8° C. on a shaker in the dark. The cells were then subjected to two different washing conditions; 2×150 µl McIlvanes buffer, pH 6.0, containing 2.5% FBS ultra low IgG or 2×150 µl PBS, pH 7.4, containing 2.5% FBS Ultra low IgG and a 20 min incubation step in PBS, pH 7.4, containing 2.5% FBS Ultra low IgG. After washing, all samples were re-suspended in 180 μl of McIlvanes, pH 6.0, containing 2.5% FBS Ultra low IgG. Data from 10,000 GFP/FcRn positive cells were obtained using a FACS Calibur (Beckman Coulter) and the data was analyzed using Flowing software 2.5.0 (Turku University).

Results

Figure 11:
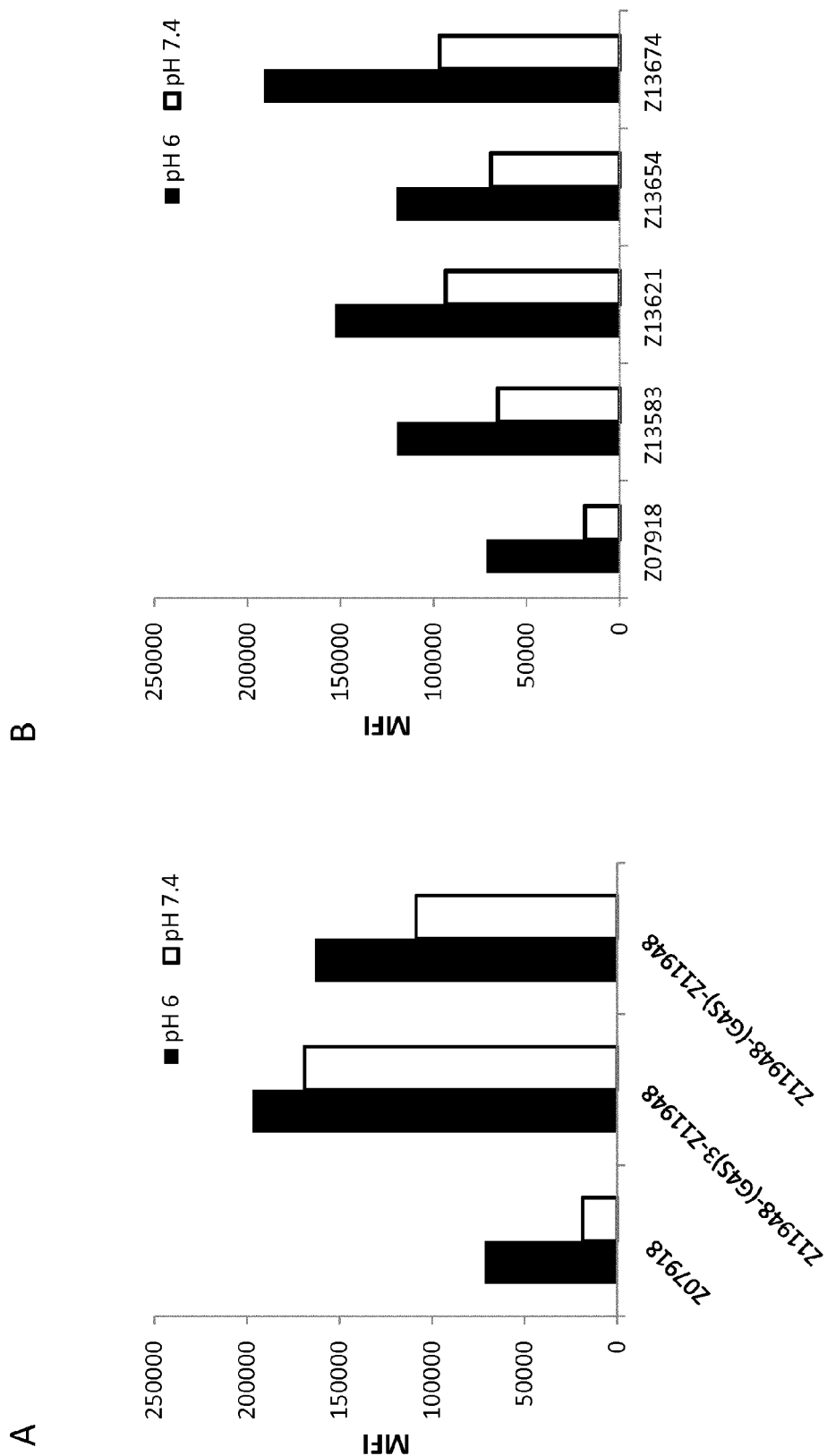
FIG. 11 shows mean fluorescence intensity (MFI) values of Alexa Fluor® 647 labeled dimeric and monomeric polypeptides binding to human FcRn-eGFP transfected HeLa cells measured as described in Example 13. (A) Dimers Z11948-$(G_4S)_3$-Z11948 (SEQ ID NO:369) and Z11948-$(G_4S)$-Z11948 (SEQ ID NO:368), and a corresponding monomer Z variant, Z07918 (SEQ ID NO:1), binding to FcRn at pH 6 (black) and pH 7.4 (white). (B) Monomer primary Z variant Z07918 (SEQ ID NO:1) and monomer maturated Z variants Z13583 (SEQ ID NO:23), Z13621 (SEQ ID NO:44), Z13654 (SEQ ID NO:65) and Z13674 (SEQ ID NO:75), binding to FcRn at pH 6 (black) and pH 7.4 (white).

Flow cytometry analysis was utilized to determine whether FcRn binding dimers could bind to human FcRn on human FcRn/eGFP transduced HeLa cells and to compare their binding ability to the monomeric FcRn binding Z variants. The analysis was also performed to determine if the pH dependent detachment from the FcRn protein was affected by the dimeric format. The experiment was performed at pH 6.0 with washings at pH 6.0 or pH 7.4 with Alexa Fluor® 647 labeled dimers Z11948-($G_4S$)$_3$-Z11948 (SEQ ID NO:369) and Z11948-($G_4S$)-Z11948 (SEQ ID NO:368), and monomers Z07918, Z13583, Z13621, Z13654 and Z13674. Z11948 and Z07918 are identical in sequence apart from the first two amino acid residues (AE vs VD). The calculated MFI values are presented in FIG. 11. The results show that the dimeric format increases the binding capacity of the FcRn binding polypeptides compared to the corresponding monomer (FIG. 11A) and that the maturated Z variants (Z13583, Z13621, Z13654 and Z13674) have a higher binding capacity than the primary Z variant Z07918 (FIG. 11B). The data shows that the pH dependent detachment from FcRn decreases with the use of the dimeric format, suggesting that FcRn binding dimers may have an improved pH dependent binding profile compared to corresponding monomeric variants.

Example 14

Comparison of Blocking Capacity of IgG Binding to FcRn

In this Example, the IgG blocking capacity of the FcRn binding dimers Z11948-($G_4S$)$_3$-Z11948 (SEQ ID NO:369) and Z11948-($G_4S$)-Z11948 (SEQ ID NO:368) was compared to that of monomeric FcRn binding Z variants, as well as to intravenous immunoglobulin (IVIg) and subcutaneous immunoglobulin (SCIg) currently used in the treatment of some autoimmune disorders.

Materials and Methods

Blocking of IgG-FcRn Immunofluorescence Staining:

Human FcRn-eGFP transduced HeLa cells were prepared as described in Example 4. Fixed cells were resuspended in 50 μl of a mix of 50 nM Alexa Fluor® 647-conjugated human IgG (Jackson laboratories, cat. no. 009-600-003) and His$_6$-tagged Z11948-($G_4S$)$_3$-Z11948 (SEQ ID NO:369), Z11948-($G_4S$)-Z11948 (SEQ ID NO:368), Z07918 (SEQ ID NO:1), Z13583 (SEQ ID NO:23), Z13621 (SEQ ID NO:44); IVIg (Octagam®, Octapharma) or SCIg (Gammanorm®, Octapharma), respectively, diluted at concentrations of 1000, 100, 10, 1, 0.1 or 0 (buffer control) nM in McIlvanes buffer, pH 6.0, containing 2.5% FBS Ultra low IgG (Life Technologies) and 0.1% saponin (AppliChem). The cells were incubated for 1 h at 37° C. in the dark, washed with 2×100 μl McIlvanes buffer, pH 6.0, containing 2.5% FBS Ultra low IgG and re-suspended in 180 μl of McIlvanes buffer, pH 6.0, containing 1% BSA. Data from 10,000 GFP/FcRn positive cells was obtained using a FACS Calibur (Beckman Coulter) and analyzed using Flowing software 2.5.0 (Turku University).

Results

Figure 12:
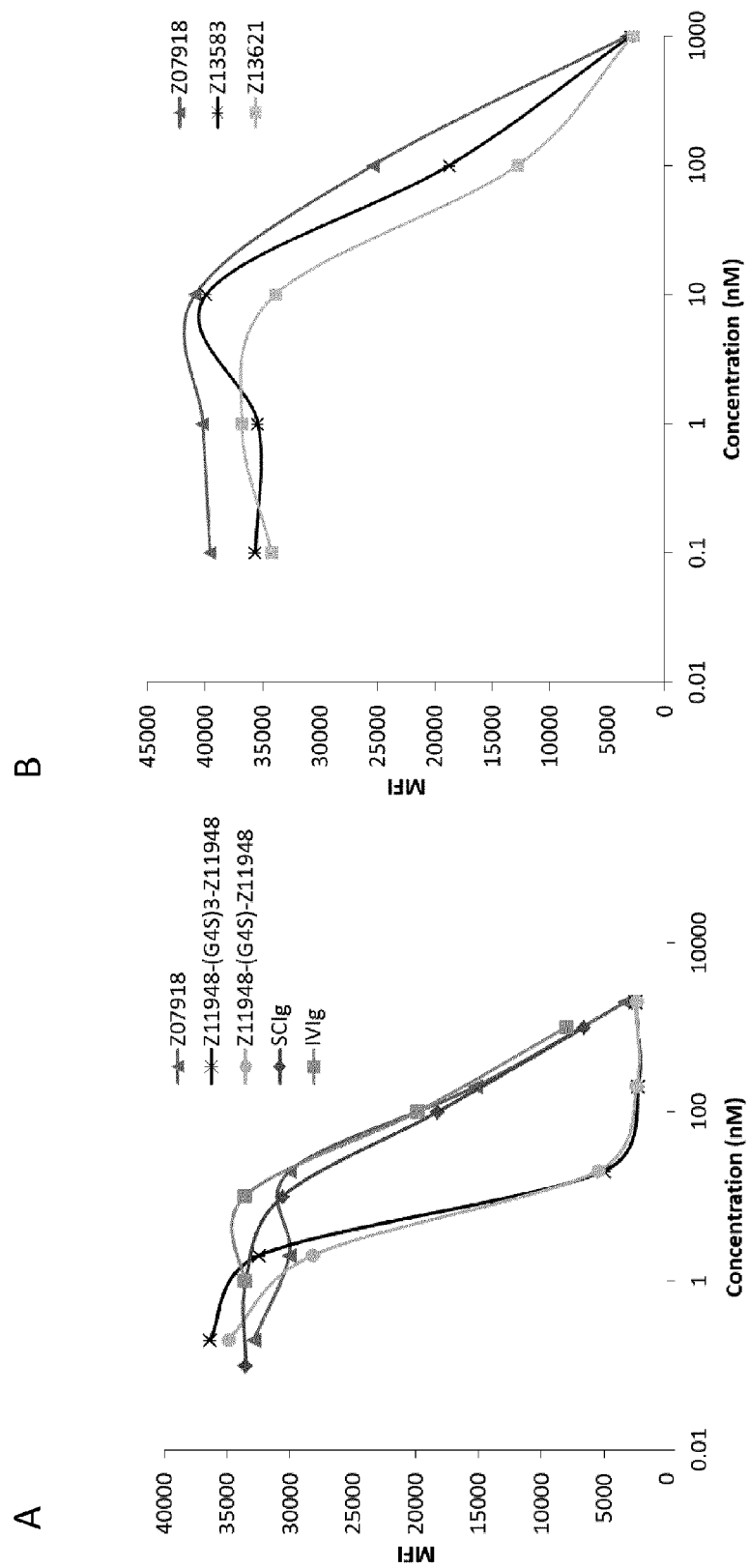
FIG. 12 shows the blocking of human IgG binding to human FcRn by dimeric and monomeric polypeptides assayed as described in Example 14. (A) Dimers Z11948-$(G_4S)_3$-Z11948 (SEQ ID NO:369) and Z11948-$(G_4S)$-Z11948 (SEQ ID NO:368); a corresponding monomer Z variant, Z07918 (SEQ ID NO:1), SCIg and IVIg. B) Monomer primary Z variant Z07918 (SEQ ID NO:1) and monomer maturated Z variants Z13583 (SEQ ID NO:23) and Z13621 (SEQ ID NO:44).

The experiment was performed to determine if the FcRn binding dimers Z11948-($G_4S$)$_3$-Z11948 (SEQ ID NO:369) and Z11948-($G_4S$)-Z11948 (SEQ ID NO:3689) block the IgG-FcRn interaction, and compare the blocking effect to that of the monomeric FcRn binding Z variants Z07918, Z13583 and Z13621, as well as IVIg and SCIg. Human FcRn-eGFP transduced HeLa cells were incubated with human Alexa Fluor® 647 conjugated IgG. The binding was blocked with unlabeled Z variants, IVIg or SCIg at different concentrations. The results showed that the FcRn binding dimers have an improved blocking effect in terms of hIgG binding to hFcRn compared to the monomeric Z variant Z07918, IVIg and SCIg (FIG. 12A). Furthermore, the blocking capacity of maturated monomeric Z variants Z13583 and Z13621 was improved compared to the blocking capacity of the primary monomeric Z variant Z07918 (FIG. 12B). The calculated IC50 values of the blocking assay are summarized in Table 15.

TABLE 15

Calculated IC50 values from HeLa cell IgG blocking assay.

| Designation | SEQ ID NO: | IC50 (M) |
|---|---|---|
| Z11948-($G_4S$)$_3$-Z11948 | 369 | $4.5 \times 10^{-9}$ |
| Z11948-($G_4S$)-Z11948 | 368 | $3.5 \times 10^{-9}$ |
| Z13583 | 23 | $3.3 \times 10^{-8}$ |
| Z13621 | 44 | $1.7 \times 10^{-8}$ |
| Z07918 | 1 | $4.8 \times 10^{-8}$ |
| IVIg | n.a. | $1.7 \times 10^{-7}$ |
| SCIg | n.a. | $1.2 \times 10^{-7}$ |

Example 15

Production of Dimeric FcRn Binding Polypeptides

Materials and Methods

The Z variants Z17303 (SEQ ID NO:357), Z18632 (SEQ ID NO:365), Z18633 (SEQ ID NO:366) and Z18634 (SEQ ID NO:367) were constructed as dimers in fusion with the albumin binding variant PP013 (SEQ ID NO:377) in the general format [Z#####]ASGS-PP013-GT-($G_4S$)-[Z#####] (SEQ ID NO:469). The resulting polypeptides were denoted ZAZ3824 (SEQ ID NO:373), ZAZ3869 (SEQ ID NO:374), ZAZ3870 (SEQ ID NO:375) and ZAZ3871 (SEQ ID NO:376), respectively. Dimeric polypeptides of the Z variant Z17303 in fusion with PP013 was also constructed with different linkers or C-terminal fusion of PP013, resulting in the polypeptides Z17303-GAP($G_4S$)$_3$TS-PP013-GT($G_4S$)$_3$PR-Z17303 and Z17303-GAP($G_4S$)$_3$TS-Z17303-GT($G_4S$)$_3$PR-PP013, denoted ZAZ3715 (SEQ ID NO:371) and ZZA3716 (SEQ ID NO:372), respectively. Furthermore, Z17303 was constructed as a dimer without PP013, but with an N-terminal His$_6$-tag resulting in the polypeptide GSS-His$_6$-LQ-Z17303-GT(G4S)$_3$-Z17303, denoted ZZ3556 (SEQ ID NO:370).

Cultivation was performed as described in Example 3. Purification of PP013 containing polypeptides was carried out by anti-ABD affinity chromatography and RPC as described in Example 6, whereas purification of His$_6$-tagged ZZ3556 was performed by IMAC as described in Example 3.

Results

The seven FcRn binding dimeric polypeptides, constructed either with a His$_6$-tag or an ABD moiety, were produced in E. coli. The amount of affinity purified protein, determined spectrophotometrically by measuring the absorbance at 280 nm, ranged from 2-18 mg per g bacterial pellet. SDS-PAGE analysis of each final protein preparation showed that these predominantly contained the FcRn binding polypeptide. The correct identity and molecular weight of each FcRn binding polypeptide was confirmed by HPLC-MS analysis.

Example 16

Binding of Homo- and/or Heterodimeric FcRn Binding Polypeptides to Human FcRn/eGFP Transfected HeLa Cells In this Example, the binding ability of homo- and/or heterodimeric FcRn binding polypeptides comprising maturated Z variants is investigated. HeLa cells expressing human FcRn-eGFP gene transgene, produced as described in Example 4, are used for flow cytometry analysis with Alexa Fluor® 647 labeled Z variants.
Materials and Methods
Alexa Fluor® 647 Labeling of FcRn Binding Z Variants:
Homo- and/or heterodimeric FcRn binding polypeptides are labeled with Alexa Fluor® 647 Carboxylic Acid Succinimidyl Ester (Invitrogen cat. no. A20106) as described in Example 13.
Immunofluorescence Staining of Human FcRn-eGFP Transfected HeLa-Cells with FcRn Binding Polypeptides:
hFcRn-eGFP HeLa cells are harvested by trypsination and washed twice in McIlvanes buffer, pH 6.0, before counting. 100,000 cells are pipetted per well of a v-bottomed 96 well plate (Nunc, cat no 277143) and the cells in the plate are subsequently pelleted at 1,700 rpm for 4 min at 4° C. The supernatants are removed and the cells are fixed with 50 µl of 2% formaldehyde (Sigma Aldrich, cat. no. F8775) in McIlvanes buffer for 10 min at RT. Cells are thereafter washed with 2×100 µl McIlvanes buffer, pH 6.0, containing 2.5% FBS Ultra low IgG (Life Technologies), and resuspended in McIlvanes buffer, pH 6.0, containing 2.5% FBS Ultra low IgG and 0.1% saponin (AppliChem, cat no A4518.0100) containing 640 nM of Alexa Fluor® 647 labeled $His_6$-tagged homo- and/or heterodimeric FcRn binding polypeptides and a corresponding monomeric Z variant.
Examples of formats for homo- and/or heterodimers include Z#1###-$(G_4S)_3$-Z##### and Z#####-$(G_4S)$-Z#####, where linker $(G_4S)_3$ is SEQ ID NO:462) and linker $G_4S$ is SEQ ID NO:441, and Z#1:14# for example is selected from Z13583 (SEQ ID NO:23), Z13621 (SEQ ID NO:44), Z13654 (SEQ ID NO:65) or Z13674 (SEQ ID NO:75), or the same Z variants starting with amino acid residues AE instead of VD, as for example in Z17303 (SEQ ID NO:357), which is identical to Z13621 (SEQ ID NO:44) apart from the N-terminal AE. Cloning may optionally be performed with a C-terminal $His_6$ tag as described in Example 3 or with an N-terminal $His_6$ tag as in SEQ ID NO:362.
Transduced HeLa cells, incubated with buffer alone, are used as control. The cells are incubated for 1 h at 8° C. on a shaker in the dark. The cells are then subjected to two different washing conditions; 2×150 µl McIlvanes buffer, pH 6.0, containing 2.5% FBS Ultra low IgG or 2×150 µl PBS, pH 7.4, containing 2.5% FBS Ultra low IgG and a 20 min incubation step in PBS, pH 7.4, containing 2.5% FBS Ultra low IgG. After washing, all samples are re-suspended in 180 µl of McIlvanes, pH 6.0, containing 2.5% FBS Ultra low IgG. Data from 10,000 GFP/FcRn positive cells are obtained using a FACS Calibur (Beckman Coulter) and the data is analyzed using Flowing software 2.5.0 (Turku University).

Results
Flow cytometry analysis is used to determine whether the homo- and/or heterodimeric FcRn binding polypeptides comprising maturated Z variants can bind to human FcRn on human FcRn/eGFP transduced HeLa cells and compare the binding ability to the monomeric FcRn binding Z variants or dimeric variants comprising primary Z variants. The analysis is also performed to determine if the pH dependent detachment from the FcRn protein is affected by the dimeric format. The experiments are performed at pH 6.0 with washings at pH 6.0 or pH 7.4 with Alexa Fluor® 647 labeled FcRn binding Z variants. The results from the experiment are expected to show that homo- and/or heterodimeric formats, as well as the inclusion of maturated Z variants with an improved affinity for FcRn, increase the binding capacity of the FcRn binding polypeptides and that the pH dependent detachment from FcRn is decreased for said polypeptides.

Example 17 pH Dependent Binding of Dimeric Polypeptides to Human FcRn

Figure 13:
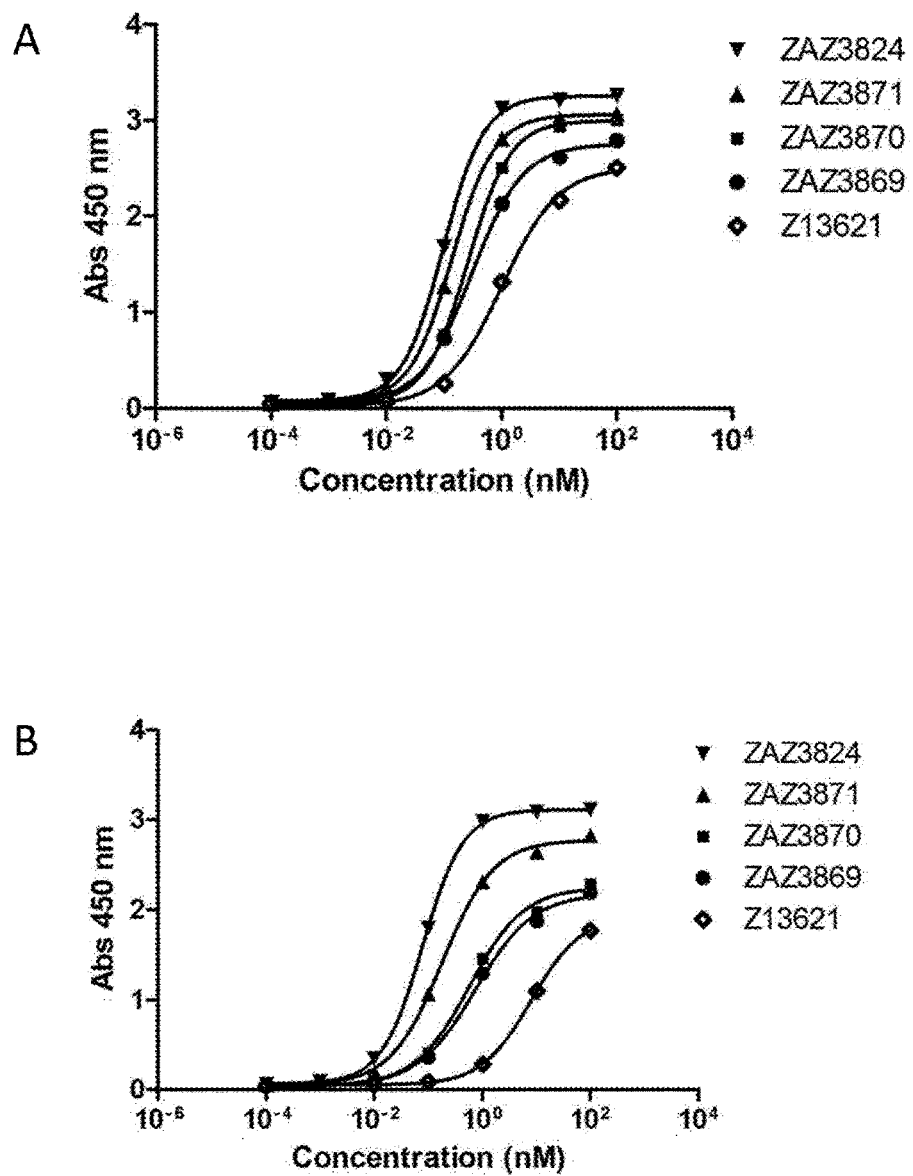
FIG. 13 shows pH dependent binding of polypeptides to hFcRn analyzed by ELISA as described in Example 17. (A) Binding of the indicated polypeptides at pH 6. (B) Binding of the indicated polypeptides at pH 7.4. At both pH values, more efficient binding was seen for the dimeric polypeptides (ZAZ####) than for the monomeric Z variant (Z13621).

In this Example, the capacity of dimeric polypetides to bind FcRn at different pH values was investigated by ELISA and compared to the binding capacity of a monomeric Z variant.
Materials and Methods
The capacity of the dimeric polypeptides ZAZ3824 (SEQ ID NO:373), ZAZ3869 (SEQ ID NO:374), ZAZ3870 (SEQ ID NO:375) and ZAZ3871 (SEQ ID NO:376), as well as the monomeric Z variant Z13621 (SEQ ID NO:44), to bind human FcRn at different pH values was tested in an ELISA where all binding and washing steps were performed at either pH 6.0 or pH 7.4. Half-area 96-well ELISA plates were coated at 4° C. overnight with 4 µg/ml of hFcRn (Biorbyt, cat. no. orb84388) diluted in PBS. The plates were washed twice in tap water and the wells were blocked with 100 µl of PBSC (PBS, pH 7.4, supplemented with 1% casein) for 1.5 h at RT. The blocking solution was poured off and the wells subjected to pH 6.0 treatment were washed once with McIlvaines phosphate-citrate buffer, pH 6.0. The different FcRn binding polypeptides were added at a concentration of 100 nM and diluted stepwise 1:10 down to 0.1 pM in either PCC (McIlvaines phosphate-citrate buffer, pH 6.0, supplemented with 1% casein) or PBSC. 50 µl of the dilutions were transferred per well and the ELISA plates were incubated for 1.5 h at RT. The plates were washed four times in either PCT (McIlvaines phosphate-citrate buffer, pH 6.0, supplemented with 0.05% Tween-20) or PBST (PBS, pH 7.4, supplemented with 0.05% Tween-20). Bound polypeptides were detected with 50 µl/well of a Z specific mouse antibody (produced in-house) diluted to 2 µg/ml in either PCC or PBSC. The plates were subsequently incubated for 1.5 h at RT followed by washing as described above. HRP-conjugated goat anti-mouse Ig obtained from DAKO (P0447), diluted 1:5000 in either PCC or PBSC, was added and the plates were incubated at RT for 1 h. After washing (as above), 50 µl of ImmunoPure TMB substrate was added to each well and the plates were developed according to the manufacturer's recommendations. After 30 min of development, the absorbance was measured at 450 nm using a multi-well plate reader (Victor$^3$) and the EC50 values were calculated using GraphPad Prism 5.
Results
The analysis was performed to compare the binding potential of monomeric versus dimeric format at different pH, but also to determine whether introduced scaffold mutations (Y5F, N52S and D53E; see further in Examples 24 and 25) would affect the pH dependent binding to FcRn. The experiment was performed in an ELISA format at pH 6.0 or pH 7.4. The results showed that the dimeric format was superior to the monomeric format in binding FcRn regardless of pH (up to 10× and 85× improvement at pH 6.0 and pH 7.4, respectively). The most potent binding, both at pH 6.0 and pH 7.4, was seen for the dimeric polypeptide ZAZ3824, which also showed a similar binding capacity (EC50 value) at pH 6.0 and pH 7.4. The ELISA titration curves are shown in FIG. 13, and the calculated EC50 values are summarized in Table 16.

Clean Version:

TABLE 16

Calculated EC50 values from binding analysis at pH 6.0 and pH 7.4

| Designation | SEQ ID NO: | EC50 (M) pH 6.0 | EC50 (M) pH 7.4 |
|---|---|---|---|
| Z13621 | 44 | $9.9 \times 10^{-10}$ | $7.7 \times 10^{-9}$ |
| ZAZ3824 | 373 | $9.9 \times 10^{-11}$ | $9.1 \times 10^{-11}$ |
| ZAZ3869 | 375 | $3.0 \times 10^{-10}$ | $7.3 \times 10^{-10}$ |
| ZAZ3870 | 375 | $2.6 \times 10^{-10}$ | $5.7 \times 10^{-10}$ |
| ZAZ3871 | 376 | $1.4 \times 10^{-10}$ | $1.8 \times 10^{-10}$ |

Example 18

Comparison of Blocking Capacity of IgG Binding to FcRn

In this Example, the potential of polypeptides to inhibit binding of IgG to FcRn was analyzed using two different in vitro methods: AlphaLISA and a cell based assay.

Materials and Methods

AlphaLISA blocking assay: The capacity of the dimeric FcRn binding polypeptides ZZ3556 (SEQ ID NO:370), ZAZ3715 (SEQ ID NO:371) and ZZA3716 (SEQ ID NO:372) as well as the monomeric Z13621 (SEQ ID NO:44) to block IgG-FcRn interaction was analyzed using an AlphaLISA assay. Human IgG (Roactemra) was immobilized on AlphaLISA acceptor beads (Perkin Elmer, cat. no. 6772002) according to the manufacurer's recommendations. Human FcRn (Biorbyt, cat. no. orb84388) was biotinylated essentially as described in Example 2. Polypeptides were serially diluted 1:3 in AlphaLISA buffer (Perkin Elmer, cat. no. AL000F) pH 6.0 (adjusted using HCl) to final concentrations of 250 nM to 13 pM in a 384-well plate (Perkin Elmer, cat. no. G6005350) and incubated for 45 min with 10 nM biotinylated hFcRn. IgG-coated acceptor beads were added to a final concentration of 10 µg/ml and incubated for 45 min. Finally, streptavidin coated donor beads (Perkin Elmer, cat. no. 6760002) were added to a final concentration of 40 µg/ml and incubated for 30 min. All incubations were performed at RT in the dark. The plate was analyzed in the EnSpire multiplate reader 2300 (Perkin Elmer) and the IC50 values were calculated using GraphPad Prism 5.

HeLa Cell IgG-FcRn Blocking Assay:

Human FcRn-eGFP transduced HeLa cells were prepared as described in Example 4. The polypeptides ZZ3556 (SEQ ID NO:370), ZAZ3715 (SEQ ID NO:371), ZZA3716 (SEQ ID NO:372), ZAZ3824 (SEQ ID NO:373), ZAZ3869 (SEQ ID NO:374), ZAZ3870 (SEQ ID NO:375), ZAZ3871 (SEQ ID NO:376), Z13621 (SEQ ID NO:44), Z18632 (SEQ ID NO:365), Z18633 (SEQ ID NO:366) and Z18634 (SEQ ID NO:367), as well as IVIg (Octagam®, Octapharma) or SCIg (Gammanorm®, Octapharma), were each diluted to concentrations of 1000, 100, 10, 1, 0.1 or 0 (buffer control) nM in McIlvanes buffer, pH 6.0, containing 2.5% FBS Ultra low IgG (Life Technologies) and 0.1% saponin (AppliChem) and 50 nM Alexa Fluor® 647-conjugated human IgG (Jackson laboratories, cat. no. 009-600-003). Fixed cells were resuspended in 100 µl of the mixture and were incubated for 1 h at 37° C. in the dark. Cells were washed and resuspended in McIlvanes buffer, pH 6.0, containing 2.5% FBS Ultra low IgG. Data from 10,000 GFP/FcRn positive cells was obtained using a FACS Calibur (Beckman Coulter), analyzed using Flowing software 2.5.0 (Turku University) and IC50 values were calculated using GraphPad Prism 5.

Results

AlphaLISA:

The ability of one monomeric and three dimeric polypeptides to inhibit IgG binding to FcRn was tested in an AlphaLISA blocking assay. The results show that the dimeric polypeptides had better IgG blocking capacity compared to the monomeric format. The two ABD fused dimeric polypeptides, ZAZ3715 and ZZA3716, had IC50 values very similar to that of ZZ3556, which does not contain an ABD moiety. The calculated IC50 values of the AlphaLISA blocking assay are summarized in Table 17.

HeLa Cell IgG Blocking Assay:

Human FcRn-eGFP transduced HeLa cells were incubated with human Alexa Fluor 647-conjugated IgG and selected polypeptides to assess the ability of the polypeptides to block IgG-FcRn interactions. Intravenous immunoglobulin (IVIg) and Subcutaneous immunoglobulin (ScIg) currently used in the treatment of some autoimmune disorders, were also included in the test. The experiment was performed at pH 6.0. The results showed that the dimeric format had an improved IgG blocking capacity compared to the monomeric format. ZAZ3715 (longer linkers) was compared to ZAZ3824 (shorter linkers), and the two constructs showed similar IC50 values. There was also no difference between IC50 values obtained for ZAZ3715 and ZZA3716, i.e. dimer constructs with ABD at different positions. All tested polypeptides had superior IgG blocking effect compared to IVIg and SCIg. The calculated IC50 values of the cell blocking assay are summarized in Table 18.

TABLE 17

Calculated IC50 values showing IgG blocking capacity of polypeptides in AlphaLISA.

| Designation | SEQ ID NO: | IC50 (M) |
|---|---|---|
| Z13621 | 44 | $1.0 \times 10^{-9}$ |
| ZZ3556 | 370 | $1.9 \times 10^{-10}$ |
| ZAZ3715 | 371 | $1.7 \times 10^{-10}$ |
| ZZA3716 | 372 | $1.8 \times 10^{-10}$ |

TABLE 18

Calculated IC50 values showing IgG blocking capacity of polypeptides in a HeLa cell based assay at pH 6.0.

| Designation | SEQ ID NO: | IC50 (M) |
|---|---|---|
| Z13621 | 44 | $2.2 \times 10^{-8}$ |
| Z18632 | 365 | $8.4 \times 10^{-8}$ |
| Z18633 | 366 | $5.7 \times 10^{-8}$ |
| Z18634 | 367 | $3.6 \times 10^{-8}$ |
| ZZ3556 | 370 | $1.9 \times 10^{-9}$ |
| ZAZ3715 | 371 | $3.6 \times 10^{-9}$ |

TABLE 18-continued

Calculated IC50 values showing IgG blocking capacity of polypeptides in a HeLa cell based assay at pH 6.0.

| Designation | SEQ ID NO: | IC50 (M) |
| --- | --- | --- |
| ZZA3716 | 372 | $3.5 \times 10^{-9}$ |
| ZAZ3824 | 373 | $3.8 \times 10^{-9}$ |
| ZAZ3869 | 374 | $4.7 \times 10^{-9}$ |
| ZAZ3870 | 375 | $5.3 \times 10^{-9}$ |
| ZAZ3871 | 376 | $4.1 \times 10^{-9}$ |
| SCIg | — | $1.2 \times 10^{-7}$ |
| IVIg | — | $1.5 \times 10^{-7}$ |

Example 19

Comparison of Blocking Capacity of IgG Recycling

In this Example, the effect of homo- and/or heterodimeric FcRn binding polypeptides on IgG recycling are investigated in FcRn transduced MDCK.2 cells.

Materials and Methods

Lentiviral transduction of MDCK.2 cells: The vector pairs 2k7$_{neo}$-CMV-hB2M and pHR-cPPT-CMV-hFcRn-eGFP are co-transfected together with VSV-G envelope and gag/pol packaging plasmid into HEK293T cells using calcium chloride transfection (Zufferey et al., supra; Jakobsson et al. (2006) supra). HEK293T culture supernatants containing formed lentiviral particles with FcRn and B2M transgenes respectively are used to sequentially transduce MDCK.2 cells (ATCC cat. no. CRL-2936) at low passage number. The resulting stably transduced MDCK.2 cell lines are denoted hFcRn-eGFP (transduced with genes for human FcRn-eGFP and hB2M).

Blocking Capacity of IgG Recycling:

Human FcRn-eGFP transduced MDCK.2 cells are plated at 25 000 cells/well in a 96-well plate and incubated overnight at 37° C., 5% $CO_2$. The cells are incubated with homo- and/or heterodimeric FcRn binding polypeptides at concentrations ranging from 200 to 0.01 nM in McIlvanes buffer, pH 6.0, containing 2.5% FBS Ultra low IgG before addition of 500 ng/ml Alexa Fluor® 647-conjugated human IgG (Jackson laboratories, cat. no. 009-600-003) and incubation for one additional hour. The cells are washed McIlvanes buffer, pH 6.0, containing 2.5% FBS Ultra low IgG and then incubated in PBS, pH 7.4, containing 2.5% FBS Ultra low IgG for 2 h in 37° C., 5% $CO_2$. The supernatants are then analyzed for the presence of the Alexa Fluor® 647-conjugated human IgG in an EnSpire multiplate reader (Perkin Elmer). The inhibition curves are analyzed by non-linear regression using the GraphPad Prism 5 software to determine the IC50 values.

Results

The results from the experiment are expected to show a dose dependent reduction in IgG recycling through the action of dimeric FcRn binding polypeptides.

Example 20

Increased IgG Catabolism by Dimeric FcRn Binding Polypeptides in FcRn Transgenic Mice In this Example, the effect of homodimeric FcRn binding polypeptides on IgG catabolism was investigated in human FcRn transgenic mice on two different occasions.

Materials and Methods

Animal Studies:

In the first study, homodimeric FcRn-binding polypeptide ZAZ3715 (SEQ ID NO:371) or ZZA3716 (SEQ ID NO:372), or vehicle (PBS buffer), was administered at 0 hours by i.v. injection to male B6.Cg-Fcgrttm1Dcr Tg(FCGRT)32Dcr/DcrJ mice (Jackson Laboratory, stock no. 14565) at a dose of 6 mg/kg. 24 hours prior to polypeptide administration, 500 mg/kg hIgG (Kiovig, Baxter) was administered by i.v. injection. Serum samples were collected at −168, 0, 24, 72, 120 and 144 h (termination of study) and stored at −20° C.

In the second study, homodimeric FcRn-binding polypeptide ZAZ3869 (SEQ ID NO:374), ZAZ3870 (SEQ ID NO:375) or ZAZ3871 (SEQ ID NO:376), or vehicle (PBS buffer), was administered at 0 hours by i.v. injection to male B6.Cg-Fcgrttm1Dcr Tg(FCGRT)32Dcr/DcrJ mice (Jackson Laboratory, stock no. 14565) at a dose of 6 mg/kg. 24 hours prior to polypeptide administration, 500 mg/kg hIgG (Kiovig, Baxter) was administered by i.v. injection. Serum samples were collected at −168, 0, 24, 72, 120 and 144 h (termination of study) and stored at −20° C.

Human IgG ELISA:

The concentration of human IgG in mouse serum samples collected from the two studies was analyzed with a human IgG AlphaLISA kit (Perkin Elmer, cat. no. AL205C) as described by the manufacturer. The concentration of hIgG was calculated from a standard curve and GraphPad Prism 5 using a non-linear regression formula.

Results

The results from the experiments show a reduction in the concentrations of human IgG over time through the action of the FcRn binding polypeptides. There were little or no difference in the reduction of IgG levels between the two groups receiving the polypeptides ZAZ3715 and ZZA3716 (FIG. 14A). These results indicate that FcRn binding polypeptides with a central or C-terminal positioning of ABD are equally efficient in increasing IgG catabolism. The polypeptides ZAZ3869, ZAZ3870 and ZAZ3871, respectively, reduced hIgG levels to a similar extent (FIG. 14B). The results from the second experiment were in the same range as the results obtained in the first experiment.

Thus, the results from the two experiments indicate that the FcRn-specific polypeptides blocked recycling of IgG, resulting in increased IgG catabolism and subsequent lower levels of IgG in human FcRn transgenic mice.

Example 21

Increased IgG Catabolism by Dimeric FcRn Binding Polypeptides in NMRI Mice

In this Example, the effect of homodimeric FcRn binding polypeptides on IgG catabolism was investigated in NMRI mice.

Materials and Methods

Animal Study:

Homodimeric FcRn-binding polypeptide ZAZ3715 (SEQ ID NO:371) or ZZA3824 (SEQ ID NO:373), or vehicle (PBS buffer), was administered at 0 hours by i.v. injection to female NMRI mice, at a dose of 0.6 or 1.7 µmol/kg. Serum samples were collected at 0, 24, 48 and 72 h (termination of study) and stored at −20° C.

Mouse IgG ELISA:

The concentration of mouse IgG in mouse serum samples was analyzed by a mouse IgG ELISA kit (Mabtech, cat.no. 3825-1AD-6) and performed as described by the manufacturer. The concentration of mIgG was calculated from a standard curve and GraphPad Prism 5 using a non-linear regression formula. The concentration of IgG in individual mice at 24, 48 and 72 h were related to the level at 0 h and the results are therefore presented as percentage of IgG (0 h).

PK ELISA:

Concentrations of FcRn-binding polypeptides in mouse serum samples were determined by ELISA. In this assay, 96-well half area plates were coated with a mouse anti Z polyclonal antibody (produced in-house) at a concentration of 4 µg/ml in PBS (50 µl/well) and incubated overnight at 4° C. Next, the plates were rinsed twice in tap water and blocked with blocking buffer for 1 hour. An in-house Z variant standard was titrated in a 3-fold dilution series (0.003-300 ng/ml) and diluted serum samples were added to the coated ELISA plates (50 µl/well) and incubated for 1.5 h at RT. The plates were washed 4 times in an automated ELISA washer and 4 µg/ml (50 µl/well) of a goat anti-ABD polyclonal antibody (produced in-house) was added. After incubation for 1 h, the plates were washed and 50 µl of anti-goat IgG-HRP (Jackson, cat. no. 711-035-152) at a concentration of 20 ng/ml was added to each well. After one additional hour of incubation and subsequent washing, the plates were developed with 50 µl TMB per well and the reactions were stopped with 50 µl 2M $H_2SO_4$. The absorbance at 450 nm was measured in a 96-well plate reader (Victor$^3$).

Results

Figure 10:
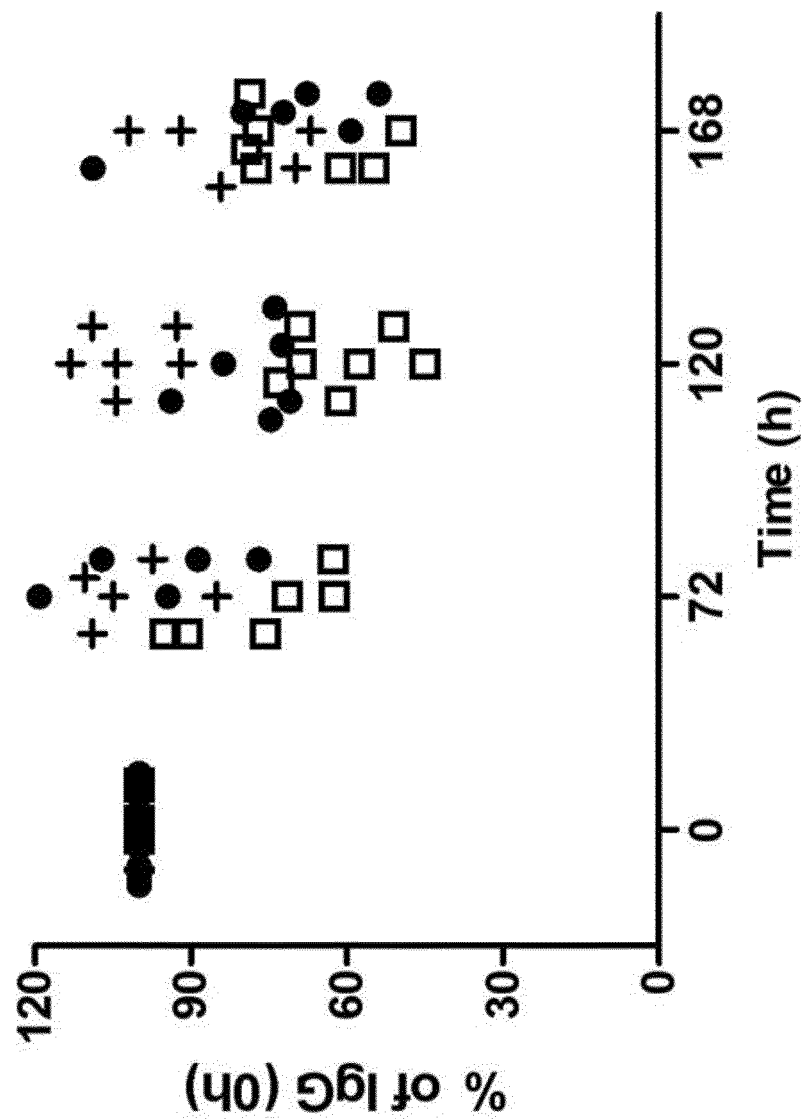
FIG. 10 shows that blocking of the IgG-FcRn interactions with FcRn specific Z variants in mice results in reduced levels of IgG. As further described in Example 11, mice were treated with five daily injections of Vehicle (+), the ABD fused Z variant Z07918-PP013 (open square) and Z11948 (SEQ ID NO:354; closed circle). The concentration of endogenous IgG was measured by ELISA. The concentration of IgG in individual mice at 24, 72, 120 and 168 h was related to the level at 0 h and the results are therefore presented as percentage of IgG at 0 h.
Figure 15:
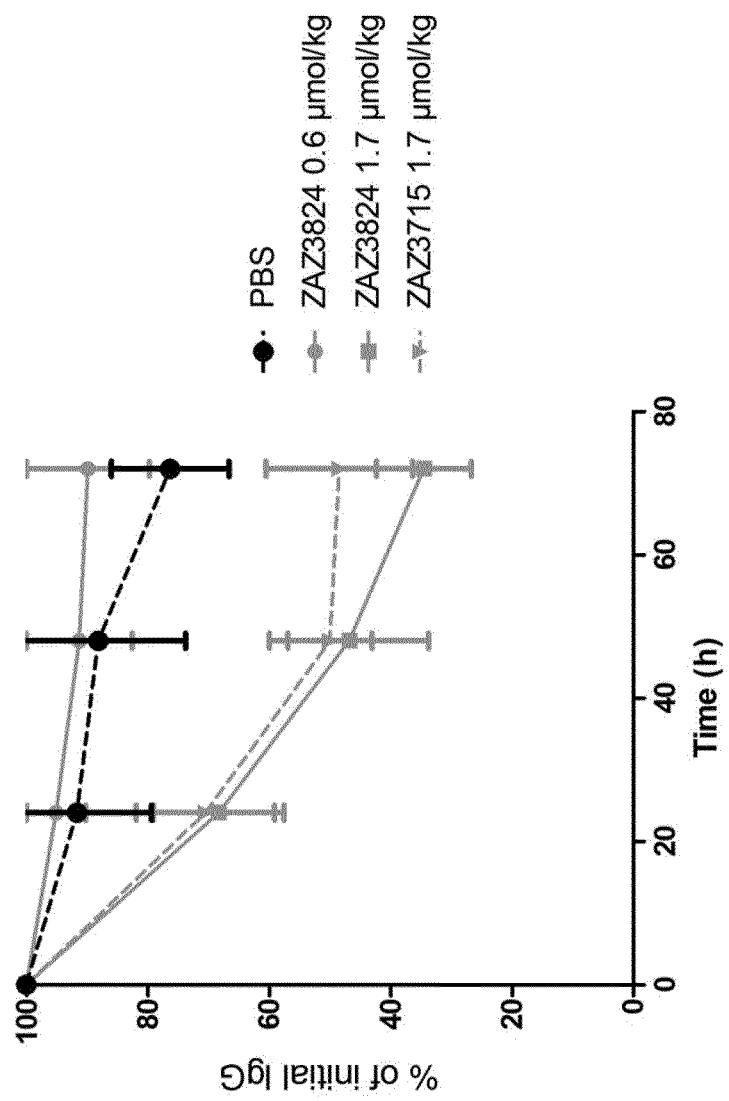
FIG. 15 shows dose dependent reduction of hIgG levels in NMRI mice treated with dimeric polypeptides ZAZ3715 (SEQ ID NO:371) and ZAZ3824 (SEQ ID NO:373) as described in Example 21.

IgG Catabolism:

The results showed a reduction of mouse IgG concentration in mice treated with the FcRn-specific polypeptides ZAZ3715 and ZAZ3824, respectively (FIG. 15). The result obtained with polypeptide ZAZ3824 shows that the reduction in endogenous IgG levels is dose dependent, and the most pronounced effect was observed at 72 h. Notably, the reduction of IgG levels obtained with the use of dimers was greater than the reduction obtained with monomeric Z07918 in Example 11, even though the monomer was administered repeatedly and at much higher dose than the dimers (compare FIGS. 15 and 10 at 72 h). Thus, the results indicate that the FcRn-specific polypeptides disclosed herein could block recycling of IgG, resulting in an increased IgG catabolism and subsequent lower levels of IgG in mice.

Figure 16:
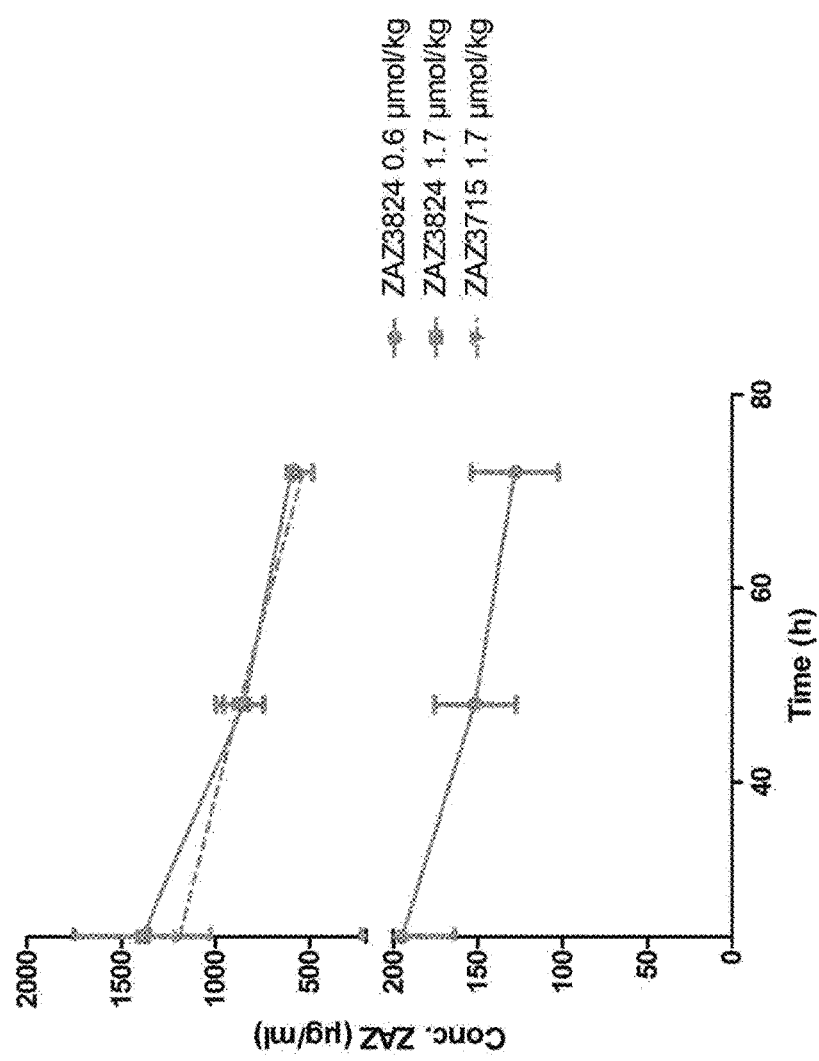
FIG. 16 shows the serum concentrations of ZAZ3715 (SEQ ID NO:371) and ZAZ3824 (SEQ ID NO:373), respectively, measured in the same IgG catabolism study as that presented in FIG. 15.

Pharmacokinetic Analysis:

The pharmacokinetic profiles of ZAZ3715 and ZAZ3824 are shown in FIG. 16. The half-life of ZAZ3824 was approximately 62 hours, which is in line with the half-life obtained in the pharmacokinetic study presented in Example 6, demonstrating that the pharmacokinetic properties of the polypeptides are further improved by binding to FcRn in addition to the prolonged half-life resulting from albumin binding.

Example 22

Increased IgG Catabolism by FcRn Binding Dimers in Cynomolgus Monkeys

In this Example, the effect of homo- or heterodimeric FcRn binding polypeptides on IgG catabolism is investigated in cynomolgus monkeys.

Materials and Methods

Animal Study:

Homo- and/or heterodimeric FcRn binding polypeptides recombinantly fused to PP013 (SEQ ID NO:377) are prepared. Examples of such FcRn binding dimers include SEQ ID NO:371-376 disclosed herein.

The FcRn binding dimers including an albumin binding domain are then administered to cynomolgus monkeys at a dose of 2, 0.4 and 0.1 µmol/kg. The dimeric polypeptides are injected intravenously at 0 hours. The monkeys are bled 1 h prior to the first administration and daily up to day 21, and then once a week up to day 50. Sera are prepared and stored at −20° C. The concentration of cynomolgus IgG is determined by ELISA.

Homo- and/or heterodimeric FcRn binding polypeptides without an albumin binding domain are administered to cynomolgus monkeys at a dose of 2, 0.4 and 0.1 µmol/kg. The dimeric polypeptides are administered three times per week for two weeks. The monkeys are bled 1 h prior to the first administration and daily up to day 21, and then once a week up to day 50. Sera are prepared and stored at −20° C. The concentration of cynomolgus IgG is determined by ELISA.

Cynomolgus IgG ELISA:

The concentration of cynomolgus IgG in serum samples is determined with a human/cynomolgus IgG ELISA kit (for example Mabtech 3850-1AD-6, which is cross-reactive with both human and cynomolgus IgG) as described by the manufacturer.

Results

The results from the experiment are expected to show a dose dependent reduction in the concentrations of cynomolgus IgG through the action of FcRn binding dimers, with a more pronounced effect for such dimers that also comprise an albumin binding domain.

Example 23

Pharmacokinetic Study of Dimeric FcRn Binding Polypeptides

In this Example, the serum half-life of homo- and/or heterodimeric FcRn binding polypeptides is investigated in a pharmacokinetic study performed in mice.

Materials and Methods

Pharmacokinetic Study:

FcRn binding polypeptides, as homo- and/or heterodimers alone or recombinantly fused to PP013 (SEQ ID NO:377) are administered intravenously (i.v.) to male NMRI mice (Charles River, Germany) at a dose of 92 nmol/. Sera from groups of three mice are obtained at 0.08, 6, 18, 78, 120, 168 and 240 hours. The concentration of respective polypeptide is determined by ELISA.

ELISA:

Half-area 96-well ELISA plates are coated at 4° C. overnight with 50 µl/well of a goat antibody specific for Z variants in general (produced in-house) diluted to 4 µg/ml in coating buffer (50 mM sodium carbonate, pH 9.6). The antibody solution is poured off and the wells are blocked with 100 µl of PBSC for 1.5 h at RT. The sera are diluted in PBSC containing 1% mouse serum (matrix) from 1:100 to 1:51,200 in a two-fold dilution series in a dilutions plate. A standard titration for respective Z variant polypeptide and four quality controls (very low, low, medium and high control) diluted in matrix are included on each plate. 50 µl of the dilutions are transferred per well and the ELISA plates are incubated for 1.5 h at RT. The plates are washed four times with PBST. Bound Z variant polypeptides are detected with 50 µl/well of rabbit anti-PP013 Ig (produced in-house) or 50 µl/well of mouse anti-Z mAb (produced in-house) diluted to 4 µg/ml in PBSC. The plates are subsequently incubated for 1.5 h at RT followed by washes as described above. HRP conjugated donkey anti-rabbit HRP (Jackson laboratories; cat. no. 711-035-152), diluted 1:20,000 in PBSC, is added and the plates are incubated for 1 h. After washing as described above, 50 µl of ImmunoPure TMB substrate is added to the wells and the plates are developed according to the manufacturer's recommendations. After 15 min of development, the absorbance is measured at 450 nm using a multi-well plate reader (Victor³). The absorbance values are analyzed using GraphPad Prism 5 to determine the concentrations (cubic-spline curve fit) and area under curve (AUC). The concentrations are then plotted as their natural logarithms against time. The resulting curves are expected to follow a two compartment model and the terminal half-life is calculated as ln2 divided by the slope based on the last three time points.

Results

The results from the experiment described herein are expected to show a two compartment elimination phase with a terminal half-life of approximately 60 min for polypeptides without ABD and approximately 90 hours for polypeptides comprising ABD.

Example 24

Generation, Stability Study and Binding Assessment of Scaffold-Modified FcRn Binding Polypeptides The following Example discloses scaffold modified FcRn binding Z variants exhibiting improved stability at elevated temperatures. The Z variants Z17347 (SEQ ID NO:358), with the amino acid substitutions N52S and D53E, and Z17348 (SEQ ID NO:359), with the amino acid substitutions D36R, D37Q, S39E, N52S and D53E, are compared to their parent molecule Z11948 (SEQ ID NO:354) in terms of stability and binding capacity to FcRn.

Materials and Methods

Generation of Scaffold-Modified Polypeptides:

Z17347 (SEQ ID NO:358), Z17348 (SEQ ID NO:359) and Z11948 (SEQ ID NO:354) were cloned with an N-terminal 6× Histidine-tag (His$_6$) and obtained constructs encoded polypeptides in the format MGSSHHHHHHLQ-[Z#####] (SEQ ID NO:470). Mutations were introduced in the plasmids of the modified Z variants using overlapping oligonucleotide primer pairs encoding the desired amino acid substitutions and by applying established molecular biology techniques. The correct plasmid sequences were verified by DNA sequencing.

E coli (strain T7E2) cells (Gene Bridge) were transformed with plasmids containing the gene fragments encoding the original and scaffold modified Z variants. The cells were cultivated at 37° C. in TSB-YE medium supplemented with 50 µg/ml kanamycin and protein expression was subsequently induced by addition of IPTG. Pelleted cells were disrupted using a FastPrep®-24 homogenizer (Nordic Biolabs) and cell debris was removed by centrifugation. Each supernatant containing the Z variant as a His$_6$-tagged protein was purified by immobilized metal ion affinity chromatography (IMAC) using His GraviTrap™ columns (GE Healthcare) according to the manufacturers instructions. Purified Z variants were buffer exchanged to phosphate-buffered saline (PBS; 1.47 mM KH$_2$PO$_4$, 8.1 mM Na$_2$HPO$_4$, 137 mM NaCl, 2.68 mM KCl, pH 7.4) using PD-10 desalting columns (GE Healthcare). The correct identity of each polypeptide was verified by SDS-PAGE and HPLC-MS.

Circular Dichroism Spectroscopy Analysis:

Circular dichroism (CD) analysis was carried out as described in Example 3 to determine the melting temperatures (Tm) and assess potential changes in the secondary structure of the inventive polypeptides as a result of the amino acid substitutions.

Comparative Stability Study:

The His$_6$-tagged Z variants, formulated in PBS pH 7.4, were diluted to 1 mg/ml and 200 µl aliquotes were incubated at 37° C. for 2 weeks. Samples collected prior to and after the stability test were analyzed by SDS-PAGE using 10% Bis-Tris NuPAGE gels (Invitrogen) and by loading 5 µg protein into each well. The stability was assessed by the appearance of new variants after incubation at the elevated temperature and mutated variants were compared to the original polypeptide.

Binding Assessment of Scaffold-Modified Polypeptides:

The His$_6$-tagged Z variants were further assessed in terms of preserved binding capacity to FcRn after introduction of alterations in the scaffold, as well as after having been subjected to the stability test, i.e. incubated at 37° C. for 2 weeks. Comparative kinetic constants ($k_{on}$ and $k_{off}$) and affinities ($K_D$) were determined using a Biacore 2000 instrument. The target protein human FcRn (Biorbyt, cat. no. orb 84388) was immobilized on the carboxylated dextran layer surface of a CM5 chip (GE Healthcare). The immobilization was performed using amine coupling chemistry according to the manufacturer's protocol and using HBS-EP as running buffer. One flow cell surface on the chip was activated and deactivated for use as blank during analyte injections. The immobilization level of hFcRn on the surface was approximately 750 RU. The Z variants were diluted in running buffer to final concentrations of 3.33, 10 and 30 nM and injected for 3 min, followed by 15 min of dissociation in running buffer. Regeneration by three pulses of HBS-EP followed by 10 min equilibration in running buffer was applied after each analyte injection. Kinetic constants were calculated from the sensorgrams using the Langmuir 1:1 model of the BiaEvaluation software 4.1 (GE Healthcare). Curves of the blank surface were subtracted from the curves of the ligand surfaces and the data from the buffer cycles were subtracted from the data of the test-sample cycles to correct for any drift in signal.

Results

Circular Dichroism Spectroscopy Analysis:

The Tm of each respective Z variant as determined from the midpoint of the transition in the CD signal vs. temperature plot is shown in Table 19. The mutated Z variants showed preserved alphahelical structure and refolded reversibly after heating to 90° C.

TABLE 19

Melting temperatures for original and mutated Z variants.

| Designation | SEQ ID NO | Tm (°C.) | Original vs modified |
|---|---|---|---|
| Z11948 | 354 | 48 | Original |
| Z17347 | 358 | 50 | Modified |
| Z17348 | 359 | 44 | Modified |

Figure 17:
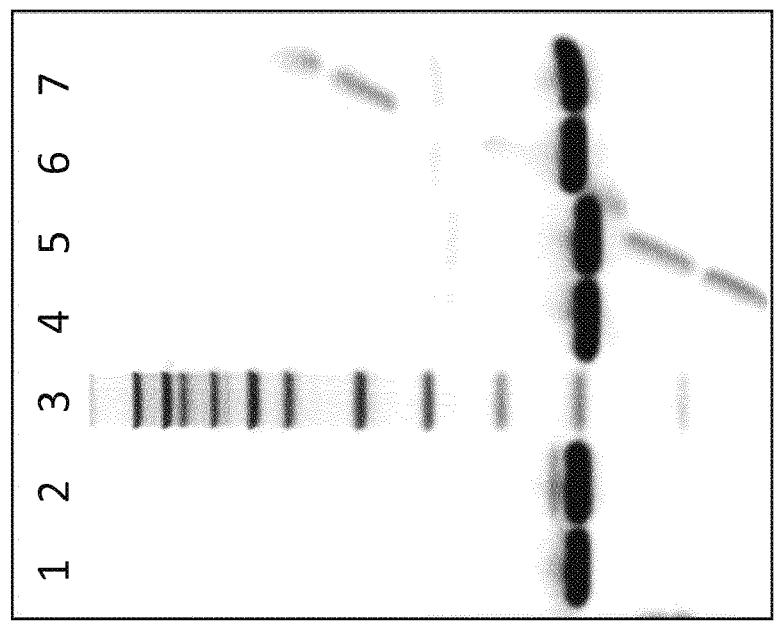
FIG. 17 is an image of an SDS-PAGE gel showing original and mutated FcRn binding Z variants before (0) and after a 2 week (2 w) stability test. Lane 1: Z11948 (0), lane 2: Z11948 (2 w), lane 3: Mw, lane 4: Z17347 (0), lane 5: Z17347 (2 w), lane 6: Z17348 (0), lane 7: Z17348 (2 w). The molecular size marker (Mw) was Novex® Sharp Pre-stained Protein Standard (216, 160, 110, 80, 60, 50, 40, 30, 20, 15, 10, 3.5 kDa). The diagonal bands seen in the figure are an artifact resulting from an imprint from a second gel stained in the same container.

Comparative Stability Study:

The scaffold modified Z variants Z17347 and Z17348 showed an improved stability compared to the original polypeptide Z11948. The second band visible on the gel just above the main band for Z11948 was not visible in samples of Z17347 and Z17348 (FIG. 17), i.e. the scaffold mutations prevent the formation of the alternative species observed for the sample in the original scaffold.

Binding Assessment of Scaffold-Modified Polypeptides:

The comparative kinetic constants for the FcRn-binding Z variants are shown in Table 20. The affinity was marginally effected by the amino acid substitutions ND to SE in position 52-53, such as in Z17347 (SEQ ID NO:358), as well as by the substitutions ND to SE in position 52-53 in combination with D36R, D37Q and S39E, such as in Z17348 (SEQ ID NO:359), and functional binders were obtained with $K_D$ in the range of $10^{-9}$M. The assessed variants also had preserved binding capabilities after 2 weeks incubation at 37° C.

TABLE 20

Comparative kinetic analysis of original and modified Z variants.

| Test sample | SEQ ID NO: | Original vs scaffold modified | $k_a$ (Ms$^{-1}$) | $k_d$ (s$^{-1}$) | $K_D$ (M)* |
|---|---|---|---|---|---|
| Z11948 (0) | 354 | Original | $1.60 \times 10^6$ | $4.56 \times 10^{-3}$ | $2.9 \times 10^{-9}$ |
| Z11948 (2w) | 354 | Original | $3.15 \times 10^6$ | $5.75 \times 10^{-3}$ | $1.8 \times 10^{-9}$ |
| Z17347 (0) | 358 | Modified | $1.18 \times 10^6$ | $7.99 \times 10^{-3}$ | $6.7 \times 10^{-9}$ |
| Z17347 (2w) | 358 | Modified | $2.27 \times 10^6$ | $8.79 \times 10^{-3}$ | $3.9 \times 10^{-9}$ |
| Z17348 (0) | 359 | Modified | $1.82 \times 10^6$ | $1.00 \times 10^{-2}$ | $5.5 \times 10^{-9}$ |
| Z17348 (2w) | 359 | Modified | $1.28 \times 10^6$ | $8.09 \times 10^{-3}$ | $6.3 \times 10^{-9}$ |

*The $K_D$ values should not be regarded as absolute, as these were determined for comparative purposes and only included a limited number of sample concentrations.

Example 25

Generation and Assessment of Additional Scaffold-Modified FcRn Binding Polypeptides In this Example, additional variants with the scaffold amino acid substitutions N52S and D53E, and some also with the amino acid substitution Y5F, were analyzed in terms of their stability and binding to FcRn as compared to their respective parent FcRn binding Z variant. The results show that the structure, stability and FcRn binding capacity are retained in the mutated variants.

Materials and Methods

Generation of Scaffold-Modified Polypeptides:

The amino acid substitutions N52S and D53E were introduced in the plasmids of His$_6$-tagged Z13578 (SEQ ID NO:20), Z13583 (SEQ ID NO:23), Z13616 (SEQ ID NO:41), Z13621 (SEQ ID NO:44) and Z13674 (SEQ ID NO:75) using established molecular biology techniques resulting in the respective Z variants Z18614 (SEQ ID NO:360), Z18615 (SEQ ID NO:361), Z18616 (SEQ ID NO:362), Z18617 (SEQ ID NO:363) and Z18618 (SEQ ID NO:364). Additional modifications at position 5, were the tyrosine residue was substituted to phenylalanine, as well as N-terminal modification to start with the amino acid residues AE instead of VD, resulted in the Z variants Z18632 (SEQ ID NO:365), Z18633 (SEQ ID NO:366) and Z18634 (SEQ ID NO:367) having binding motifs (BM) identical to Z13578, Z13616 and Z13621, respectively. Cultivation and purification was performed essentially as described in Example 3 and Example 9. The five Z variants Z18614-Z18618 were purified by IMAC only, whereas the three Z variants Z18632-Z18634 were further purified by RPC.

CD Analysis:

CD analysis was carried out as described in Example 3 to determine the melting temperatures (Tm) and assess potential changes in the secondary structure of the mutated Z variants compared to their respective parent Z variant.

Biacore Binding Analysis:

A binding analysis at pH 6.0, using a Biacore instrument, was performed essentially as described in Example 3. A concentration series (270, 90, 30, 10 and 3.3 nM) of the His$_6$-tagged Z variants Z18632, Z18633 and Z18634 and their respective corresponding parent Z variants Z13578, Z13616 and Z13621, were injected during 4 min at 30 µl/min over hFcRn (Biorbyt, cat. no. orb84388) and cFcRn (Biorbyt, cat.no. orb99075), immobilized in different flow cells of a CM5 chip surface. 0.005% PCT pH 6.0 was used as running buffer and for dilutions of the His$_6$-tagged Z variants. Dissociation in running buffer was allowed for 20 min, followed by surface regeneration by injection of 3×30 second pulses of 0.005% PCT pH 7.4 and equilibration for 15 min before the start of next cycle.

Results

Cultivation and Purification:

The FcRn binding Z variants were constructed with an N-terminal His$_6$-tag and produced in E. coli. SDS-PAGE analysis of each final protein preparation showed that it predominantly contained the Z variant. The correct identity and molecular weight of each FcRn binding Z variant was confirmed by HPLC-MS analysis.

CD Analysis:

The Tm of the mutated FcRn binding Z variants were identical, or nearly identical, to the Tm of the respective parent Z variant (Table 21). Furthermore, reversible folding was observed for all seven Z variants by overlaying spectra obtained before and after heating to 90° C.

Figure 18:
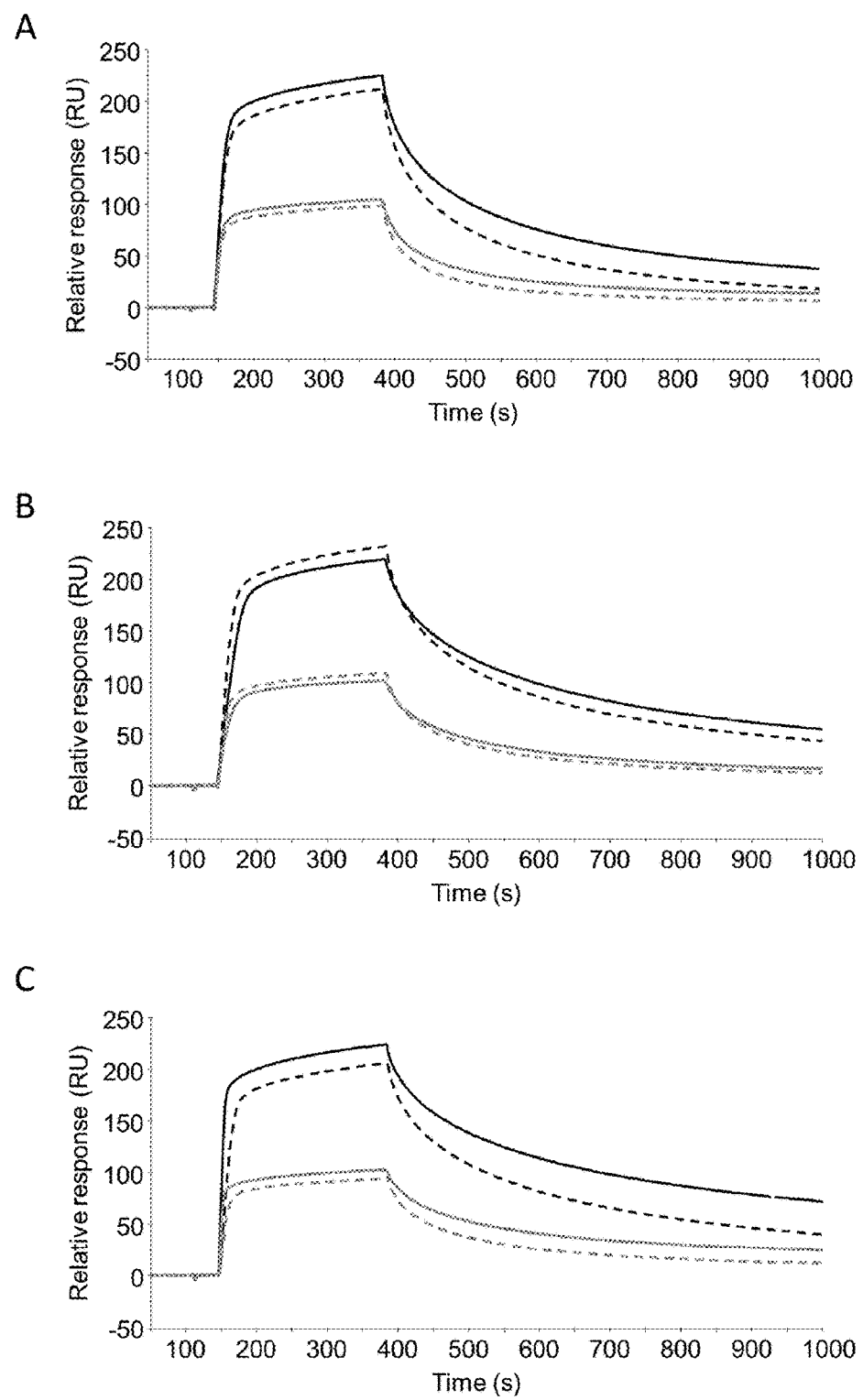
FIG. 18 shows the binding to human and cynomolgus FcRn at pH 6.0 as described in Example 25. Overlays of sensorgrams obtained from a Biacore instrument representing responses from injection of 90 nM $His_6$-tagged Z variant over hFcRn (black) and cFcRn (grey) are displayed for (A) Z13578 (solid line) and Z18632 (dashed line), (B) Z13616 (solid line) and Z18633 (dashed line), and (C) Z13621 (solid line) and Z18634 (dashed line).

Biacore Binding Analysis:

The binding profiles for interactions with FcRn at pH 6.0 were compared pairwise for three mutated Z variants and their respective parent Z variants; Z18632/Z13578 (SEQ ID NO:365/20), Z18633/Z13616 (SEQ ID NO:366/41) and Z18634/Z13621 (SEQ ID NO:367/44). Overlays of sensorgrams from the 90 nM injections of the Z variants over hFcRn and cFcRn surfaces show that the mutated Z variants retained their ability to bind to human and cynomolgus FcRn (FIG. 18A-C). The FcRn immobilization levels of the chip surfaces were 1577 RU for human FcRn and 1098 RU for cynomolgus FcRn.

TABLE 21

Melting temperatures for scaffold mutated and parent Z variants.

| Mutated Z variant | SEQ ID NO: | Tm (°C.) | Parent Z variant | SEQ ID NO: | Tm (°C.) |
|---|---|---|---|---|---|
| Z18614 | 360 | 57 | Z13578 | 20 | 55 |
| Z18615 | 361 | 50 | Z13583 | 23 | 51 |
| Z18616 | 362 | 62 | Z13616 | 41 | 60 |
| Z18617 | 363 | 49 | Z13621 | 44 | 49 |
| Z18618 | 364 | 50 | Z13674 | 75 | 50 |
| Z18632 | 365 | 56 | Z13578 | 20 | 57 |
| Z18633 | 366 | 61 | Z13616 | 41 | 60 |
| Z18634 | 367 | 48 | Z13621 | 44 | 49 |

Itemized Listing of Embodiments

1. FcRn binding dimer, comprising a first monomer unit, a second monomer unit and an amino acid linker, wherein said first and second monomer unit each comprises an FcRn binding motif (BM), which motif consists of the amino acid sequence EX$_2$ X$_3$ X$_4$ AX$_6$ X$_7$ EIR WLPNLX$_{16}$X$_{17}$ X$_{18}$ QR X$_{21}$ AFIX$_{25}$ X$_{26}$LX$_{28}$ X$_{29}$ (SEQ ID NO:389)

wherein, independently from each other,
- $X_2$ is selected from A, D, E, F, H, I, K, L, N, Q, R, S, T, V, W and Y;
- $X_3$ is selected from A, D, E, F, G, H, I, K, L, M, N, Q, R, S, T, V, W and Y;
- $X_4$ is selected from A, D, E, F, G, H, I, K, L, N, Q, R, S, T, V, W and Y;
- $X_6$ is selected from A, E, F, G, H, I, K, Q, R, S and V;
- $X_7$ is selected from A, F, H, K, N, Q, R, S and V;
- $X_{16}$ is selected from N and T;
- $X_{17}$ is selected from F, W and Y;
- $X_{18}$ is selected from A, D, E and N;
- $X_{21}$ is selected from A, S, V and W;
- $X_{25}$ is selected from D, E, G, H, I, K, L, N, Q, R, S, T, V, W and Y;
- $X_{26}$ is selected from K and S;
- $X_{28}$ is selected from A, D, E, F, H, I, K, L, N, Q, R, S, T, V, W and Y; and
- $X_{29}$ is selected from D and R, and wherein said FcRn binding dimer binds FcRn with a higher binding capacity compared to said first monomer unit or said second monomer unit alone.

2. FcRn binding dimer according to item 1, wherein, independently from each other,
- $X_2$ is selected from A, D, E, F, H, I, K, L, N, Q, R, S, T, V, W and Y;
- $X_3$ is selected from A, D, E, F, H, I, K, L, M, N, Q, R, S, T, V, W and Y;
- $X_4$ is selected from A, D, E, F, H, I, K, L, N, Q, R, S, T, V, W and Y;
- $X_6$ is selected from A, E, F, G, H, I, K, Q, R and S;
- $X_7$ is selected from A, F, H, K, N, Q, R, S and V;
- $X_{16}$ is selected from N and T;
- $X_{17}$ is selected from F and Y;
- $X_{18}$ is D;
- $X_{21}$ is V;
- $X_{25}$ is selected from D, E, H, I, K, L, N, Q, R, S, T, V, W and Y;
- $X_{26}$ is selected from K and S;
- $X_{28}$ is selected from A, D, E, F, H, I, K, L, N, Q, R, S, T, V and W; and
- $X_{29}$ is selected from D and R.

3. FcRn binding dimer according to item 1, wherein the BM of at least one of said first and second monomer units consists of an amino acid sequence selected from
  i) EX$_2$ X$_3$ X$_4$ AX$_6$ HEIR WLPNLTX$_{17}$ X$_{18}$ QR X$_{21}$ AFIX$_{25}$ KLX$_{28}$ D (SEQ ID NO:391)
wherein, independently from each other,
- $X_2$ is selected from A, D, E, F, H, I, K, L, N, Q, R, S, T, V, W and Y;
- $X_3$ is selected from A, D, E, G, H, K, L, M, N, Q, R, S, T, V and Y;
- $X_4$ is selected from A, D, E, F, G, I, K, L, N, Q, R, S, T, V and Y;
- $X_6$ is selected from A, G, K, R, S and V;
- $X_{17}$ is selected from F, W and Y;
- $X_{18}$ is selected from A, D, E and N;
- $X_{21}$ is selected from A, S, V and W;
- $X_{25}$ is selected from D, G, H, K, L, N, R, V and W;
- $X_{28}$ is selected from A, D, E, H, K, L, N, Q, R, S, T, W and Y;
and
  ii) an amino acid sequence which has at least 96% identity to a sequence defined by i).

4. FcRn binding dimer according to any one of items 1-3, wherein $X_6X_7$ is selected from AH and GH in at least one of said first and second monomer units.

5. FcRn binding dimer according to item 4, wherein $X_6X_7$ is AH in at least one of said first and second monomer units.

6. FcRn binding dimer according to item 4, wherein $X_6X_7$ is GH in at least one of said first and second monomer units.

7. FcRn binding dimer according to any preceding item, wherein $X_{17}X_{18}$ is selected from FD and YD in at least one of said first and second monomer units.

8. FcRn binding dimer according to item 7, wherein $X_{17}X_{18}$ is FD in at least one of said first and second monomer units.

9. FcRn binding dimer according to any preceding item, wherein the sequence of the BM of at least one of said first and second monomer units fulfills at least three of the six conditions I-VI:
- I. $X_6$ is selected from A, G, K and S, such as in particular A;
- II. $X_7$ is H;
- III. $X_{17}$ is selected from F and Y, such as in particular F;
- IV. $X_{18}$ is D;
- V. $X_{21}$ is selected from V and W, such as in particular V;
- VI. $X_{25}$ is selected from H and R, such as in particular H.

10. FcRn binding dimer according to item 9, wherein the sequence fulfills at least four of the six conditions I-VI.

11. FcRn binding dimer according to item 10, wherein the sequence fulfills at least five of the six conditions I-VI.

12. FcRn binding dimer according to item 11, wherein the sequence fulfills all of the six conditions I-VI.

13. FcRn binding dimer according to any preceding item, wherein said first and second monomer units comprise identical BM sequences.

14. FcRn binding dimer according to any one of items 1-12, wherein said first and second monomer units comprise different BM sequences.

15. FcRn binding dimer according to any preceding item, wherein at least one of said first and second monomer units comprises an FcRn binding motif BM corresponding to the sequence from position 8 to position 36 in a sequence selected from the group consisting of SEQ ID NO:1-353, such as the group consisting of SEQ ID NO:17-352.

16. FcRn binding dimer according to item 15, wherein at least one of said first and second monomer units comprises a BM corresponding to the sequence from position 8 to position 36 in a sequence selected from the group consisting of SEQ ID NO:1-15, SEQ ID NO:17-140 and SEQ ID NO:353.

17. FcRn binding dimer according to item 16, wherein at least one of said first and second monomer units comprises a BM corresponding to the sequence from position 8 to position 36 in a sequence selected from the group consisting of SEQ ID NO:1-2 and SEQ ID NO:17-140, such as the group consisting of SEQ ID NO:17-140.

18. FcRn binding dimer according to item 17, wherein at least one of said first and second monomer units comprises a BM corresponding to the sequence from position 8 to position 36 in a sequence selected from the group consisting of SEQ ID NO:1-2, SEQ ID NO:17-92, SEQ ID NO:94-103, SEQ ID NO:105-125 and SEQ ID NO:127-140, such as the group consisting of SEQ ID NO:17-92, SEQ ID NO:94-103, SEQ ID NO:105-125 and SEQ ID NO:127-140.

19. FcRn binding dimer according to item 16, wherein at least one of said first and second monomer units comprises a BM corresponding to the sequence from position 8 to position 36 in a sequence selected from the group consisting of SEQ ID NO:1-8, SEQ ID NO:13, SEQ ID NO:19-20, SEQ ID NO:23, SEQ ID NO:28, SEQ ID NO:41, SEQ ID NO:44, SEQ ID NO:65, SEQ ID NO:70, SEQ ID NO:73, SEQ ID NO:75-77 and SEQ ID NO:353, such as the group consisting of SEQ ID NO:19-20, SEQ ID NO:23, SEQ ID NO:28, SEQ ID NO:41, SEQ ID NO:44, SEQ ID NO:65, SEQ ID NO:70, SEQ ID NO:73 and SEQ ID NO:75-77.

20. FcRn binding dimer according to item 18 or 19, wherein at least one of said first and second monomer units comprises a BM corresponding to the sequence from position 8 to position 36 in a sequence selected from the group consisting of SEQ ID NO:1, SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77, such as the group consisting of SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77.

21. FcRn binding dimer according to item 20, wherein at least one of said first and second monomer units comprises a BM corresponding to the sequence from position 8 to position 36 in a sequence selected from the group consisting of SEQ ID NO:1, SEQ ID NO:20, SEQ ID NO:23, SEQ ID NO:41, SEQ ID NO:44, SEQ ID NO:65, SEQ ID NO:75 and SEQ ID NO:77, such as the group consisting of SEQ ID NO:20, SEQ ID NO:23, SEQ ID NO:41, SEQ ID NO:44, SEQ ID NO:65, SEQ ID NO:75 and SEQ ID NO:77.

22. FcRn binding dimer according to item 21, wherein at least one of said first and second monomer units comprises a BM corresponding to the sequence from position 8 to position 36 in a sequence selected from the group consisting of SEQ ID NO:1, SEQ ID NO:20, SEQ ID NO:23, SEQ ID NO:41, SEQ ID NO:44, SEQ ID NO:65 and SEQ ID NO:75, such as the group consisting of SEQ ID NO:20, SEQ ID NO:23, SEQ ID NO:41, SEQ ID NO:44, SEQ ID NO:65 and SEQ ID NO:75.

23. FcRn binding dimer according to item 22, wherein at least one of said first and second monomer units comprises a BM corresponding to the sequence from position 8 to position 36 in a sequence selected from the group consisting of SEQ ID NO:1, SEQ ID NO:23 and SEQ ID NO:75, such as the group consisting of SEQ ID NO:23 and SEQ ID NO:75.

24. FcRn binding dimer according to item 22, wherein at least one of said first and second monomer units comprises a BM corresponding to the sequence from position 8 to position 36 in a sequence selected from the group consisting of SEQ ID NO:20, SEQ ID NO:41 and SEQ ID NO:44, such as the group consisting of SEQ ID NO:20 and SEQ ID NO:41; the group consisting of SEQ ID NO:20 and SEQ ID NO:44; or the group consisting of SEQ ID NO:41 and SEQ ID NO:44.

25. FcRn binding dimer according to item 22, wherein at least one of said first and second monomer units comprises a BM corresponding to the sequence from position 8 to position 36 in a sequence selected from the group consisting of SEQ ID NO:1, SEQ ID NO:23 and SEQ ID NO:44, such as the group consisting of SEQ ID NO:23 and SEQ ID NO:44.

26. FcRn binding dimer according to item 24 or 25, wherein at least one of said first and second monomer units comprises a BM corresponding to the sequence from position 8 to position 36 in sequence SEQ ID NO:44.

27. FcRn binding dimer according to any preceding item, wherein both said first and second monomer units independently comprise a BM corresponding to the sequence from position 8 to position 36 in a sequence selected as defined in any one of items 15-26.

28. FcRn binding dimer according to item 27, wherein both said first and second monomer units independently comprise a BM corresponding to the sequence from position 8 to position 36 in a sequence selected from the group consisting of SEQ ID NO:20, SEQ ID NO:23, SEQ ID NO:41, SEQ ID NO:44 and SEQ ID NO:75, such as the group consisting of SEQ ID NO:20, SEQ ID NO:41 and SEQ ID NO:44.

29. FcRn binding dimer according to item 28, wherein both said first and second monomer units comprise a BM corresponding to the sequence from position 8 to position 36 in SEQ ID NO:44.

30. FcRn binding dimer according to any preceding item, wherein said FcRn binding motif BM in at least one of said first and second monomers forms part of a three-helix bundle protein domain.

31. FcRn binding dimer according to item 30, wherein said BM essentially forms part of two helices with an interconnecting loop, within said three-helix bundle protein domain.

32. FcRn binding dimer according to item 31, wherein said three-helix bundle protein domain is selected from bacterial receptor domains.

33. FcRn binding dimer according to item 32, wherein said three-helix bundle protein domain is selected from domains of protein A from *Staphylococcus aureus* or derivatives thereof.

34. FcRn binding dimer according to any preceding item, wherein at least one of said first and second monomer units comprises a binding module (BMod), which module consists of an amino acid sequence selected from:
    iii) K-[BM]-DPSQS $X_aX_bLLX_c$ EAKKL $X_dX_eX_fQ$ (SEQ ID NO:392);
wherein
  [BM] is an FcRn binding motif as defined in any one of items 1-29,
  provided that $X_{29}$ is D;
  $X_a$ is selected from A and S;
  $X_b$ is selected from N and E;
  $X_c$ is selected from A, S and C;
  $X_d$ is selected from E, N and S;
  $X_e$ is selected from D, E and S;
  $X_f$ is selected from A and S;
and
  iv) an amino acid sequence which has at least 93% identity to a sequence defined by iii).

35. FcRn binding dimer according to any one of items 1-33, wherein at least one of said first and second monomer units comprises a binding module (BMod), which module consists of an amino acid sequence selected from:
    v) K-[BM]-QPEQS $X_aX_bLLX_c$ EAKKL $X_dX_eX_fQ$ (SEQ ID NO:393);
wherein
  [BM] is an FcRn binding motif as defined in any one of items 1-29,
  provided that $X_{29}$ is R;
  $X_a$ is selected from A and S;
  $X_b$ is selected from N and E;
  $X_c$ is selected from A, S and C;
  $X_d$ is selected from E, N and S;
  $X_e$ is selected from D, E and S;
  $X_f$ is selected from A and S;
and
  vi) an amino acid sequence which has at least 93% identity to a sequence defined by v).

36. FcRn binding dimer according to item 34, wherein at least one of said first and second monomer units comprises a BMod corresponding to the sequence from position 7 to position 55 in a sequence selected from the group consisting of SEQ ID NO:1-353, SEQ ID NO:358 and SEQ ID NO:360-364, such as the group consisting of SEQ ID NO:17-352 and SEQ ID NO:360-364.

37. FcRn binding dimer according to item 36, wherein at least one of said first and second monomer units comprises a BMod corresponding to the sequence from position 7 to position 55 in a sequence selected from the group consisting of SEQ ID NO:1-15, SEQ ID NO:17-140, SEQ ID NO:353, SEQ ID NO:358 and SEQ ID NO:360-364.

38. FcRn binding dimer according to item 37, wherein at least one of said first and second monomer units comprises a BMod corresponding to the sequence from position 7 to position 55 in a sequence selected from the group consisting of SEQ ID NO:1-2, SEQ ID NO:17-140, SEQ ID NO:358 and SEQ ID NO:360-364, such as the group consisting of SEQ ID NO:17-140 and SEQ ID NO:360-364.

39. FcRn binding dimer according to item 38, wherein at least one of said first and second monomer units comprises a BMod corresponding to the sequence from position 7 to position 55 in a sequence selected from the group consisting of SEQ ID NO:1-2, SEQ ID NO:17-92, SEQ ID NO:94-103, SEQ ID NO:105-125, SEQ ID NO:127-140, SEQ ID NO:358 and SEQ ID NO:360-364, such as the group consisting of SEQ ID NO:17-92, SEQ ID NO:94-103, SEQ ID NO:105-125, SEQ ID NO:127-140 and SEQ ID NO:360-364.

40. FcRn binding dimer according to item 36, wherein at least one of said first and second monomer units comprises a BMod corresponding to the sequence from position 7 to position 55 in a sequence selected from the group consisting of SEQ ID NO:1-8, SEQ ID NO:13, SEQ ID NO:19-20, SEQ ID NO:23, SEQ ID NO:28, SEQ ID NO:41, SEQ ID NO:44, SEQ ID NO:65, SEQ ID NO:70, SEQ ID NO:73, SEQ ID NO:75-77, SEQ ID NO:353, SEQ ID NO:358 and SEQ ID NO:360-364, such as the group consisting of SEQ ID NO:19-20, SEQ ID NO:23, SEQ ID NO:28, SEQ ID NO:41, SEQ ID NO:44, SEQ ID NO:65, SEQ ID NO:70, SEQ ID NO:73, SEQ ID NO:75-77 and SEQ ID NO:360-364.

41. FcRn binding dimer according to item 39 or 40, wherein at least one of said first and second monomer units comprises a BMod corresponding to the sequence from position 7 to position 55 in a sequence selected from the group consisting of SEQ ID NO:1, SEQ ID NO:20, SEQ ID NO:23, SEQ ID NO:28, SEQ ID NO:41, SEQ ID NO:44, SEQ ID NO:65, SEQ ID NO:73, SEQ ID NO:75-77, SEQ ID NO:358 and SEQ ID NO:360-364, such as the group consisting of SEQ ID NO:20, SEQ ID NO:23, SEQ ID NO:28, SEQ ID NO:41, SEQ ID NO:44, SEQ ID NO:65, SEQ ID NO:73, SEQ ID NO:75-77 and SEQ ID NO:360-364.

42. FcRn binding dimer according to item 41, wherein at least one of said first and second monomer units comprises a BMod corresponding to the sequence from position 7 to position 55 in a sequence selected from the group consisting of SEQ ID NO:1, SEQ ID NO:20, SEQ ID NO:23, SEQ ID NO:41, SEQ ID NO:44, SEQ ID NO:65, SEQ ID NO:75, SEQ ID NO:77, SEQ ID NO:358 and SEQ ID NO:360-364, such as the group consisting of SEQ ID NO:20, SEQ ID NO:23, SEQ ID NO:41, SEQ ID NO:44, SEQ ID NO:65, SEQ ID NO:75, SEQ ID NO:77 and SEQ ID NO:360-364.

43. FcRn binding dimer according to item 42, wherein at least one of said first and second monomer units comprises a BMod corresponding to the sequence from position 7 to position 55 in a sequence selected from the group consisting of SEQ ID NO:1, SEQ ID NO:20, SEQ ID NO:23, SEQ ID NO:41, SEQ ID NO:44, SEQ ID NO:65, SEQ ID NO:75, SEQ ID NO:358 and SEQ ID NO:360-364, such as the group consisting of SEQ ID NO:20, SEQ ID NO:23, SEQ ID NO:41, SEQ ID NO:44, SEQ ID NO:75 and SEQ ID NO:360-364.

44. FcRn binding dimer according to item 43, wherein at least one of said first and second monomer units comprises a BMod corresponding to the sequence from position 7 to position 55 in a sequence selected from the group consisting of SEQ ID NO:1, SEQ ID NO:23, SEQ ID NO:75, SEQ ID NO:358, SEQ ID NO:361 and SEQ ID NO:364, such as the group consisting of SEQ ID NO:23, SEQ ID NO:75, SEQ ID NO:361 and SEQ ID NO:364.

45. FcRn binding dimer according to item 43, wherein at least one of said first and second monomer units comprises a BMod corresponding to the sequence from position 7 to position 55 in a sequence selected from the group consisting of SEQ ID NO:20, SEQ ID NO:41, SEQ ID NO:44, SEQ ID NO:360, SEQ ID NO:362 and SEQ ID NO:363, such as the group consisting of SEQ ID NO:20, SEQ ID NO:41, SEQ ID NO:360 and SEQ ID NO:362; the group consisting of SEQ ID NO:20, SEQ ID NO:44, SEQ ID NO:360 and SEQ ID NO:363; or the group consisting of SEQ ID NO:41, SEQ ID NO:44, SEQ ID NO:362 and SEQ ID NO:363.

46. FcRn binding dimer according to item 43, wherein at least one of said first and second monomer units comprises a BMod corresponding to the sequence from position 7 to position 55 in a sequence selected from the group consisting of SEQ ID NO:1, SEQ ID NO:23, SEQ ID NO:44, SEQ ID NO:358, SEQ ID NO:361 and SEQ ID NO:363, such as the group consisting of SEQ ID NO:23, SEQ ID NO:44, SEQ ID NO:361 and SEQ ID NO:363.

47. FcRn binding dimer according to item 46, wherein at least one of said first and second monomer units comprises a BMod corresponding to the sequence from position 7 to position 55 in SEQ ID NO:44.

48. FcRn binding dimer according to any one of items 1-13 and 15-47, wherein both said first and second monomer units comprise a BMod corresponding to the sequence from position 7 to position 55 in a sequence selected from the group as defined in any one of items 36-47.

49. FcRn binding dimer according to item 48, wherein both said first and second monomer units comprise a BMod corresponding to the sequence from position 7 to position 55 in a sequence selected from the group consisting of SEQ ID NO:20, SEQ ID NO:23, SEQ ID NO:41, SEQ ID NO:44, SEQ ID NO:75 and SEQ ID NO:360-364, such as the group consisting of SEQ ID NO:20, SEQ ID NO:41, SEQ ID NO:44, SEQ ID NO:360, SEQ ID NO:362 and SEQ ID NO:363.

50. FcRn binding dimer according to item 49, wherein both said first and second monomer units comprise a BMod corresponding to the sequence from position 7 to position 55 in SEQ ID NO:44.

51. FcRn binding dimer according to any preceding item, wherein at least one of said first and second monomer units comprises a sequence selected from the group consisting of:
  vii) YAK[BM]-DPSQS SELLX$_c$ EAKKL NDSQA P (SEQ ID NO:394);
wherein [BM] is an FcRn binding motif as defined in any one of items 1-29 and X$_c$ is selected from A, S and C; and
  viii) an amino acid sequence which has at least 94% identity to a sequence defined by vii).

52. FcRn binding dimer according to any one of items 1-50, wherein at least one of said first and second monomer units comprises a sequence selected from the group consisting of:
  ix) FAK-[BM]-DPSQS SELLX$_c$ EAKKL SESQA P (SEQ ID NO:395);

wherein [BM] is an FcRn binding motif as defined in any one of items 1-29 and $X_c$ is selected from A, S and C; and
  x) an amino acid sequence which has at least 94% identity to a sequence defined by ix).
53. FcRn binding dimer according to any one of items 1-50, wherein at least one of said first and second monomer units comprises a sequence selected from the group consisting of:
  xi) FNK-[BM]-DPSQS ANLL$X_c$ EAKKL NDAQA P (SEQ ID NO:463);
wherein [BM] is an FcRn binding motif as defined in any one of items 1-29 and $X_c$ is selected from A and C; and
  xii) an amino acid sequence which has at least 94% identity to a sequence defined by xi).
54. FcRn binding dimer according to item 33, wherein at least one of said first and second monomer units comprises a sequence selected from:
  ADNNFNK-[BM]-DPSQSANLLSEAKKLNESQAPK (SEQ ID NO:396);
  ADNKFNK-[BM]-DPSQSANLLAEAKKLNDAQAPK (SEQ ID NO:397);
  ADNKFNK-[BM]-DPSVSKEILAEAKKLNDAQAPK (SEQ ID NO:398);
  ADAQQNNFNK-[BM]-DPSQSTNVLGEAKKL-NESQAPK (SEQ ID NO:399);
  AQHDE-[BM]-DPSQSANVLGEAQKLNDSQAPK (SEQ ID NO:400);
  VDNKFNK-[BM]-DPSQSANLLAEAKKLNDAQAPK (SEQ ID NO:401);
  AEAKYAK-[BM]-DPSESSELLSEAKKLNKSQAPK (SEQ ID NO:402);
  VDAKYAK-[BM]-DPSQSSELLAEAKKLNDAQAPK (SEQ ID NO:403);
  VDAKYAK-[BM]-DPSQSSELLAEAKKLNDSQAPK (SEQ ID NO:404);
  AEAKYAK-[BM]-DPSQSSELLSEAKKLNDSQAPK (SEQ ID NO:405);
  AEAKYAK-[BM]-DPSQSSELLSEAKKLNDSQAP (SEQ ID NO:406);
  AEAKFAK-[BM]-DPSQSSELLSEAKKLNDSQAPK (SEQ ID NO:407);
  AEAKFAK-[BM]-DPSQSSELLSEAKKLNDSQAP (SEQ ID NO:408);
  AEAKYAK-[BM]-DPSQSSELLAEAKKLNDAQAPK (SEQ ID NO:409);
  AEAKYAK-[BM]-DPSQSSELLSEAKKLSESQAPK (SEQ ID NO:410);
  AEAKYAK-[BM]-DPSQSSELLSEAKKLSESQAP (SEQ ID NO:411);
  AEAKFAK-[BM]-DPSQSSELLSEAKKLSESQAPK (SEQ ID NO:412);
  AEAKFAK-[BM]-DPSQSSELLSEAKKLSESQAP (SEQ ID NO:413);
  AEAKYAK-[BM]-DPSQSSELLAEAKKLSEAQAPK (SEQ ID NO:414);
  AEAKYAK-[BM]-QPEQSSELLSEAKKLSESQAPK (SEQ ID NO:415);
  AEAKYAK-[BM]-DPSQSSELLSEAKKLESSQAPK (SEQ ID NO:416);
  AEAKYAK-[BM]-DPSQSSELLSEAKKLESSQAP (SEQ ID NO:417);
  AEAKYAK-[BM]-DPSQSSELLAEAKKLESAQAPK (SEQ ID NO:418);
  AEAKYAK-[BM]-QPEQSSELLSEAKKLESSQAPK (SEQ ID NO:419);
  AEAKYAK-[BM]-DPSQSSELLSEAKKLSDSQAPK (SEQ ID NO:420);
  AEAKYAK-[BM]-DPSQSSELLSEAKKLSDSQAP (SEQ ID NO:421);
  AEAKYAK-[BM]-DPSQSSELLAEAKKLSDAQAPK (SEQ ID NO:422);
  AEAKYAK-[BM]-QPEQSSELLSEAKKLSDSQAPK (SEQ ID NO:423);
  VDAKYAK-[BM]-DPSQSSELLSEAKKLNDSQAPK (SEQ ID NO:424);
  VDAKFAK-[BM]-DPSQSSELLSEAKKLNDSQAPK (SEQ ID NO:425);
  VDAKYAK-[BM]-DPSQSSELLAEAKKLNDAQAPK (SEQ ID NO:426);
  VDAKYAK-[BM]-DPSQSSELLSEAKKLSESQAPK (SEQ ID NO:427);
  VDAKFAK-[BM]-DPSQSSELLSEAKKLSESQAPK (SEQ ID NO:428);
  VDAKYAK-[BM]-DPSQSSELLAEAKKLSEAQAPK (SEQ ID NO:429);
  VDAKYAK-[BM]-QPEQSSELLSEAKKLSESQAPK (SEQ ID NO:430);
  VDAKYAK-[BM]-DPSQSSELLSEAKKLESSQAPK (SEQ ID NO:431);
  VDAKYAK-[BM]-DPSQSSELLAEAKKLESAQAPK (SEQ ID NO:432);
  VDAKYAK-[BM]-QPEQSSELLSEAKKLESSQAPK (SEQ ID NO:433);
  VDAKYAK-[BM]-DPSQSSELLSEAKKLSDSQAPK (SEQ ID NO:434);
  VDAKYAK-[BM]-DPSQSSELLAEAKKLSDAQAPK (SEQ ID NO:435);
  VDAKYAK-[BM]-QPEQSSELLSEAKKLSDSQAPK (SEQ ID NO:436);
  VDAKYAK-[BM]-DPSQSSELLAEAKKLNKAQAPK (SEQ ID NO:437);
  AEAKYAK-[BM]-DPSQSSELLAEAKKLNKAQAPK (SEQ ID NO:438); and
  ADAKYAK-[BM]-DPSQSSELLSEAKKLNDSQAPK (SEQ ID NO:439);
wherein [BM] is an FcRn binding motif as defined in any one of items 1-29.
55. FcRn binding dimer according to any preceding item, wherein at least one of said first and second monomer units comprises a sequence selected from the group consisting of:
  xiii) AEAKYAK-[BM]-DPSQSSELLSEAKKLND-SQAPK (SEQ ID NO:405);
wherein [BM] is an FcRn binding motif as defined in any one of items 1-29; and
  xiv) an amino acid sequence which has at least 94% identity to the sequence defined in xiii).
56. FcRn binding dimer according to item 55, wherein at least one of said first and second monomer units comprises a sequence xiii) selected from the group consisting of SEQ ID NO:354-357, such as selected from SEQ ID NO:354 and 357.
57. FcRn binding dimer according to item 56, wherein at least one of said first and second monomer units comprises a sequence xiii) which is SEQ ID NO:357.
58. FcRn binding dimer according to any one of items 1-54, wherein at least one of said first and second monomer units comprises a sequence selected from the group consisting of:
  xv) AEAKFAK-[BM]-DPSQSSELLSEAKKLSESQAPK (SEQ ID NO:412);
wherein [BM] is an FcRn binding motif as defined in any one of items 1-29; and
  xvi) an amino acid sequence which has at least 94% identity to the sequence defined in xv).

59. FcRn binding dimer according to item 58, wherein at least one of said first and second monomer units comprises a sequence xv) selected from the group consisting of SEQ ID NO:365-367.

60. FcRn binding dimer according to any one of items 1-54, wherein at least one of said first and second monomer units comprises a sequence selected from the group consisting of:
  xvii)     VDAKYAK-[BM]-DPSQSSELLSEAKKLS-ESQAPK (SEQ ID NO:427);
wherein [BM] is an FcRn binding motif as defined in any one of items 1-29; and
  xviii) an amino acid sequence which has at least 94% identity to the sequence defined in xvii).

61. FcRn binding dimer according to item 60, wherein at least one of said first and second monomer units comprises a sequence xvii) selected from the group consisting of SEQ ID NO:360-364.

62. FcRn binding dimer according to any preceding item, wherein at least one of said first and second monomer units comprises a sequence selected from the group consisting of:
  xix)     AEAKYAK-[BM]-RQPESSELLSEAKKLS-ESQAPK (SEQ ID NO:440);
wherein [BM] is an FcRn binding motif as defined in any one of items 1-29; and
  xx) an amino acid sequence which has at least 94% identity to the sequence defined in xix).

63. FcRn binding dimer according to item 62, wherein at least one of said first and second monomer units comprises a sequence xix) which is SEQ ID NO:359.

64. FcRn binding dimer according to any one of items 1-54, wherein at least one of said first and second monomer units comprises a sequence selected from the group consisting of:
  xxi)     VDAKYAK-[BM]-DPSQSSELLSEAKKLND-SQAPK (SEQ ID NO:424);
wherein [BM] is an FcRn binding motif as defined in any one of items 1-29; and
  xxii) an amino acid sequence which has at least 94% identity to the sequence defined in xxi).

65. FcRn binding dimer according to item 64, wherein at least one of said first and second monomer units comprises a sequence xxi) selected from the group consisting of SEQ ID NO:1-353, such as the group consisting of SEQ ID NO:17-352.

66. FcRn binding dimer according to item 65, wherein at least one of said first and second monomer units comprises a sequence xxi) selected from the group consisting of SEQ ID NO:1-15, SEQ ID NO:17-140 and SEQ ID NO:353, or comprises a sequence xxi) selected from the group consisting of SEQ ID NO:1-2 and SEQ ID NO:17-140, such as the group consisting of SEQ ID NO:17-140.

67. FcRn binding dimer according to item 66, wherein at least one of said first and second monomer units comprises a sequence xxi) selected from the group consisting of SEQ ID NO:1-2, SEQ ID NO:17-92, SEQ ID NO:94-103, SEQ ID NO:105-125 and SEQ ID NO:127-140, such as the group consisting of SEQ ID NO:17-92, SEQ ID NO:94-103, SEQ ID NO:105-125 and SEQ ID NO:127-140.

68. FcRn binding dimer according to item 67, wherein at least one of said first and second monomer units comprises a sequence xxi) selected from the group consisting of SEQ ID NO:1-8, SEQ ID NO:13, SEQ ID NO:19-20, SEQ ID NO:23, SEQ ID NO:28, SEQ ID NO:41, SEQ ID NO:44, SEQ ID NO:65, SEQ ID NO:70, SEQ ID NO:73, SEQ ID NO:75-77 and SEQ ID NO:353, such as the group consisting of SEQ ID NO:19-20, SEQ ID NO:23, SEQ ID NO:28, SEQ ID NO:41, SEQ ID NO:44, SEQ ID NO:65, SEQ ID NO:70, SEQ ID NO:73 and SEQ ID NO:75-77.

69. FcRn binding dimer according to item 66 or 68, wherein at least one of said first and second monomer units comprises a sequence xxi) selected from the group consisting of SEQ ID NO:1, SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77, such as the group consisting of SEQ ID NO:20, SEQ ID NO:23, SEQ ID NO:28, SEQ ID NO:41, SEQ ID NO:44, SEQ ID NO:65, SEQ ID NO:73 and SEQ ID NO:75-77.

70. FcRn binding dimer according to item 69, wherein at least one of said first and second monomer units comprises a sequence xxi) selected from the group consisting of SEQ ID NO:1, SEQ ID NO:20, SEQ ID NO:23, SEQ ID NO:41, SEQ ID NO:44, SEQ ID NO:65, SEQ ID NO:75 and SEQ ID NO:77, such as the group consisting of SEQ ID NO:20, SEQ ID NO:23, SEQ ID NO:41, SEQ ID NO:44, SEQ ID NO:65, SEQ ID NO:75 and SEQ ID NO:77.

71. FcRn binding dimer according to item 70 wherein at least one of said first and second monomer units comprises a sequence xxi) selected from the group consisting of SEQ ID NO:1, SEQ ID NO:20, SEQ ID NO:23, SEQ ID NO:41, SEQ ID NO:44, SEQ ID NO:65 and SEQ ID NO:75, such as the group consisting of SEQ ID NO:20, SEQ ID NO:23, SEQ ID NO:41, SEQ ID NO:44, SEQ ID NO:65 and SEQ ID NO:75, such as the group consisting of SEQ ID NO:20, SEQ ID NO:23, SEQ ID NO:41, SEQ ID NO:44 and SEQ ID NO:75.

72. FcRn binding dimer according to item 71, wherein at least one of said first and second monomer units comprises a sequence xxi) selected from the group consisting of SEQ ID NO:1, SEQ ID NO:23 and SEQ ID NO:75, such as the group consisting of SEQ ID NO:23 and SEQ ID NO:75.

73. FcRn binding dimer according to item 71, wherein at least one of said first and second monomer units comprises a sequence xxi) selected from the group consisting of SEQ ID NO:20, SEQ ID NO:41 and SEQ ID NO:44.

74. FcRn binding dimer according to item 71, wherein at least one of said first and second monomer units comprises a sequence xxi) selected from the group consisting of SEQ ID NO:1, SEQ ID NO:23 and SEQ ID NO:44, such as the group consisting of SEQ ID NO:23 and SEQ ID NO:44.

75. FcRn binding dimer according to item 73 or 74, wherein at least one of said first and second monomer units comprises a sequence xxi) which is SEQ ID NO:44.

76. FcRn binding dimer according to any one of items 1-13 and 15-75, wherein both said first and second monomer units correspond to a sequence selected from the group as defined in any one of items 55, 56 and 62-75.

77. FcRn binding dimer according to item 76, wherein both said first and second monomer units correspond to a sequence selected from the group consisting of SEQ ID NO:1, SEQ ID NO:20, SEQ ID NO:23, SEQ ID NO:41, SEQ ID NO:44, SEQ ID NO:65, SEQ ID NO:75, SEQ ID NO:354, SEQ ID NO:357 and SEQ ID NO:360-367, such as the group consisting of SEQ ID NO:20, SEQ ID NO:41, SEQ ID NO:44, SEQ ID NO:360, SEQ ID NO:362, SEQ ID NO:363, SEQ ID NO:365, SEQ ID NO:366 and SEQ ID NO:367.

78. FcRn binding dimer according to item 77, wherein both said first and second monomer units correspond to SEQ ID NO:1 or SEQ ID NO:357.

79. FcRn binding dimer according to item 77, wherein both said first and second monomer units correspond to SEQ ID NO:20, SEQ ID NO:360 or SEQ ID NO:365.

80. FcRn binding dimer according to item 77, wherein both said first and second monomer units correspond to SEQ ID NO:41, SEQ ID NO:362 or SEQ ID NO:366.

81. FcRn binding dimer according to item 77, wherein both said first and second monomer units correspond to SEQ ID NO:44, SEQ ID NO:363 or SEQ ID NO:367.

82. FcRn binding dimer according to any preceding item, wherein said linker is selected from the group consisting of flexible amino acid linkers, rigid amino acid linkers and cleavable amino acid linkers.

83. FcRn binding dimer according to item 82, wherein said linker is arranged between said first monomer unit and said second monomer unit.

84. FcRn binding dimer according to item 82 or 83, wherein said linker is a flexible linker comprising amino acid residues selected from the group consisting of glycine, serine and threonine.

85. FcRn binding dimer according to claim 84, wherein said linker has a general formula selected from $$(G_nS_m)_p \text{ and } (S_nG_m)_p,$$

wherein, independently,
n=1-7,
m=0-7,
n+m≤8 and
p=1-7.

86. FcRn binding dimer according to claim 85, wherein n=1-5.

87. FcRn binding dimer according to any one of claims 85-86, wherein m=0-5.

88. FcRn binding dimer according to any one of claims 85-87, wherein p=1-5.

89. FcRn binding dimer according to any one of claims 86-88, wherein n=4, m=1 and p=1-4.

90. FcRn binding dimer according to claim 89, wherein said linker is $(G_4S)_3$.

91. FcRn binding dimer according item 89, wherein said linker is $G_4S$.

92. FcRn binding dimer according to any preceding item, which is capable of binding to FcRn with at least 2 times, such as at least 3 times, such as at least 4 times, such as at least 5 times, such as at least 6 times, such as at least 7 times, such as at least 8 times, such as at least 9 times, such as at least 10 times, such as at least 25 times, such as at least 50 times, such as at least 100 times higher capacity than the corresponding first monomer unit or second monomer unit alone.

93. FcRn binding dimer according to item 92, which is capable of binding to FcRn at pH 6.0 with at least 2 times, such as at least 3 times higher capacity than the corresponding first monomer unit or second monomer unit alone.

94. FcRn binding dimer according to item 92, which is capable of binding to FcRn at pH 7.4 with at least 2 times, such as at least 3 times, such as at least 4 times, such as at least 5 times, such as at least 6 times, such as at least 7 times, such as at least 8 times, such as at least 9 times, such as at least 10 times higher capacity than the corresponding first monomer unit or second monomer unit alone.

95. FcRn binding dimer according to any preceding item, which is capable of binding to FcRn at pH 6.0 such that the $K_D$ value of the interaction is at most $1 \times 10^{-7}$ M, such as at most $1 \times 10^{-8}$ M, such as at most $1 \times 10^{-9}$ M, such as at most $1 \times 10^{-10}$ M, such as at most $1 \times 10^{-11}$ M, such as at most $1 \times 10^{-12}$ M.

96. FcRn binding dimer according to any preceding item, wherein the $K_D$ value of the interaction between FcRn binding polypeptide and FcRn at pH 7.4 is higher than the $K_D$ value of said interaction at pH 6.0, such as at least 2 times higher, such as at least 5 times higher, such as at least 10 times higher, such as at least 50 times higher, such as at least 100 times higher than the $K_D$ value of said interaction at pH 6.0.

97. FcRn binding dimer according to any preceding item, wherein the $K_D$ value of the interaction between FcRn binding polypeptide and FcRn at pH 7.4 is at least $1 \times 10^{-10}$ M, such as at least $1 \times 10^{-9}$ M, such as at least $1 \times 10^{-8}$ M, such as at least $1 \times 10^{-7}$ M, such as at least $1 \times 10^{-6}$ M, such as at least $1 \times 10^{-5}$ M.

98. FcRn binding dimer according to any one of items 1-94, wherein the $K_D$ value of said interaction at pH 7.4 is the same as or lower than the $K_D$ value of said interaction at pH 6.0.

99. FcRn binding dimer according to any one of items 1-94, wherein the $K_D$ value of said interaction at pH 7.4 is at most $1 \times 10^{-7}$ M, such as at most $1 \times 10^{-8}$ M, such as at most $1 \times 10^{-9}$ M, such as at most $1 \times 10^{-10}$ M, such as at most $1 \times 10^{-11}$ M, such as at most $1 \times 10^{-12}$ M.

100. FcRn binding dimer according to any preceding item, wherein at least one of said first and second monomer units comprises at least one additional amino acid at the C-terminal and/or N-terminal end.

101. FcRn binding dimer according to item 100, wherein said at least one additional amino acid extension improves or simplifies production, purification, stabilization in vivo or in vitro, coupling or detection of the polypeptide.

102. Fusion protein or conjugate comprising
    a first moiety consisting of an FcRn binding dimer according to any preceding item; and
    a second moiety consisting of a polypeptide having a desired biological activity.

103. Fusion protein or conjugate according to item 102, wherein the in vivo half-life of said fusion protein or conjugate is longer than the in vivo half-life of the polypeptide having a desired biological activity per se.

104. Fusion protein or conjugate according to any one of items 102-103, wherein said desired biological activity is a therapeutic activity.

105. Fusion protein or conjugate according to any one of items 100-102, wherein said desired biological activity is a binding activity to a selected target.

106. Fusion protein or conjugate according to item 105, wherein said selected target is albumin.

107. Fusion protein or conjugate according to item 106, wherein said albumin binding activity is provided by the albumin binding domain of streptococcal protein G, or a derivative thereof.

108. Fusion protein or conjugate according to any one of items 106-107, wherein said albumin binding activity increases in vivo half-life of the fusion protein or conjugate.

109. Fusion protein or conjugate according to any one of items 103-104, wherein said desired biological activity is an enzymatic activity.

110. Fusion protein or conjugate according to any one of items 103-105, wherein the second moiety having a desired biological activity is a therapeutically active polypeptide.

111. Fusion protein or conjugate according to any one of items 103-105 and 109-110, wherein the second moiety having a desired biological activity is selected from the group consisting of enzymes, hormones, growth factors, chemokines and cytokines.

112. FcRn binding dimer, fusion protein or conjugate according to any preceding item, which inhibits binding of IgG to FcRn.

113. FcRn binding dimer, fusion protein or conjugate according to item 112, which binds FcRn such that the ability of the FcRn binding dimer to block IgG binding to FcRn is at least 2 times higher, such as at least 3 times higher, such as at least 4 times higher, such as at least 5 times higher, such as at least 10 times, such as at least 15 times, such as at least 20 times, such as at least 25 times higher compared to the blocking ability of the corresponding first or second monomer unit alone.

114. FcRn binding dimer, fusion protein or conjugate according to item 112 or 113, wherein the $K_D$ value of the interaction between said FcRn binding polypeptide, fusion protein or conjugate and FcRn is lower than the $K_D$ value of the interaction between IgG and FcRn.

115. FcRn binding dimer, fusion protein or conjugate according to any preceding item, further comprising a label.

116. FcRn binding dimer, fusion protein or conjugate according to item 115, wherein said label is selected from the group consisting of fluorescent dyes and metals, chromophoric dyes, chemiluminescent compounds and bioluminescent proteins, enzymes, radionuclides and radioactive particles.

117. FcRn binding dimer, fusion protein or conjugate according to any preceding item, comprising a chelating environment provided by a polyaminopolycarboxylate chelator conjugated to the FcRn binding polypeptide via a thiol group of a cysteine residue or an amine group of a lysine residue.

118. FcRn binding dimer, fusion protein or conjugate according to item 117, wherein the polyaminopolycarboxylate chelator is 1,4,7,10-tetraazacyclododecane-1,4,7,10-tetraacetic acid or a derivative thereof.

119. FcRn binding dimer, fusion protein or conjugate according to item 118, wherein the 1,4,7,10-tetraazacyclododecane-1,4,7,10-tetraacetic acid derivative is 1,4,7,10-tetraazacyclododecane-1,4,7-tris-acetic acid-10-maleimidoethylacetamide.

120. FcRn binding dimer, fusion protein or conjugate according to item 117, wherein the polyaminopolycarboxylate chelator is 1,4,7-triazacyclononane-1,4,7-triacetic acid or a derivative thereof.

121. FcRn binding dimer, fusion protein or conjugate according to item 117, wherein the polyaminopolycarboxylate chelator is diethylenetriaminepentaacetic acid or derivatives thereof.

122. A polynucleotide encoding a polypeptide according to any one of items 1-114.

123. Expression vector comprising a polynucleotide according to item 122.

124. Host cell comprising an expression vector according to item 123.

125. Method of producing a polypeptide according to any one of items 1-114, comprising
culturing a host cell according to item 124 under conditions permissive of expression of said polypeptide from said expression vector, and
isolating said polypeptide.

126. Composition comprising an FcRn binding dimer, fusion protein or conjugate according to any one of items 1-121 and at least one pharmaceutically acceptable excipient or carrier.

127. Composition according to item 126, further comprising at least one additional active agent.

128. Composition according to any one of items 126-127, which is adapted for administration by a route selected from the group consisting of oral administration, intranasal administration, pulmonar administration, vaginal administration, rectal administration, intravenous injection, intraperitoneal injection, intramuscular injection, subcutaneous injection and intradermal injection.

129. FcRn binding dimer, fusion protein or conjugate according to any one of items 1-121 or composition according to any one of items 126-128 for use as a medicament.

130. FcRn binding dimer, fusion protein, conjugate or composition for use according to item 129, wherein said medicament is intended for treatment or prophylaxis of an auto-immune condition.

131. FcRn binding dimer, fusion protein, conjugate or composition for use according to item 129, wherein said medicament is intended for treatment or prophylaxis of an allo-immune condition.

132. FcRn binding dimer, fusion protein, conjugate or composition for use according to item 129, wherein said medicament is intended for treatment or prophylaxis of a condition selected from the group consisting of epilepsy and seizures.

133. Method of treatment or prophylaxis of a subject in need thereof, comprising administering to the subject a therapeutically or prophylactically active amount of an FcRn binding dimer, fusion protein or conjugate according to any one of items 1-121 or composition according to any one of items 126-128.

134. Method according to item 133, for treatment or prophylaxis of an auto-immune condition.

135. Method according to item 133, for treatment or prophylaxis of an allo-immune condition.

136. Method according to item 133, for treatment or prophylaxis of a condition selected from the group consisting of epilepsy and seizures.

The invention claimed is:

1. A neonatal Fc receptor (FcRn) binding dimer, comprising a first monomer unit, a second monomer unit and an amino acid linker, wherein said first and second monomer unit each comprises an FcRn binding motif (BM), which motif consists of the amino acid sequence $EX_2\ X_3\ X_4\ AX_6\ X_7$ EIR WLPNL$X_{16}X_{17}\ X_{18}$ QR $X_{21}$ AFI$X_{25}\ X_{26}$L$X_{28}\ X_{29}$ (SEQ ID NO:389)

wherein, independently from each other,
- $X_2$ is selected from A, D, E, F, H, I, K, L, N, Q, R, S, T, V, W and Y;
- $X_3$ is selected from A, D, E, F, G, H, I, K, L, M, N, Q, R, S, T, V, W and Y;
- $X_4$ is selected from A, D, E, F, G, H, I, K, L, N, Q, R, S, T, V, W and Y;
- $X_6$ is selected from A, E, F, G, H, I, K, Q, R, S and V;
- $X_7$ is selected from A, F, H, K, N, Q, R, S and V;
- $X_{16}$ is selected from N and T;
- $X_{17}$ is selected from F, W and Y;
- $X_{18}$ is selected from A, D, E and N;
- $X_{21}$ is selected from A, S, V and W;
- $X_{25}$ is selected from D, E, G, H, I, K, L, N, Q, R, S, T, V, W and Y;
- $X_{26}$ is selected from K and S;
- $X_{28}$ is selected from A, D, E, F, H, I, K, L, N, Q, R, S, T, V, W and Y; and
- $X_{29}$ is selected from D and R, and wherein said FcRn binding dimer binds FcRn with a higher binding capacity compared to said first monomer or said second monomer alone.

2. The FcRn binding dimer according to claim 1, wherein the BM of at least one of said first and second monomer units consists of an amino acid sequence selected from i) $EX_2\ X_3\ X_4\ AX_6$ HEIR WLPNLT$X_{17}\ X_{18}$ QR $X_{21}$ AFI$X_{25}$ KL$X_{28}$ D (SEQ ID NO:391)

wherein, independently from each other,
- $X_2$ is selected from A, D, E, F, H, I, K, L, N, Q, R, S, T, V, W and Y;
- $X_3$ is selected from A, D, E, G, H, K, L, M, N, Q, R, S, T, V and Y;
- $X_4$ is selected from A, D, E, F, G, I, K, L, N, Q, R, S, T, V and Y;
- $X_6$ is selected from A, G, K, R, S and V;
- $X_{17}$ is selected from F, W and Y;
- $X_{18}$ is selected from A, D, E and N;
- $X_{21}$ is selected from A, S, V and W;
- $X_{25}$ is selected from D, G, H, K, L, N, R, V and W;
- $X_{28}$ is selected from A, D, E, H, K, L, N, Q, R, S, T, W and Y;
and ii) an amino acid sequence which has at least 96% identity to a sequence defined by i).

3. The FcRn binding dimer according to claim 1, wherein said first and second monomer units comprise identical BM sequences.

4. The FcRn binding dimer according to claim 1, wherein said first and second monomer units comprise different BM sequences.

5. The FcRn binding dimer according to claim 1, wherein at least one of said first and second monomer units comprises an FcRn binding motif BM corresponding to the sequence from position 8 to position 36 in a sequence selected from the group consisting of SEQ ID NO:1-353.

6. The FcRn binding dimer according to claim 5, wherein at least one of said first and second monomer units comprises an FcRn binding motif BM corresponding to the sequence from position 8 to position 36 in a sequence selected from the group consisting of SEQ ID NO:1, SEQ ID NO:20, SEQ ID NO:23, SEQ ID NO:41, SEQ ID NO:44, SEQ ID NO:65, SEQ ID NO:75 and SEQ ID NO:77.

7. The FcRn binding dimer according to claim 1, wherein at least one of said first and second monomer units comprises a sequence selected from the group consisting of:
- xi) AEAKYAK-[BM]-DPSQSSELLSEAKKLND-SQAPK (SEQ ID NO:405);
- xv) AEAKFAK-WW-DPSQSSELLSEAKKLSESQAPK (SEQ ID NO:412);
- xvii) VDAKYAK-WW-DPSQSSELLSEAKKLS-ESQAPK (SEQ ID NO:427);

wherein [BM] is an FcRn binding motif as defined in claim 1; and an amino acid sequence which has at least 94% identity to the sequence defined in xi), xv) or xvii).

8. The FcRn binding dimer according to claim 7, wherein at least one of said first and second monomer units comprises a sequence xi) selected from the group consisting of SEQ ID NO:354-357 and SEQ ID NO:360-367.

9. The FcRn binding dimer according to claim 1, wherein at least one of said first and second monomer units comprises a sequence selected from the group consisting of:

xxi) VDAKYAK-[B4]-DPSQS SELL SEAKKLNDSQAPK (SEQ ID NO:424);

wherein [BM] is an FcRn binding motif as defined in claim 1; and xxii) an amino acid sequence which has at least 94% identity to the sequence defined in xxi).

10. The FcRn binding dimer according to claim 9, wherein at least one of said first and second monomer units comprises a sequence xxi) selected from the group consisting of SEQ ID NO:1-353.

11. The FcRn binding dimer according to claim 10, wherein at least one of said first and second monomer units comprises a sequence xxi) selected from the group consisting of SEQ ID NO:1, SEQ ID NO:20, SEQ ID NO:23, SEQ ID NO:41, SEQ ID NO:44, SEQ ID NO:65, SEQ ID NO:75 and SEQ ID NO:77.

12. The FcRn binding dimer according to claim 8, wherein said first and second monomer units comprise SEQ ID NO:365 and SEQ ID NO:365; SEQ ID NO:366 and SEQ ID NO:366; or SEQ ID NO:367 and SEQ ID NO:367, respectively.

13. The FcRn binding dimer according to claim 1, wherein said linker has a general formula selected from $$(G_nS_m)_p \text{ and } (S_nG_m)_p,$$

wherein, independently,
n=1-7,
m=0-7,
n+m≤8 and
p=1-7.

14. The FcRn binding dimer according to claim 1, which is capable of binding to FcRn with at least 2 times higher capacity than the corresponding first monomer unit or second monomer unit alone.

15. A fusion protein or conjugate comprising
   a first moiety consisting of the FcRn binding dimer according to claim 1; and
   a second moiety consisting of a polypeptide having a desired biological activity.

16. The FcRn binding dimer according to claim 1, which inhibits binding of IgG to FcRn.

17. The FcRn binding dimer according to claim 1, which binds FcRn such that the ability of the FcRn binding dimer to block IgG binding to FcRn is at least 2 times higher compared to the blocking ability of the corresponding first or second monomer unit alone.

18. A composition comprising the FcRn binding dimer according to claim 1 and at least one pharmaceutically acceptable excipient or carrier.

19. A method of blocking IgG binding to FcRn, the method comprising
   contacting the FcRn binding dimer according to claim 1 with FcRn under conditions such that the FcRn binding dimer binds to FcRn.

20. The fusion protein or conjugate according to claim 15, which inhibits binding of IgG to FcRn.

21. The fusion protein or conjugate according to claim 15 which binds FcRn such that the ability of the FcRn binding dimer to block IgG binding to FcRn is at least 2 times higher compared to the blocking ability of the corresponding first or second monomer unit alone.

22. A composition comprising the fusion protein or conjugate according to claim 15 and at least one pharmaceutically acceptable excipient or carrier.

23. A method of blocking IgG binding to FcRn, the method comprising
   contacting the fusion protein or conjugate according to claim 15 with FcRn under conditions such that the FcRn binding dimer binds to FcRn.

* * * * *